US012427135B2

(12) United States Patent
Tumer et al.

(10) Patent No.: US 12,427,135 B2
(45) Date of Patent: Sep. 30, 2025

(54) COMPOSITIONS AND METHODS FOR INHIBITING RIBOSOME INACTIVATING PROTEINS

(71) Applicant: Rutgers, The State University of New Jersey, New Brunswick, NJ (US)

(72) Inventors: Nilgun E. Tumer, Belle Mead, NJ (US); Xiao-Ping Li, Flemington, NJ (US); Jacques Roberge, Piscataway, NJ (US); David Augeri, Princeton, NJ (US); Bin Cao, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/690,251

(22) Filed: Mar. 9, 2022

(65) Prior Publication Data

US 2022/0202772 A1 Jun. 30, 2022

Related U.S. Application Data

(63) Continuation-in-part of application No. PCT/US2020/049957, filed on Sep. 9, 2020.

(60) Provisional application No. 62/897,851, filed on Sep. 9, 2019.

(51) Int. Cl.
| | |
|---|---|
| *A61K 31/34* | (2006.01) |
| *A61K 31/381* | (2006.01) |
| *A61K 31/40* | (2006.01) |
| *A61K 31/41* | (2006.01) |
| *A61K 31/426* | (2006.01) |
| *A61K 31/69* | (2006.01) |
| *A61K 45/06* | (2006.01) |
| *A61P 39/02* | (2006.01) |
| *C07D 207/337* | (2006.01) |
| *C07D 277/56* | (2006.01) |
| *C07D 307/54* | (2006.01) |
| *C07D 333/24* | (2006.01) |
| *C07D 333/34* | (2006.01) |
| *C07D 333/38* | (2006.01) |
| *C07D 333/40* | (2006.01) |
| *C07D 333/70* | (2006.01) |
| *C07D 409/04* | (2006.01) |
| *C07F 5/02* | (2006.01) |

(52) U.S. Cl.
CPC ............ *A61K 31/381* (2013.01); *A61K 31/34* (2013.01); *A61K 31/40* (2013.01); *A61K 31/41* (2013.01); *A61K 31/426* (2013.01); *A61K 31/69* (2013.01); *A61K 45/06* (2013.01); *A61P 39/02* (2018.01); *C07D 207/337* (2013.01); *C07D 277/56* (2013.01); *C07D 307/54* (2013.01); *C07D 333/24* (2013.01); *C07D 333/34* (2013.01); *C07D 333/38* (2013.01); *C07D 333/40* (2013.01); *C07D 333/70* (2013.01); *C07D 409/04* (2013.01); *C07F 5/025* (2013.01)

(58) Field of Classification Search
CPC ........ A61K 31/69; A61K 31/381; A61P 39/02
See application file for complete search history.

(56) References Cited

U.S. PATENT DOCUMENTS

| | | | |
|---|---|---|---|
| 4,983,619 | A | 1/1991 | Gallagher et al. |
| 2002/0165264 | A1 | 11/2002 | Kort et al. |
| 2005/0288336 | A1 | 12/2005 | Graupe et al. |
| 2011/0263540 | A1 | 10/2011 | Pang et al. |

OTHER PUBLICATIONS

Wahome et al., Curr. Top. Microbiol. Immunol. (2011) 357:179-207. (Year: 2011).*

Chiou , et al., "The ribosomal stalk is required for ribosome binding, depurination of the rRNA and cytotoxicity of ricin A chain in *Saccharomyces cerevisiae*", Mol Microbiol, 70(6), 2008, pp. 1441-1452.

Jetzt , et al., "Toxicity of ricin A chain can be reduced in mammalian cells by inhibiting its interaction with the ribosome", Toxicol Appl Pharmacol, 310, 2016, pp. 120-128.

Li , et al., "Small Molecule Inhibitors Targeting the Interaction of Ricin Toxin A Subunit with Ribosomes", ACS Infect Dis, 6, 2020, pp. 1894-1905.

Li , et al., "Synthesis and Structural Characterization of Ricin Inhibitors Targeting Ribosome Binding Using Fragment-Based Methods and Structure-Based Design", J Med Chem, 64, 2021, pp. 15334-15348.

May , et al., "The P1/P2 proteins of the human ribosomal stalk are required for ribosome binding and depurination by ricin in human cells", FEBS Journal, 279, 2012, pp. 3925-3936.

Park , et al., "Chemical Structure of Retro-2, a Compound that Protects Cells against Ribosome-Inactivating Proteins", Scientific Reports 2, 631, 2012, pp. 1-4.

Pruet , et al., "7-substituted pterins provide a new direction for ricin A chain inhibitors", Eur J Med Chem, 46(9), 2011, pp. 3608-3615.

(Continued)

*Primary Examiner* — Marcos L Sznaidman
(74) *Attorney, Agent, or Firm* — Saul Ewing LLP; Kathryn Doyle; Domingos J. Silva

(57) ABSTRACT

The disclosure provides in one aspect a method of treating, ameliorating, and/or preventing toxicity caused by a ribosome inactivating protein (RIP) in a subject. In certain embodiments, the method comprises administering to the subject a therapeutically effective amount of at least one compound of the disclosure.

23 Claims, 79 Drawing Sheets

Specification includes a Sequence Listing.

(56) References Cited

OTHER PUBLICATIONS

Saenz, et al., "Identification and Characterization of Small Molecules that Inhibit Intracellular Toxin Transport", Infect Immun, vol. 75, No. 9, 2007, pp. 4552-4561.
Baito, et al., "Peptide-conjugated pterins as inhibitors of Ricin Toxin A", J Med Chem, 56(1), 2013, pp. 320-329.
Stechmann, et al., "Inhibition of Retrograde Transport Protects Mice from Lethal Ricin Challenge", Cell, 141, 2010, pp. 231-242.
Wahome, et al., "Small-Molecule Inhibitors of Ricin and Shiga Toxins", Curr Top Microbiol Immunol, 357, 2012, pp. 179-207.
Yan, et al., "Structure-based Identification of a Ricin Inhibitor", J Mol Biol, vol. 266, 1997, pp. 1043-1049.
"PubChem CID 78598", 5-Methoxybenzimidzole, Mar. 27, 2005.
PCT International Search Report & Written Opinion dated Dec. 22, 2020 for corresponding PCT International Application PCT/US2020/049957.

* cited by examiner

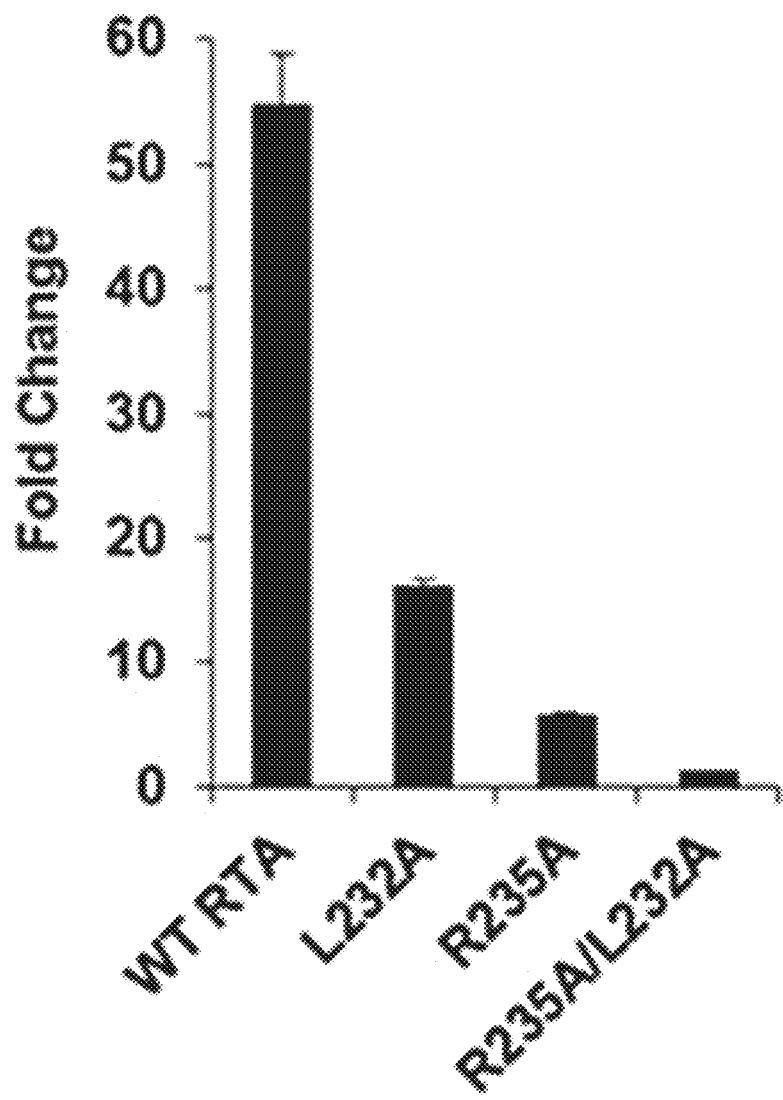

FIG. 3
Adenine
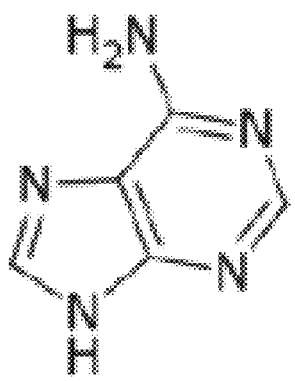
135.127 Da
P11
SDDDMGFGLFD
1218.25 Da
myo-inositol
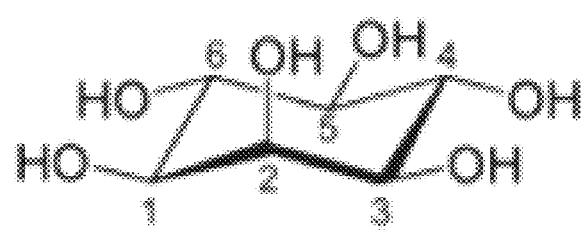
180.16 Da
PT
RGWGHPSGYS
1103.15 Da

FIG. 6

| Fragment | K_D | Percent Inhibition (%) Yeast | Percent Inhibition (%) Rat liver | Fragment | K_D | Percent Inhibition (%) Yeast | Percent Inhibition (%) Rat liver |
|---|---|---|---|---|---|---|---|
| RF1 | 3.28E-07 | 29 | 29 | RF41 | 2.47E-03 | -5 | 25 |
| RF2 | 4.05E-05 | 98 | 93 | RF42 | 2.67E-03 | 77 | 99 |
| RF3 | 4.36E-05 | -1 | 10 | RF43 | 2.70E-03 | 31 | 18 |
| RF4 | 7.88E-05 | -35 | 50 | RF44 | 2.87E-03 | 34 | 43 |
| RF5 | 1.28E-04 | -22 | 49 | RF45 | 3.04E-03 | 98 | 100 |
| RF6 | 1.29E-04 | 90 | 11 | RF46 | 3.33E-03 | 70 | 90 |
| RF7 | 1.37E-04 | 69 | 91 | RF47 | 3.37E-03 | -3 | 23 |
| RF8 | 2.81E-04 | 54 | -18 | RF48 | 3.50E-03 | 60 | 98 |
| RF9 | 3.21E-04 | 50 | 15 | RF49 | 3.57E-03 | 27 | 94 |
| RF10 | 3.63E-04 | -26 | 13 | RF50 | 3.61E-03 | 34 | 94 |
| RF11 | 3.78E-04 | 64 | 18 | RF51 | 3.84E-03 | 64 | 16 |
| RF12 | 3.94E-04 | 99 | 97 | RF52 | 3.92E-03 | 85 | 96 |
| RF13 | 4.54E-04 | 67 | 12 | RF53 | 4.06E-03 | 34 | -17 |
| RF14 | 4.77E-04 | -32 | 39 | RF54 | 4.09E-03 | -20 | 23 |
| RF15 | 5.62E-04 | 89 | 87 | RF55 | 4.20E-03 | 57 | 84 |
| RF16 | 6.24E-04 | 73 | 99 | RF56 | 4.26E-03 | 72 | 73 |
| RF17 | 6.87E-04 | 75 | 96 | RF57 | 4.57E-03 | 59 | -2 |
| RF18 | 7.39E-04 | -21 | -8 | RF58 | 5.32E-03 | 25 | 54 |
| RF19 | 7.97E-04 | -50 | 26 | RF59 | 6.55E-03 | 100 | 98 |
| RF20 | 8.46E-04 | -9 | 40 | RF60 | 6.56E-03 | -24 | -8 |
| RF21 | 9.17E-04 | 52 | -20 | RF61 | 6.87E-03 | 98 | 99 |
| RF22 | 9.30E-04 | 60 | 99 | RF62 | 9.53E-03 | 32 | 72 |
| RF23 | 1.06E-03 | 99 | 100 | RF63 | 1.17E-02 | -82 | 31 |
| RF24 | 1.14E-03 | 99 | 99 | RF64 | 4.80E-02 | 1 | 61 |
| RF25 | 1.16E-03 | 62 | 3 | RF65 | 8.65E-02 | -41 | 53 |
| RF26 | 1.26E-03 | 63 | -15 | RF66 | 3.73E+0 | 12 | 36 |
| RF27 | 1.32E-03 | -18 | 38 | RF67 | 6.53E+0 | 90 | 98 |
| RF28 | 1.54E-03 | 93 | 96 | RF68 | 1.39E+01 | 91 | 99 |
| RF29 | 1.55E-03 | 43 | 94 | RF69 | 1.51E+01 | -8 | -1 |
| RF30 | 1.65E-03 | 34 | 6 | RF70 | 2.98E+01 | 96 | 100 |
| RF31 | 1.68E-03 | 79 | 91 | RF71 | 3.02E+01 | 16 | 76 |
| RF32 | 1.68E-03 | -36 | 51 | RF72 | 3.02E+01 | -53 | 33 |
| RF33 | 1.69E-03 | -16 | 36 | RF73 | 3.23E+01 | 85 | 77 |
| RF34 | 1.71E-03 | 83 | 99 | RF74 | 3.60E+01 | -38 | 46 |
| RF35 | 1.77E-03 | -14 | 15 | RF75 | 3.71E+01 | 98 | 99 |
| RF36 | 1.98E-03 | 86 | 99 | RF76 | 3.85E+01 | 71 | 38 |
| RF37 | 2.08E-03 | 93 | 93 | RF77 | - | -1 | 38 |
| RF38 | 2.11E-03 | 15 | 44 | RF78 | - | -55 | 34 |
| RF39 | 2.34E-03 | -3 | 14 | RF79 | - | -39 | 41 |
| RF40 | 2.44E-03 | 100 | 50 | | | | - |

FIG. 9
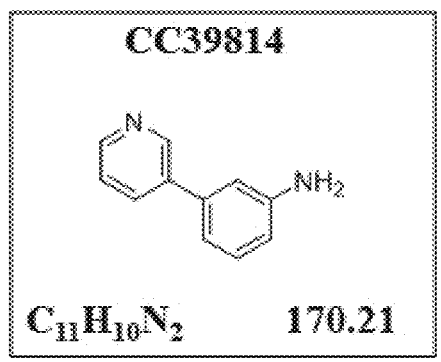
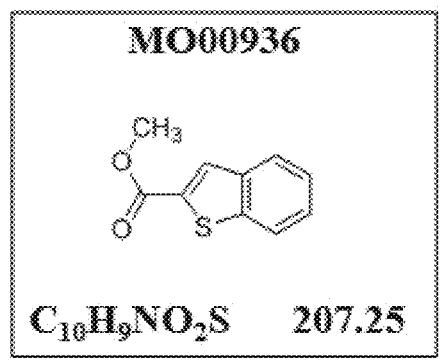
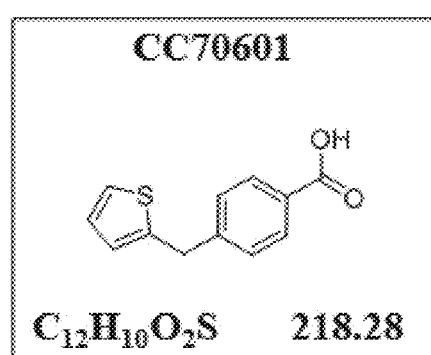
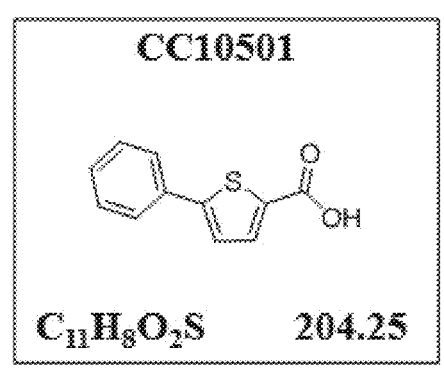
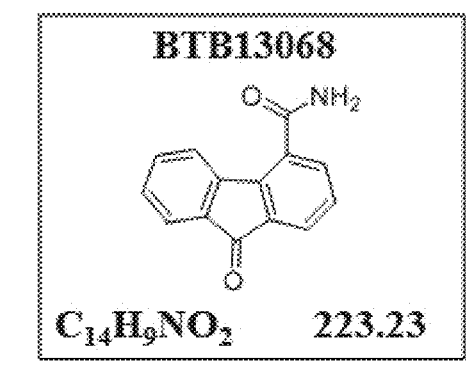
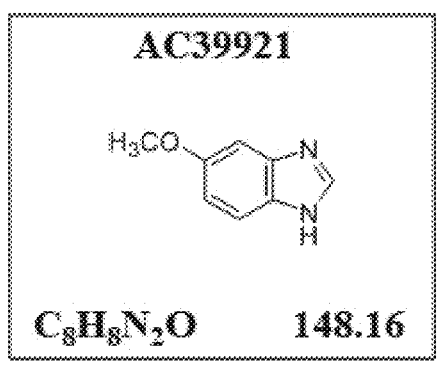
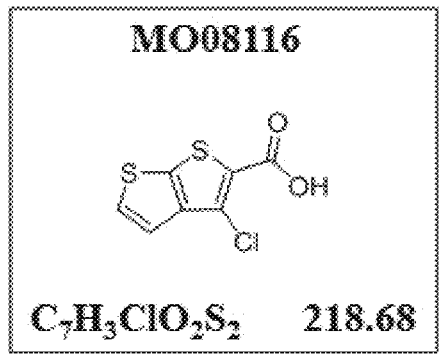
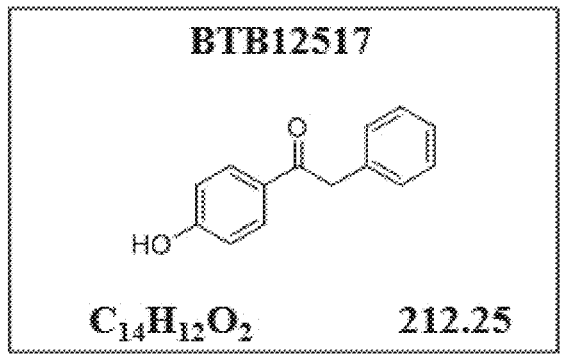

FIG. 12A

RTA-CC10501

FIG. 12B

RTA-CC70601

FIG. 13A

|  | Ricin catalytic subunit | | |
|---|---|---|---|
| Data set | RTA + CC10501 | RTA + CC70601 | RTA + BTB13068 |
| Unit Cell Data | | | |
| Space group | $P6_322$ | $P6_311$ | $P4_32_12$ |
| Cell parameters (Å,°) | $a = 168.35$, $b = 168.35$, $c = 54.83$, $\alpha,\beta = 90$, $\gamma = 120.0$ | $a = 168.62$, $b = 168.62$, $c = 54.66$, $\alpha,\beta = 90$, $\gamma = 120.0$ | $a = 66.23$, $b = 66.23$, $c = 264.57$, $\alpha,\beta,\gamma = 90$ |
| $V_m$ (Å$^3$/Dalton) | 3.7 | 3.7 | 2.4 |
| # of subunits in the asymmetric unit | 1 | 1 | 2 |
| Data Collection | | | |
| Beamline | LRL-CAT | LRL-CAT | LRL-CAT |
| Wavelength (Å) | 0.97931 | 0.97931 | 0.97931 |
| Temperature (K) | 100 | 100 | 100 |
| Resolution Range (Å) | 145.80-1.99 (2.04-1.99) | 146.02-2.40 (2.49-2.40) | 66.14-1.54 (1.57-1.54) |
| Total # of observed reflections | 775660 (53962) | 411233 (26050) | 2238366 (46300) |
| Number of unique reflections | 31903 (2190) | 18435 (1891) | 88500 (4211) |
| $R_{merge}$ (%) | 19.9 (222.4) | 13.8 (153.9) | 12.4 (117.4) |
| $R_{pim}$ (%) | 4.1 (45.5) | 2.9 (42.9) | 2.5 (35.6) |
| CC1/2 (%) | 0.99 (0.81) | 0.99 (0.75) | 0.99 (0.75) |
| $<I/\sigma(I)>$ | 17.6 (2.0) | 20.9 (1.9) | 18.2 (2.0) |
| Completeness (%) | 100 (100) | 100 (100) | 100 (99.4) |
| Multiplicity | 24.3 (24.6) | 22.3 (13.8) | 25.3 (11) |
| Wilson B-factor (Å$^2$) | 25.8 | 33.1 | 12.1 |

FIG. 13B

| Data set | Ricin catalytic subunit | | |
|---|---|---|---|
| | RTA + CC10501 | RTA + CC70601 | RTA + BTB13068 |
| Refinement | | | |
| R-work (%) | 18.4 | 18.5 | 16.4 |
| R-free (%) | 21.8 | 23.5 | 19.5 |
| # of atoms | 2336 | 2248 | 5083 |
| Protein atoms | 2060 | 2042 | 4202 |
| Ligand atoms | 14 | 15 | 17 |
| Solvent atoms | 262 | 191 | 864 |
| Model Quality | | | |
| RMS Deviation from Ideal Value | | | |
| Bond length (Å) | 0.01 | 0.01 | 0.01 |
| Bond angle (deg) | 1.43 | 1.49 | 1.48 |
| Average B-factor | | | |
| Protein atoms (Å$^2$) | 34.3 | 45.6 | 16.8 |
| Ligand atoms (Å$^2$) | 42.2 | 88.3 | 10.7 |
| Waters (Å$^2$) | 52.1 | 65.3 | 31.1 |
| Ramanchandran Plot | | | |
| Most favored regions (%) | 98.1 | 97.7 | 99.6 |
| Allowed regions (%) | 1.5 | 1.9 | 0.4 |
| Outlier regions (%) | 0.4 | 0.4 | 0.0 |
| PDB entries | 6URX | 6URW | 6URY |

FIG. 28

| CODE | MW | STRUCTURE | KD (μM) | IC50 | INHIBITORY RTA ACTIVITY |
|---|---|---|---|---|---|
| CC10501 | | 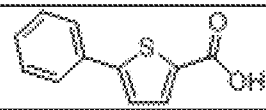 | 270 | 37 | |
| RU-NT-047 | 246 | 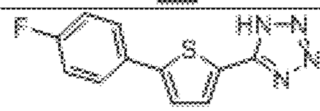 | 80 | 36 | |
| RU-NT-057 | 242 | 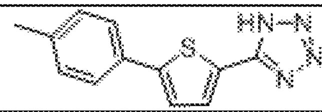 | 106 | 6 | |
| RU-NT-059 | 248 | 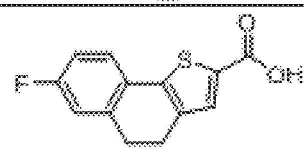 | | 20 | |
| RU-NT-061 | 308 | 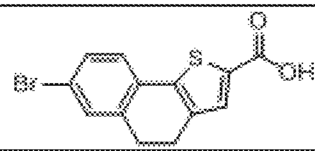 | 94 | 33 | |
| RU-NT-062 | 244 | 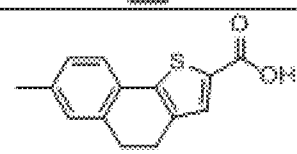 | 70 | 35 | |
| RU-NT-070 | 281 | 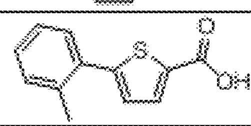 | 65 | 30 | |
| RU-NT-075 | 246 | 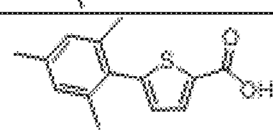 | 190 | | More than CC1501 |
| RU-NT-082 | 254 | 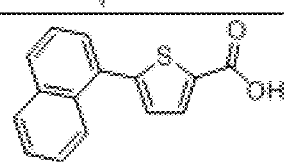 | 209 | | Similar as CC10501 |
| RU-NT-085 | 258 | 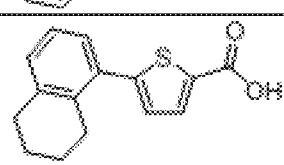 | 224 | | More than CC1501 |
| RU-NT-093 | 232 | 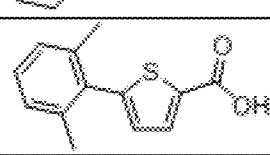 | 62 | | |

FIG. 29A

Ricin

PDB: 2AAI

FIG. 29B

Shiga toxin

PDB:1R4P

FIG. 32
Model of yeast and human stalk
Yeast ribosomal stalk
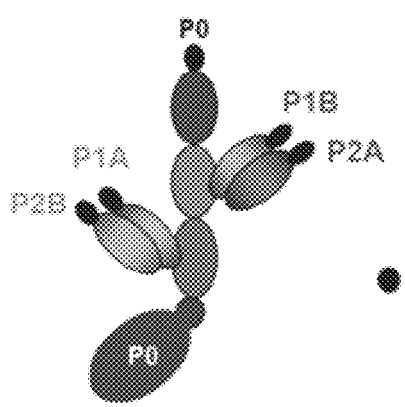
P0(P1A-P2B)(P1B/P2A)
Human ribosomal stalk
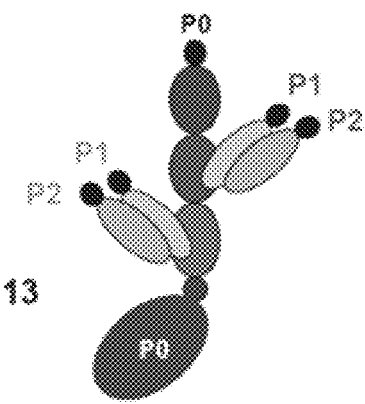
● Conserved last 13 amino acids
P0(P1-P2)$_2$ FIG. 33
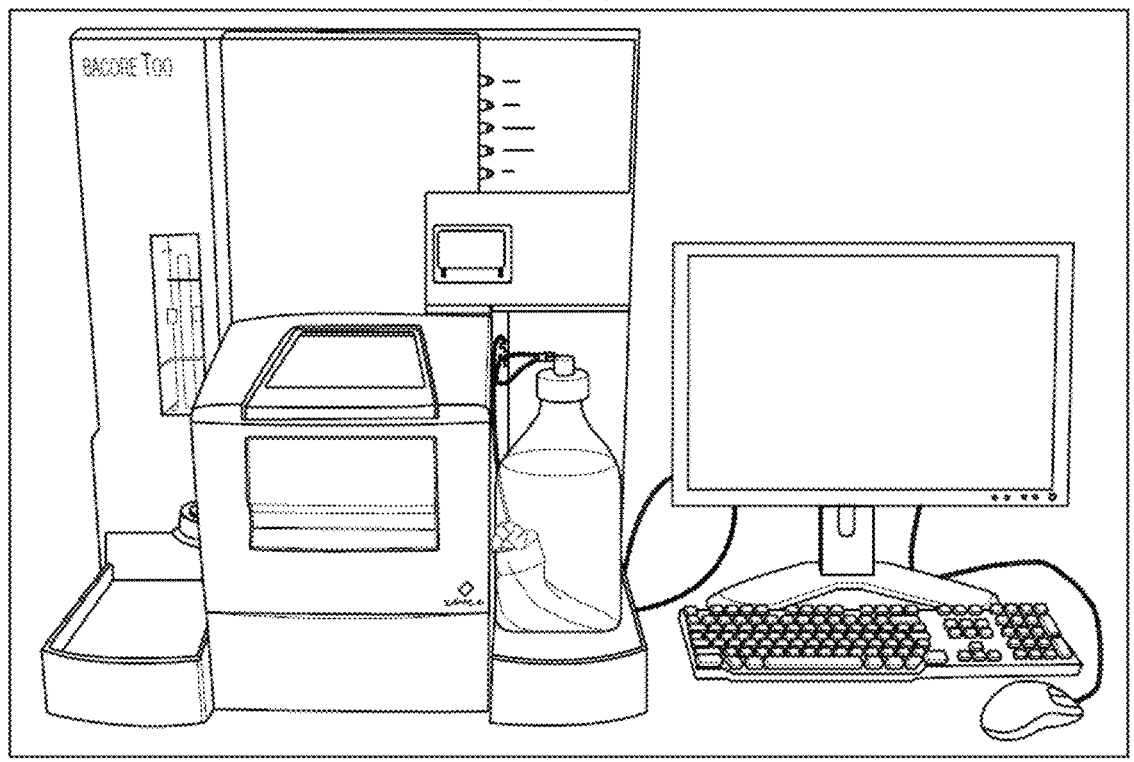
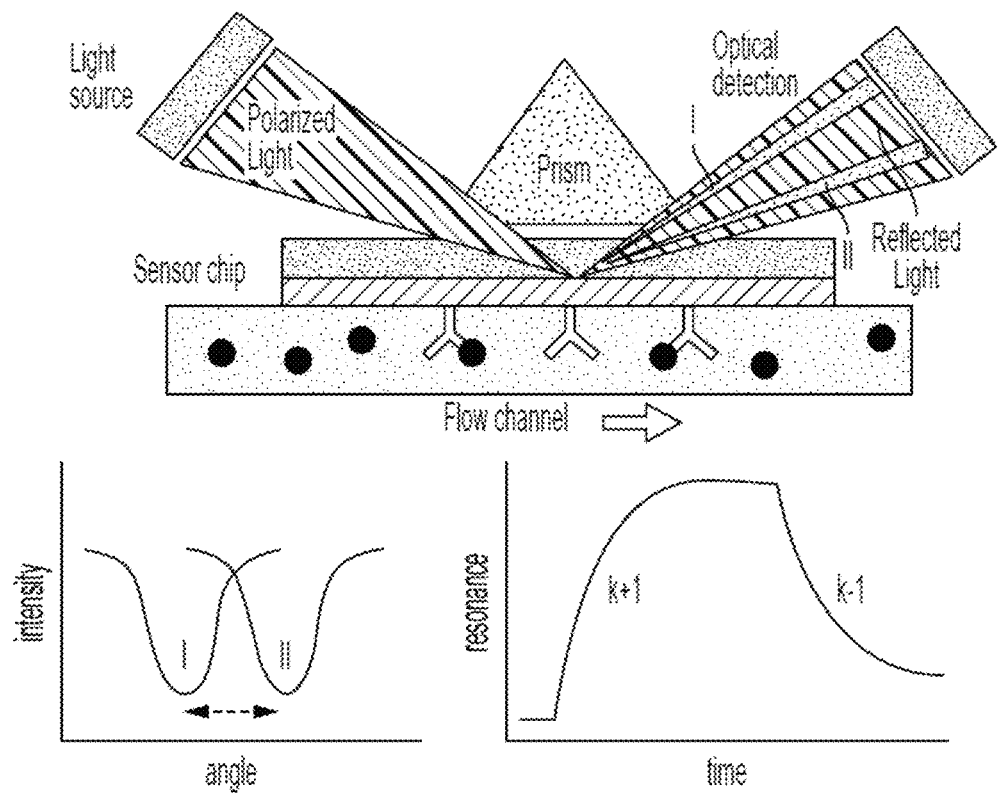

Structure of the RTA-P6 complex

Ricin uses arginine 235 interact with the last Asp of P6, GFGLFD

P-protein C termini: SDDDMGFGLFD
P6: GFGLFD

PDB ID: 5GU4

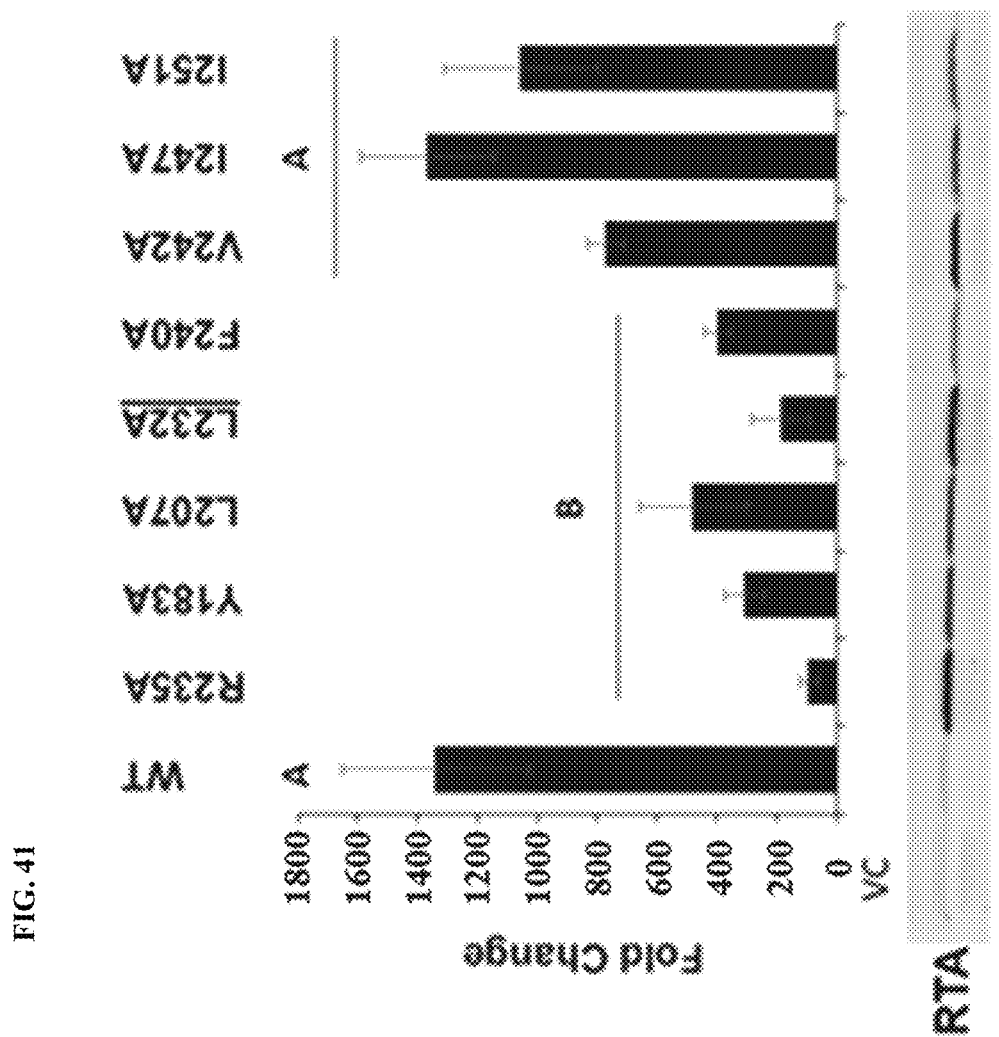
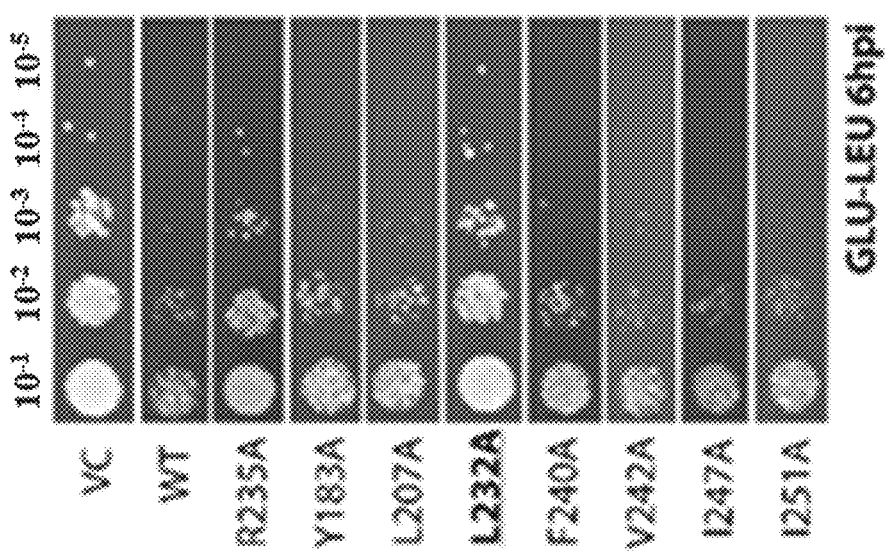
FIG. 41

FIG. 43
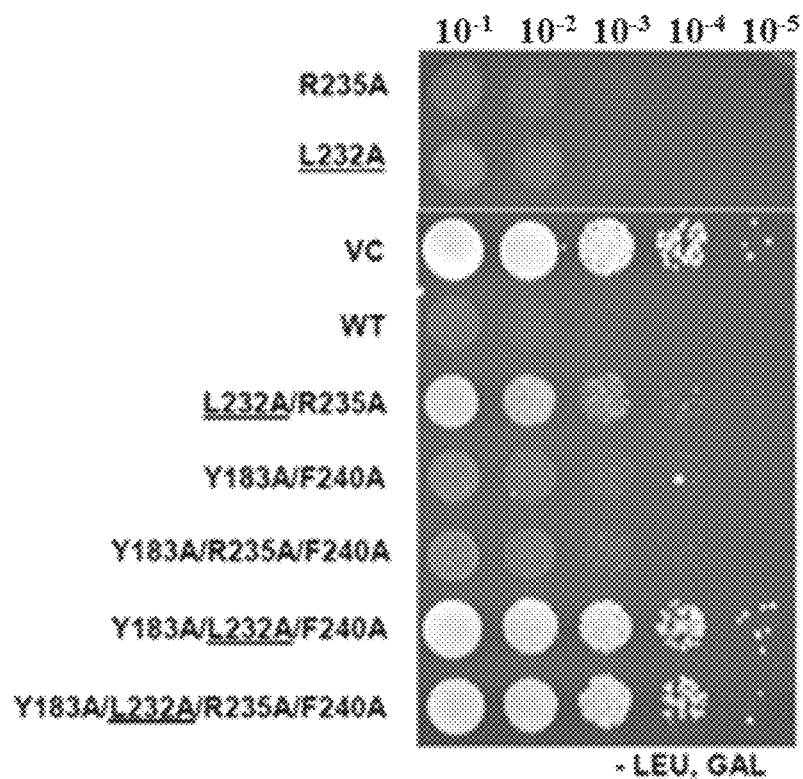
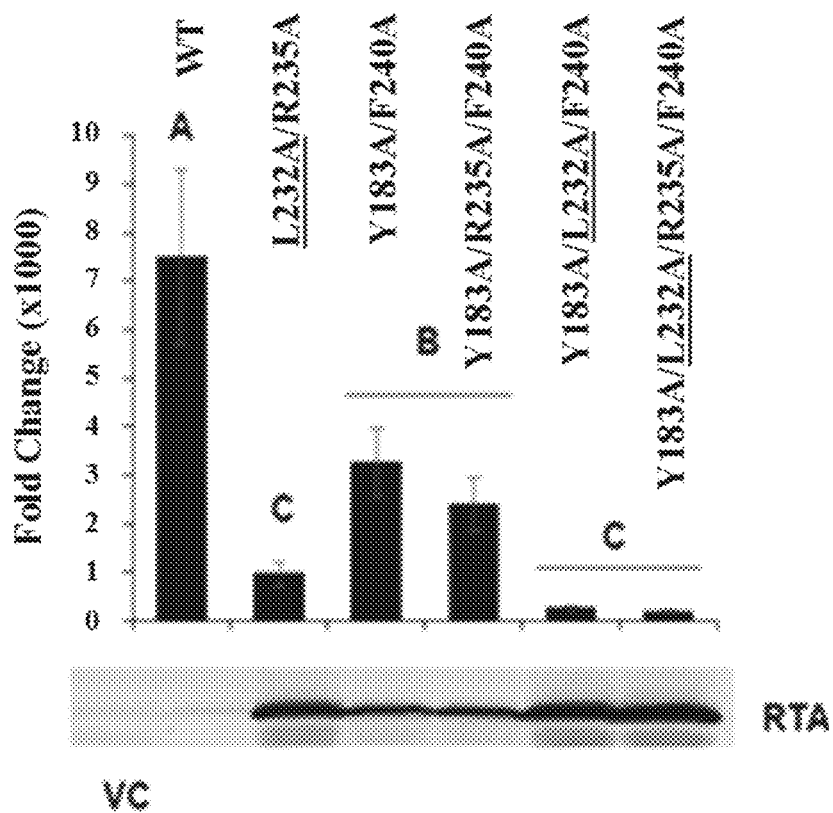

FIG. 45

| Peptides | Sequence | $K_D$ (μM)* | Yeast ribosome $IC_{50}$ (μM)* |
|---|---|---|---|
| P11 | SDDDMGFGLFD | 196 ± 17 | 4.7 ± 0.9 |
| P10 | DDDMGFGLFD | 272 ± 6 | 7.9 ± 1.7 |
| P9 | DDMGFGLFD | 309 ± 7 | 15 ± 1.5 |
| P8 | DMGFGLFD | 299 ± 5 | 23 ± 4.4 |
| P7 | MGFGLFD | 294 ± 47 | 34 ± 9.5 |
| P6 | GFGLFD | 399 ± 20 | 63 ± 13 |
| P5 | FGLFD | 497 ± 30 | 121 ± 44 |
| P4 | GLFD | 451 ± 17 | 102 ± 45 |
| P3 | LFD | > 10 mM | |

FIG. 48

SEQUENCE LISTING

<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: Chemically synthesized

<400> SEQUENCE: 1

Ser Asp Asp Asp Met Gly Phe Gly Leu Phe Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically synthesized

<400> SEQUENCE: 2

Arg Gly Trp Gly His Pro Ser Gly Tyr Ser
1               5                   10

<210> SEQ ID NO 3
<211> LENGTH: 24
<212> TYPE: PRT
<213> ORGANISM: Artificial Sequence
<220> FEATURE:
<223> OTHER INFORMATION: Chemically synthesized

<400> SEQUENCE: 3

Ala Pro Ala Lys Val Glu Ala Lys Glu Ser Glu Glu Ser Asp Glu
1               5                   10                  15

Asp Met Gly Phe Gly Leu Phe Asp
            20

<210> SEQ ID NO 4
<211> LENGTH: 24
<212> TYPE: PRT
<213> ORGANISM: Artificial Sequence
<220> FEATURE:
<223> OTHER INFORMATION: Chemically synthesized

<400> SEQUENCE: 4

Glu Lys Lys Val Glu Ala Lys Lys Glu Ser Glu Glu Ser Asp Asp
1               5                   10                  15

Asp Met Gly Phe Gly Leu Phe Asp
            20

<210> SEQ ID NO 5
<211> LENGTH: 24
<212> TYPE: PRT
<213> ORGANISM: Artificial Sequence
<220> FEATURE:
<223> OTHER INFORMATION: Chemically synthesized

<400> SEQUENCE: 5

Glu Glu Lys Lys Asp Glu Lys Lys Glu Ser Glu Glu Ser Asp Asp
1               5                   10                  15

Asp Met Gly Phe Gly Leu Phe Asp
            20

<210> SEQ ID NO 6
<211> LENGTH: 24
<212> TYPE: PRT
<213> ORGANISM: Artificial Sequence
<220> FEATURE:
<223> OTHER INFORMATION: Chemically synthesized

<400> SEQUENCE: 6

Ala Pro Ala Glu Glu Ala Ala Ala Glu Glu Glu Glu Ser Asp Asp
1               5                   10                  15

Asp Met Gly Phe Gly Leu Phe Asp
            20

<210> SEQ ID NO 7
<211> LENGTH: 21
<212> TYPE: PRT
<213> ORGANISM: Artificial Sequence
<220> FEATURE:
<223> OTHER INFORMATION: Chemically synthesized

<400> SEQUENCE: 7

Glu Lys Glu Glu Glu Glu Ala Lys Glu Ser Asp Asp Asp Met Gly
1               5                   10                  15

Phe Gly Leu Phe Asp
            20

<210> SEQ ID NO 8
<211> LENGTH: 21
<212> TYPE: PRT
<213> ORGANISM: Artificial Sequence
<220> FEATURE:
<223> OTHER INFORMATION: Chemically synthesized

<400> SEQUENCE: 8

Glu Glu Lys Glu Glu Glu Ala Ala Glu Glu Ser Asp Asp Asp Met Gly
1               5                   10                  15

Phe Gly Leu Phe Asp
            20

<210> SEQ ID NO 9
<211> LENGTH: 22
<212> TYPE: PRT
<213> ORGANISM: Artificial Sequence
<220> FEATURE:

<223> OTHER INFORMATION: Chemically synthesized

<400> SEQUENCE: 9

Glu Glu Glu Lys Glu Glu Glu Ala Ala Glu Glu Ser Asp Asp Asp Met
1               5                   10                  15

Gly Phe Gly Leu Phe Asp
            20

<210> SEQ ID NO 10
<211> LENGTH: 22
<212> TYPE: PRT
<213> ORGANISM: Artificial Sequence
<220> FEATURE:
<223> OTHER INFORMATION: Chemically synthesized

<400> SEQUENCE: 10

Glu Glu Glu Lys Glu Glu Glu Ala Lys Glu Glu Ser Asp Asp Asp Met
1               5                   10                  15

Gly Phe Gly Leu Phe Asp
            20

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized

<400> SEQUENCE: 11

Asp Asp Asp Met Gly Phe Gly Leu Phe Asp
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Chemically synthesized

<400> SEQUENCE: 12

Asp Asp Met Gly Phe Gly Leu Phe Asp
1               5

<210> SEQ ID NO 13
<211> LENGTH: 8
<212> TYPE: PRT
<213> ORGANISM: Artificial Sequence
<220> FEATURE:
<223> OTHER INFORMATION: Chemically synthesized

<400> SEQUENCE: 13

Asp Met Gly Phe Gly Leu Phe Asp
1               5

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized

<400> SEQUENCE: 14

Met Gly Phe Gly Leu Phe Asp
1               5

```
<210> SEQ ID NO 15
<211> LENGTH: 6
<212> TYPE: PRT
<213> ORGANISM: Artificial Sequence
<220> FEATURE:
<223> OTHER INFORMATION: Chemically synthesized

<400> SEQUENCE: 15

Gly Phe Gly Leu Phe Asp
1               5

<210> SEQ ID NO 16
<211> LENGTH: 5
<212> TYPE: PRT
<213> ORGANISM: Artificial Sequence
<220> FEATURE:
<223> OTHER INFORMATION: Chemically synthesized

<400> SEQUENCE: 16

Phe Gly Leu Phe Asp
1               5

<210> SEQ ID NO 17
<211> LENGTH: 4
<212> TYPE: PRT
<213> ORGANISM: Artificial Sequence
<220> FEATURE:
<223> OTHER INFORMATION: Chemically synthesized

<400> SEQUENCE: 17

Gly Leu Phe Asp
1

<210> SEQ ID NO 18
<211> LENGTH: 3
<212> TYPE: PRT
<213> ORGANISM: Artificial Sequence
<220> FEATURE:
<223> OTHER INFORMATION: Chemically synthesized

<400> SEQUENCE: 18

Leu Phe Asp
1
```

COMPOSITIONS AND METHODS FOR INHIBITING RIBOSOME INACTIVATING PROTEINS

CROSS-REFERENCE TO RELATED APPLICATIONS

This application is a continuation-in-part of, and claims priority to, PCT Application No. PCT/US2020/049957, filed Sep. 9, 2020, which claims priority under 35 U.S.C. § 119(e) to U.S. Provisional Patent Application No. 62/897,851, filed Sep. 9, 2019, all of which is hereby incorporated by reference in its entirety herein.

STATEMENT REGARDING FEDERALLY SPONSORED RESEARCH OR DEVELOPMENT

This invention was made with government support under grant number AI072425 awarded by the National Institutes of Health. The government has certain rights in the invention.

SEQUENCE LISTING

The ASCII text file named "370602-7018US1_Sequence_Listing.txt" created on Mar. 8, 2022, comprising 4.6 Kbytes, is hereby incorporated by reference in its entirety.

BACKGROUND OF THE DISCLOSURE

Ribosome inactivating proteins (RIPs) are a class of protein synthesis inhibitors that act at the ribosome. Trichosanthin, a plant toxin derived from *Trichosanthes kirilowii*, is an example of a type I ribosome inactivating protein (RIP), which comprises an active A chain (RTA). The plant toxin ricin and Shiga toxins (Stxs) are type II ribosome inactivating proteins (RIPs) or AB-toxins, which comprise an active A chain (RTA) or A1 chain (Stx2A1) covalently linked to a cell binding B chain (RTB or Stx2B). Ricin is one of the most lethal substances known, and Stxs produced by *Shigella dysenteriae* and *E. coli* O157:H7 (STEC) are responsible for food-borne outbreaks of dysentery and hemolytic-uremic syndrome (HUS). HUS is the most common cause of renal failure in infants and young children in the US. Both Ricin and Stxs depurinate a universally conserved adenine in the highly conserved sarcin-ricin loop (SRL) of the large rRNA and inhibit protein synthesis. Currently, no FDA-approved vaccine or therapeutic exists to protect against ricin or Shiga toxins. In light of the spreading of multi-drug resistant *Shigella* and *E. coli* infections in the US, the length of time required for diagnosis (around a month), and vulnerability of children and elderly, quick diagnosis and treatment are national and international research priorities.

Although small-molecule RIP inhibitors have been reported, none of them exhibit potent protection against RIPs. Hence, there is an unmet need in the art to develop potent RIP-inhibitors to treat toxicity caused by RIPs. The present disclosure addresses this unmet need.

BRIEF SUMMARY OF THE DISCLOSURE

The present disclosure relates in part to methods of treating, ameliorating, or preventing toxicity caused by a ribosome inactivating protein (RIP) in a subject, the method comprising administering to the subject a therapeutically effective amount of a compound of Formula (I), or a salt, solvate, stereoisomer, geometric isomer, and/or tautomer thereof:

$$R^1 \underset{X^2}{\overset{X^1}{\diagdown}} {*}{-}A{-}B\overset{**}{-}R^2, \quad (I)$$

wherein A, B, $R^1$, $R^2$, $X^1$, and $X^2$ are defined elsewhere herein. In certain embodiments, the RIP is a type I RIP. On other embodiments, the RIP is a type II RIP. The present disclosure further relates to pharmaceutical compositions comprising at least one pharmaceutically acceptable carrier and at least one compound contemplated herein, or a salt, solvate, stereoisomer, geometric isomer, and/or tautomer thereof.

BRIEF DESCRIPTION OF THE DRAWINGS

The following detailed description of certain embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIGS. 2A-2B show cytotoxicity and depurination level of RTA mutants in yeast. FIG. 2A: viability of yeast at 8 hpi (hours post-injection). FIG. 2B: Depurination level was measured at 1 hpi using qRT-PCR and expressed relative to no toxin control.

FIG. 3 provides binding controls for the fragment screen with Biacore. Adenine and P11 peptide (SEQ ID NO: 1) were used as positive controls and myo-inositol and PT peptide (SEQ ID NO: 2) were used as negative controls. The molecular weights of each are indicated. The structure of the last 6 amino acids of P11 (underlined) with RTA have been solved.

FIG. 6 is a table showing illustrative dissociation constant ($K_D$) and percent inhibition of 79 fragments with yeast and rat liver ribosomes at 100 µM fragment concentration.

FIG. 9 depicts chemical structures of eight illustrative fragments.

FIG. 10A provides CC10501 (5-phenylthiophene-2-carboxylic acid; CC70601 (4-(thien-2-ylmethyl) benzoic acid); and BTB13068 (9-oxofluorene-4-carboxamide). FIG. 10B provides inhibitor bound structures (stereoviews), the superposition of RTA structures in complex with CC10501, CC70601, and BTB13068.

FIG. 12A shows illustrative X-ray crystal structure of CC10501 with RTA. It binds at the ribosome binding site and makes a key interaction with Arg235 imitating the interaction of Arg235 with the last Asp of P6.

FIG. 12B shows illustrative X-ray crystal structure of CC70601 with RTA. It binds at the ribosome-binding site and makes a key interaction with Arg235.

FIGS. 13A-13B show an illustrative table of the data collection and refinement statistics of RTA complexes of RTA+CC10501, RTA+CC70601, and RTA+BTB13068.

FIG. 15A shows the electrostatic surface representation of CC10501, CC70601, and C-terminal stalk protein (P2) in the hydrophobic pocket of RTA. FIG. 15B shows a cartoon representation (zoomed in) of CC10501 (stick), CC70601 (stick), and C-terminal stalk protein (P2, stick) in the hydrophobic pocket of RTA.

FIG. 18A shows superposition of RTA structure in complex with CC10501, CC70601, BTB13068 with the RTA-RTB complex. FIG. 18B shows close views of CC10501 and CC70601 binding in the hydrophobic pocket. The binding position of Phe262 from RTB into the hydrophobic RTA pocket is indicated.

FIG. 28 is a table showing a illustrative nalogues of CC10501 having a higher affinity and inhibitory activity against RTA compared to CC10501.

Figure 29A:
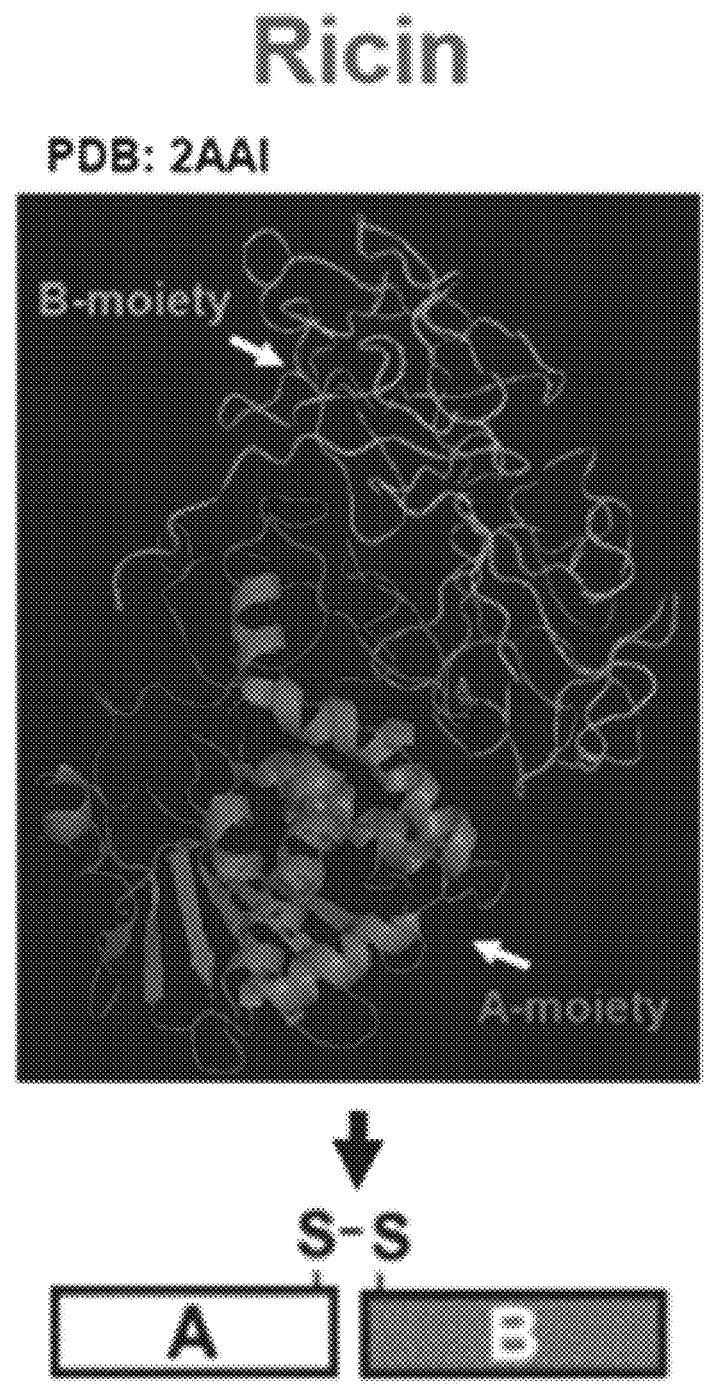
Figure 29B:
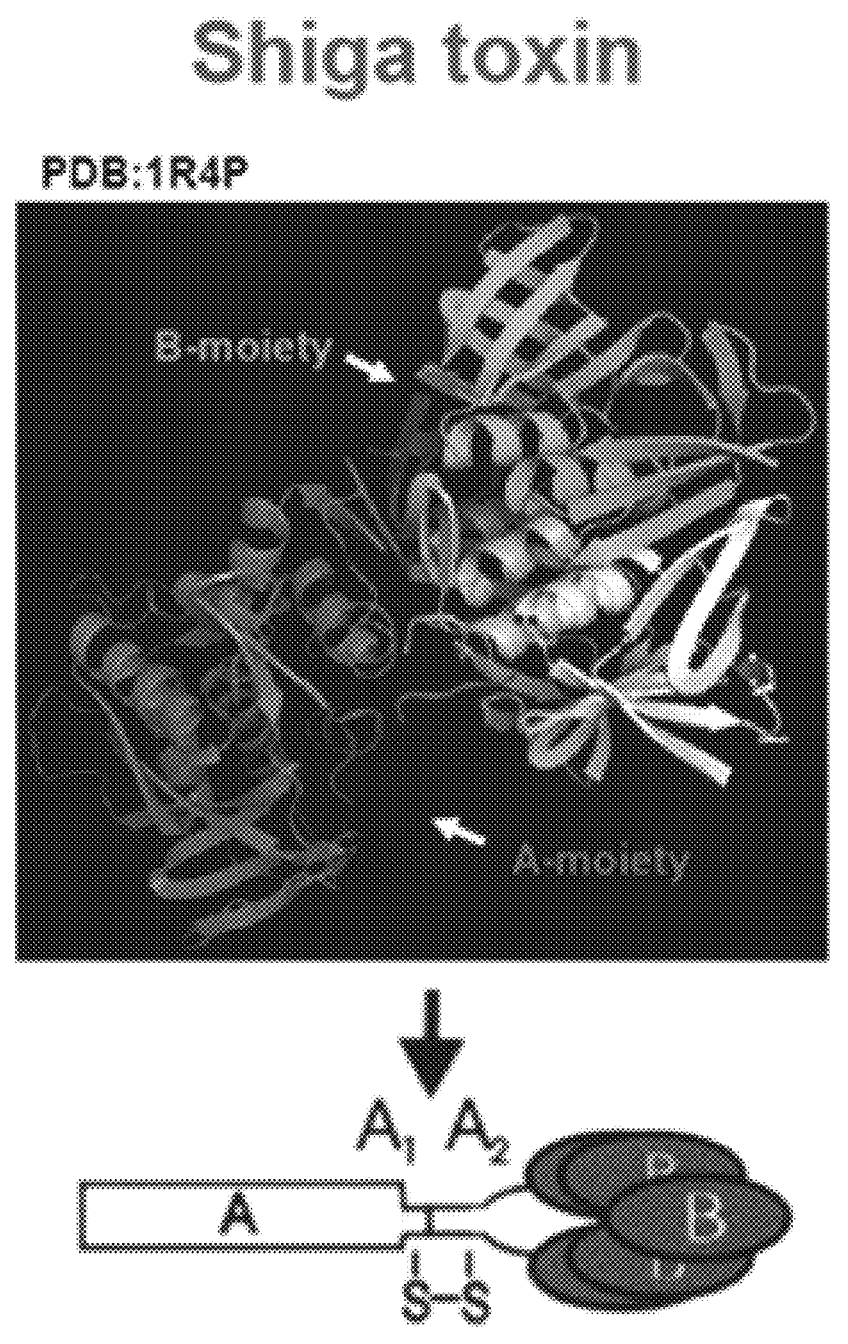

FIGS. 29A-29B show illustrative structures of ricin (FIG. 29A) and shiga toxin (FIG. 29B).

FIG. 32 show illustrative models of yeast and human stalk and overlapping conserved amino acid sequences: Hs-P0 (SEQ ID NO: 3), Hs-P1 (SEQ ID NO: 4), Hs-P2 (SEQ ID NO: 5), Sc-P0 (SEQ ID NO: 6), Sc-P1α (SEQ ID NO: 7), Sc-P1β (SEQ ID NO: 8), Sc-P2a (SEQ ID NO: 9), and Sc-P2β (SEQ ID NO: 10).

FIG. 33 illustrates a set-up and working principle of surface plasmon resonance. Thin gold film deposited on glass is excited by plane polarized light to induce an evanescent wave; an increase in mass on the sensor surface causes an increase in the refractive index; measures change in the resonance angle in real time as a change in response units (ΔRU); the sensor gram is a continuous display of RU over time.

Figure 36:
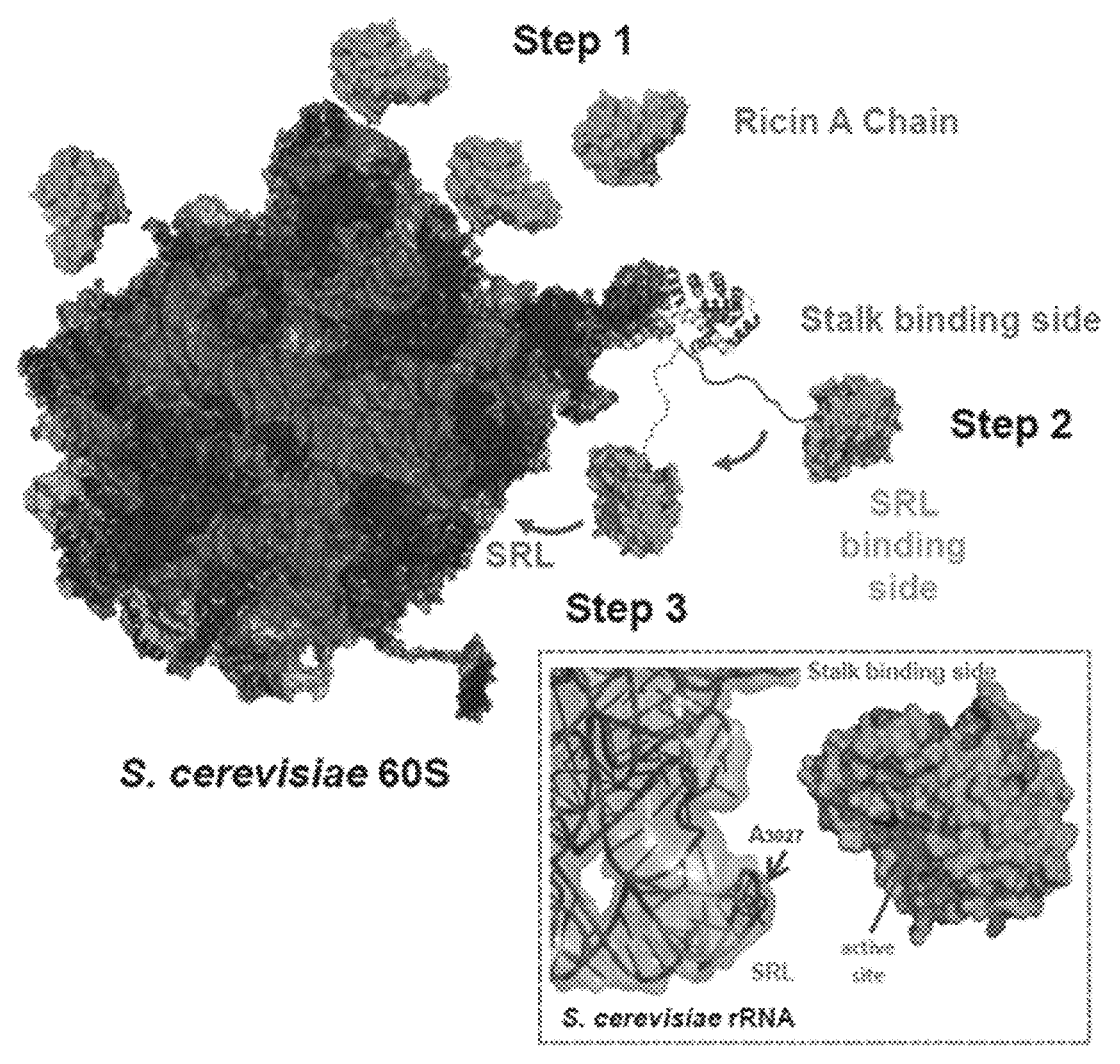

FIG. 36 Illustrates a model of how RTA depurinates the ribosome. Step 1: RTA molecules are concentrated on the ribosomal surface by electrostatic interactions. Step 2: Interaction with the C-termini of P stalk proteins reorient the active site of RTA towards the SRL. Step 3: P stalk binding stimulates the catalysis of depurination by delivering RTA to the SRL.

FIG. 40 shows an illustrative structure of the RTA-P6 complex with C-terminal sequence (SEQ ID NO: 1).

Figure 1:
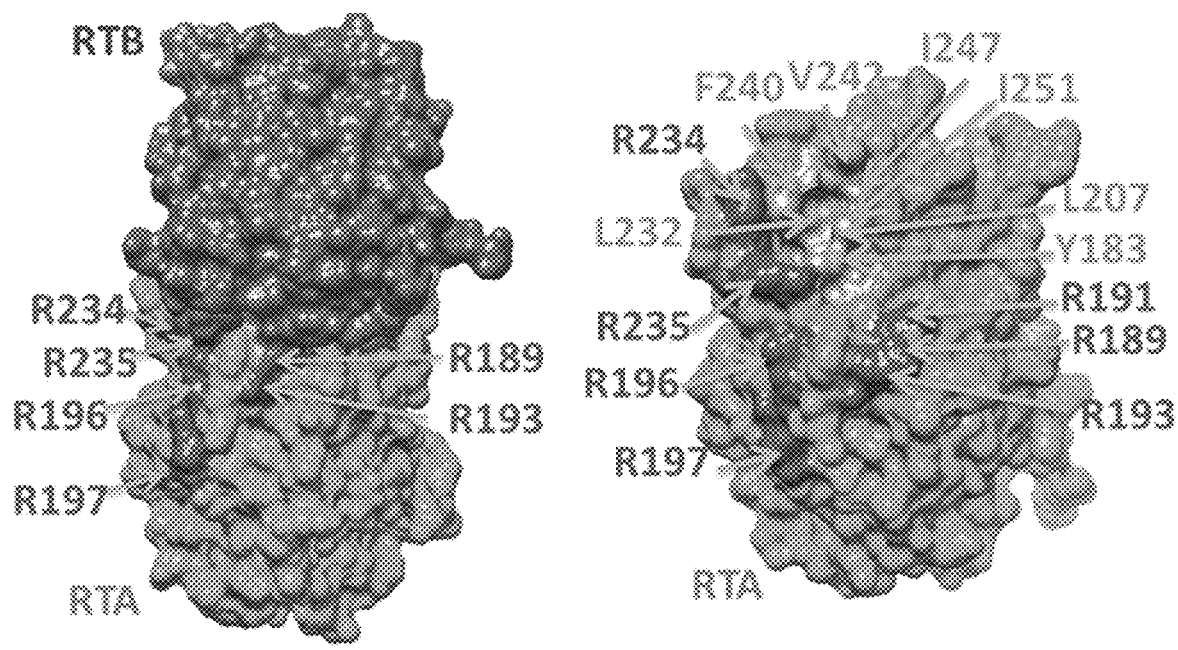
FIG. 1 shows structure of ricin holotoxin (left PDB ID: 2AAI) and RTA (right PDB ID: 1RTC). Arginine residues at the RTA/RTB interface are labeled and residues in the hydrophobic pocket are also labeled.
Figure 2A:
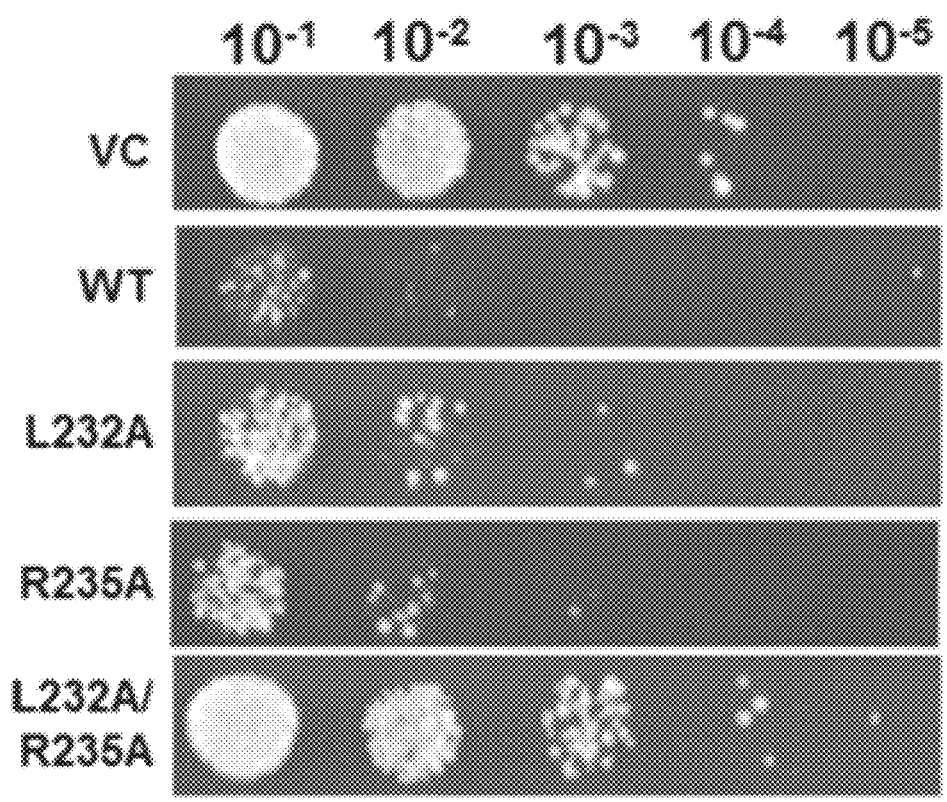
Figure 4A:
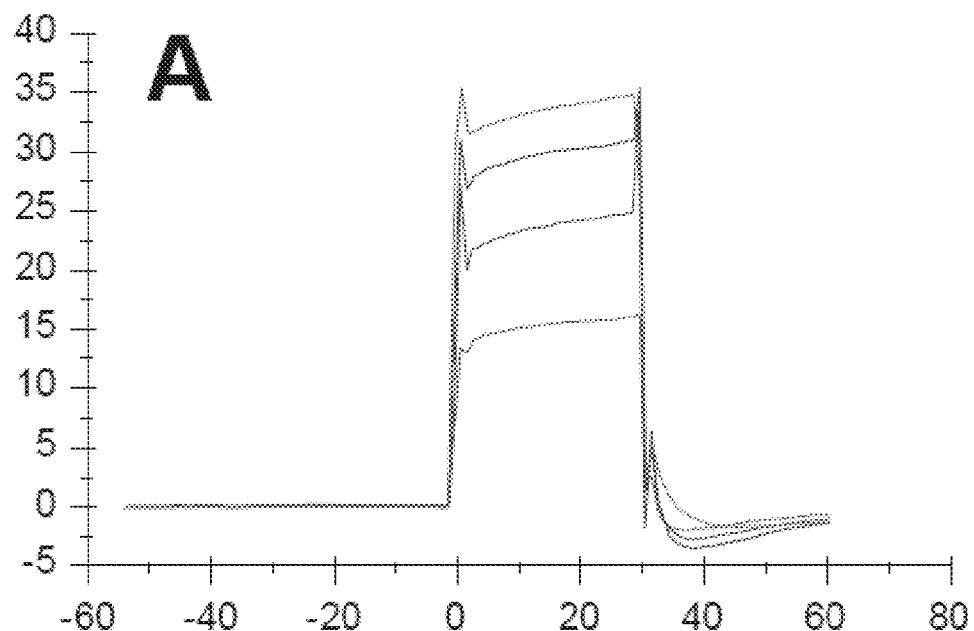
FIGS. 4A-4P provide illustrative results of kinetic screening from one plate, including the sensorgrams of fragment inhibitors at 62.5, 125, 250, and 500 µM.
Figure 4B:
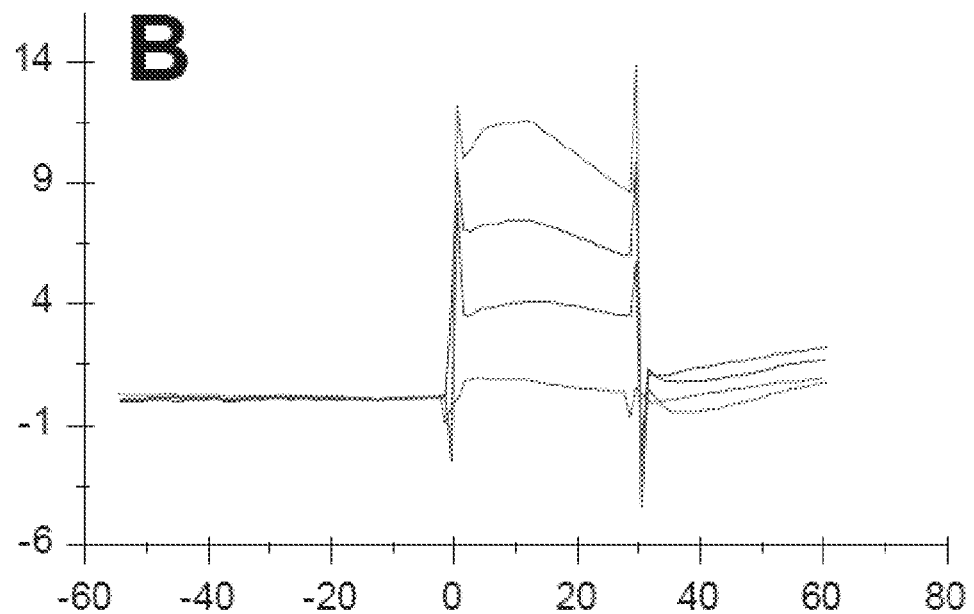
Figure 4C:
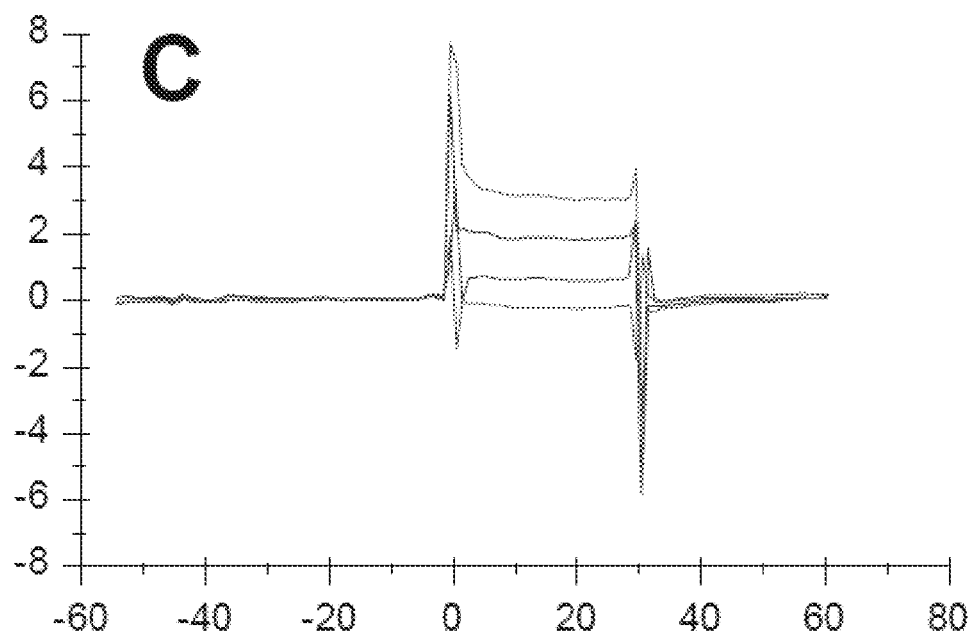
Figure 4D:
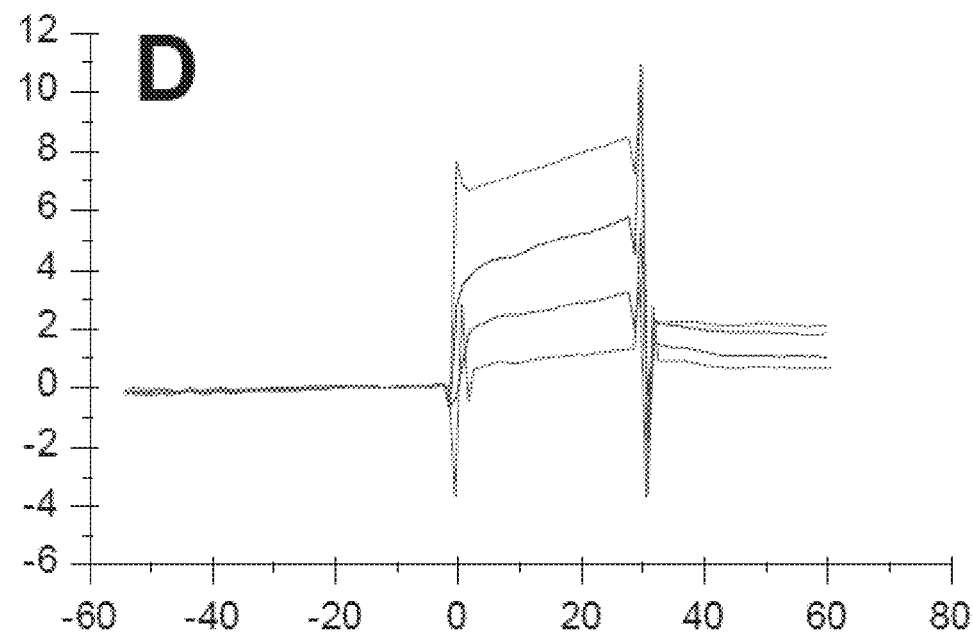
Figure 4E:
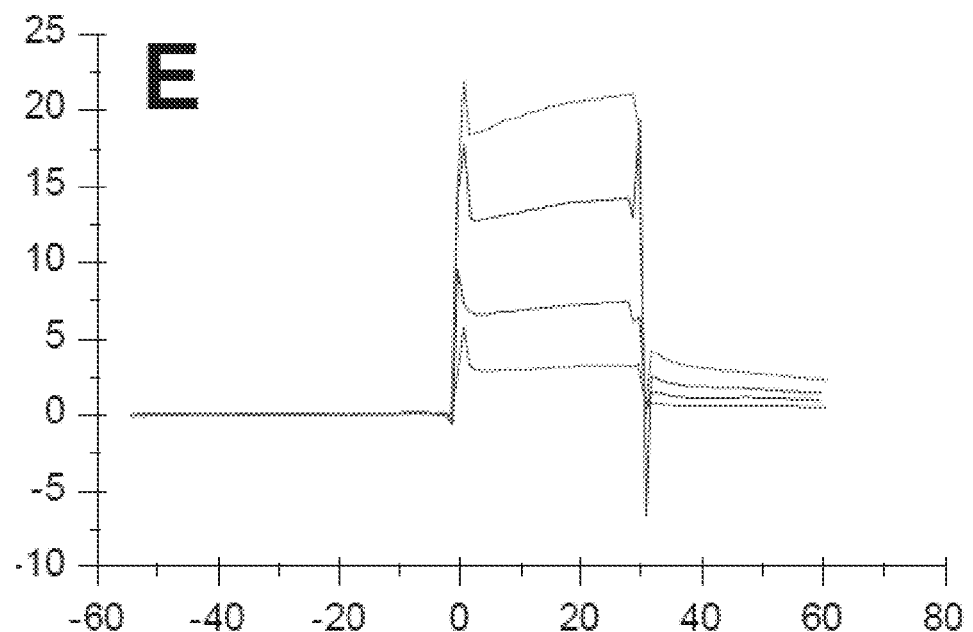
Figure 4F:
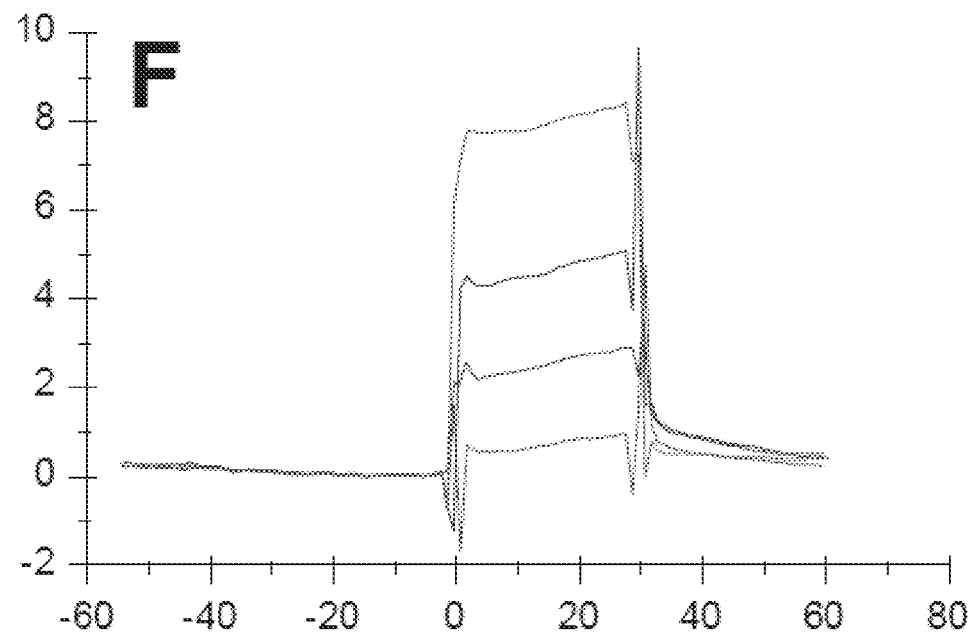
Figure 4G:
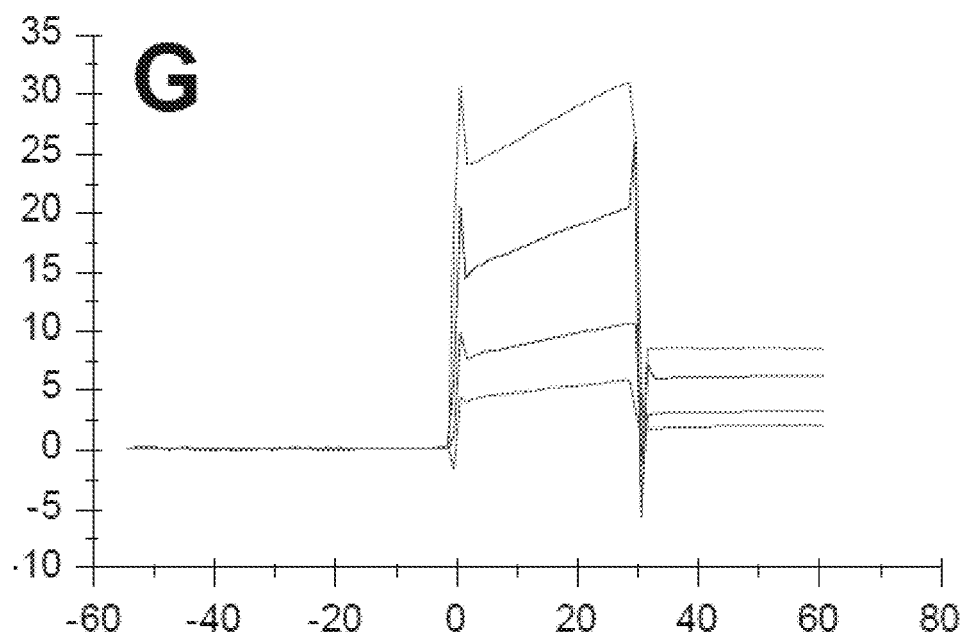
Figure 4H:
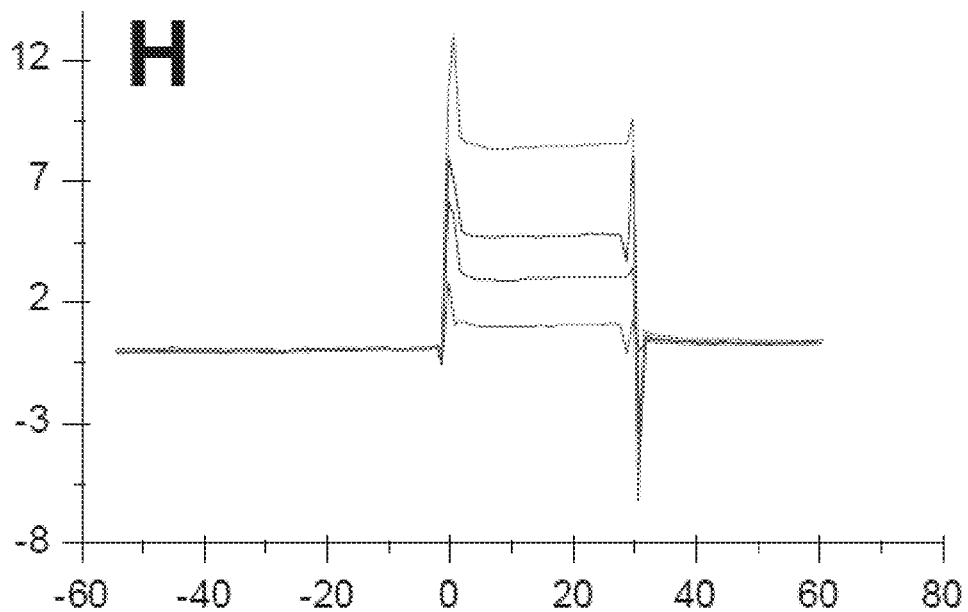
Figure 4I:
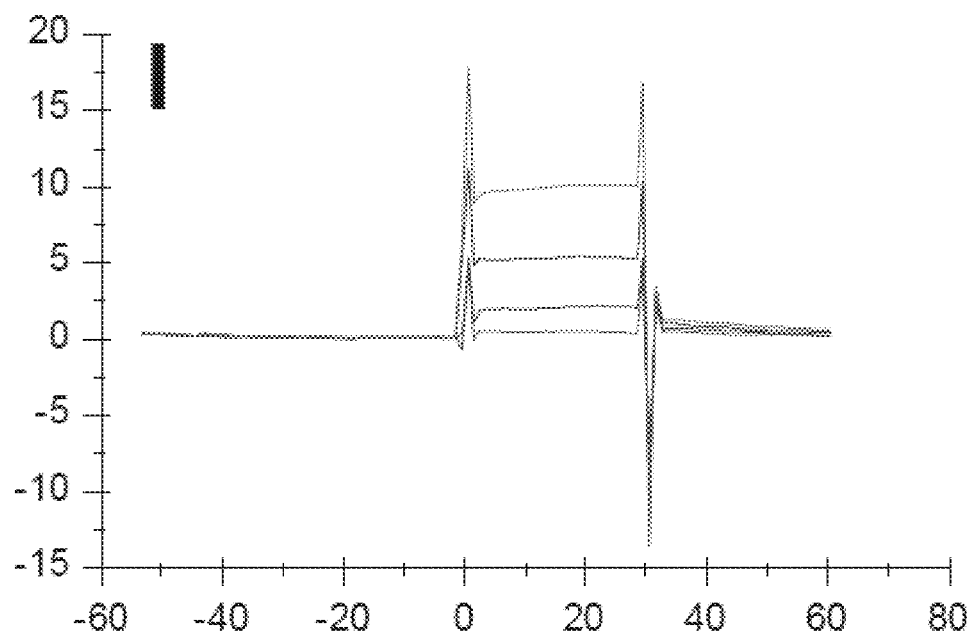
Figure 4J:
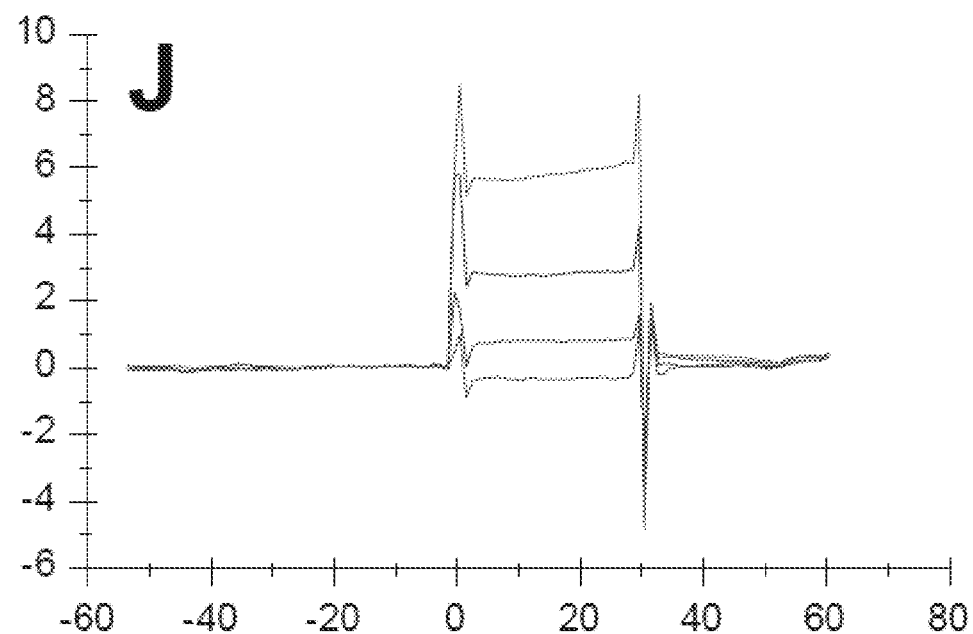
Figure 4K:
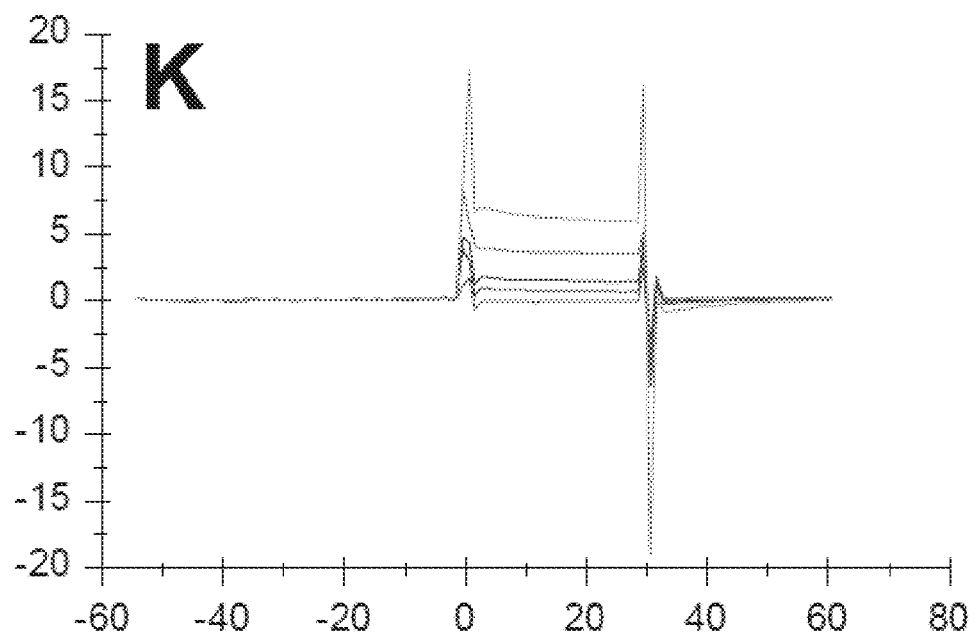
Figure 4L:
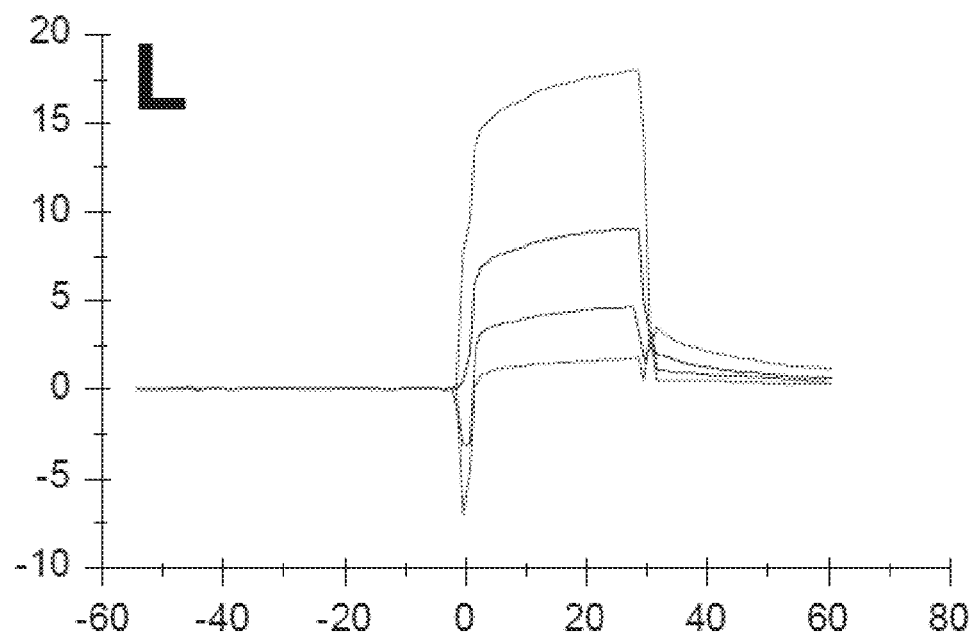
Figure 4M:
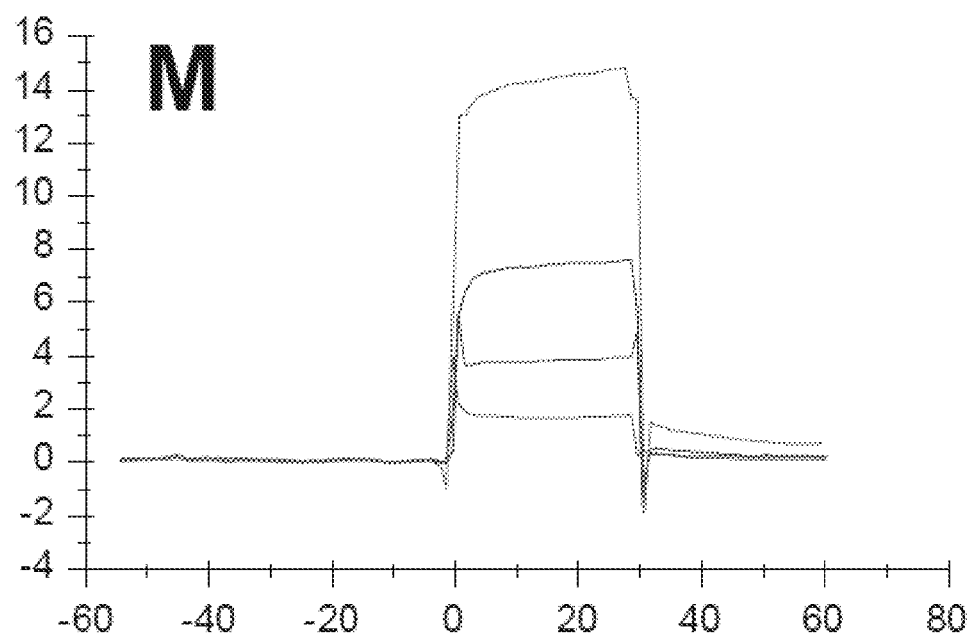
Figure 4N:
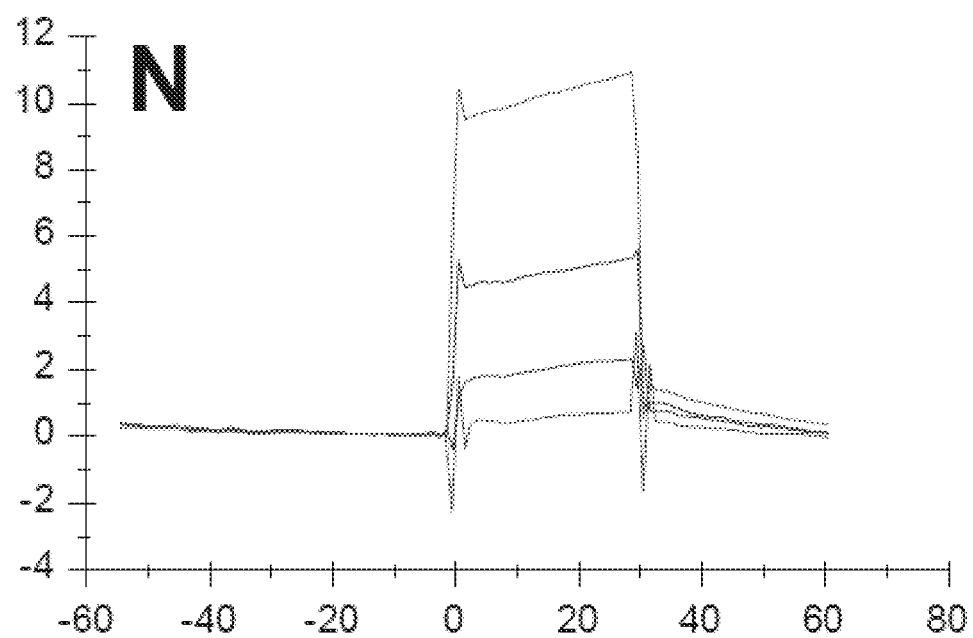
Figure 4O:
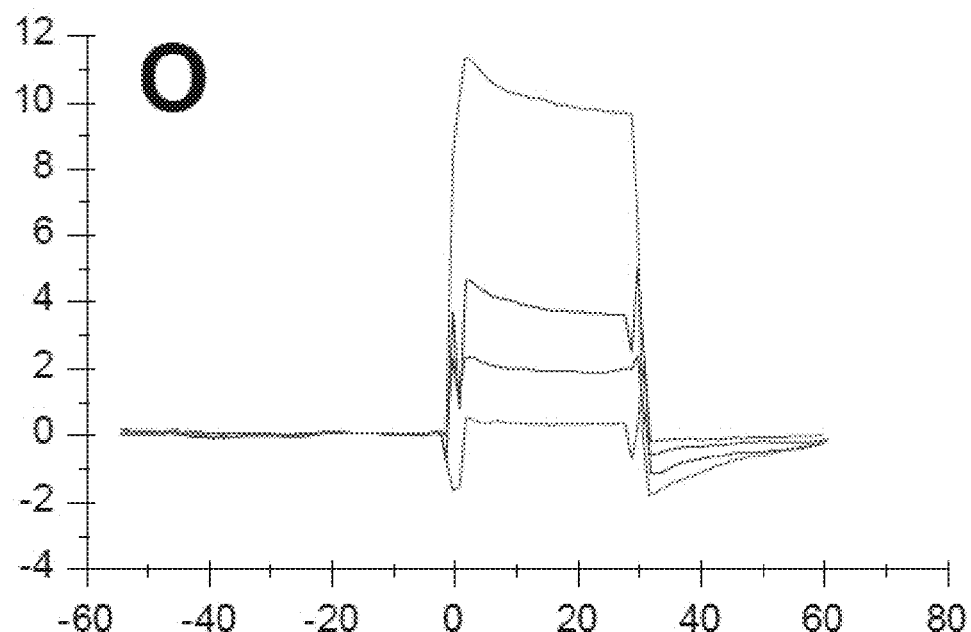
Figure 4P:
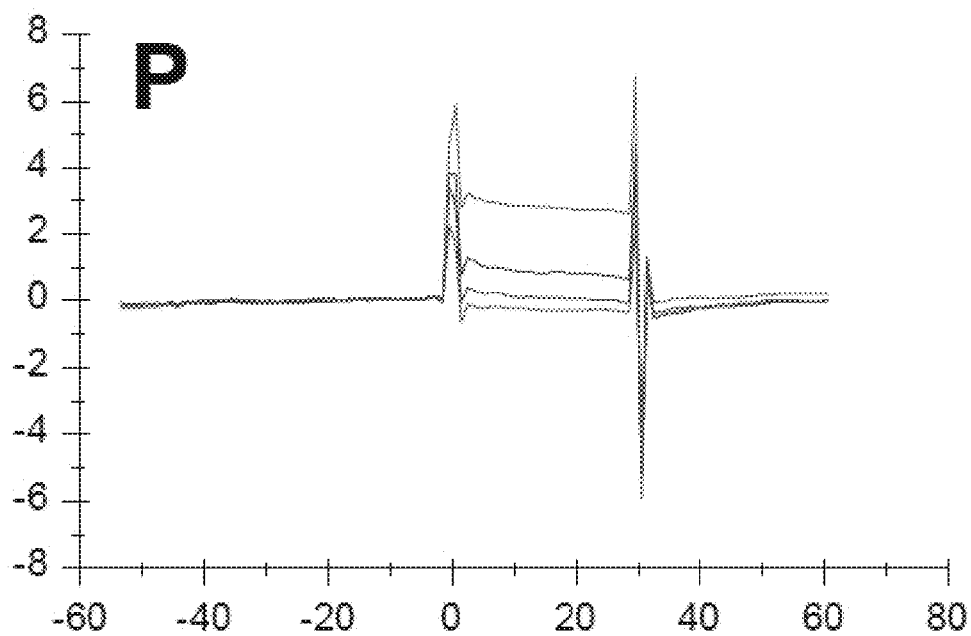
Figure 5A:
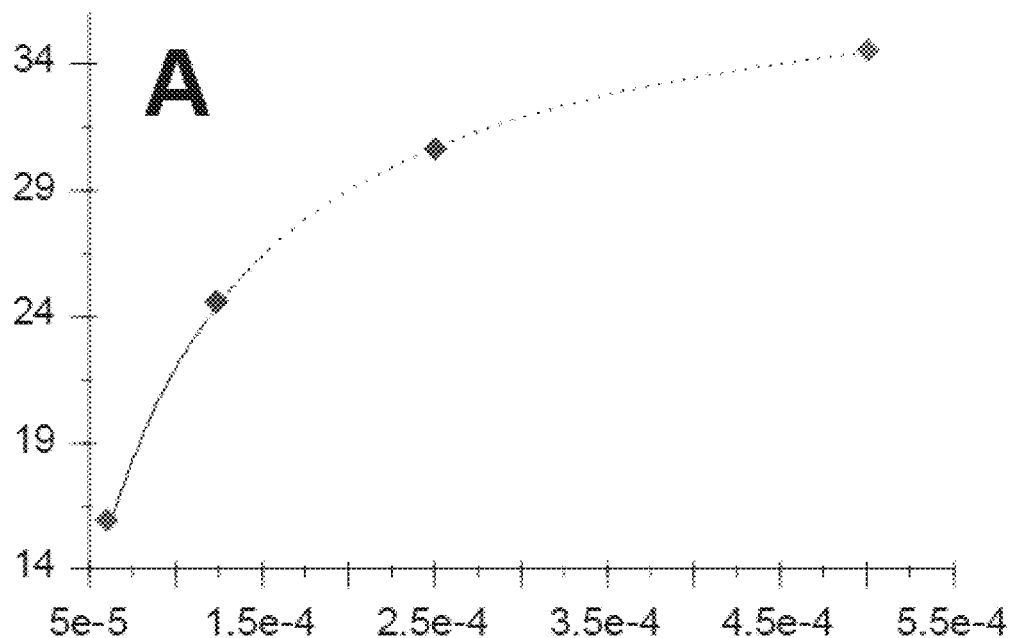
FIGS. 5A-5P provide illustrative results of kinetic screening from one plate, including the kinetic fittings of the sensorgrams of fragment inhibitors at 62.5, 125, 250, and 500 µM.
Figure 5B:
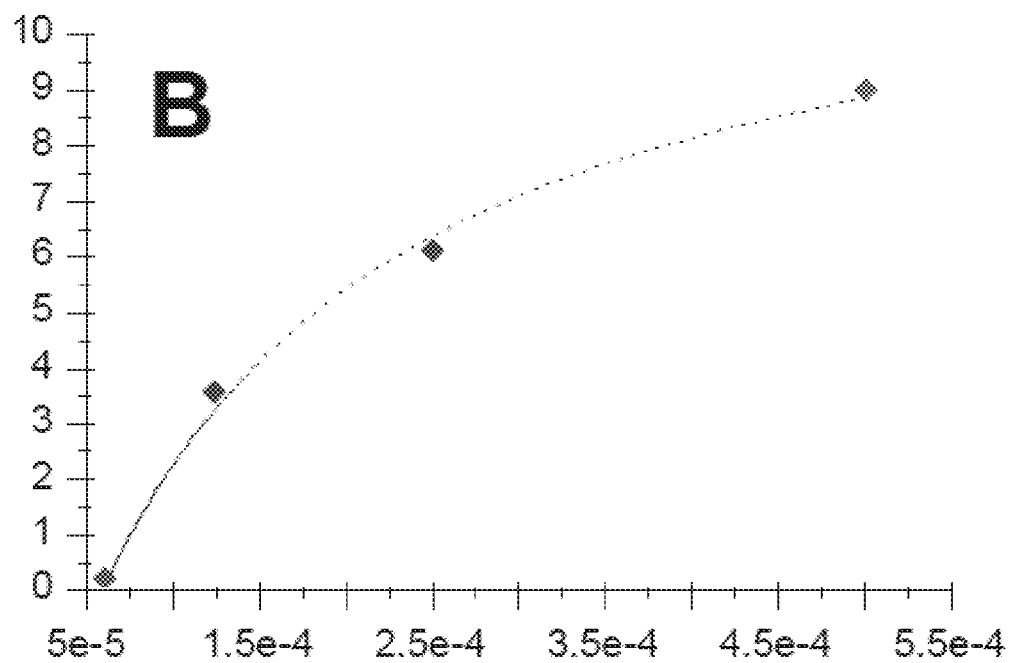
Figure 5C:
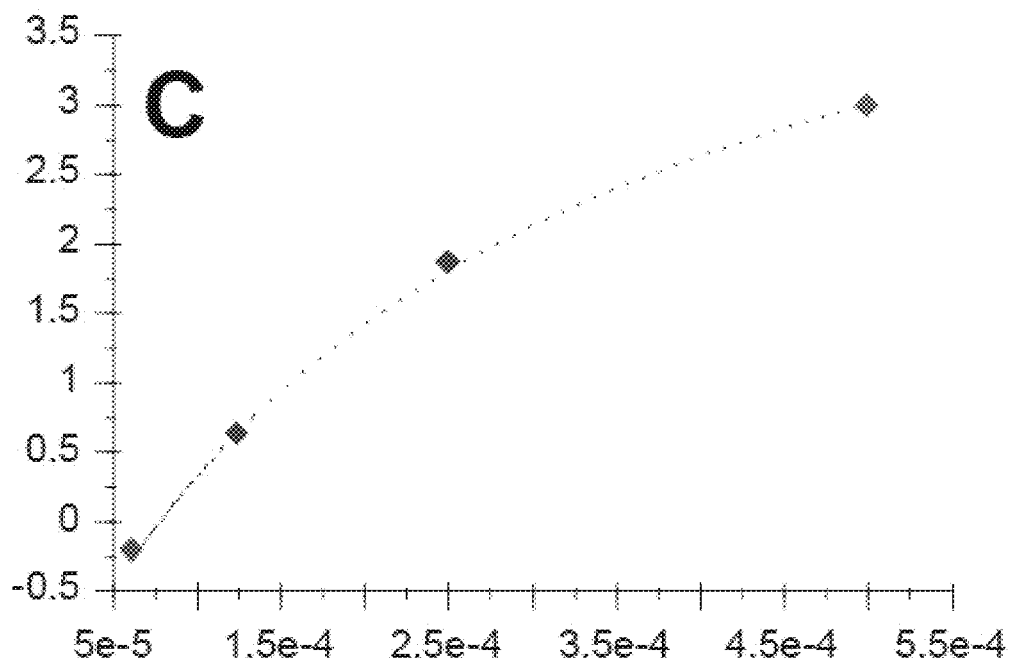
Figure 5D:
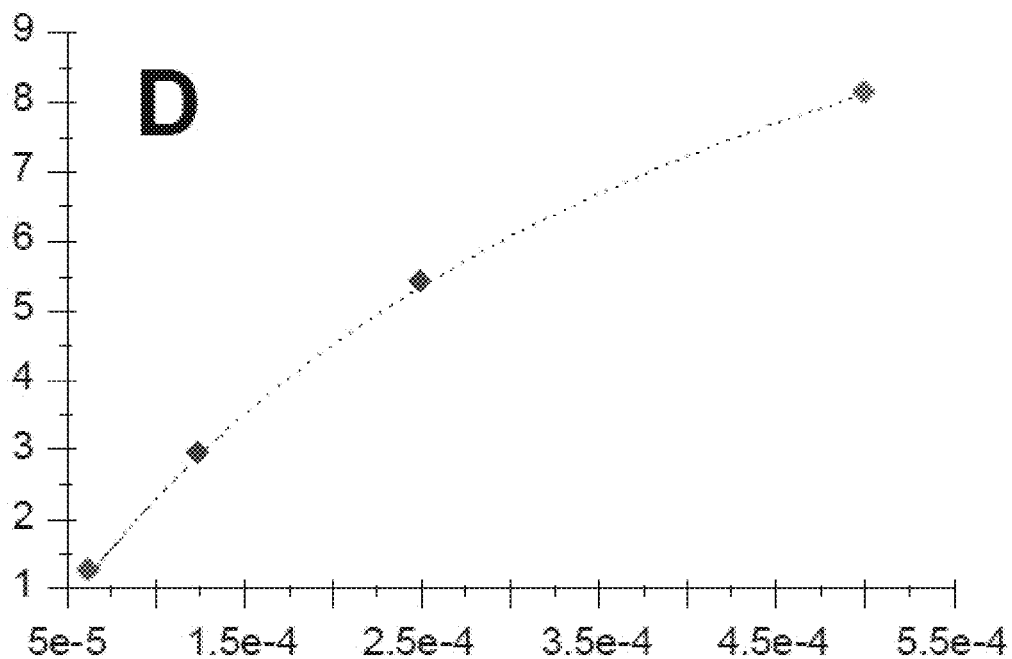
Figure 5E:
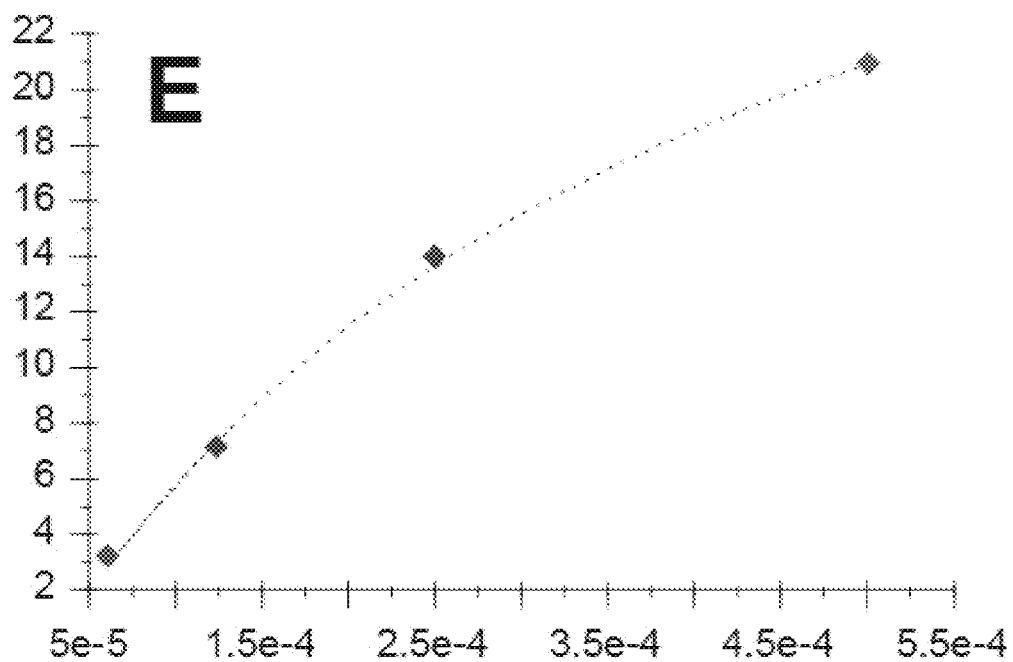
Figure 5F:
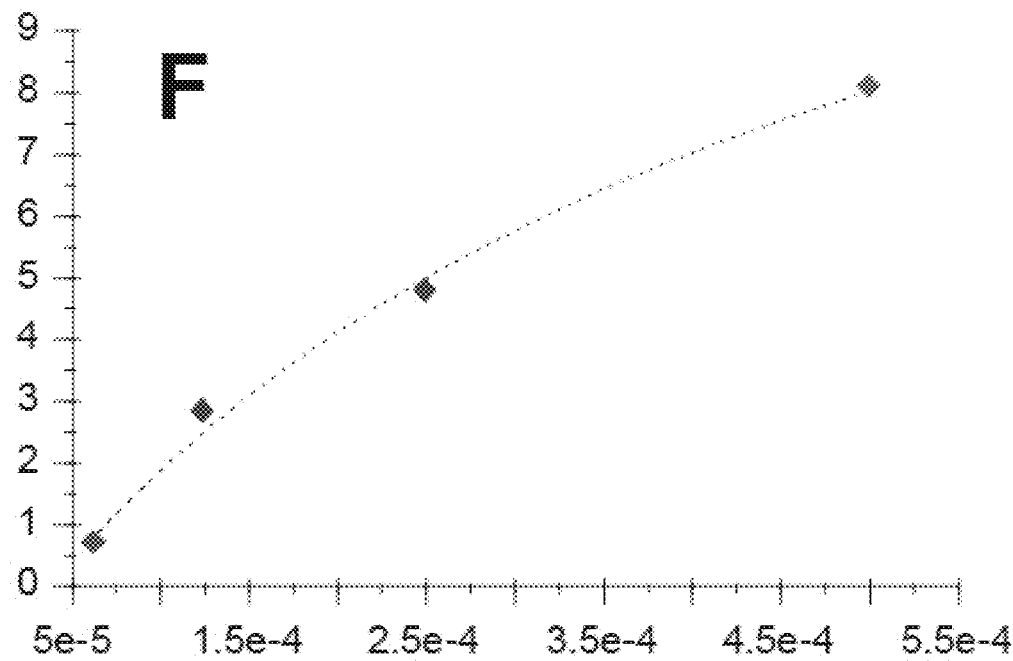
Figure 5G:
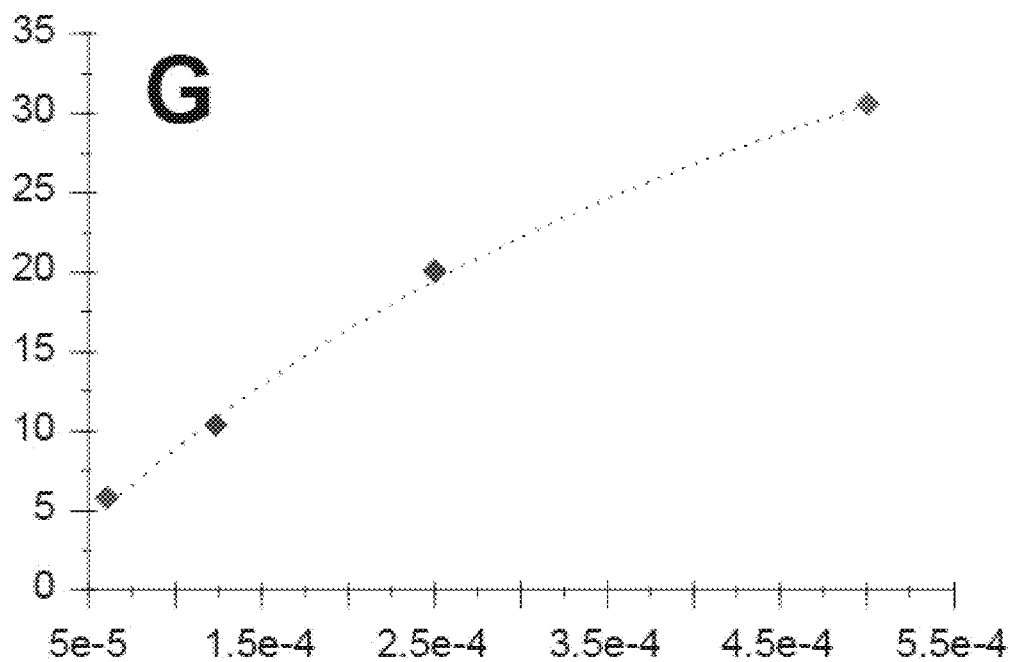
Figure 5H:
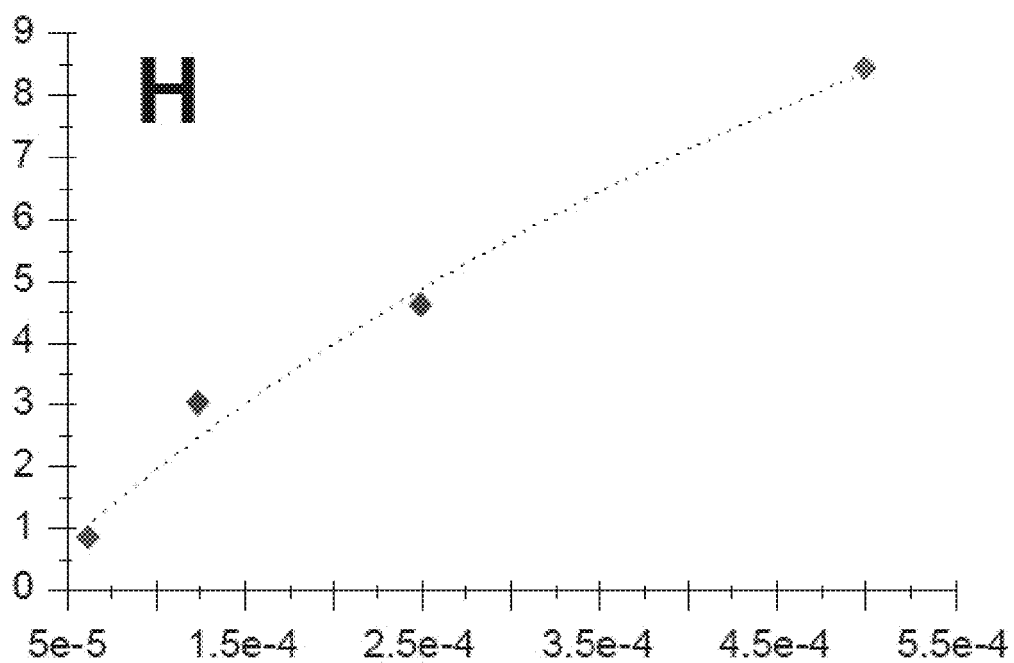
Figure 5I:
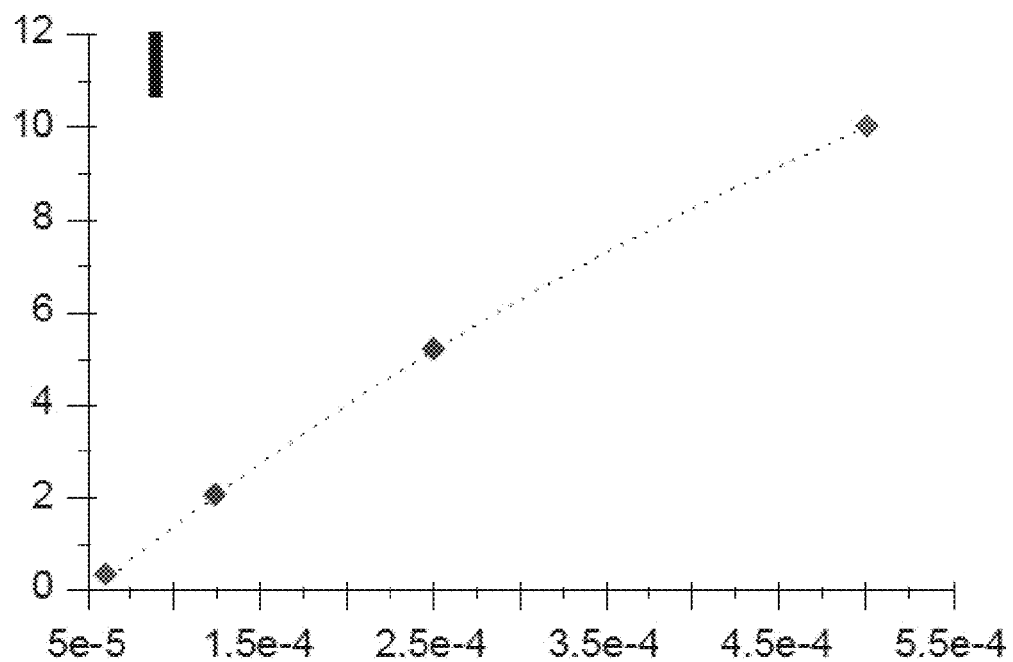
Figure 5J:
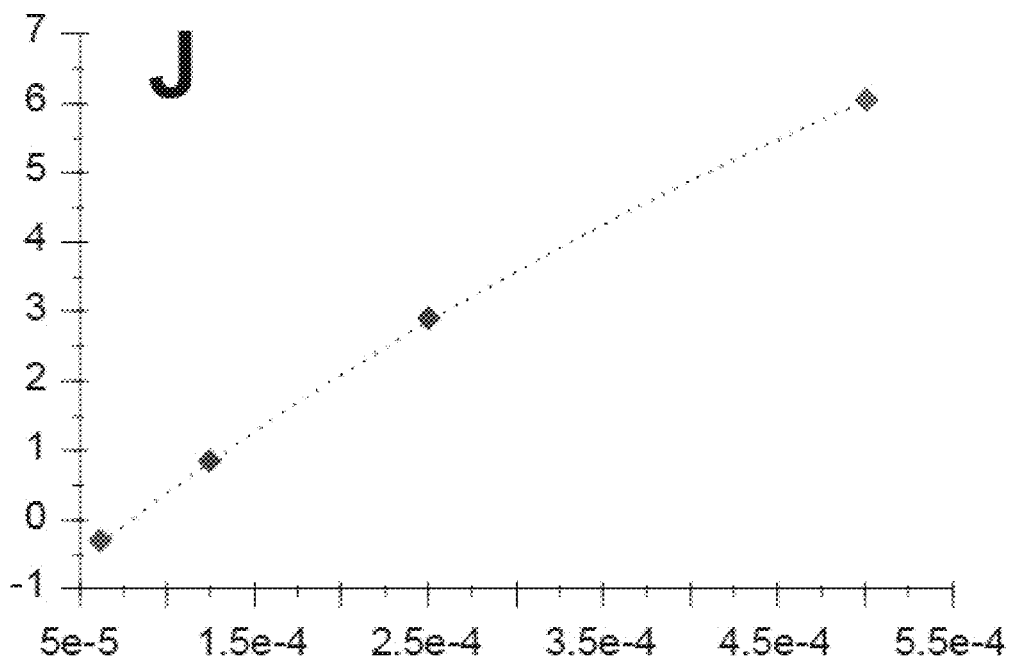
Figure 5K:
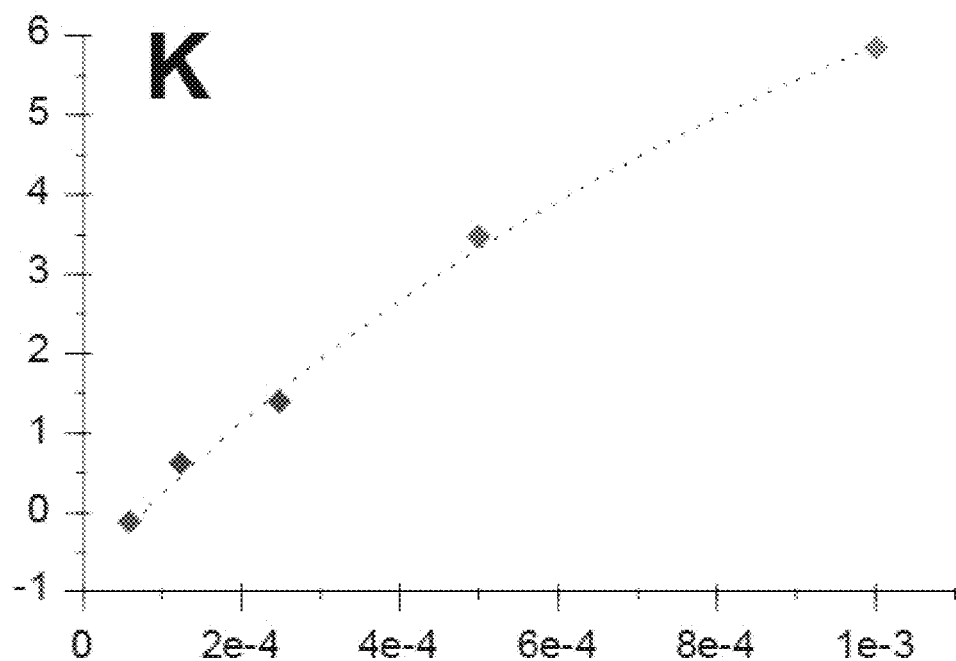
Figure 5L:
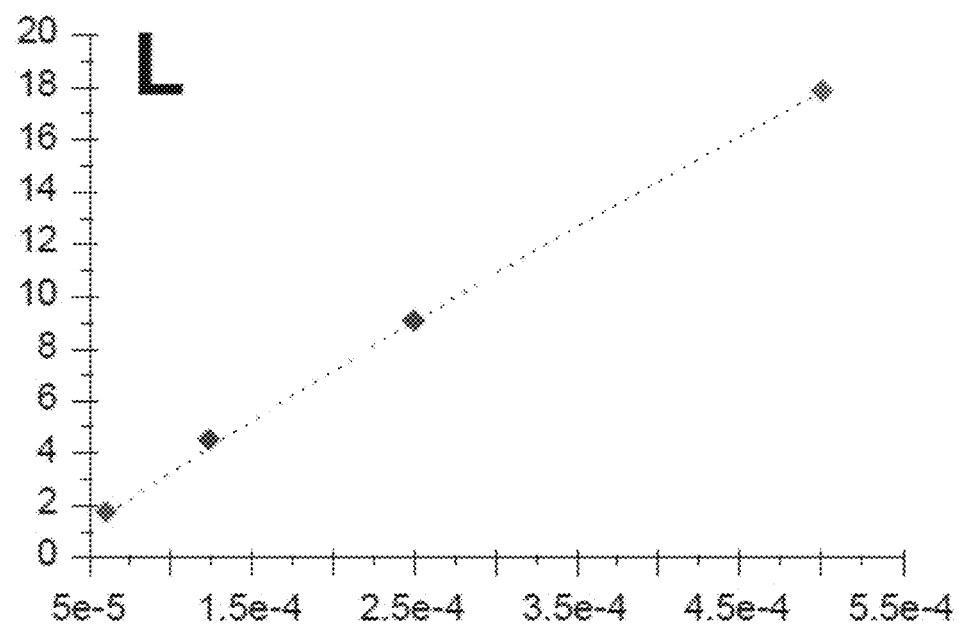
Figure 5M:
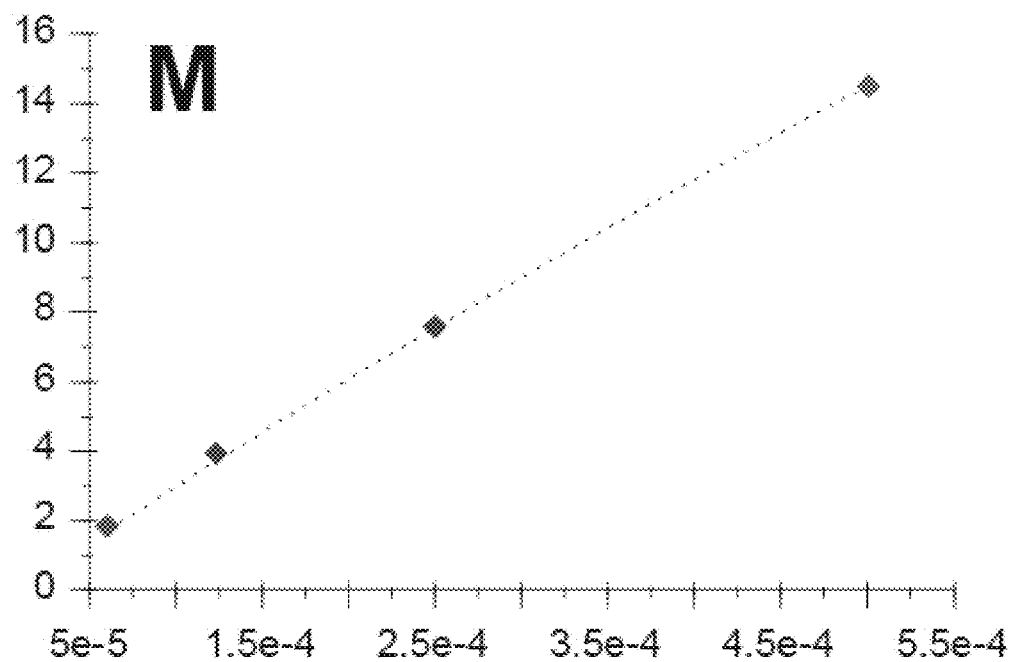
Figure 5N:
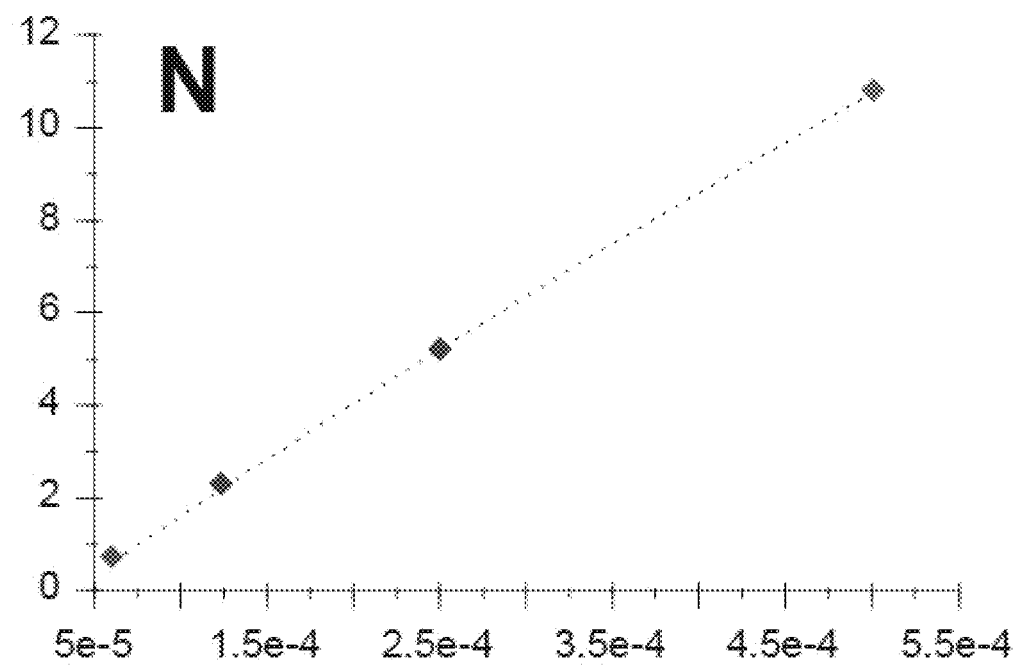
Figure 5O:
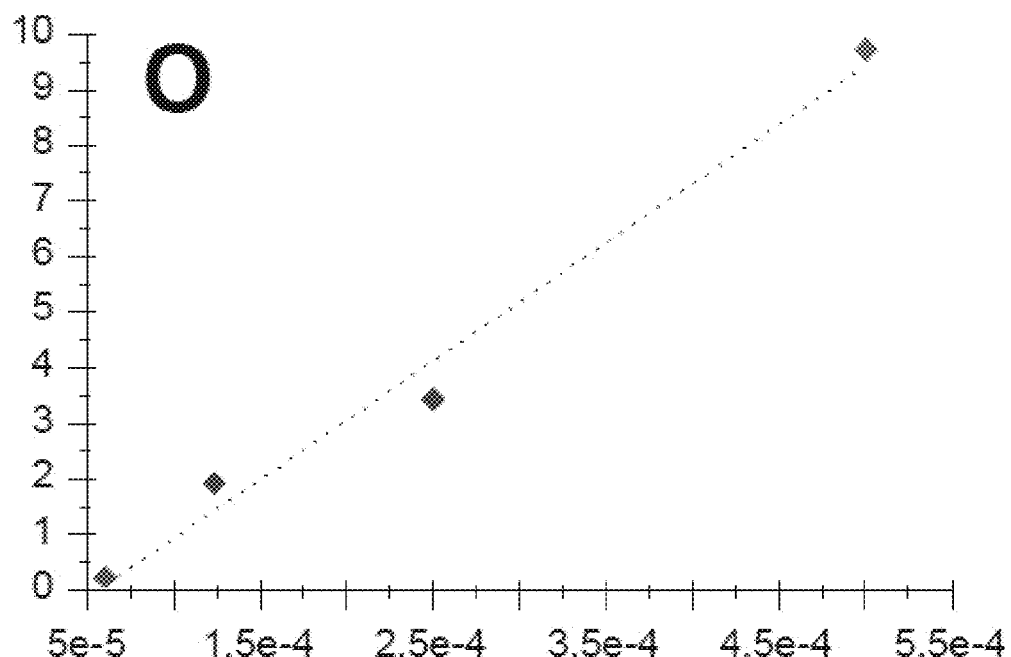
Figure 5P:
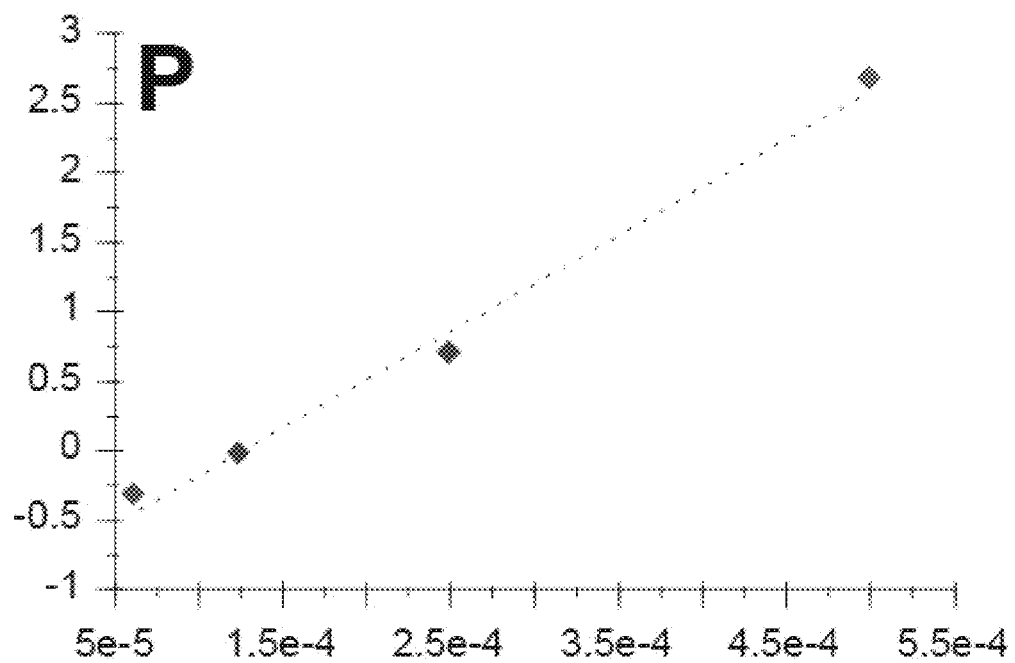

FIG. 41 shows that L232A mutation reduces toxicity more than the other residues in the hydrophobic pocket.

FIG. 42 shows that the conserved LF motif of P6 is inserted in a pocket lined by Tyr183 and Phe240. C-terminal sequence (SEQ ID NO: 1) FIG. 43 demonstrates that double, triple, and quadruple mutants containing L232A show further reduction in toxicity and activity in yeast.

FIG. 44 illustrates that combining hydrophobic mutations with R235A eliminates activity of RTA in Vero cells.

FIG. 45 is a table showing that illustrative peptide mimics of the P stalk C-termini inhibit the activity of RTA by preventing ribosome binding. Peptide mimics P11 (SEQ ID NO: 1), P10 (SEQ ID NO: 11), P9 (SEQ ID NO: 12), P8 (SEQ ID NO: 13), P7 (SEQ ID NO: 14), P6 (SEQ ID NO: 15), P5 (SEQ ID NO: 16), P4 (SEQ ID NO: 17), and P3 (SEQ ID NO: 18).

FIGS. 46A-46D shows illustrative X-ray crystal structure of RTA with C-termini of ribosomal P protein (PDB ID: 5GU4, FIG. 46A) with three different fragments bound to RTA (FIG. 46B; FIG. 46C; and FIG. 46D).

FIGS. 47A-47C show the hydrophobic pocket of ricin toxin A subunit: with P protein peptide (FIG. 47A); with an inhibitor (FIG. 47B); and covered by the B subunit (FIG. 47C).

Figure 48:
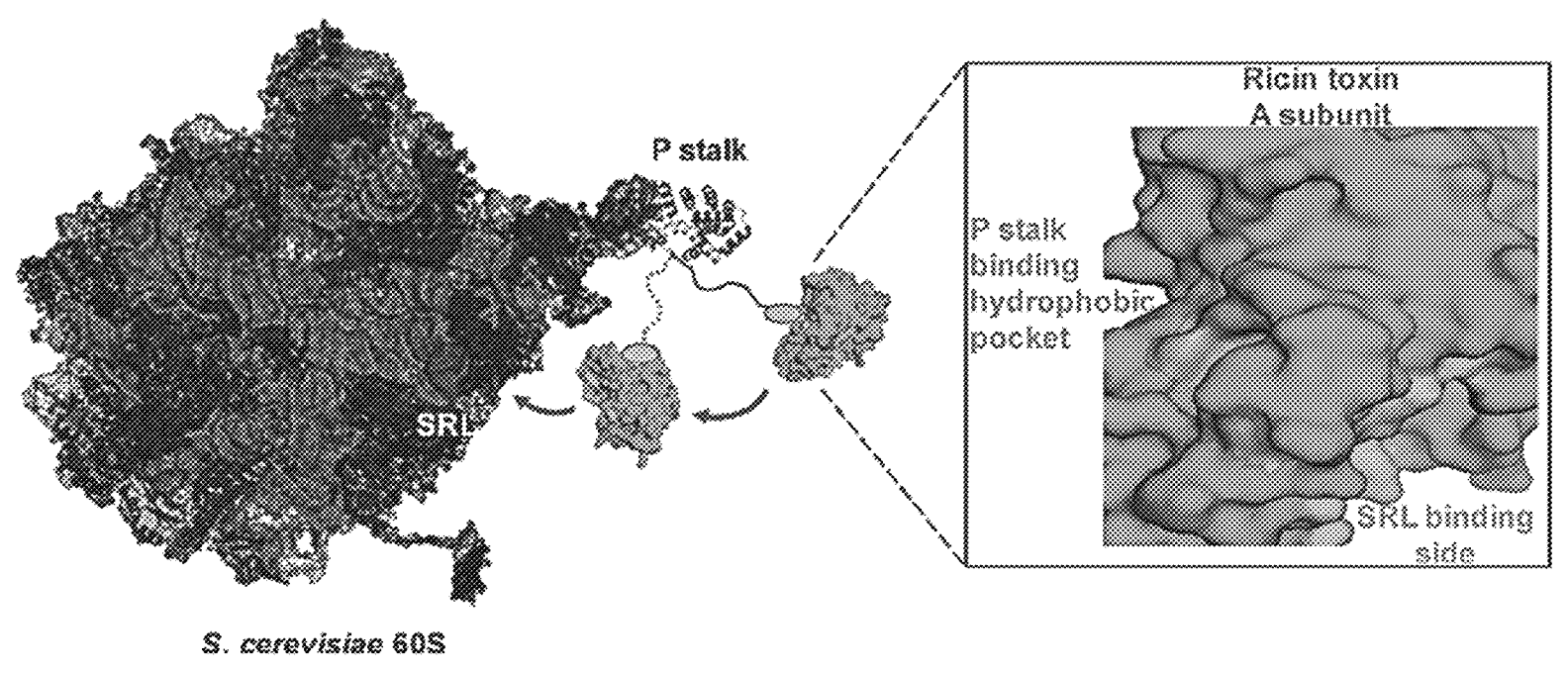

FIG. 48 shows an illustrative interaction of RTA with the P stalk to access SRL.

FIG. 49A: Structures of Stx2A1 with citrate; FIG. 49B: shows citrate together with P11; FIG. 49C: shows Stx2A1 with BTB13086; FIG. 49D: shows BTB13086 together with P11.

FIG. 50 shows a comparison of RU-NT-93 with Retro2 in Vero cells. Vero cells (0.5 mL/well) were plated at $10^5$ cells/mL and grown for 24 h, then media with serum was removed and replaced by serum free media, vortexed with additions of compounds from 100% DMSO stocks to a final DMSO concentration of 0.5%. After 1 h, ricin was add (200 pM). Wells were harvested 2 h after ricin addition, with addition of 350 μL lysis buffer, as described for Qiagen Plus RNA Mammalian cell kid. Total RNA was extracted from Vero cells using the RNeasy Plus Mini Kit (Qiagen) either immediately or after storage at −80° C. The high capacity cDNA reverse transcription kit (Thermo Fisher Scientific) was used for cDNA conversion of approximately 375 ng of total RNA in a 20 μL reaction. Percent depurination was measured by qRT-bars showing the standard error. A Dunnet test was used to compare each compound to control (−cpd) ***P<0.001.

FIG. 51 shows protection in A549 cells against ricin administration with administration of compounds of the present disclosure. Human epithelial lung cells (A549) were grown and treated with holotoxin as described elsewhere herein. Cells were exposed to ricin (200 pm) for 2 h, within the linear range for dose and time.

FIG. 52 shows protection in Vero cells against ricin administration with administration of RU-NT-47 and RU-NT-57. Vero cell protection from ricin holotoxin was performed as described elsewhere herein, except that the compound (i.e., RU-NT-47 or RU-NT-57) and toxin were administered simultaneously.

DETAILED DESCRIPTION OF THE DISCLOSURE

The present disclosure is related to the discovery of RIP inhibitors that exhibit potent (nanomolar) protection against RIPs. The paucity of promising RIP inhibitor candidates is primarily due to the large active site pocket and the strong electrostatic interactions at the interface between RIP and ribosome that make some drug-like molecules ineffective in competing with the ribosome for binding to RIPs. This technical barrier to developing small-molecule inhibitors of protein/ribosome complex has stymied the progress of RIP inhibitor development.

To address this barrier at the root level, P-proteins of the ribosomal stalk were identified as the host target of ricin and Stxs, then it was shown that the ribosome binding surface of RTA is on the opposite face of the active site. Further, it was demonstrated that blocking the interaction of RTA with the ribosome reduces its depurination activity and cytotoxicity. These studies established toxin/ribosome interactions as a new target for drug discovery and arginine 235 as a key interacting residue at the ribosome-binding site of RTA as an initial step in inhibitor discovery.

Fragment-based lead discovery (FBLD), using surface plasmon resonance (SPR) together with nuclear magnetic resonance (NMR), has emerged as an important tool for discovery of inhibitors of protein function. FBLD has not previously been used to identify inhibitors of ricin. FBLD involves screening small molecules (100-300 Da) with expected affinities in 0.1-10 mM range, which may become fragments for constructing drug-like compounds. Its advantages over conventional high throughput screening (HTS) are that: 1) a tremendous chemical diversity can be represented in fragment collections of as few as 1000 molecules; 2) observed hit rates for fragment screens are 10-1000× higher than conventional HTS due to greater exploration of chemical space; 3) low molecular weight compounds tend to be more soluble; and 4) the method of detection, SPR is simpler, more robust and is more reliable than HTS because it is less prone to artifacts.

Low molecular mass fragments tend to bind with low affinity. Thus, compounds require screening at high concentrations to be detected, which can lead to high false positive hit rates in biochemical assays. Therefore, to detect low affinity interactions, SPR was employed. The primary advantage of SPR versus complementary biophysical screening methods, such as NMR, X-ray crystallography, and calorimetry, is its low reagent requirements. Typically, 1-5 µg of target protein is immobilized on the SPR chip surface, and each fragment is used at 100-500 µM.

FBLD is used in combination with SPR and NMR to identify ricin-specific inhibitors that target ribosome binding and/or depurination activity. Eight fragments that show dose-dependent binding to RTA and inhibit its activity in a cell-free depurination assay are identified herein. The selectivity of fragments to RTA was verified and these ligands validated using NMR.

Toxin-specific inhibitors of ricin that target the ribosome-binding site have not been previously identified. These inhibitors reveal previously undescribed ribosome and SRL binding mechanisms and are useful in providing important insights into the mechanism of toxicity. These inhibitors can be used alone or in synergetic combination with immunotherapeutics or vaccines as pre-therapeutics against ricin. These inhibitors can also be used as immunotoxin rescue therapeutics since they can inhibit off-target effects of RTA containing immunotoxins.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, exemplary methods and materials are described. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that can be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof. Pharmaceutically unacceptable salts may nonetheless possess properties such as high crystallinity, which have utility in the practice of the present disclosure, such as for example utility in process of synthesis, purification or formulation of compounds useful within the methods of the disclosure. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Suitable pharmaceutically acceptable base addition salts of compounds of the disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the terms "pharmaceutically effective amount" and "effective amount" and "therapeutically effective amount" refer to a nontoxic but sufficient amount of an agent to provide the desired biological result. That result can be reduction and/or alleviation of the signs, symptoms, or causes of a disease, or any other desired alteration of a biological system. An appropriate therapeutic amount in any individual case can be determined by one of ordinary skill in the art using routine experimentation.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments can be specifically tailored or modified, based on knowledge obtained from the field of pharmacogenomics.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

As used herein, the term "alkyl," by itself or as part of another substituent means, unless otherwise stated, a straight or branched chain hydrocarbon having the number of carbon atoms designated (i.e. C1-6 means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. A non-limiting example is (C$_1$-C$_6$)alkyl, particularly ethyl, methyl, isopropyl, isobutyl, n-pentyl, n-hexyl and cyclopropylmethyl.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies. Heteroalkenylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkenyl group, including between the rest of the heteroalkenyl group and the fragment to which it is attached, as well as attached to the most distal carbon atom in the heteroalkenyl group.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies. Heteroalkynylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkynyl group, including between the rest of the heteroalkynyl group and the fragment to which it is attached, as well as attached to the most distal carbon atom in the heteroalkynyl group.

As used herein, the term "substituted alkyl" means alkyl as defined above, substituted by one, two or three substituents selected from halogen, —OH, alkoxy, —$NH_2$, —$N(CH_3)_2$, —C(=O)OH, trifluoromethyl, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, $CF_3$, $OCF_3$, R, C(O), methylenedioxy, ethylenedioxy, N(R)$_2$, SR, SOR, $SO_2$R, $SO_2$N(R)$_2$, $SO_3$R, C(O)R, C(O)C(O)R, C(O)$CH_2$C(O)R, C(S)R, C(O)OR, OC(O)R, C(O)N(R)$_2$, OC(O)N(R)$_2$, C(S)N(R)$_2$, ($CH_2$)$_{0-2}$N(R)C(O)R, ($CH_2$)$_{0-2}$N(R)N(R)$_2$, N(R)N(R)C(O)R, N(R)N(R)C(O)OR, N(R)N(R)CON(R)$_2$, N(R)$SO_2$R, N(R)$SO_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted ($C_1$-$C_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, $NO_2$, $ONO_2$, azido, $CF_3$, $OCF_3$, R, O (oxo), S (thiono), C(O), S(O), methylenedioxy, ethylenedioxy, N(R)$_2$, SR, SOR, $SO_2$R, $SO_2$N(R)$_2$, $SO_3$R, C(O)R, C(O)C(O)R, C(O)$CH_2$C(O)R, C(S)R, C(O)OR, OC(O)R, C(O)N(R)$_2$, OC(O)N(R)$_2$, C(S)N(R)$_2$, ($CH_2$)$_{0-2}$N(R)C(O)R, ($CH_2$)$_{0-2}$N(R)N(R)$_2$, N(R)N(R)C(O)R, N(R)N(R)C(O)OR, N(R)N(R)CON(R)$_2$, N(R)$SO_2$R, N(R)$SO_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, ($C_1$-$C_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H- dibenz[b,f]azepine-3-yl, 10,11-dihydro-5H-dibenz[b,f] azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

As used herein, the term "optionally substituted" means that the referenced group can be substituted or unsubstituted. In certain embodiments, the referenced group is optionally substituted with zero substituents, i.e., the referenced group is unsubstituted. In other embodiments, the referenced group is optionally substituted with one or more additional group (s) individually and independently selected from groups described herein.

In certain embodiments, the substituents are independently selected from the group consisting of halogen, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl] C(=O)[substituted or unsubstituted alkyl], —NHC(=O) [substituted or unsubstituted alkyl], —C(OH)[substituted or unsubstituted alkyl]$_2$, and —C(NH$_2$)[substituted or unsubstituted alkyl]$_2$. In other embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_1$-6 alkyl, —OH, C$_1$-6 alkoxy, halo, amino, acetamido, oxo and nitro. In yet other embodiments, the substituents are independently selected from the group consisting of C$_1$-6 alkyl, C$_1$-6 alkoxy, halo, acetamido, and nitro. As used herein, where a substituent is an alkyl or alkoxy group, the carbon chain can be branched, straight or cyclic.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "type I ribosome inactivating protein" refers to a single polypeptide chain, comprising an A (active) domain capable of inhibiting protein translation.

As used herein, the term "type II ribosome inactivating protein" refers to a heterodimeric species consisting of an A chain, functionally equivalent to that of a type I ribosome-inactivating protein, linked to a B subunit by a disulfide bond, endowed with lectin-binding properties, and capable of inhibiting protein translation.

The following abbreviations are used herein: RIP=ribosome inactivating protein; RTA=active A; Stxs=Shiga toxins; SRL=sarcin-ricin loop; SPR=surface plasmon resonance; and FBLD=Fragment-based lead discovery.

Compounds and Compositions

In certain embodiments, the compound has the structure of Formula (I), or a salt, solvate, stereoisomer, geometric isomer, and/or tautomer thereof:

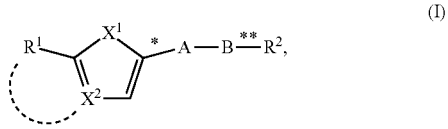
(I)

wherein:
A is a bond or an optionally substituted $C_1$-$C_2$ linker selected from the group consisting of optionally substituted $C_1$-$C_2$ alkylene, —CH═CH—, —C≡C—,

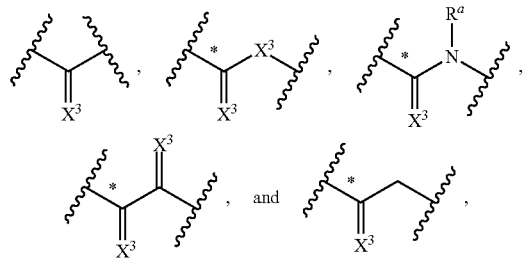

wherein, if present, the $C_1$-$C_2$ alkylene is optionally substituted with at least one substituent selected from the group consisting of hydroxyl, $C_1$-$C_6$ alkoxy, $N(R^a)(R^a)$, and halogen,
wherein * indicates the bond from A to the 5-membered ring;
B is selected from the group consisting of a bond,

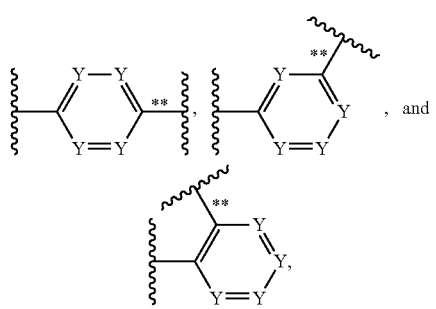

wherein ** indicates the bond from B to $R^2$;
$R^1$ is selected from the group consisting of H, optionally substituted aryl, optionally substituted heteroaryl, optionally substituted benzyl, optionally substituted $C_1$-$C_6$ alkyl, optionally substituted $C_3$-$C_6$ cycloalkyl, optionally substituted heterocycloalkyl, optionally substituted $C_2$-$C_6$ alkenyl, optionally substituted $C_2$-$C_6$ alkynyl, C(O)—$C_1$-$C_6$ alkyl, C(O)-aryl, C(O)$NR^a_2$, cyano, and halogen,
wherein each optional substituent comprises at least one substituent selected from the group consisting of $C_1$-$C_6$ alkyl, $C_2$-$C_6$ alkenyl, $C_1$-$C_6$ cycloalkyl, $C_1$-$C_6$ alkoxy, hydroxyl, $NR^a_2$, C(O)—$C_1$-$C_6$ alkyl, CN, $CF_3$, $NO_2$, and C(O)-aryl, wherein two adjacent optional $C_1$-$C_6$ alkyl, $C_1$-$C_6$ cycloalkyl, $C_1$-$C_6$ alkoxy, and C(O)—$C_1$-$C_6$ alkyl substituents may optionally combine to form a 5 or 6-membered fused ring,
wherein each optionally substituted aryl, optionally substituted heteroaryl, optionally substituted benzyl, optionally substituted $C_1$-$C_6$ alkyl, optionally substituted $C_2$-$C_6$ alkenyl, or optional substituent thereof, may optionally combine with $X^2$ to form a 5, 6, or 7-membered fused ring;
$R^2$ is selected from the group consisting of

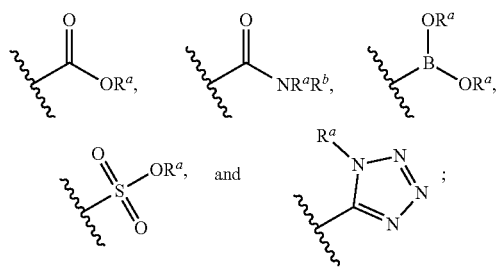

each occurrence of $R^a$ is independently selected from the group consisting of H, $C_1$-$C_6$ alkyl, $C_1$-$C_6$ alkoxy, benzyl, and aryl;
$R^b$ is selected from the group consisting of H, $C_1$-$C_6$ alkyl, $C_1$-$C_6$ alkoxy, benzyl, aryl, hydroxyl, and $C_1$-$C_6$ hydroxyalkyl;
$X^1$ is selected from the group consisting of S, O, and $NR^a$;
$X^2$ is CH or N;
each occurrence of $X^3$ is independently O or S;
each occurrence of Y is independently CH or N, wherein 0-3 Y are N in a given ring.

In certain embodiments, the compound of Formula (I) is the compound of Formula (II):

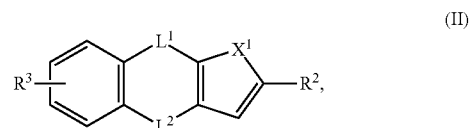
(II)

wherein:
$R^3$ is selected from the group consisting of $C_1$-$C_6$ alkyl, $C_2$-$C_6$ alkenyl, $C_1$-$C_6$ cycloalkyl, $C_1$-$C_6$ alkoxy, hydroxyl, $NR^a_2$, C(O)—$C_1$-$C_6$ alkyl, CN, $CF_3$, $NO_2$, and C(O)-aryl;
$L^1$ and $L^2$ are each independently a bond or optionally substituted $C_1$-$C_2$ alkyl.

In certain embodiments, the compound of Formula (I) is not 4-(thiophen-2-ylmethyl)benzoic acid. In certain embodiments, the compound of Formula (I) is 4-(thiophen-2-ylmethyl)benzoic acid.

In certain embodiments, A is a bond. In certain embodiments, A is optionally substituted $C_1$-$C_2$ alkylene. In certain embodiments, A is optionally substituted —CH═CH—. In certain embodiments, A is —CH═CH—. In certain embodiments, A is —C≡C—. In certain embodiments, A is

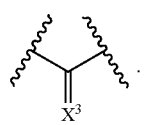

In certain embodiments, A is

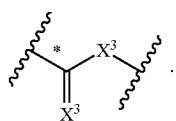

In certain embodiments, A is

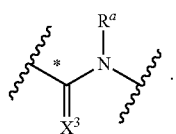

In certain embodiments, A is

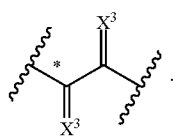

In certain embodiments, A is

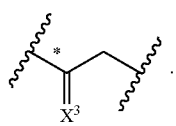

In certain embodiments, B is a bond. In certain embodiments, B is

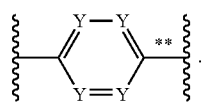

In certain embodiments, B is

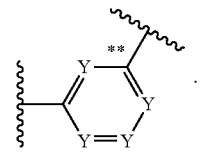

In certain embodiments, B is

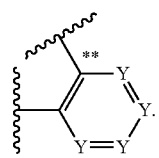

In certain embodiments, $R^2$ is

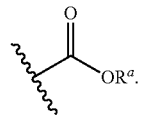

In certain embodiments, $R^2$ is

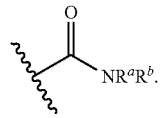

In certain embodiments, $R^2$ is

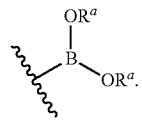

In certain embodiments, $R^2$ is

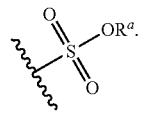

In certain embodiments, $R^2$ is

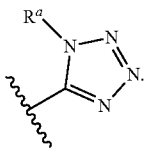

In certain embodiments, $R^1$ is CN. In certain embodiments, $R^1$ is Br. In certain embodiments, $R^1$ is Me. In certain embodiments, $R^1$ is Et. In certain embodiments, $R^1$ is Ph. In certain embodiments, $R^1$ is

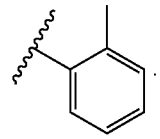

In certain embodiments, $R^1$ is

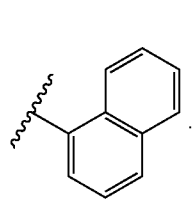 [SMILES: *c1cccc2ccccc12]

In certain embodiments, $R^1$ is

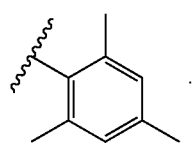 [SMILES: *c1c(C)cc(C)cc1C]

In certain embodiments, $R^1$ is

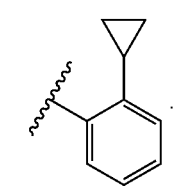

In certain embodiments, $R^1$ is

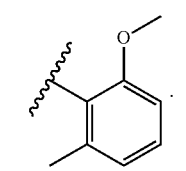

In certain embodiments, $R^1$ is

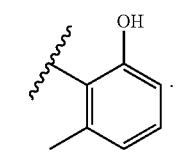

In certain embodiments, $R^1$ is

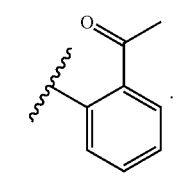

In certain embodiments, $R^1$ is

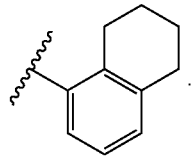 [SMILES: *c1cccc2c1CCCC2]

In certain embodiments, $R^1$ is

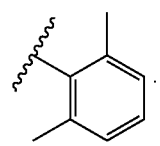

In certain embodiments, $R^1$ is

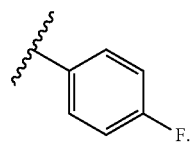 [SMILES: *c1ccc(F)cc1]

In certain embodiments, $R^1$ is

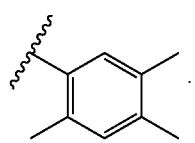 [SMILES: *c1cc(C)c(C)cc1C]

In certain embodiments, $R^1$ is

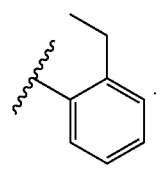

In certain embodiments, $R^1$ is

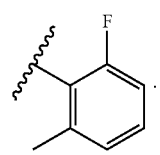

In certain embodiments, $R^1$ is

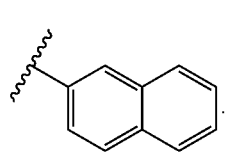 [SMILES: *c1ccc2ccccc2c1]

In certain embodiments, R¹ is
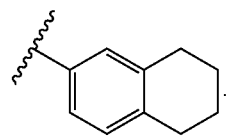 [SMILES: *c1ccc2c(c1)CCCC2]
In certain embodiments, R¹ is
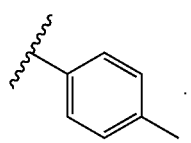 [SMILES: *c1ccc(C)cc1]
In certain embodiments, R¹ is
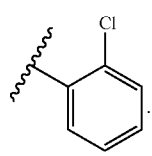
In certain embodiments, R¹ is
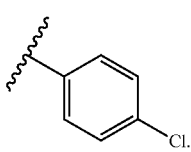 [SMILES: *c1ccc(Cl)cc1]
In certain embodiments, R¹ is
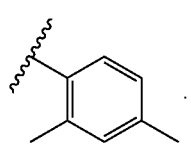 [SMILES: *c1ccc(C)cc1C]
In certain embodiments, R¹ is
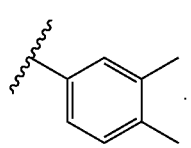 [SMILES: *c1ccc(C)c(C)c1]
In certain embodiments, R¹ is
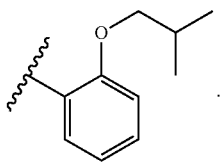 [SMILES: *c1ccccc1OCC(C)C]
In certain embodiments, R¹ is
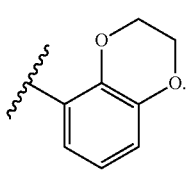 [SMILES: *c1cccc2c1OCCO2]
In certain embodiments, R¹ is
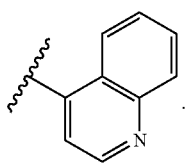 [SMILES: *c1ccnc2ccccc12]
In certain embodiments, R¹ is
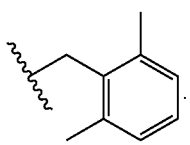 [SMILES: *Cc1c(C)cccc1C]
In certain embodiments, R¹ is
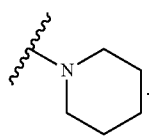 [SMILES: *N1CCCCC1]
In certain embodiments, R¹ is
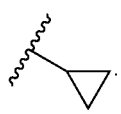

In certain embodiments, R¹ is

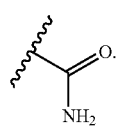

In certain embodiments, R¹ is

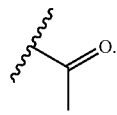 [SMILES: *C(C)=O]

In certain embodiments, R¹ is

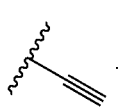

In certain embodiments, R¹ is

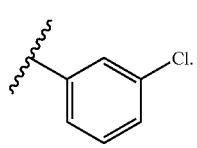 [SMILES: *c1cccc(Cl)c1]

In certain embodiments, R¹ is

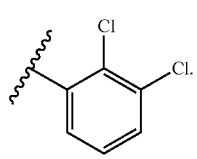

In certain embodiments, R¹ is

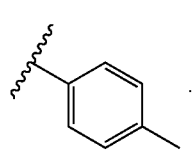 [SMILES: *c1ccc(C)cc1]

In certain embodiments, R¹ is

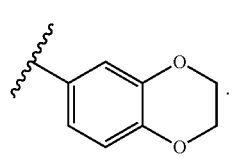 [SMILES: *c1ccc2c(c1)OCCO2]

In certain embodiments, R¹ is

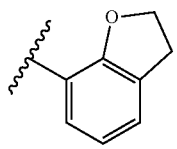

In certain embodiments, R¹ is

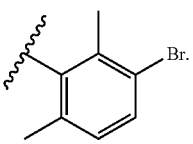 [SMILES: *c1c(C)ccc(Br)c1C]

In certain embodiments, R¹ is

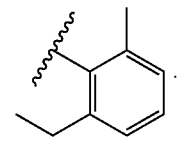 [SMILES: *c1c(C)cccc1CC]

In certain embodiments, R is

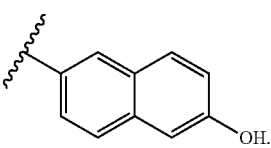 [SMILES: *c1ccc2cc(O)ccc2c1]

In certain embodiments, R¹ is

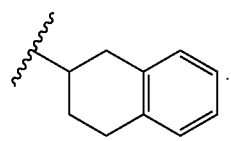 [SMILES: *C1CCc2ccccc2C1]

In certain embodiments R² is

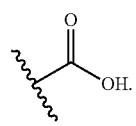 [SMILES: *C(=O)O]

In certain embodiments, R² is

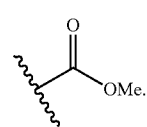 [SMILES: *C(=O)OC]

In certain embodiments, R² is

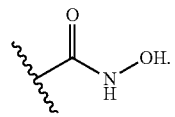

In certain embodiments, R² is

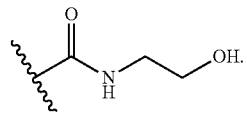 [SMILES: *C(=O)NCCO]

In certain embodiments, R²

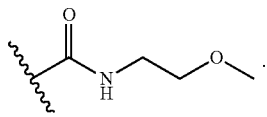 [SMILES: *C(=O)NCCOC]

In certain embodiments, R² is

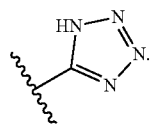 [SMILES: *c1nnn[nH]1]

In certain embodiments, R² is

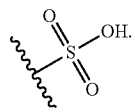

In certain embodiments, R² is

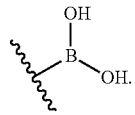

In certain embodiments, A is a bond.
In certain embodiments, A is

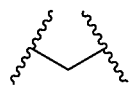

In certain embodiments A is

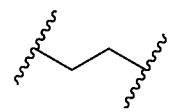

In certain embodiments, A is

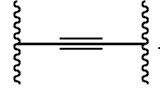

In certain embodiments, A is

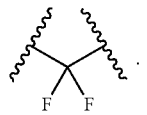 [SMILES: *C(*)(F)F]

In certain embodiments, A is

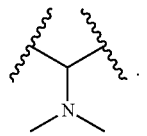 [SMILES: *C(*)N(C)C]

In certain embodiments, A is

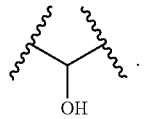 [SMILES: *C(*)O]

In certain embodiments, A is

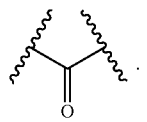 [SMILES: *C(*)=O]

In certain embodiments, A is

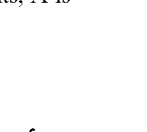

In certain embodiments, A is

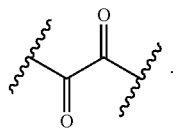 [SMILES: *C(=O)C(*)=O]

In certain embodiments, A is

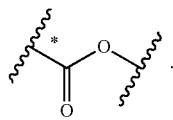 [SMILES: *OC(*)=O]

In certain embodiments, A is

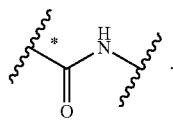 [SMILES: *NC(*)=O]

In certain embodiments, B is a bond. In certain embodiments, B is

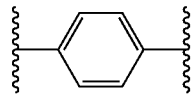

In certain embodiments, B is

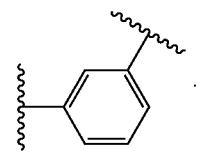 [SMILES: *c1cccc(*)c1]

In certain embodiments, $R^3$ is F. In certain embodiments, $R^3$ is Br. In certain embodiments, $R^3$ is Me. In certain embodiments, $R^3$ is $NMe_2$. In certain embodiments, $R^3$ is OMe.

In certain embodiments, $L^1$ is a bond. In certain embodiments, $L^1$ is —$CH_2$—.

In certain embodiments, $L^2$ is —$CH_2$—. In certain embodiments, $L^2$ is —$CH_2CH_2$—.

In certain embodiments, the compound is selected from the group consisting of:

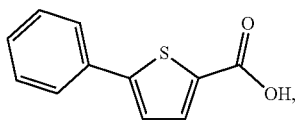

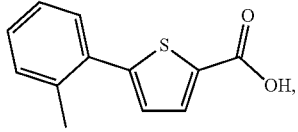

-continued

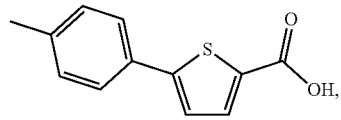

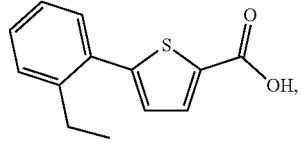

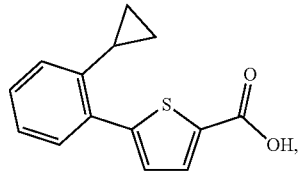

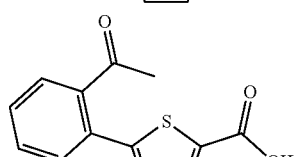

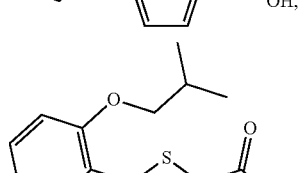

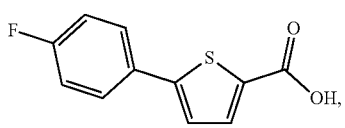

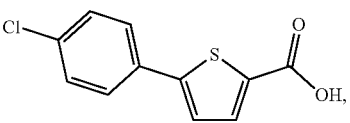

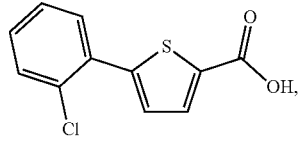

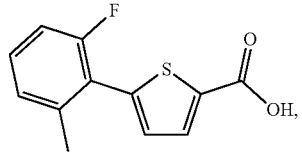

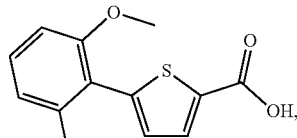

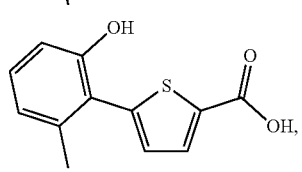

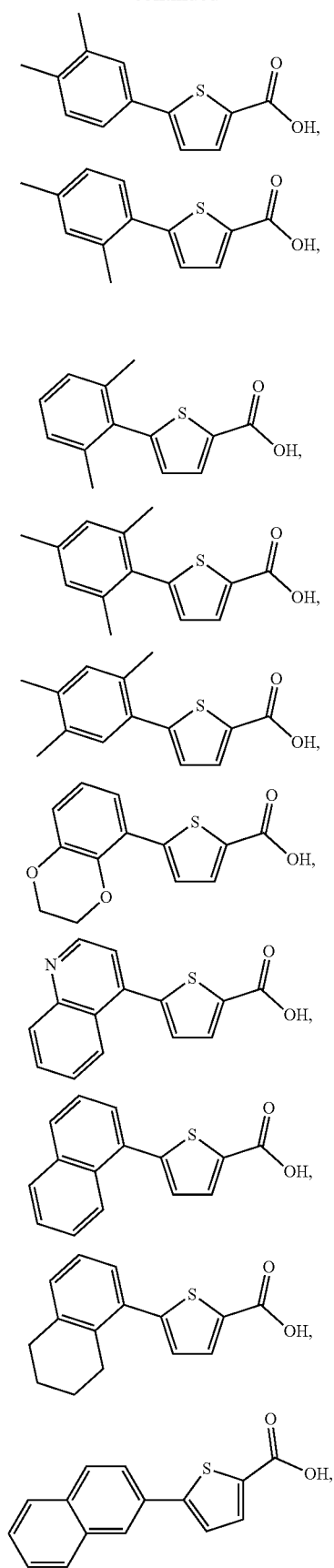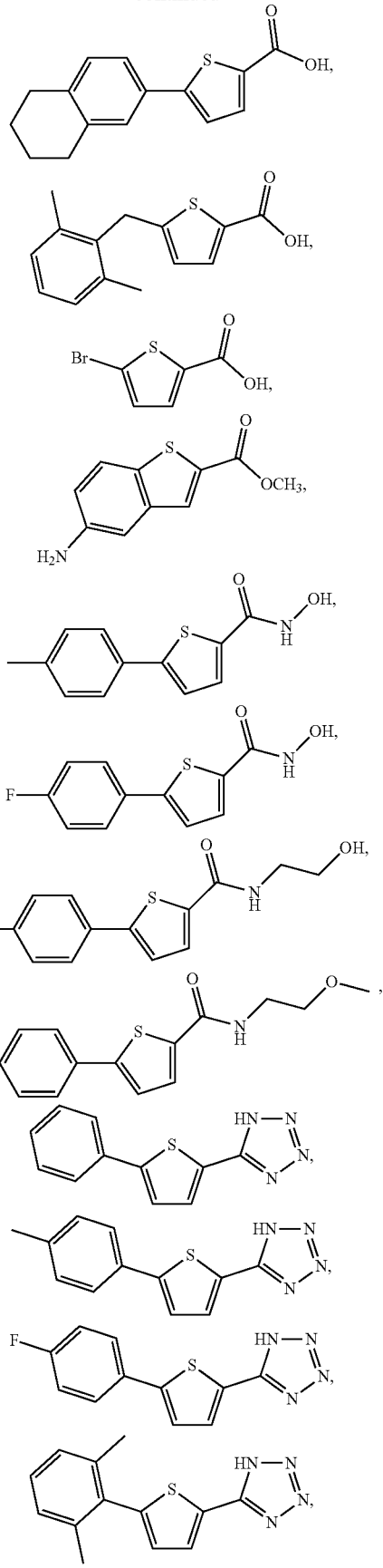

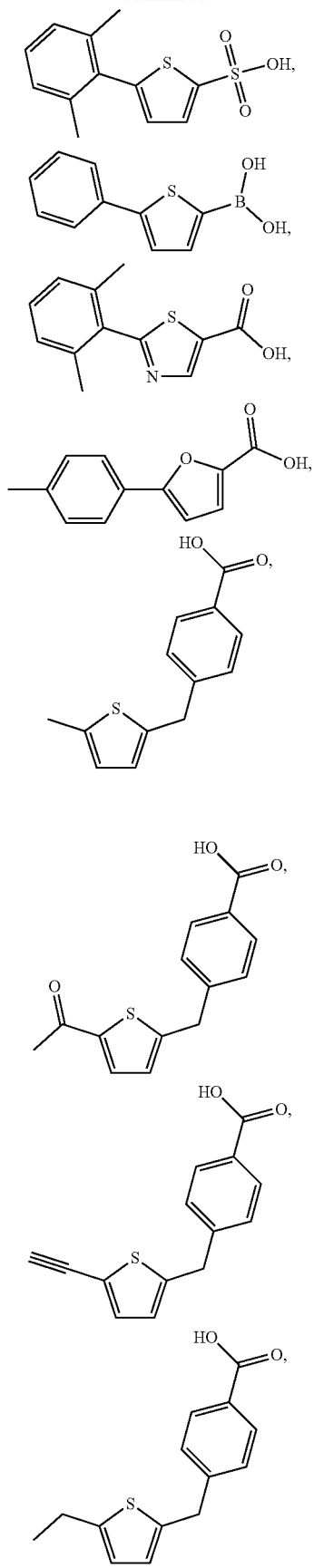
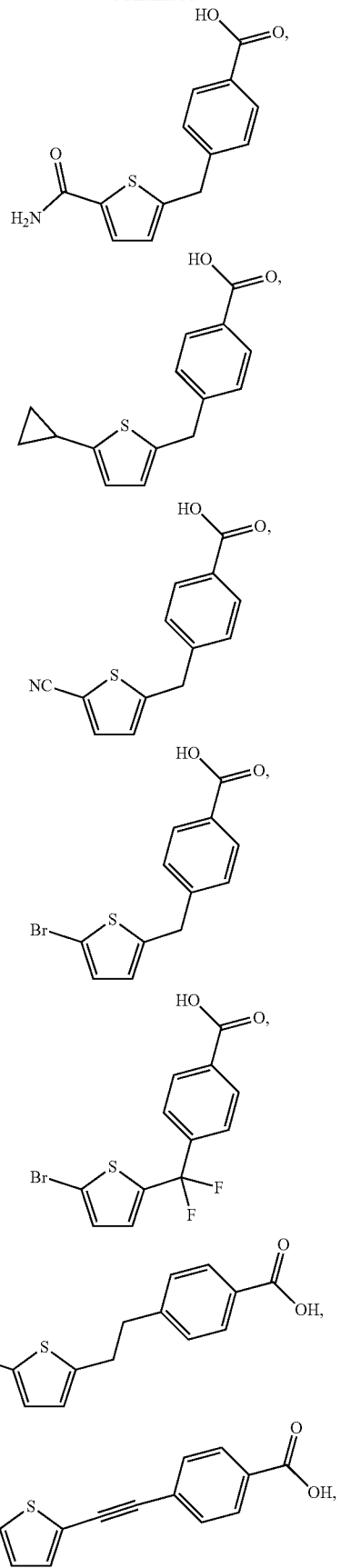

-continued
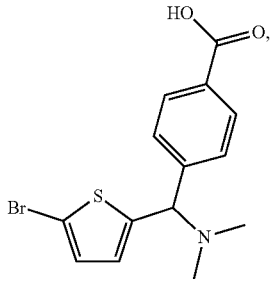
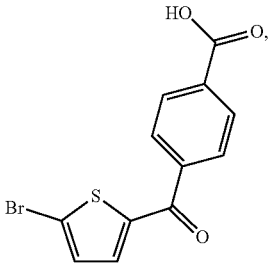
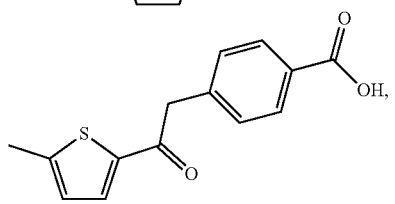
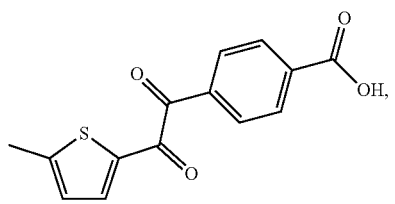
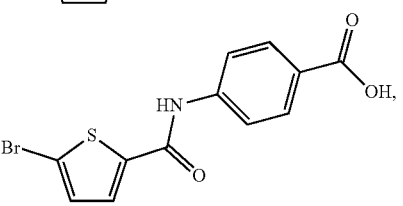
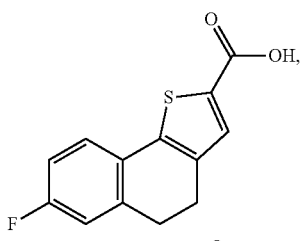
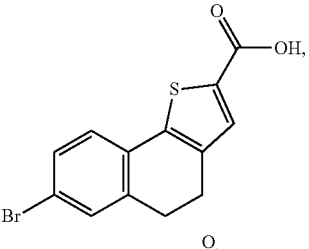
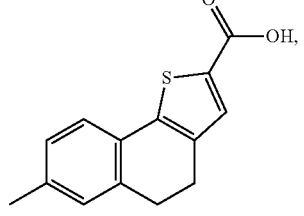

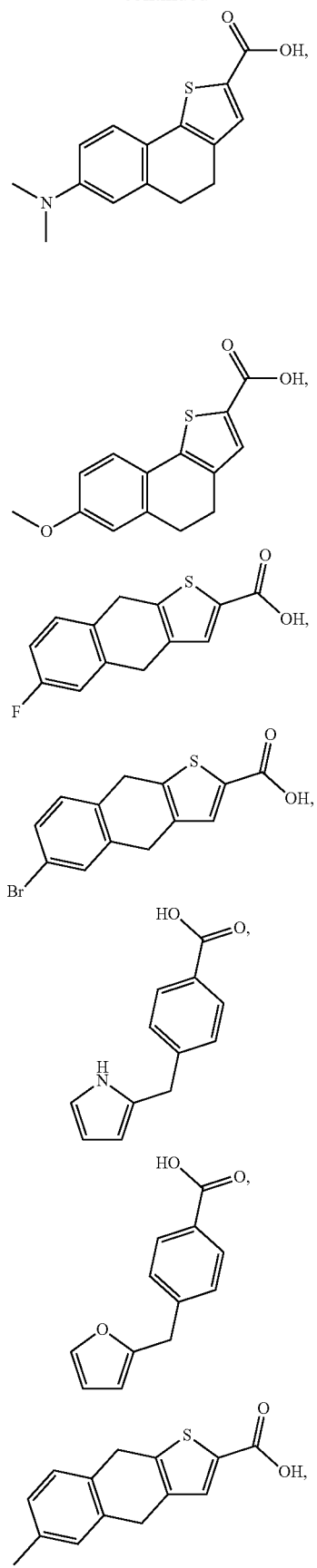
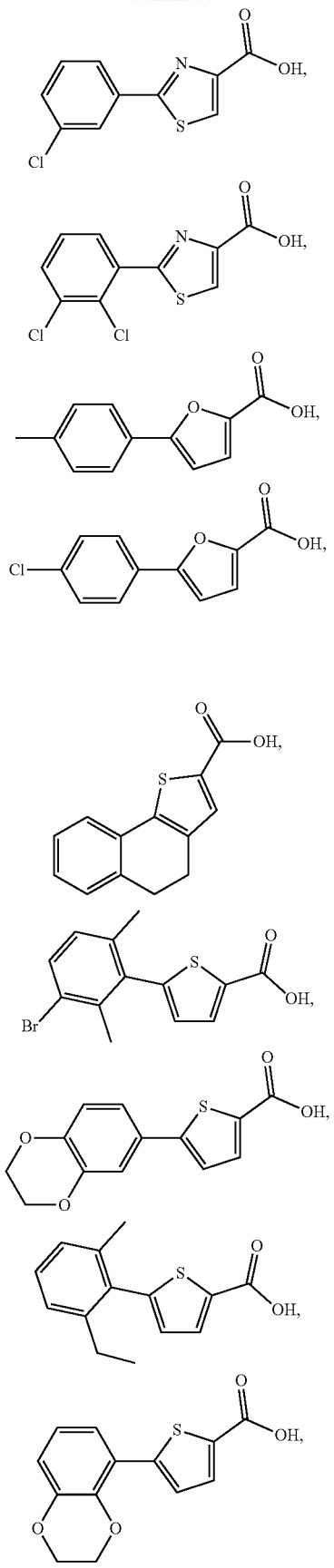

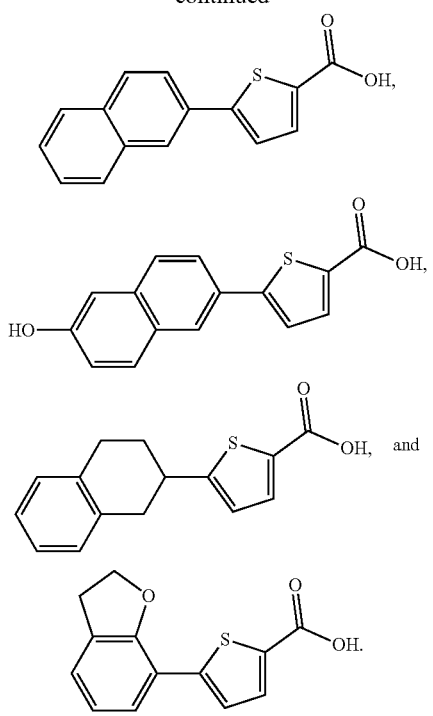
In certain embodiments, the compound is selected from the group consisting of:
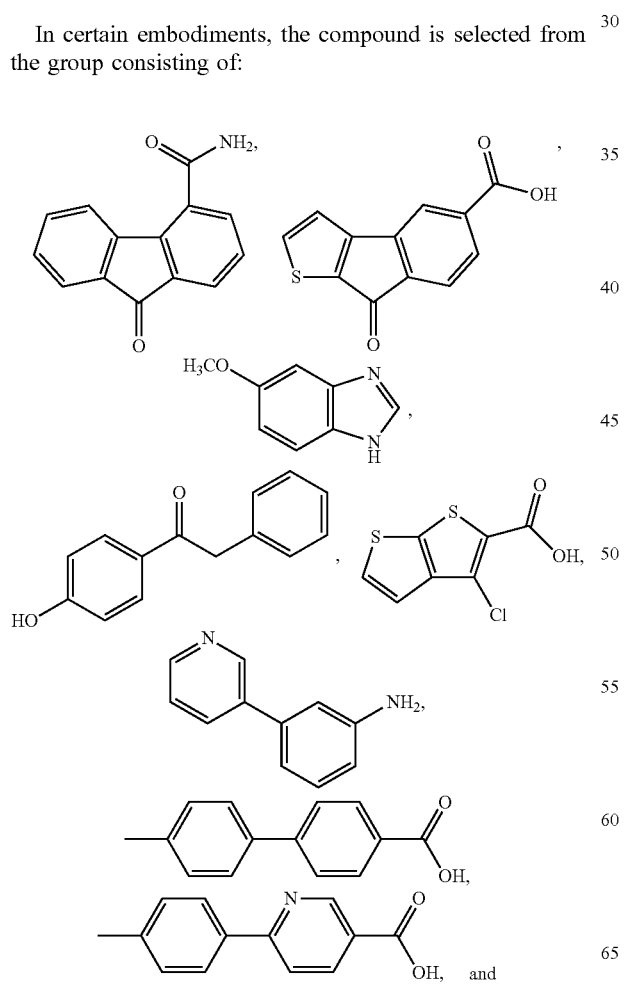
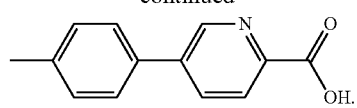
In certain embodiments, the compound is selected from the group consisting of:
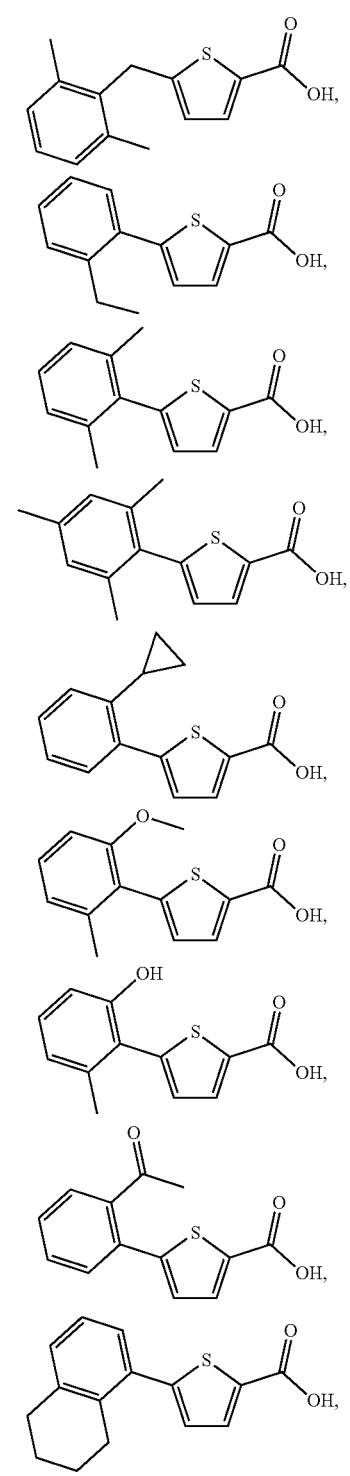

-continued
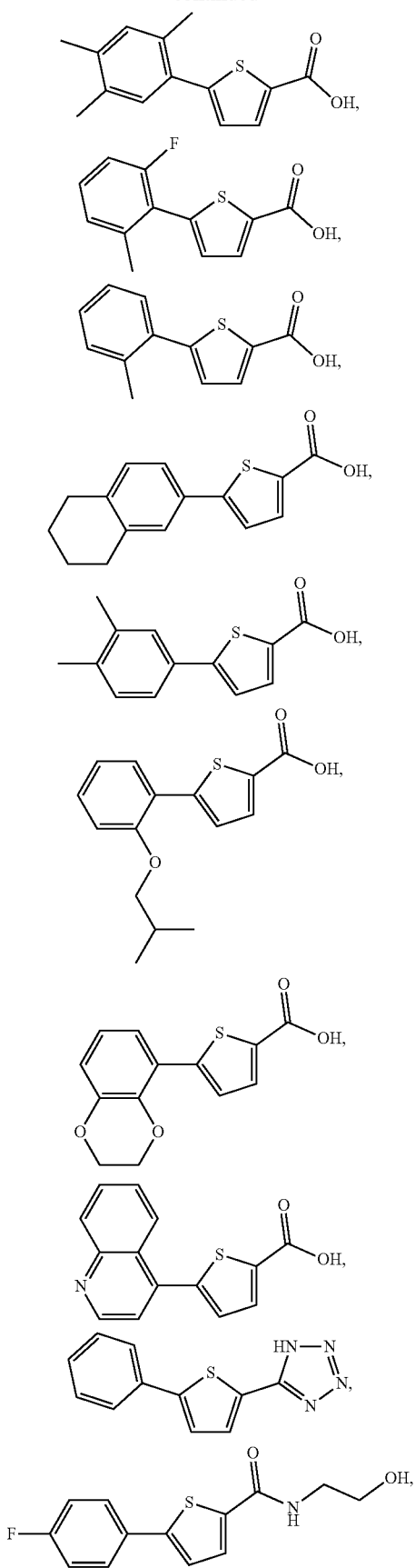
-continued
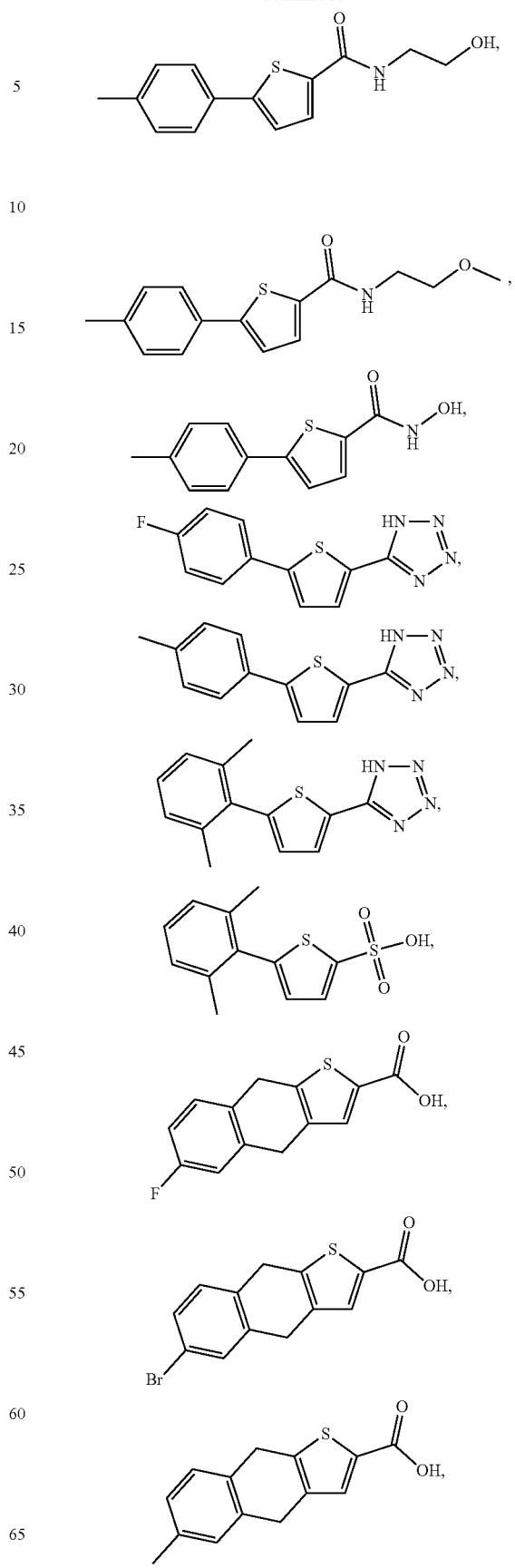

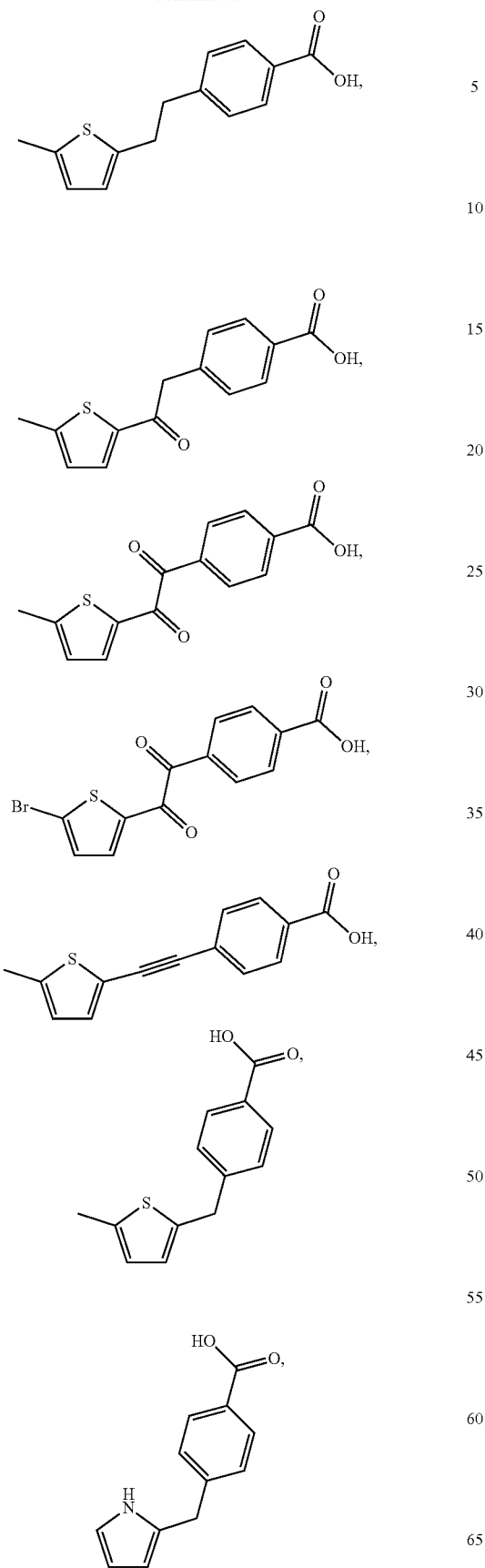
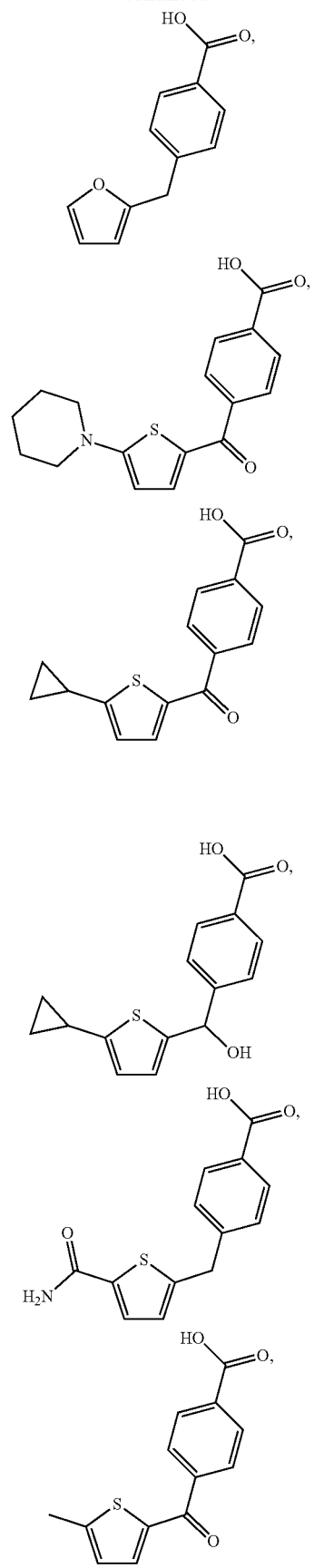

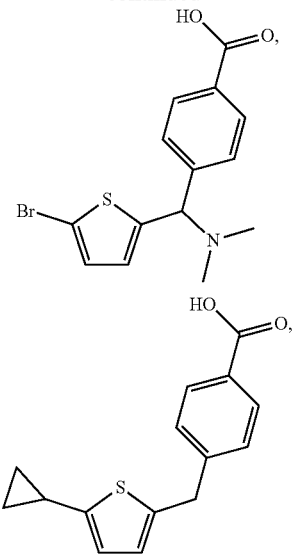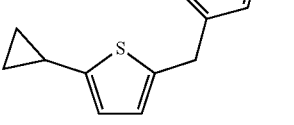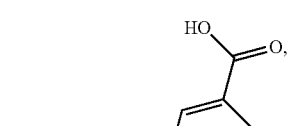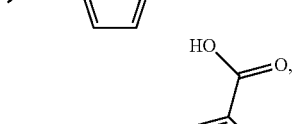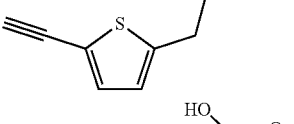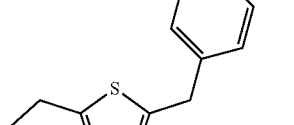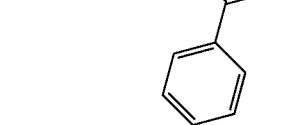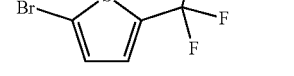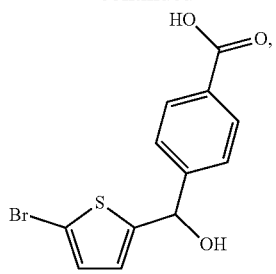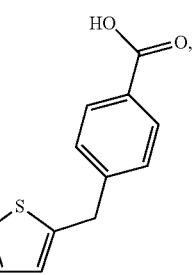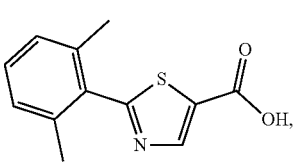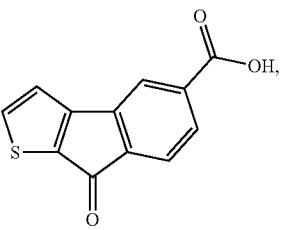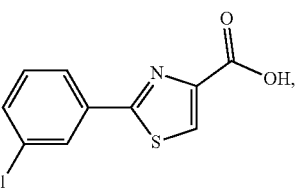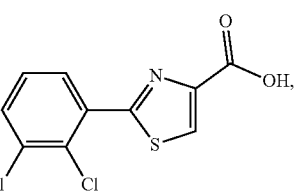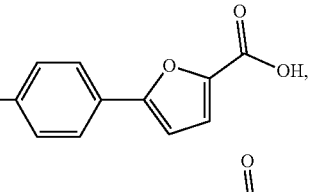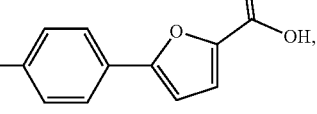

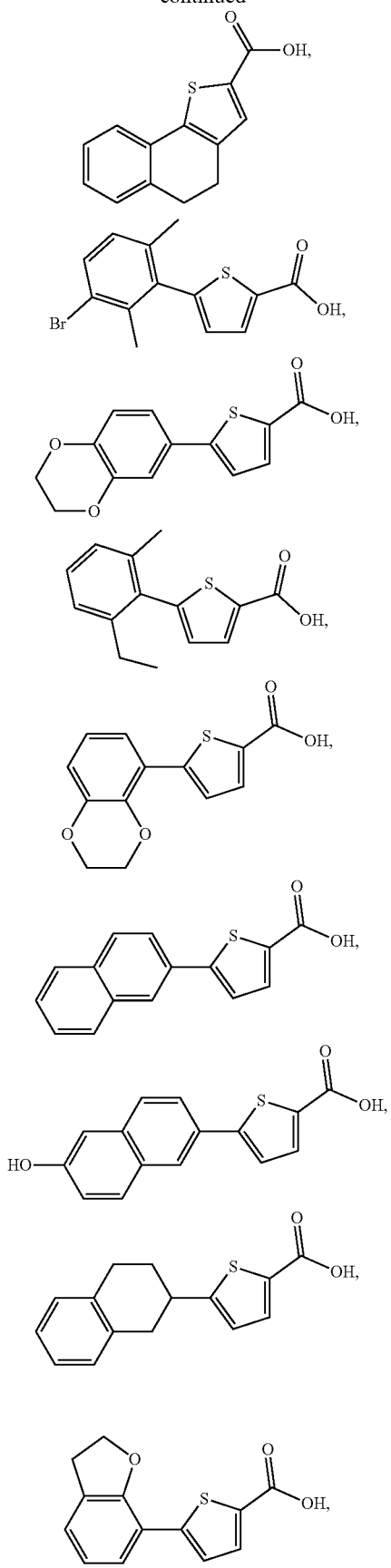
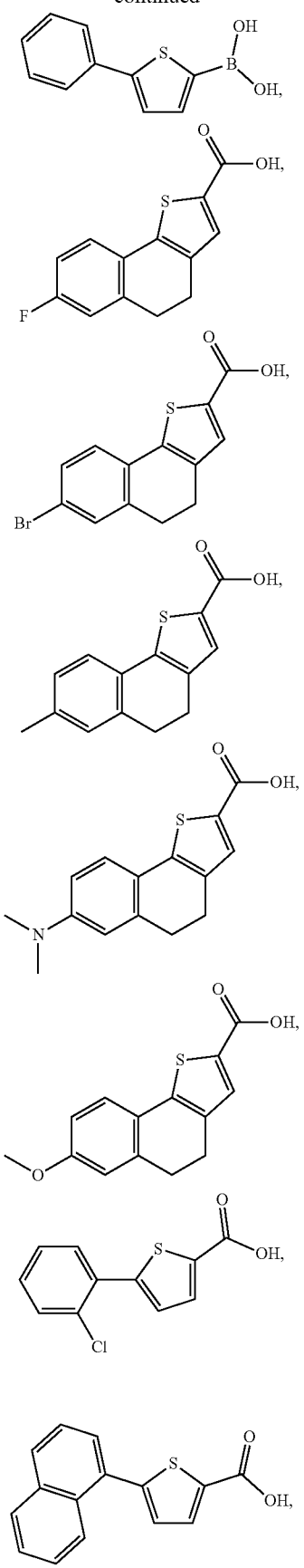

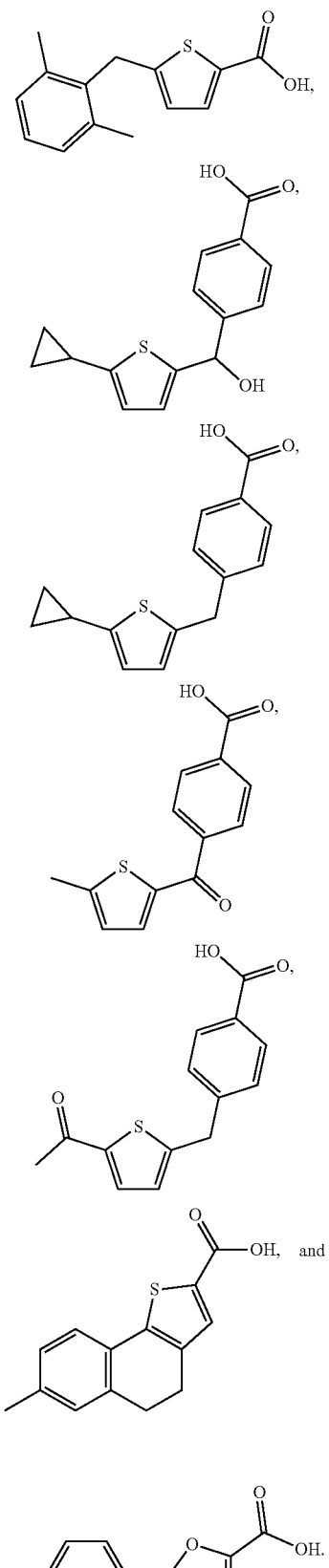
In certain embodiments, the compound is
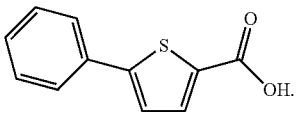 [SMILES: O=C(O)c1ccc(-c2ccccc2)s1]
In certain embodiments, the compound is
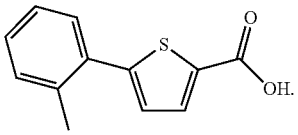
In certain embodiments, the compound is
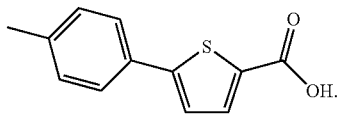
In certain embodiments, the compound is
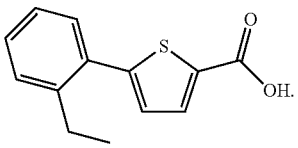 [SMILES: CCc1ccccc1-c1ccc(C(=O)O)s1]
In certain embodiments, the compound is
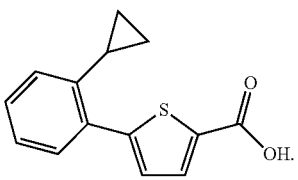 [SMILES: O=C(O)c1ccc(-c2ccccc2C2CC2)s1]
In certain embodiments, the compound is
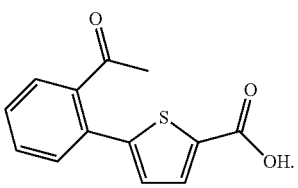 [SMILES: CC(=O)c1ccccc1-c1ccc(C(=O)O)s1]
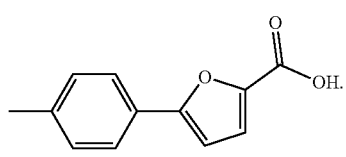

In certain embodiments, the compound is

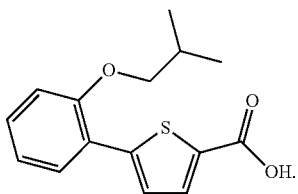 [SMILES: CC(C)COc1ccccc1-c1ccc(C(=O)O)s1]

In certain embodiments, the compound is

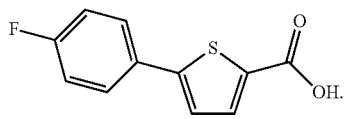 [SMILES: O=C(O)c1ccc(-c2ccc(F)cc2)s1]

In certain embodiments, the compound is

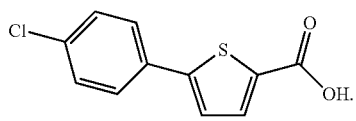 [SMILES: O=C(O)c1ccc(-c2ccc(Cl)cc2)s1]

In certain embodiments, the compound is

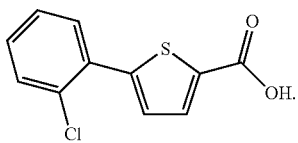 [SMILES: O=C(O)c1ccc(-c2ccccc2Cl)s1]

In certain embodiments, the compound is

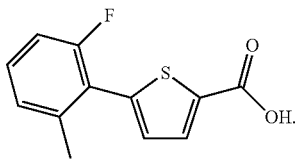

In certain embodiments, the compound is

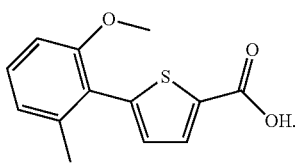 [SMILES: COc1cccc(C)c1-c1ccc(C(=O)O)s1]

In certain embodiments, the compound is

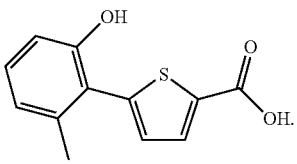 [SMILES: Cc1cccc(O)c1-c1ccc(C(=O)O)s1]

In certain embodiments, the compound is

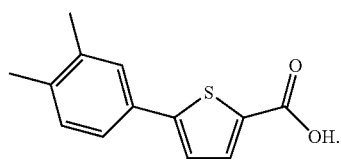 [SMILES: Cc1ccc(-c2ccc(C(=O)O)s2)cc1C]

In certain embodiments, the compound is

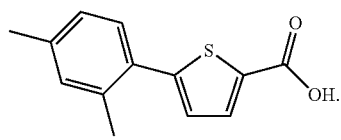 [SMILES: Cc1ccc(-c2ccc(C(=O)O)s2)c(C)c1]

In certain embodiments, the compound is

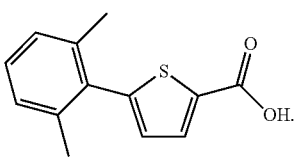 [SMILES: Cc1cccc(C)c1-c1ccc(C(=O)O)s1]

In certain embodiments, the compound is

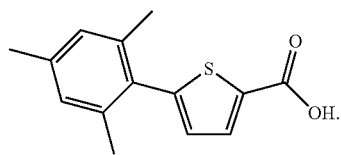 [SMILES: Cc1cc(C)c(-c2ccc(C(=O)O)s2)c(C)c1]

In certain embodiments, the compound is

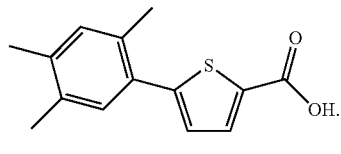 [SMILES: Cc1cc(C)c(-c2ccc(C(=O)O)s2)cc1C]

In certain embodiments, the compound is

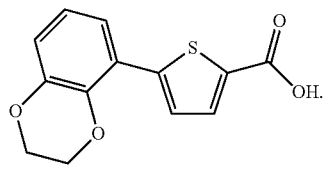 [SMILES: O=C(O)c1ccc(-c2cccc3c2OCCO3)s1]

In certain embodiments, the compound is

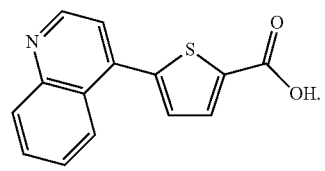 [SMILES: O=C(O)c1ccc(-c2ccnc3ccccc23)s1]

In certain embodiments, the compound is

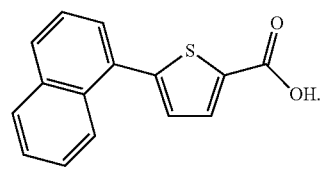 [SMILES: O=C(O)c1ccc(-c2cccc3ccccc23)s1]

In certain embodiments, the compound is

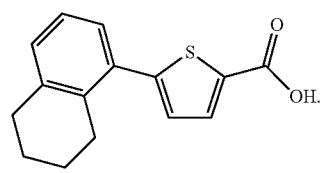 [SMILES: O=C(O)c1ccc(-c2cccc3c2CCCC3)s1]

In certain embodiments, the compound is

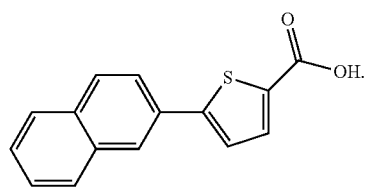 [SMILES: O=C(O)c1ccc(-c2ccc3ccccc3c2)s1]

In certain embodiments, the compound is

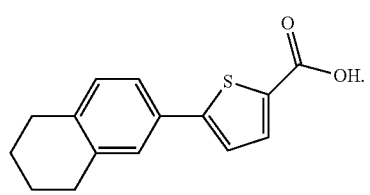 [SMILES: O=C(O)c1ccc(-c2ccc3c(c2)CCCC3)s1]

In certain embodiments, the compound is

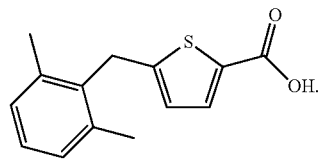 [SMILES: Cc1cccc(C)c1Cc1ccc(C(=O)O)s1]

In certain embodiments, the compound is

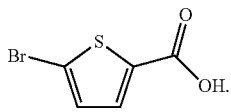

In certain embodiments, the compound is

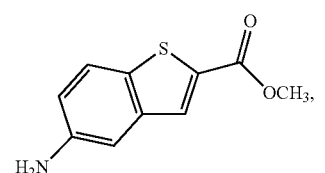

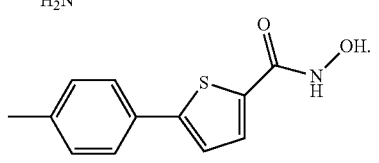

In certain embodiments, the compound is

In certain embodiments, the compound is

In certain embodiments, the compound is

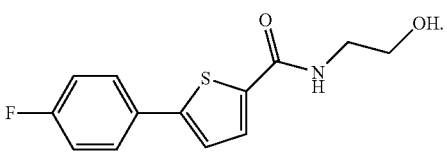

In certain embodiments, the compound is

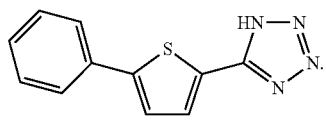 [SMILES: c1ccc(-c2ccc(-c3nnn[nH]3)s2)cc1]

In certain embodiments, the compound is

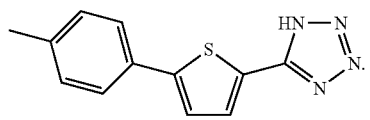 [SMILES: Cc1ccc(-c2ccc(-c3nnn[nH]3)s2)cc1]

In certain embodiments, the compound is

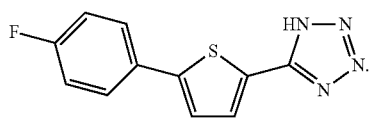 [SMILES: Fc1ccc(-c2ccc(-c3nnn[nH]3)s2)cc1]

In certain embodiments, the compound is

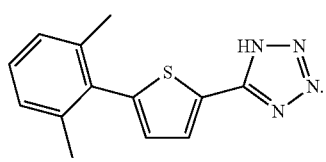 [SMILES: Cc1cccc(C)c1-c1ccc(-c2nnn[nH]2)s1]

In certain embodiments, the compound is

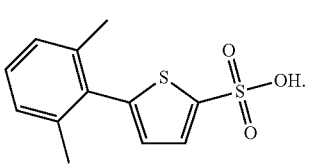 [SMILES: Cc1cccc(C)c1-c1ccc(S(=O)(=O)O)s1]

In certain embodiments, the compound is

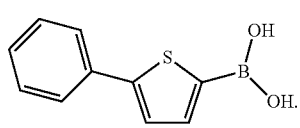 [SMILES: OB(O)c1ccc(-c2ccccc2)s1]

In certain embodiments, the compound is

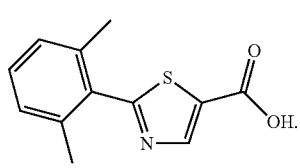 [SMILES: Cc1cccc(C)c1-c1ncc(C(=O)O)s1]

In certain embodiments, the compound is

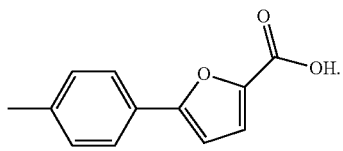

In certain embodiments, the compound is

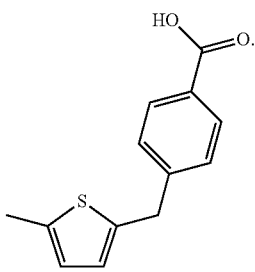 [SMILES: Cc1ccc(Cc2ccc(C(=O)O)cc2)s1]

In certain embodiments, the compound is

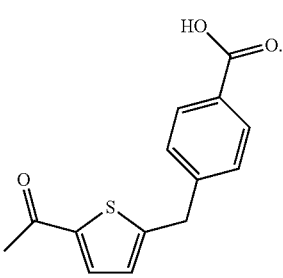 [SMILES: CC(=O)c1ccc(Cc2ccc(C(=O)O)cc2)s1]

In certain embodiments, the compound is

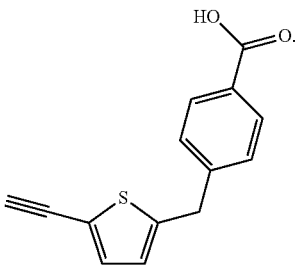 [SMILES: C#Cc1ccc(Cc2ccc(C(=O)O)cc2)s1]

In certain embodiments, the compound is

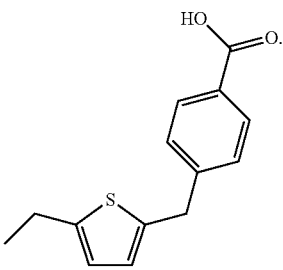 [SMILES: CCc1ccc(Cc2ccc(C(=O)O)cc2)s1]

In certain embodiments, the compound is
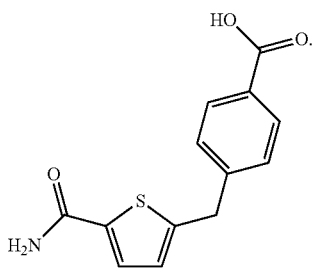 [SMILES: NC(=O)c1ccc(Cc2ccc(C(=O)O)cc2)s1]
In certain embodiments, the compound is
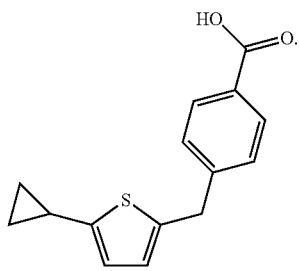 [SMILES: O=C(O)c1ccc(Cc2ccc(C3CC3)s2)cc1]
In certain embodiments, the compound is
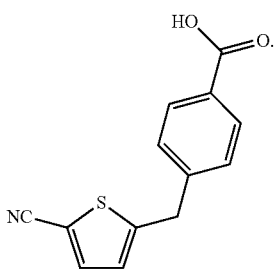 [SMILES: N#Cc1ccc(Cc2ccc(C(=O)O)cc2)s1]
In certain embodiments, the compound is
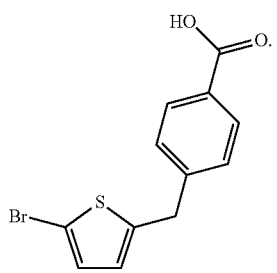 [SMILES: O=C(O)c1ccc(Cc2ccc(Br)s2)cc1]
In certain embodiments, the compound is
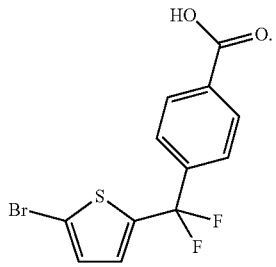 [SMILES: O=C(O)c1ccc(C(F)(F)c2ccc(Br)s2)cc1]
In certain embodiments, the compound is
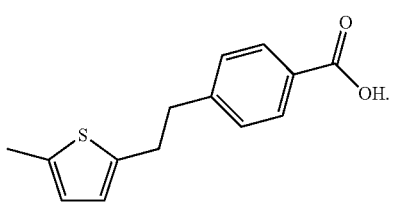 [SMILES: Cc1ccc(CCc2ccc(C(=O)O)cc2)s1]
In certain embodiments, the compound is
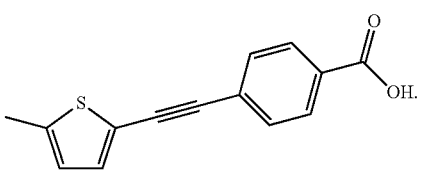 [SMILES: Cc1ccc(C#Cc2ccc(C(=O)O)cc2)s1]
In certain embodiments, the compound is
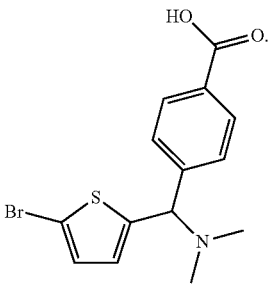 [SMILES: CN(C)C(c1ccc(C(=O)O)cc1)c1ccc(Br)s1]
In certain embodiments, the compound is
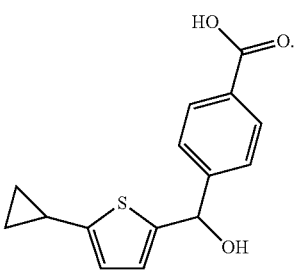

In certain embodiments, the compound is
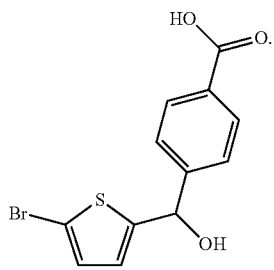 [SMILES: O=C(O)c1ccc(C(O)c2ccc(Br)s2)cc1]
In certain embodiments, the compound is
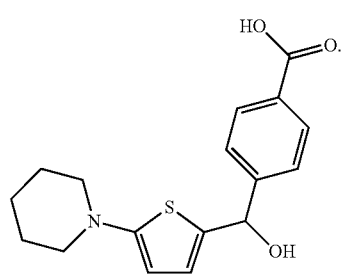
In certain embodiments, the compound is
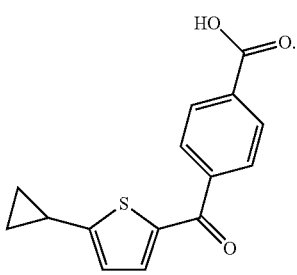 [SMILES: O=C(O)c1ccc(C(=O)c2ccc(C3CC3)s2)cc1]
In certain embodiments, the compound is
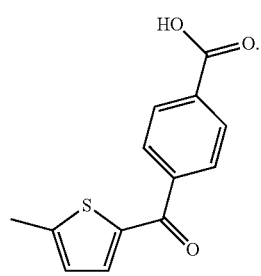 [SMILES: Cc1ccc(C(=O)c2ccc(C(=O)O)cc2)s1]
In certain embodiments, the compound is
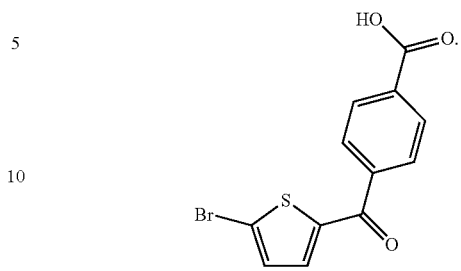
In certain embodiments, the compound is
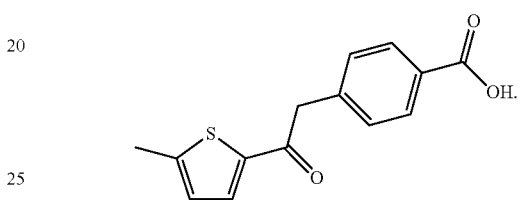
In certain embodiments, the compound is
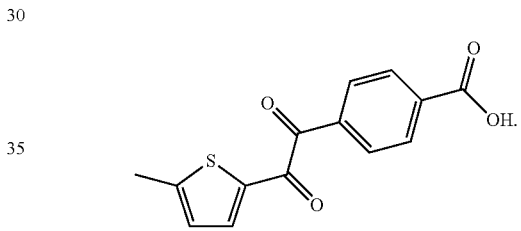
In certain embodiments, the compound is
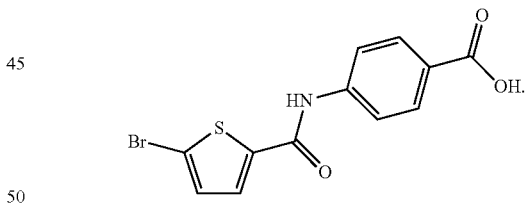
In certain embodiments, the compound is
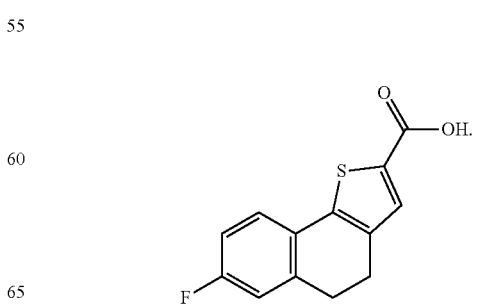

In certain embodiments, the compound is

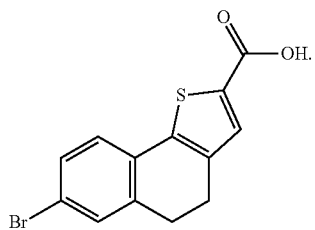 [SMILES: O=C(O)c1cc2c(s1)-c1ccc(Br)cc1CC2]

In certain embodiments, the compound is

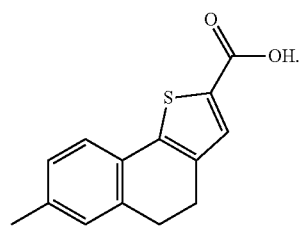 [SMILES: Cc1ccc2c(c1)CCc1cc(C(=O)O)sc1-2]

In certain embodiments, the compound is

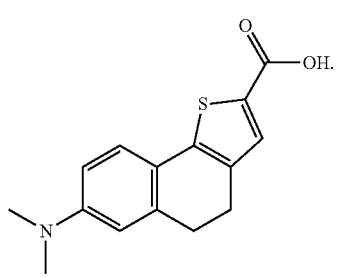 [SMILES: CN(C)c1ccc2c(c1)CCc1cc(C(=O)O)sc1-2]

In certain embodiments, the compound is

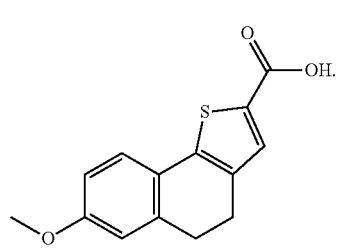 [SMILES: COc1ccc2c(c1)CCc1cc(C(=O)O)sc1-2]

In certain embodiments, the compound is

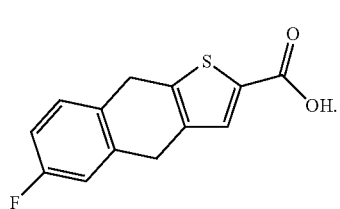 [SMILES: O=C(O)c1cc2c(s1)Cc1ccc(F)cc1C2]

In certain embodiments, the compound is

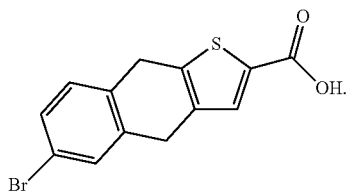 [SMILES: O=C(O)c1cc2c(s1)Cc1ccc(Br)cc1C2]

In certain embodiments, the compound is

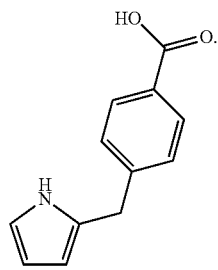 [SMILES: O=C(O)c1ccc(Cc2ccc[nH]2)cc1]

In certain embodiments, the compound is

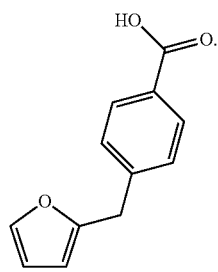 [SMILES: O=C(O)c1ccc(Cc2ccco2)cc1]

In certain embodiments, the compound is

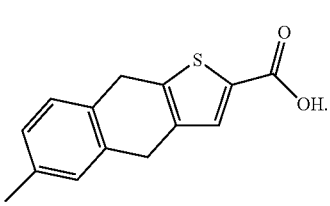 [SMILES: Cc1ccc2c(c1)Cc1cc(C(=O)O)sc1C2]

In certain embodiments, the compound is

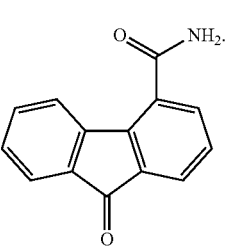 [SMILES: NC(=O)c1cccc2c1-c1ccccc1C2=O]

In certain embodiments, the compound is

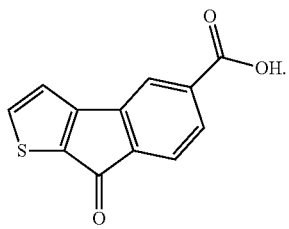 [SMILES: O=C(O)c1ccc2c(c1)-c1ccsc1C2=O]

In certain embodiments, the compound is

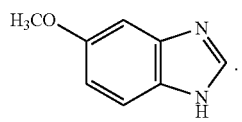 [SMILES: COc1ccc2[nH]cnc2c1]

In certain embodiments, the compound is

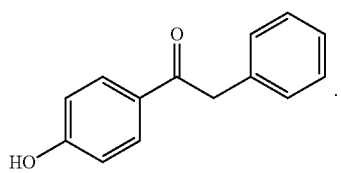

In certain embodiments, the compound is

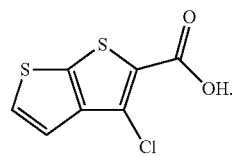

In certain embodiments, the compound is

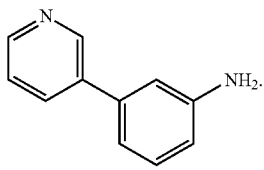 [SMILES: Nc1cccc(-c2cccnc2)c1]

In certain embodiments, the compound is

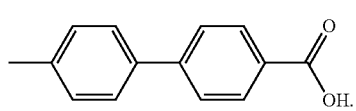 [SMILES: Cc1ccc(-c2ccc(C(=O)O)cc2)cc1]

In certain embodiments, the compound is

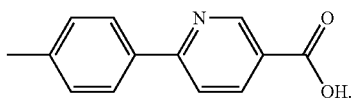 [SMILES: Cc1ccc(-c2ccc(C(=O)O)cn2)cc1]

In certain embodiments, the compound is

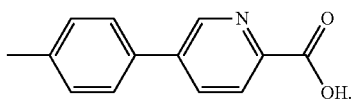

In certain embodiments, the compound is

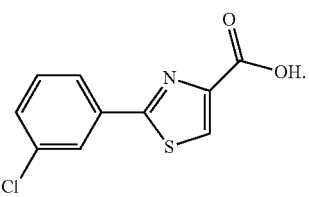 [SMILES: O=C(O)c1csc(-c2cccc(Cl)c2)n1]

In certain embodiments, the compound is

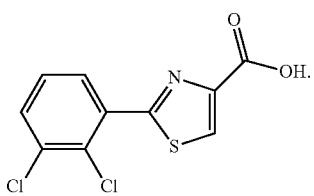 [SMILES: O=C(O)c1csc(-c2cccc(Cl)c2Cl)n1]

In certain embodiments, the compound is

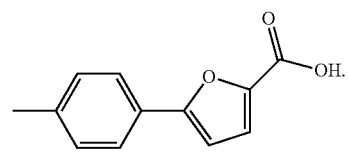

In certain embodiments, the compound is

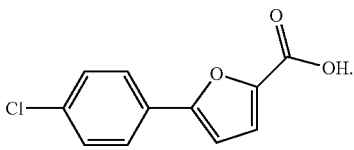 [SMILES: O=C(O)c1ccc(-c2ccc(Cl)cc2)o1]

In certain embodiments, the compound is

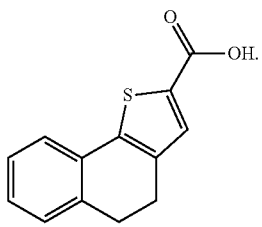 [SMILES: O=C(O)c1cc2c(s1)-c1ccccc1CC2]

In certain embodiments, the compound is

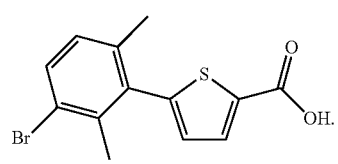 [SMILES: Cc1ccc(Br)c(C)c1-c1ccc(C(=O)O)s1]

In certain embodiments, the compound is

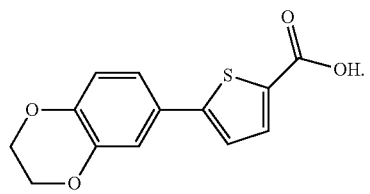 [SMILES: O=C(O)c1ccc(-c2ccc3c(c2)OCCO3)s1]

In certain embodiments, the compound is

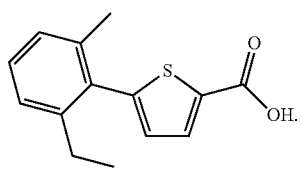 [SMILES: CCc1cccc(C)c1-c1ccc(C(=O)O)s1]

In certain embodiments, the compound is

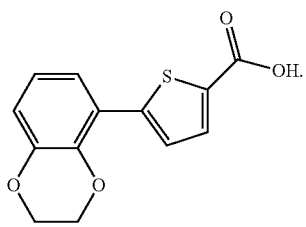 [SMILES: O=C(O)c1ccc(-c2cccc3c2OCCO3)s1]

In certain embodiments, the compound is

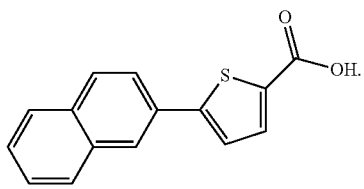 [SMILES: O=C(O)c1ccc(-c2ccc3ccccc3c2)s1]

In certain embodiments, the compound is

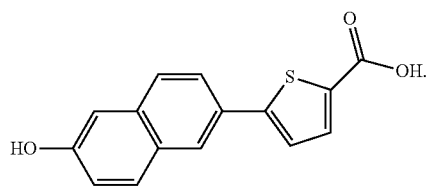

In certain embodiments, the compound is

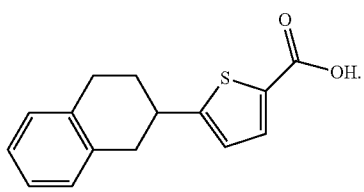 [SMILES: O=C(O)c1ccc(C2CCc3ccccc3C2)s1]

In certain embodiments, the compound is

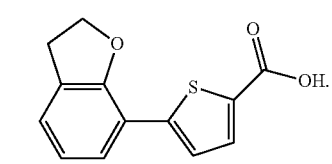 [SMILES: O=C(O)c1ccc(-c2cccc3c2OCC3)s1]

In certain embodiments, the compound is

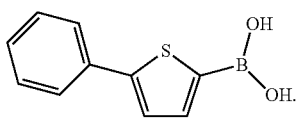 [SMILES: OB(O)c1ccc(-c2ccccc2)s1]

In certain embodiments, the compound is

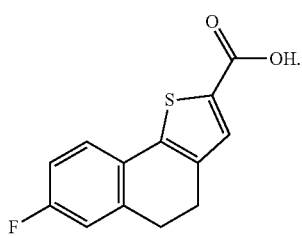 [SMILES: O=C(O)c1cc2c(s1)-c1ccc(F)cc1CC2]

In certain embodiments, the compound is

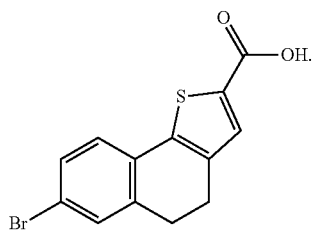 [SMILES: O=C(O)c1cc2c(s1)-c1ccc(Br)cc1CC2]

In certain embodiments, the compound is

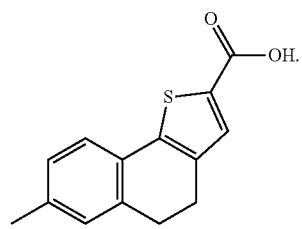 [SMILES: Cc1ccc2c(c1)CCc1cc(C(=O)O)sc1-2]

In certain embodiments, the compound is

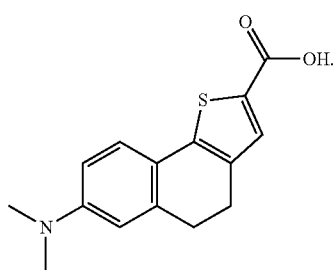 [SMILES: CN(C)c1ccc2c(c1)CCc1cc(C(=O)O)sc1-2]

In certain embodiments, the compound is

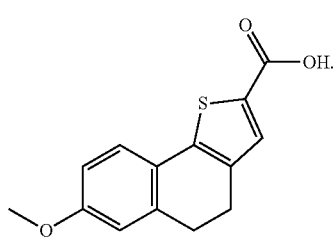 [SMILES: COc1ccc2c(c1)CCc1cc(C(=O)O)sc1-2]

In certain embodiments, the compound is

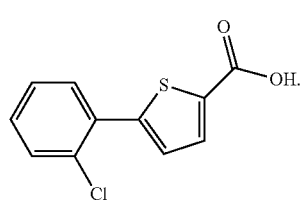 [SMILES: O=C(O)c1ccc(-c2ccccc2Cl)s1]

In certain embodiments, the compound is

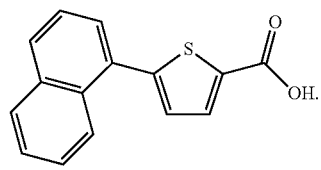

In certain embodiments, the compound is

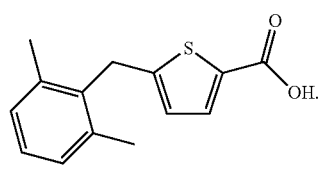 [SMILES: Cc1cccc(C)c1Cc1ccc(C(=O)O)s1]

In certain embodiments, the compound is

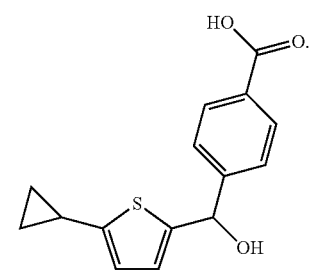 [SMILES: O=C(O)c1ccc(C(O)c2ccc(C3CC3)s2)cc1]

In certain embodiments, the compound is

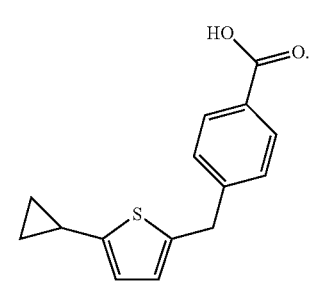 [SMILES: O=C(O)c1ccc(Cc2ccc(C3CC3)s2)cc1]

In certain embodiments, the compound is

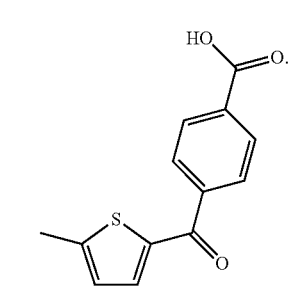 [SMILES: Cc1ccc(C(=O)c2ccc(C(=O)O)cc2)s1]

In certain embodiments, the compound is

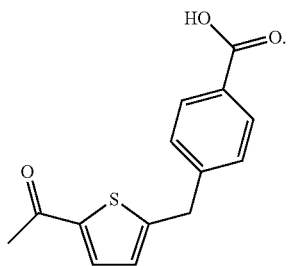 [SMILES: CC(=O)c1ccc(Cc2ccc(C(=O)O)cc2)s1]

In certain embodiments, the compound is

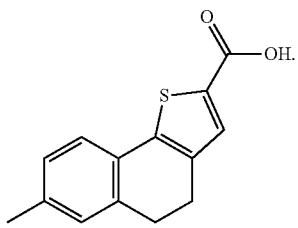 [SMILES: Cc1ccc2c(c1)CCc1cc(C(=O)O)sc1-2]

In certain embodiments, the compound is

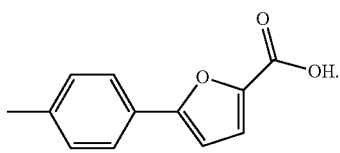

In certain embodiments, the compound is not

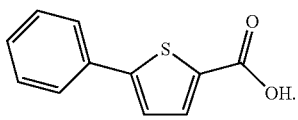 [SMILES: O=C(O)c1ccc(-c2ccccc2)s1]

In certain embodiments, the compound is not

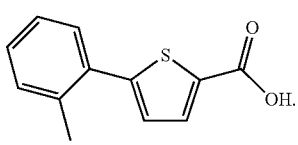

In certain embodiments, the compound is not

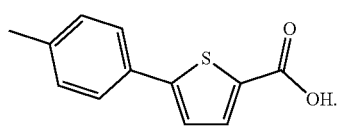

In certain embodiments, the compound is no

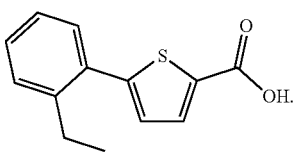 [SMILES: CCc1ccccc1-c1ccc(C(=O)O)s1]

In certain embodiments, the compound is not

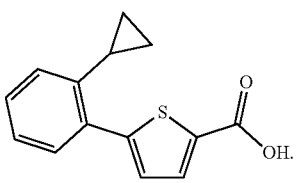 [SMILES: O=C(O)c1ccc(-c2ccccc2C2CC2)s1]

In certain embodiments, the compound is not

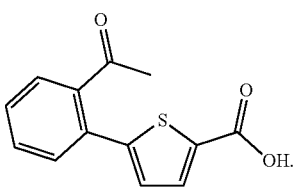 [SMILES: CC(=O)c1ccccc1-c1ccc(C(=O)O)s1]

In certain embodiments, the compound is not

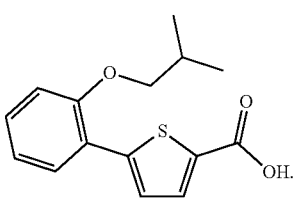 [SMILES: CC(C)COc1ccccc1-c1ccc(C(=O)O)s1]

In certain embodiments, the compound is not

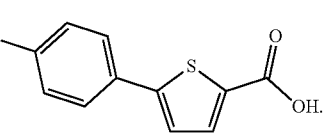

In certain embodiments, the compound is not

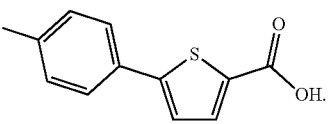

In certain embodiments, the compound is not

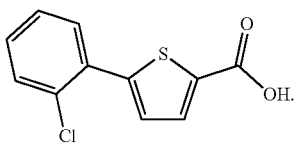 [SMILES: O=C(O)c1ccc(-c2ccccc2Cl)s1]

In certain embodiments, the compound is not

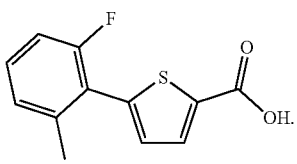 [SMILES: Cc1cccc(F)c1-c1ccc(C(=O)O)s1]

In certain embodiments, the compound is not

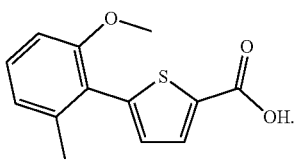 [SMILES: COc1cccc(C)c1-c1ccc(C(=O)O)s1]

In certain embodiments, the compound is not

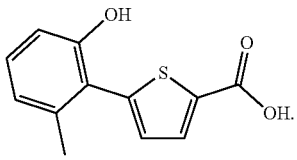 [SMILES: Cc1cccc(O)c1-c1ccc(C(=O)O)s1]

In certain embodiments, the compound is not

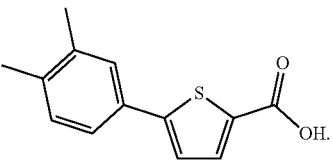 [SMILES: Cc1ccc(-c2ccc(C(=O)O)s2)cc1C]

In certain embodiments, the compound is not

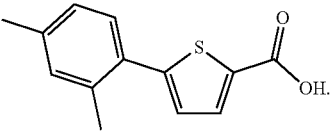 [SMILES: Cc1ccc(-c2ccc(C(=O)O)s2)c(C)c1]

In certain embodiments, the compound is not

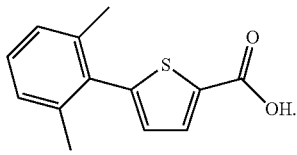 [SMILES: Cc1cccc(C)c1-c1ccc(C(=O)O)s1]

In certain embodiments, the compound is not

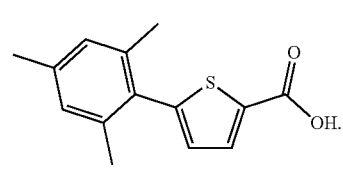 [SMILES: Cc1cc(C)c(-c2ccc(C(=O)O)s2)c(C)c1]

In certain embodiments, the compound is not

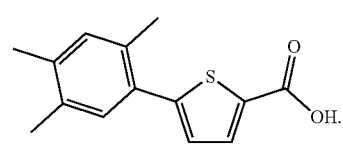 [SMILES: Cc1cc(C)c(-c2ccc(C(=O)O)s2)cc1C]

In certain embodiments, the compound is not

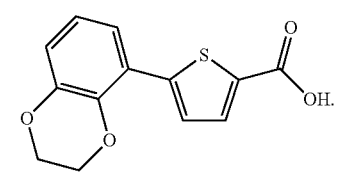

In certain embodiments, the compound is not

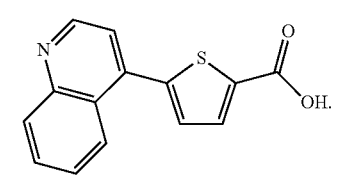 [SMILES: O=C(O)c1ccc(-c2ccnc3ccccc23)s1]

In certain embodiments, the compound is not

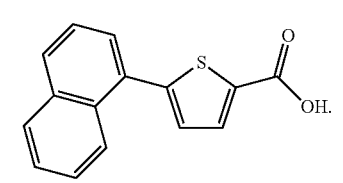 [SMILES: O=C(O)c1ccc(-c2cccc3ccccc23)s1]

In certain embodiments, the compound is not

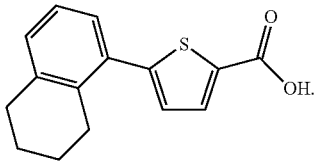 [SMILES: O=C(O)c1ccc(-c2cccc3c2CCCC3)s1]

In certain embodiments, the compound is not

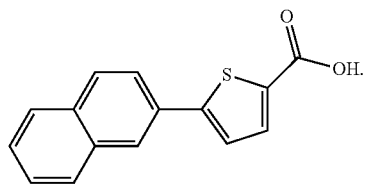 [SMILES: O=C(O)c1ccc(-c2ccc3ccccc3c2)s1]

In certain embodiments, the compound is not

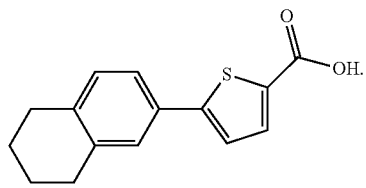 [SMILES: O=C(O)c1ccc(-c2ccc3c(c2)CCCC3)s1]

In certain embodiments, the compound is not

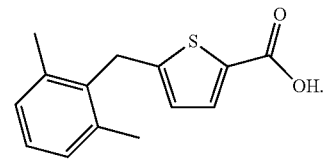 [SMILES: Cc1cccc(C)c1Cc1ccc(C(=O)O)s1]

In certain embodiments, the compound is not

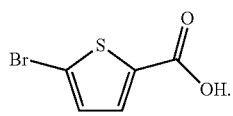

In certain embodiments, the compound is not

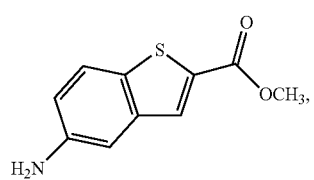 [SMILES: COC(=O)c1cc2cc(N)ccc2s1]

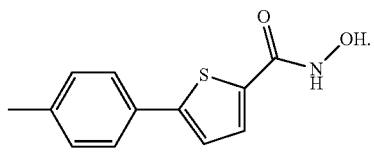 [SMILES: Cc1ccc(-c2ccc(C(=O)NO)s2)cc1]

In certain embodiments, the compound is not

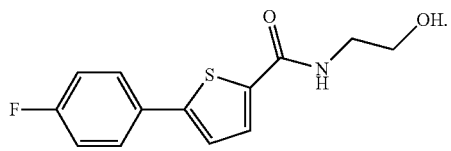 [SMILES: O=C(NCCO)c1ccc(-c2ccc(F)cc2)s1]

In certain embodiments, the compound is not

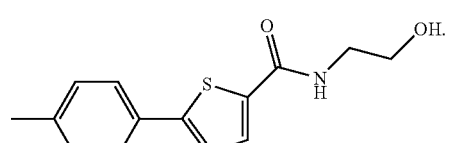

In certain embodiments, the compound is not

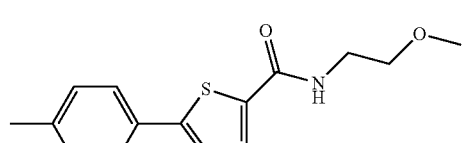

In certain embodiments, the compound is not

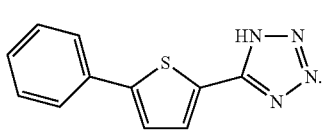 [SMILES: c1ccc(-c2ccc(-c3nnn[nH]3)s2)cc1]

In certain embodiments, the compound is not

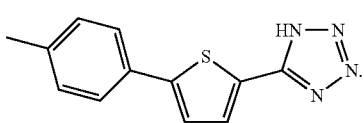 [SMILES: Cc1ccc(-c2ccc(-c3nnn[nH]3)s2)cc1]

In certain embodiments, the compound is not

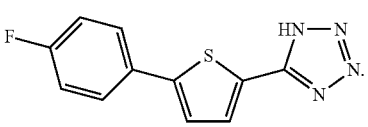

In certain embodiments, the compound is not

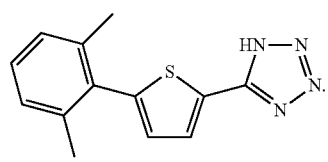 [SMILES: Cc1cccc(C)c1-c1ccc(-c2nnn[nH]2)s1]

In certain embodiments, the compound is not

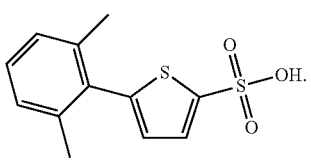 [SMILES: Cc1cccc(C)c1-c1ccc(S(=O)(=O)O)s1]

In certain embodiments, the compound is not

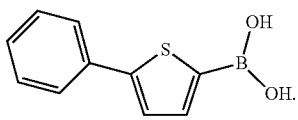 [SMILES: OB(O)c1ccc(-c2ccccc2)s1]

In certain embodiments, the compound is not

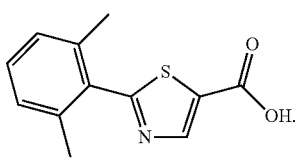 [SMILES: Cc1cccc(C)c1-c1ncc(C(=O)O)s1]

In certain embodiments, the compound is not

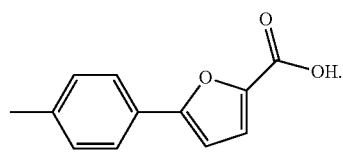

In certain embodiments, the compound is not

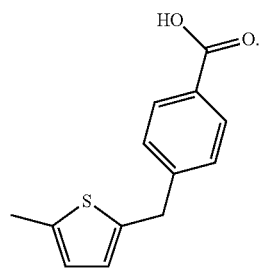 [SMILES: Cc1ccc(Cc2ccc(C(=O)O)cc2)s1]

In certain embodiments, the compound is not

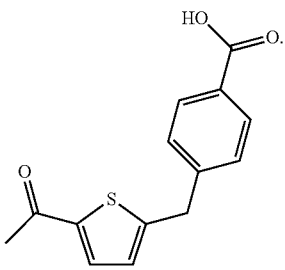 [SMILES: CC(=O)c1ccc(Cc2ccc(C(=O)O)cc2)s1]

In certain embodiments, the compound is not

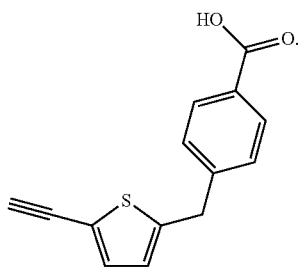 [SMILES: C#Cc1ccc(Cc2ccc(C(=O)O)cc2)s1]

In certain embodiments, the compound is not

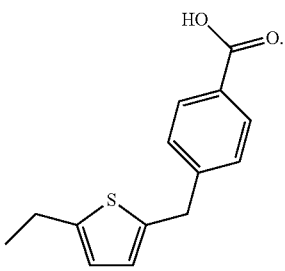 [SMILES: CCc1ccc(Cc2ccc(C(=O)O)cc2)s1]

In certain embodiments, the compound is not

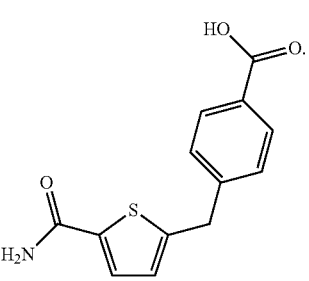 [SMILES: NC(=O)c1ccc(Cc2ccc(C(=O)O)cc2)s1]

In certain embodiments, the compound is not

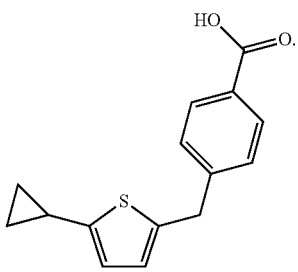 [SMILES: O=C(O)c1ccc(Cc2ccc(C3CC3)s2)cc1]

In certain embodiments, the compound is not

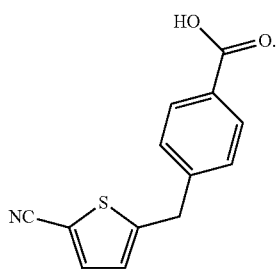 [SMILES: N#Cc1ccc(Cc2ccc(C(=O)O)cc2)s1]

In certain embodiments, the compound is not

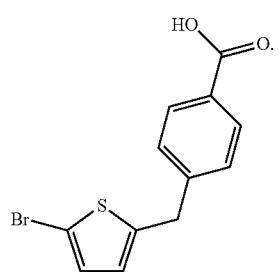 [SMILES: O=C(O)c1ccc(Cc2ccc(Br)s2)cc1]

In certain embodiments, the compound is not

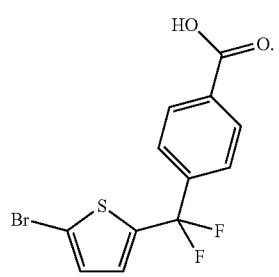 [SMILES: O=C(O)c1ccc(C(F)(F)c2ccc(Br)s2)cc1]

In certain embodiments, the compound is not

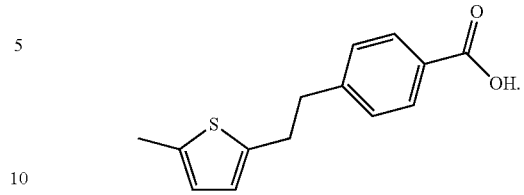

In certain embodiments, the compound is not

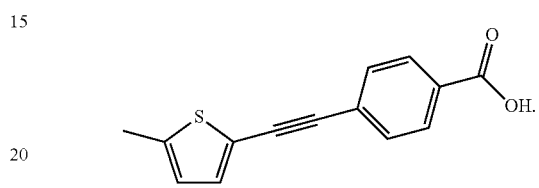

In certain embodiments, the compound is not

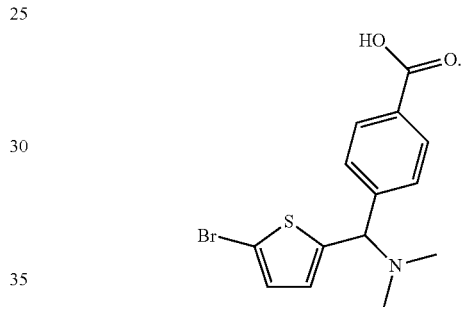

In certain embodiments, the compound is not

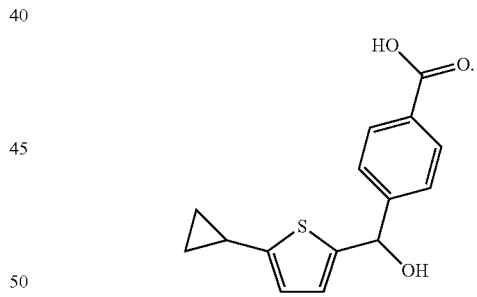

In certain embodiments, the compound is not

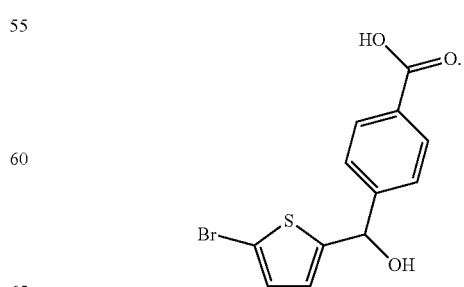

In certain embodiments, the compound is not

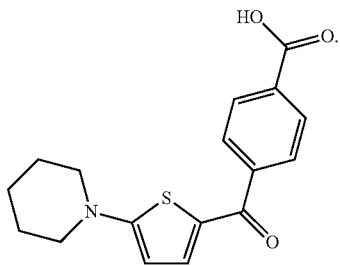 [SMILES: O=C(O)c1ccc(C(=O)c2ccc(N3CCCCC3)s2)cc1]

In certain embodiments, the compound is not

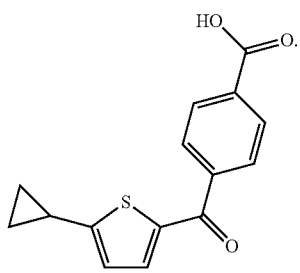 [SMILES: O=C(O)c1ccc(C(=O)c2ccc(C3CC3)s2)cc1]

In certain embodiments, the compound is not

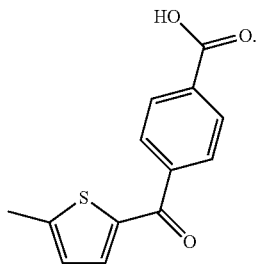 [SMILES: Cc1ccc(C(=O)c2ccc(C(=O)O)cc2)s1]

In certain embodiments, the compound is not

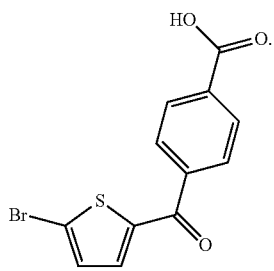 [SMILES: O=C(O)c1ccc(C(=O)c2ccc(Br)s2)cc1]

In certain embodiments, the compound is not

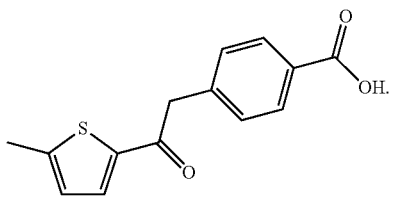 [SMILES: Cc1ccc(C(=O)Cc2ccc(C(=O)O)cc2)s1]

In certain embodiments, the compound is not

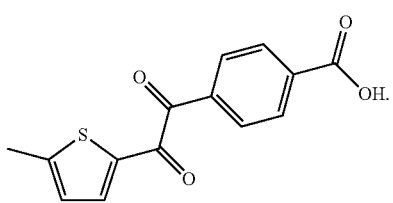 [SMILES: Cc1ccc(C(=O)C(=O)c2ccc(C(=O)O)cc2)s1]

In certain embodiments, the compound is not

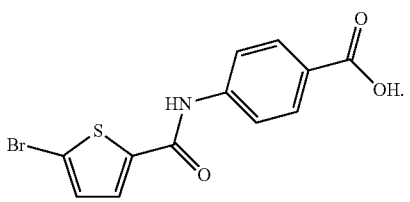 [SMILES: O=C(O)c1ccc(NC(=O)c2ccc(Br)s2)cc1]

In certain embodiments, the compound is not

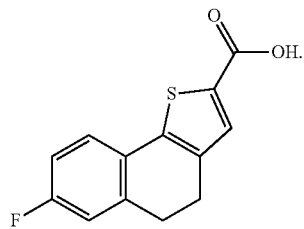 [SMILES: O=C(O)c1cc2c(s1)-c1ccc(F)cc1CC2]

In certain embodiments, the compound is not

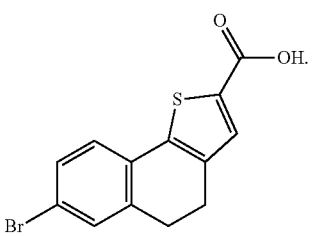 [SMILES: O=C(O)c1cc2c(s1)-c1ccc(Br)cc1CC2]

In certain embodiments, the compound is not

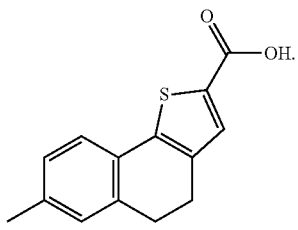 [SMILES: Cc1ccc2c(c1)CCc1cc(C(=O)O)sc1-2]

In certain embodiments, the compound is not

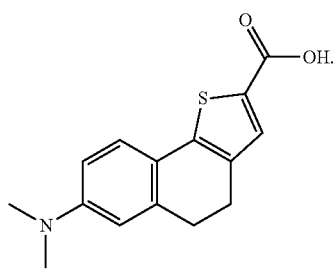 [SMILES: CN(C)c1ccc2c(c1)CCc1cc(C(=O)O)sc1-2]

In certain embodiments, the compound is not

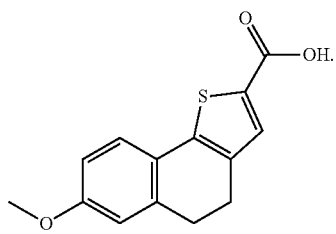 [SMILES: COc1ccc2c(c1)CCc1cc(C(=O)O)sc1-2]

In certain embodiments, the compound is not

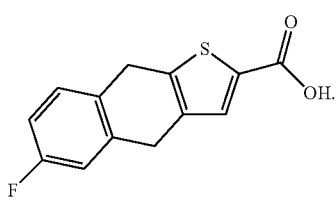 [SMILES: O=C(O)c1cc2c(s1)Cc1ccc(F)cc1C2]

In certain embodiments, the compound is not

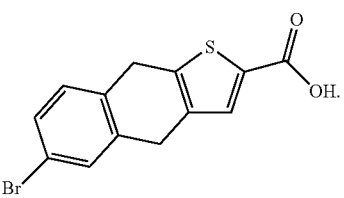 [SMILES: O=C(O)c1cc2c(s1)Cc1ccc(Br)cc1C2]

In certain embodiments, the compound is not

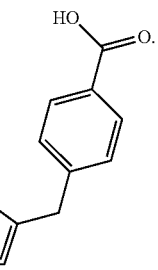

In certain embodiments, the compound is not

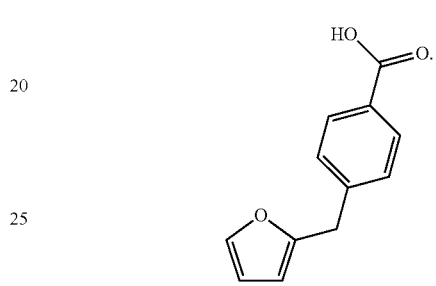

In certain embodiments, the compound is not

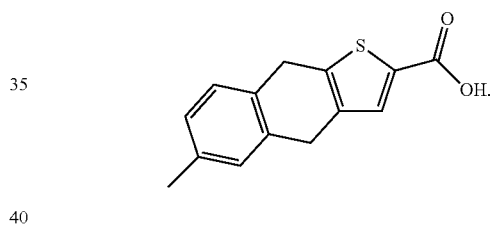

In certain embodiments, the compound is not

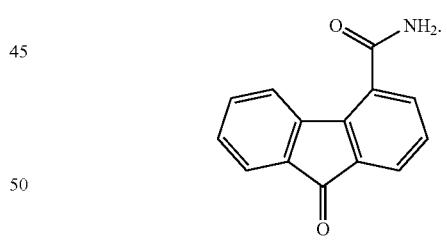

In certain embodiments, the compound is not

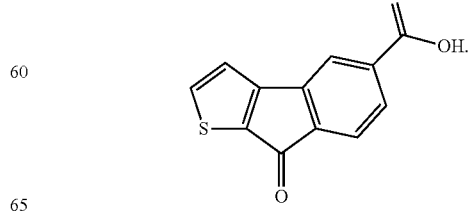

In certain embodiments, the compound is not

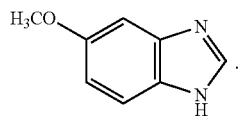

In certain embodiments, the compound is not

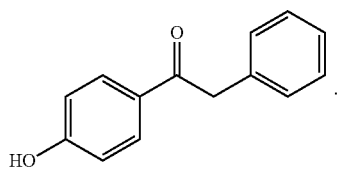 [SMILES: O=C(Cc1ccccc1)c1ccc(O)cc1]

In certain embodiments, the compound is not

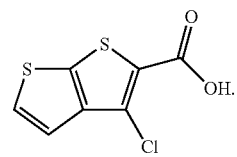 [SMILES: O=C(O)c1sc2sccc2c1Cl]

In certain embodiments, the compound is not

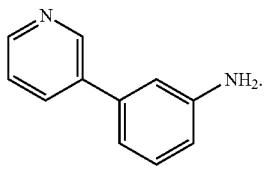 [SMILES: Nc1cccc(-c2cccnc2)c1]

In certain embodiments, the compound is not

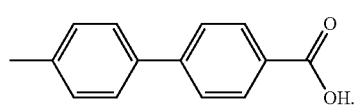 [SMILES: Cc1ccc(-c2ccc(C(=O)O)cc2)cc1]

In certain embodiments, the compound is not

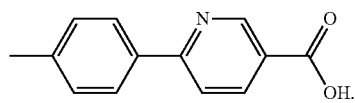

In certain embodiments, the compound is not

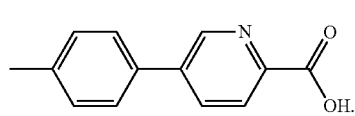

In certain embodiments, the compound is not

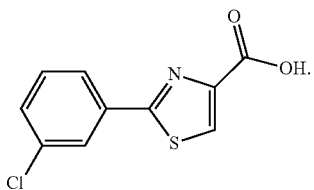 [SMILES: O=C(O)c1csc(-c2cccc(Cl)c2)n1]

In certain embodiments, the compound is not

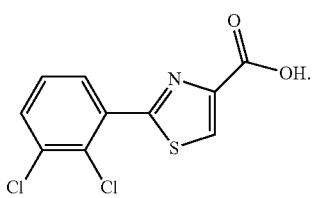 [SMILES: O=C(O)c1csc(-c2cccc(Cl)c2Cl)n1]

In certain embodiments, the compound is not

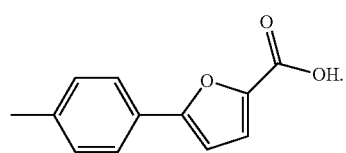

In certain embodiments, the compound is not

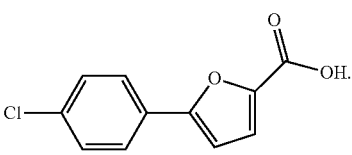 [SMILES: O=C(O)c1ccc(-c2ccc(Cl)cc2)o1]

In certain embodiments, the compound is not

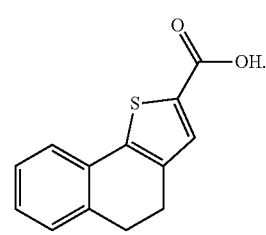 [SMILES: O=C(O)c1cc2c(s1)-c1ccccc1CC2]

In certain embodiments, the compound is not

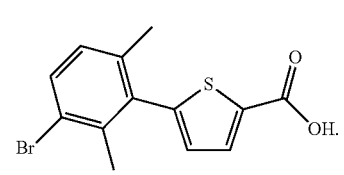 [SMILES: Cc1ccc(Br)c(C)c1-c1ccc(C(=O)O)s1]

In certain embodiments, the compound is not

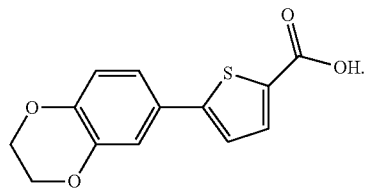 [SMILES: O=C(O)c1ccc(-c2ccc3c(c2)OCCO3)s1]

In certain embodiments, the compound is not

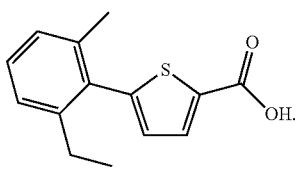 [SMILES: CCc1cccc(C)c1-c1ccc(C(=O)O)s1]

In certain embodiments, the compound is not

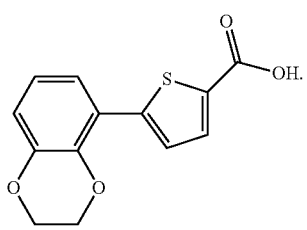 [SMILES: O=C(O)c1ccc(-c2cccc3c2OCCO3)s1]

In certain embodiments, the compound is not

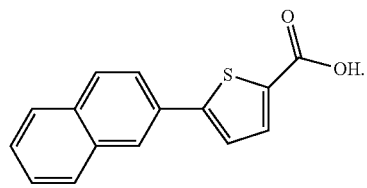 [SMILES: O=C(O)c1ccc(-c2ccc3ccccc3c2)s1]

In certain embodiments, the compound is not

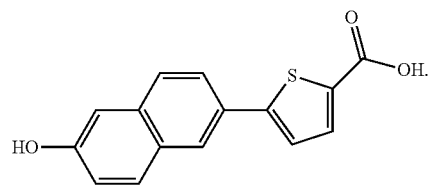 [SMILES: O=C(O)c1ccc(-c2ccc3cc(O)ccc3c2)s1]

In certain embodiments, the compound is not

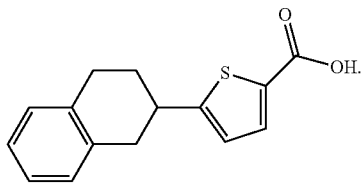 [SMILES: O=C(O)c1ccc(C2CCc3ccccc3C2)s1]

In certain embodiments, the compound is not

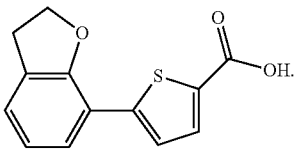 [SMILES: O=C(O)c1ccc(-c2cccc3c2OCC3)s1]

In certain embodiments, the compound is not

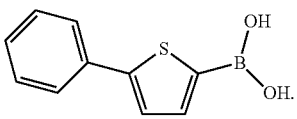 [SMILES: OB(O)c1ccc(-c2ccccc2)s1]

In certain embodiments, the compound is not

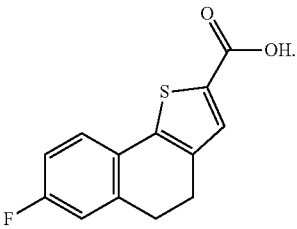 [SMILES: O=C(O)c1cc2c(s1)-c1ccc(F)cc1CC2]

In certain embodiments, the compound is not

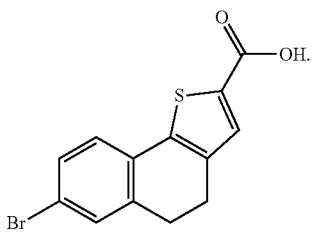 [SMILES: O=C(O)c1cc2c(s1)-c1ccc(Br)cc1CC2]

In certain embodiments, the compound is not

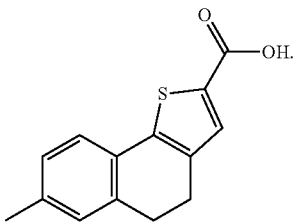

In certain embodiments, the compound is not

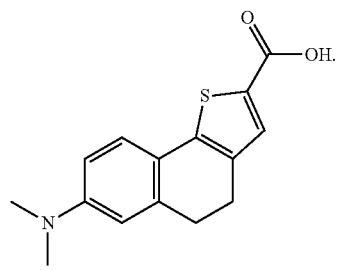 [SMILES: CN(C)c1ccc2c(c1)CCc1cc(C(=O)O)sc1-2]

In certain embodiments, the compound is not

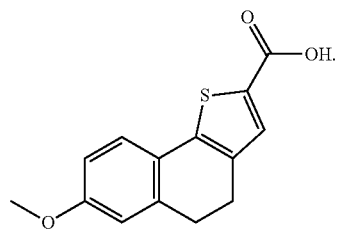 [SMILES: COc1ccc2c(c1)CCc1cc(C(=O)O)sc1-2]

In certain embodiments, the compound is not

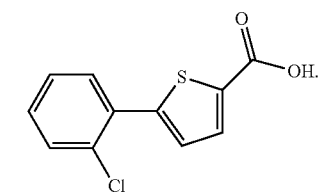 [SMILES: O=C(O)c1ccc(-c2ccccc2Cl)s1]

In certain embodiments, the compound is not

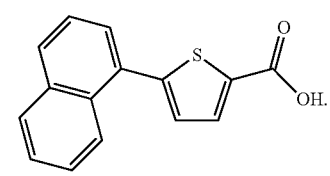 [SMILES: O=C(O)c1ccc(-c2cccc3ccccc23)s1]

In certain embodiments, the compound is not

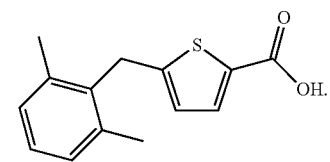 [SMILES: Cc1cccc(C)c1Cc1ccc(C(=O)O)s1]

In certain embodiments, the compound is not

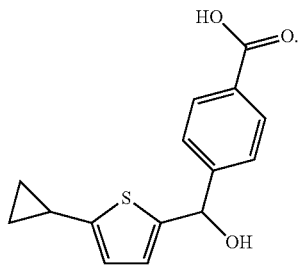 [SMILES: O=C(O)c1ccc(C(O)c2ccc(C3CC3)s2)cc1]

In certain embodiments, the compound is not

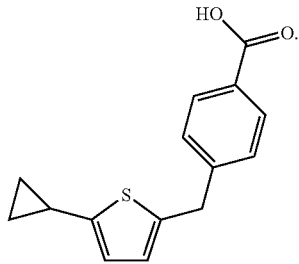 [SMILES: O=C(O)c1ccc(Cc2ccc(C3CC3)s2)cc1]

In certain embodiments, the compound is not

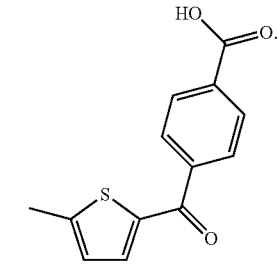 [SMILES: Cc1ccc(C(=O)c2ccc(C(=O)O)cc2)s1]

In certain embodiments, the compound is not

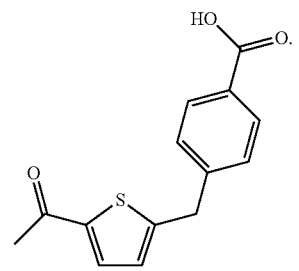 [SMILES: CC(=O)c1ccc(Cc2ccc(C(=O)O)cc2)s1]

In certain embodiments, the compound is not

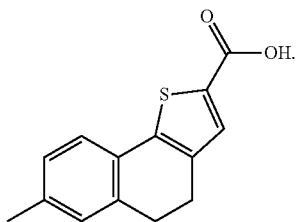 [SMILES: Cc1ccc2c(c1)CCc1cc(C(=O)O)sc1-2]

In certain embodiments, the compound is not

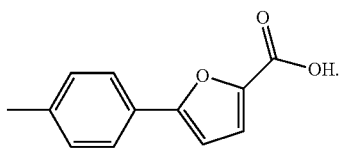

In certain embodiments, the compound inhibits depurination activity of the RIP. In certain embodiments, the RIP is ricin. In certain embodiments, the rip is Shiga toxin 2a (Stx2a). In certain embodiments, the compound inhibits interaction of the RIP with a ribosome. In certain embodiments, the compound inhibits interaction of active A chain (RTA) of the RIP with a ribosome. In certain embodiments, the compound binds to the ribosome binding site of the RTA.

In certain embodiments, the compound binds to the ribosome binding site of RTA with dissociation constant ranging from about 0.1 μM to about 300 μM. In certain embodiments, the compound binds to the ribosome binding site of RTA with dissociation constant of about 0.1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 μM.

In certain embodiments, the compound inhibits RTA depurination activity with an $IC_{50}$ ranging from about 2 μM to about 150 μM. In certain embodiments, the compound inhibits RTA depurination activity with an $IC_{50}$ of about 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150 μM.

In another aspect, the disclosure provides a composition comprising at least one pharmaceutically acceptable carrier and the compound of the disclosure, or a salt, solvate, stereoisomer, geometric isomer, and/or tautomer thereof.

In certain embodiment, the compound or the composition of the disclosure is formulated for administration by a route selected from the group consisting of oral, parenteral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

In certain embodiments, the composition further comprising at least one additional agent useful for treating, ameliorating, or preventing toxicity caused by RIPs in a subject.

In certain embodiments, the at least one additional agent is selected from the group consisting of immunotherapeutics and vaccines.

The compounds of the disclosure can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In certain embodiments, the compounds of the disclosure may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the disclosure are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Methods

In certain embodiments, the disclosure is a method of treating, ameliorating, or preventing toxicity caused by a ribosome inactivating protein (RIP) in a subject by administering to the subject a therapeutically effective amount of the compound of the disclosure. In certain embodiments, the RIP is ricin. In certain embodiments, the ribosome inactivating protein (RIP) is either a type I or type II RIP.

In certain embodiment, the compound is administered as a therapeutic composition. In certain embodiments, the compound and the compositions are as described elsewhere herein.

In other embodiments, the method further comprises administering to the subject an additional therapeutic agent that treats, ameliorates, or prevents toxicity caused by RIPs in a subject. In certain embodiment, the additional therapeutic agent is as described elsewhere herein.

In certain embodiments, administering the compound of the disclosure to the subject allows for administering a lower dose of the additional therapeutic agent compared to the dose of the additional therapeutic agent alone that is required for achieving similar results in treating, ameliorating, or preventing toxicity caused by RIPs in a subject. For example, in other embodiments, the compound of the disclosure enhances the activity of the additional therapeutic compound, thereby allowing for a lower dose of the additional therapeutic compound to provide the same effect.

In certain embodiments, the compound of the disclosure and the additional therapeutic agent are co-administered to the subject. In other embodiments, the compound of the disclosure and the additional therapeutic agent are co-formulated and co-administered to the subject.

In certain embodiments, the subject is a mammal. In other embodiments, the mammal is a human.

Administration/Dosage/Formulations

The regimen of administration may affect what constitutes an effective amount. The therapeutic formulations can be administered to the subject either prior to or after the onset of toxicity caused by RIP. Further, several divided dosages, as well as staggered dosages can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

Administration of the compositions of the present disclosure to a patient, preferably a mammal, more preferably a human, can be carried out using known procedures, at dosages and for periods of time effective to treat, ameliorate, or prevent toxicity caused by RIP. An effective amount of the therapeutic compound necessary to achieve a therapeutic effect may vary according to factors such as the state of the disease or disorder in the patient; the age, sex, and weight of the patient; and the ability of the therapeutic compound to treat, ameliorate, or prevent toxicity caused by RIP. Dosage regimens can be adjusted to provide the optimum therapeutic response. For example, several divided doses can be administered daily or the dose can be proportionally reduced as indicated by the exigencies of the therapeutic situation. A non-limiting example of an effective dose range for a therapeutic compound of the disclosure is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this disclosure can be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of heart failure in a patient.

In certain embodiments, the compositions of the disclosure are formulated using one or more pharmaceutically acceptable excipients or carriers. In certain embodiments, the pharmaceutical compositions of the disclosure comprise a therapeutically effective amount of a compound of the disclosure and a pharmaceutically acceptable carrier.

The carrier can be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the disclosure are administered to the patient in dosages that range from one to five times per day or more. In other embodiments, the compositions of the disclosure are administered to the patient in range of dosages that include, but are not limited to, once every day, every two, days, every three days to once a week, and once every two weeks. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration can be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of toxicity caused by RIP.

Formulations can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the disclosure include oral, nasal, rectal, intravaginal, parenteral, buccal, sublingual or topical. The compounds for use in the disclosure can be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, suppositories, or capsules, caplets and gelcaps. The compositions intended for oral use can be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets can be uncoated or they can be coated by known techniques for elegance or to delay the release of the active ingredients. Formulations for oral use may also be presented as hard gelatin capsules wherein the active ingredient is mixed with an inert diluent.

Parenteral Administration

For parenteral administration, the compounds of the disclosure can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present disclosure can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material which provides sustained release properties to the compounds. As such, the compounds for use the method of the disclosure can be administered in the form of microparticles, for example, by injection or in the form of wafers or discs by implantation.

In certain embodiments of the disclosure, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of heart failure in the patient being treated. The skilled artisan is able to determine appropriate dosages depending on these and other factors.

A suitable dose of a compound of the present disclosure can be in the range of from about 0.01 mg to about 5,000 mg per day, such as from about 0.1 mg to about 1,000 mg, for example, from about 1 mg to about 500 mg, such as about 5 mg to about 250 mg per day. The dose can be administered in a single dosage or in multiple dosages, for example from 1 to 4 or more times per day. When multiple dosages are used, the amount of each dosage can be the same or different. For example, a dose of 1 mg per day can be administered as two 0.5 mg doses, with about a 12-hour interval between doses.

It is understood that the amount of compound dosed per day can be administered, in non-limiting examples, every day, every other day, every 2 days, every 3 days, every 4 days, or every 5 days. For example, with every other day administration, a 5 mg per day dose can be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the disclosure can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

The disclosures of each and every patent, patent application, and publication cited herein are hereby incorporated herein by reference in their entirety. While this disclosure has been disclosed with reference to specific embodiments, it is apparent that other embodiments and variations of this disclosure can be devised by others skilled in the art without departing from the true spirit and scope of the disclosure. The appended claims are intended to be construed to include all such embodiments and equivalent variations.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

Example 1: Fragment-Based Lead Discovery to Identify Fragments that Bind to the Critical Pockets of RTA and Inhibit its Depurination Activity and Toxicity It is shown here that the simultaneous mutation of at least two arginines (R193A/R235A) at the interface of RTB (FIG.

1) inhibits RTA-ribosome interaction, and reduces the activity and cytotoxicity of RTA in yeast and in mammalian cells. To identify the key interacting arginines at the RTA/RTB interface, each arginine was mutated at the interface shown in FIG. 1 and the effect of these mutations on ribosome binding, depurination activity and toxicity was examined. The R235A mutation reduced toxicity and depurination more than the other alanine substitutions, indicating that R235 is more critical than the other arginines. WT RTA and each Arg mutant were expressed in *E. coli*. Purified Arg mutants depurinated yeast RNA and a stem loop mimic of the SRL (A-10) at a similar catalytic rate as WT RTA, indicating that they folded properly in *E. coli* and retained full catalytic activity. However, their activity on ribosomes was reduced. The R235A mutant showed the greatest reduction in activity on ribosomes and bound yeast ribosomes at a lower level compared with WT RTA and the other arginine mutants.

The X-ray crystal structure of the P11 peptide [SDDDMGFGLFD] (SEQ ID NO: 1) corresponding to the conserved last 11 residues of P-proteins of the ribosomal stalk in a complex with trichosanthin (TCS), a single chain RIP, is available (PDB ID: 2JDL). The complex of RTA (PDB ID: 1RTC) with P11 was modeled using the P11-TCS complex as a template and identified a pocket lined by hydrophobic residues Y183, L207, L232, F240, V242, I247 and I251 in close proximity of the arginine residues on RTA (FIG. 1 pink). Hydrophobic residues were systematically mutated to alanine and expressed in yeast from the GAL1 promoter. L232A mutation led to the greatest reduction in depurination activity and toxicity. To determine if toxicity and depurination activity can be reduced further, L232A with R235A were combined. Yeast expressing R235A/L232A was able to grow on galactose containing media at a similar level as yeast harboring the vector, indicating that it was not toxic (FIG. 2A). Depurination activity of L232A/R235A was reduced by 98% relative to WT RTA (FIG. 2B).

It was found that Leu232, Tyr183 and Phe240 all contribute cumulatively to toxicity, with Leu232 being the most significant. A quadruple mutant, Y183A/L232A/R235A/F240A, which combined mutations in critical hydrophobic residues with the R235A mutation completely abolished inhibition of protein synthesis and depurination activity of RTA in mammalian cells. These results indicated that electrostatic and hydrophobic interactions with the P stalk are both required for full biological activity of RTA. The ribosome interaction surface of RTA is formed by arginines in combination with the hydrophobic pocket and identified Arg235, Leu232, tyr183 and Phe240 as the key interacting residues at the ribosome binding site.

Example 2: Binding Level and Affinity Screen of the Fragment Library Against RTA The Ro3 core library obtained from Maybridge (Waltham, MA, USA) contains 1000 fragments, representing the diversity of their 2500 fragment library. A clean screen was performed by GE Life Sciences to remove fragments that show persistent binding and behave promiscuously.

N-terminal 6×-His tagged RTA was obtained from Bireources (Manassas, VA, USA). Untagged RTA was purified by Nexomics (Nexomics Biosciences, New Brunswick, NJ, USA).

A Biacore T-200 (GE Healthcare Life Sciences, Marlborough, Massachusetts, USA) was used for screening 1000 fragments from the Maybridge Ro3 core library and for the affinity measurements. The 6×-His-tagged RTA was immobilized on a carboxymethyl dextran (CM5) chip to around 6000 RU using the amine coupling kit (GE Healthcare). The reference surface was activated and blocked in the same way as the active surface without RTA. The running buffer was PBS-P (20 mM phosphate, 2.7 mM KCl, 137 mM NaCl, and 0.05% surfactant P20, pH 7.4) with 2% DMSO for both screens. For the Binding Level Screen, the fragments were passed over both reference and RTA surfaces in phosphate buffer (PBS-P) with 2% DMSO at a 200 μM concentration, and binding levels and sensorgram shapes were analyzed using Biacore T2000 Evaluation Software 3.0. Solvent correction against DMSO was run in Binding Level Screen and Affinity Screen.

One thousand fragments from the Maybridge Ro3 core library, which has been prescreened for promiscuous binders using Biacore instruments with different chips, were screened against RTA using Biacore T200 in a binding level screen to identify fragments that bind to RTA. Fragments were passed over both reference and RTA surfaces at a single concentration of 200 μM, and binding levels and sensorgram shapes were analyzed. Since there are no known small molecules that bind at the ribosome binding site of RTA, an 11-mer peptide (P11) mimicking the last 11 amino acids of P proteins (molecular weight 1218.25 Da) was used as a positive control, and myoinositol, which does not bind to the chip surface or RTA, has a high solubility, and has a similar molecular weight as the fragments, was used as a negative control (FIG. 3). Due to the low affinity of P11 (80 μM in this buffer) and limited solubility, a concentration of 200 μM was used. Even at this concentration, the surface activity for P11 binding decreased gradually. The PT peptide (SEQ ID NO: 2), which was reported to bind to the active site of RTA, showed the opposite behavior, with a gradual increase of binding activity from an initial very low level. PT did not bind when RTA was freshly immobilized, but did show binding as the binding of P11 decreased, indicating that PT can bind to partially deactivated RTA. Both P11 and PT were used to monitor the surface activity, which is critical for picking reliable binders because, once the surface lost activity, it became sticky and generated false positives. Adenine was used as a positive control for the active site of RTA.

Sample results from the screening of the 13 plates have been provided (FIG. 11). The binding level of each fragment and control was solvent corrected against DMSO, normalized for molecular weight, and shown as the relative response compared to adenine. The binding level of P11 decreased slightly with the cycle time, indicating that RTA gradually lost binding activity to P11. The binding level of adenine was relatively stable during the screen. Promising binders were selected on the basis of the binding strength as well as binding behavior by analyzed sensorgram shape. The fragments with binding levels higher than 80 response units were analyzed manually for sensorgram shape. The fragments that showed square sensorgrams due to fast on and off rates (Fragment A) were picked as good binders for further testing (FIG. 11). The fragments with sloped sensorgrams indicated super stoichiometric sticky binders (Fragment B), which were not tested further (FIG. 11).

Seventy-nine fragments were selected from the binding level screen for the affinity screen. The 79 fragments were run at five different concentrations from 65.2 to 1000 μM to verify binding and to determine the equilibrium dissociation constant ($K_D$). The binding level data up to 500 μM was used in the fitting to avoid the effect of aggregation or sticky fragments. The $K_D$ values were obtained by fitting the binding levels at steady state, since the kinetic rate constants could not be resolved due to fast on and fast off binding. The binders were ranked from high to low affinity. Three out of 79 fragments either did not show dose-dependent binding (two fragments) or showed no binding (one fragment), indicating that the result of the single dose screening was reliable. Some fragments showed gradually saturated fitting curves and maximal binding levels with relatively low $K_D$, indicating relatively few binding sites (FIGS. 4A-4F and FIGS. 5A-5F). Most of the fragments showed a linear increase in the binding level with increasing fragment concentration and projected very high maximal binding, indicating multiple binding sites, aggregation, or both (FIGS. 4G-4P and FIGS. 5G-5P).

Example 3: Inhibition of the Depurination Activity of RTA by the Fragment Inhibitors Depurination inhibitory activity of the fragments was determined by qRT-PCR at 500, 200, and 100 μM using both yeast and rat liver ribosomes. Depurination reaction buffer contained 10 mM Tris-HCl, pH 7.4, 60 mM KCl, 10 mM $MgCl_2$, and 0.5% DMSO. RTA was used at 1.0 and 0.2 nM for yeast and rat liver ribosomes, respectively. RTA and fragments were first preincubated at room temperature for 5 min followed by the addition of ribosomes (50 nM) to start the reaction. The reaction was incubated at room temperature for 5 min. 100 μL of 2× extraction buffer (240 mM NaCl, 50 mM Tris-HCl, pH 8.8, 20 mM EDTA, 2% SDS) was added to stop the reaction. RNA was extracted using phenol/chloroform, precipitated with ethanol, and dissolved in 30 μL of RNase-free water. The depurination level was determined using qRT-PCR. The reaction mixture without RTA was used as no depurination control (0%), and the reaction mixture with RTA but without the fragment was used as the 100% depurination control. The data were fitted to the Michaelis-Menten equation using Origin (OriginLab, Northampton, Massachusetts, USA).

The $IC_{50}$ value was determined for each fragment by qRT-PCR by measuring the percent inhibition at different fragment concentrations. RTA (1 nM) and fragments were preincubated for 5 min at room temperature before the addition of yeast ribosomes (50 nM). The reaction was incubated at room temperature for 5 min in the depurination buffer (20 mM Tris-HCl, pH 7.4, 25 mM KCl, 5 mM $MgCl_2$, 0.5% DMSO). Fragment concentrations varied, depending on the inhibitory activity of each fragment. The highest concentrations were 300 μM for CC10501 and 100 μM for CC70601, and BTB13068 was used at 400 μM due to the limited solubility of this fragment. The measurements were repeated 4 to 6 times.

Figure 7:
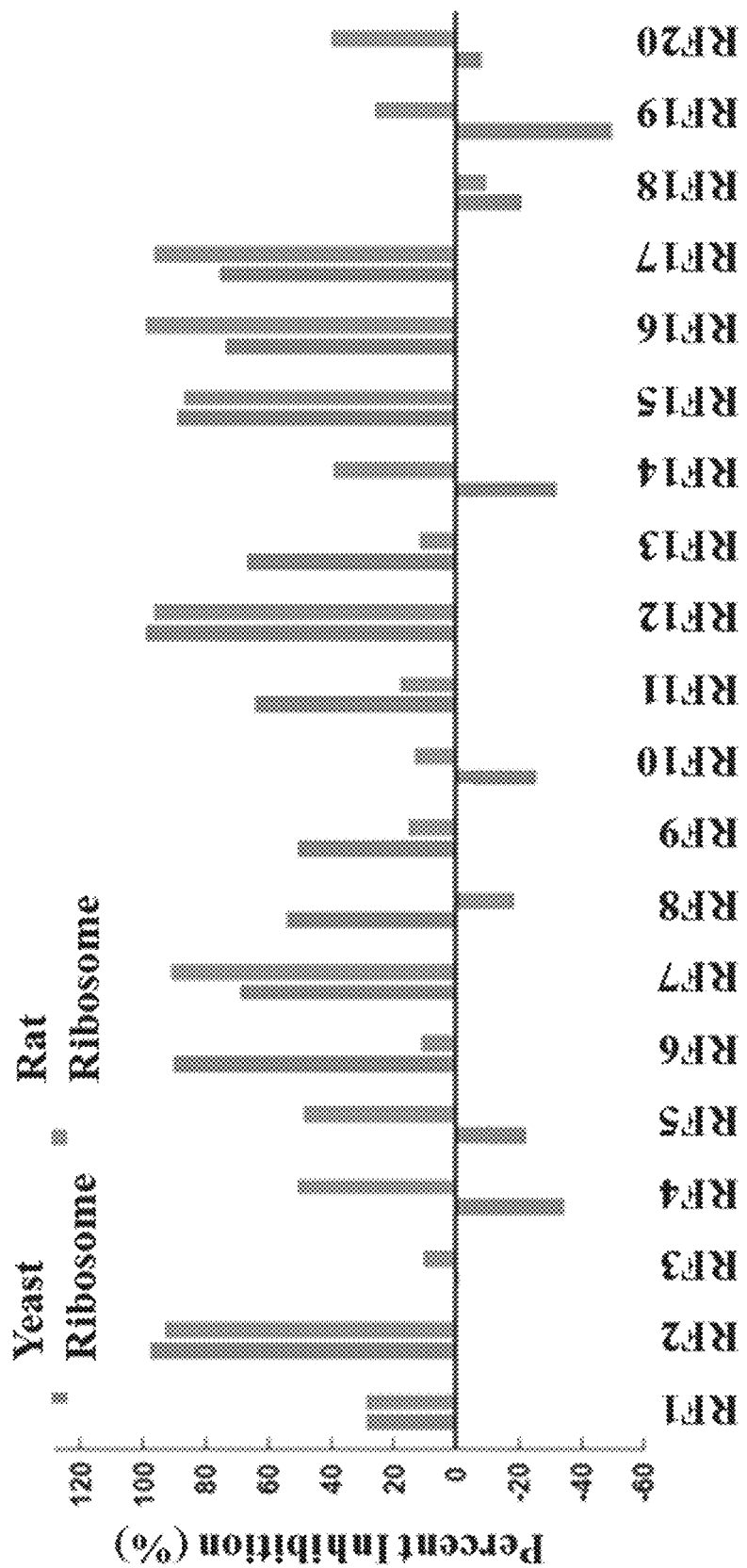
FIG. 7 shows illustrative inhibition of RTA depurination by fragment inhibitors as determined by qRT-PCR, wherein yeast or rat ribosomes were treated with 1.0 or 0.2 nM RTA, respectively, in the presence of each fragment at 100 µM concentration. Five inhibitors were selected for X-ray crystallography.
Figure 8:
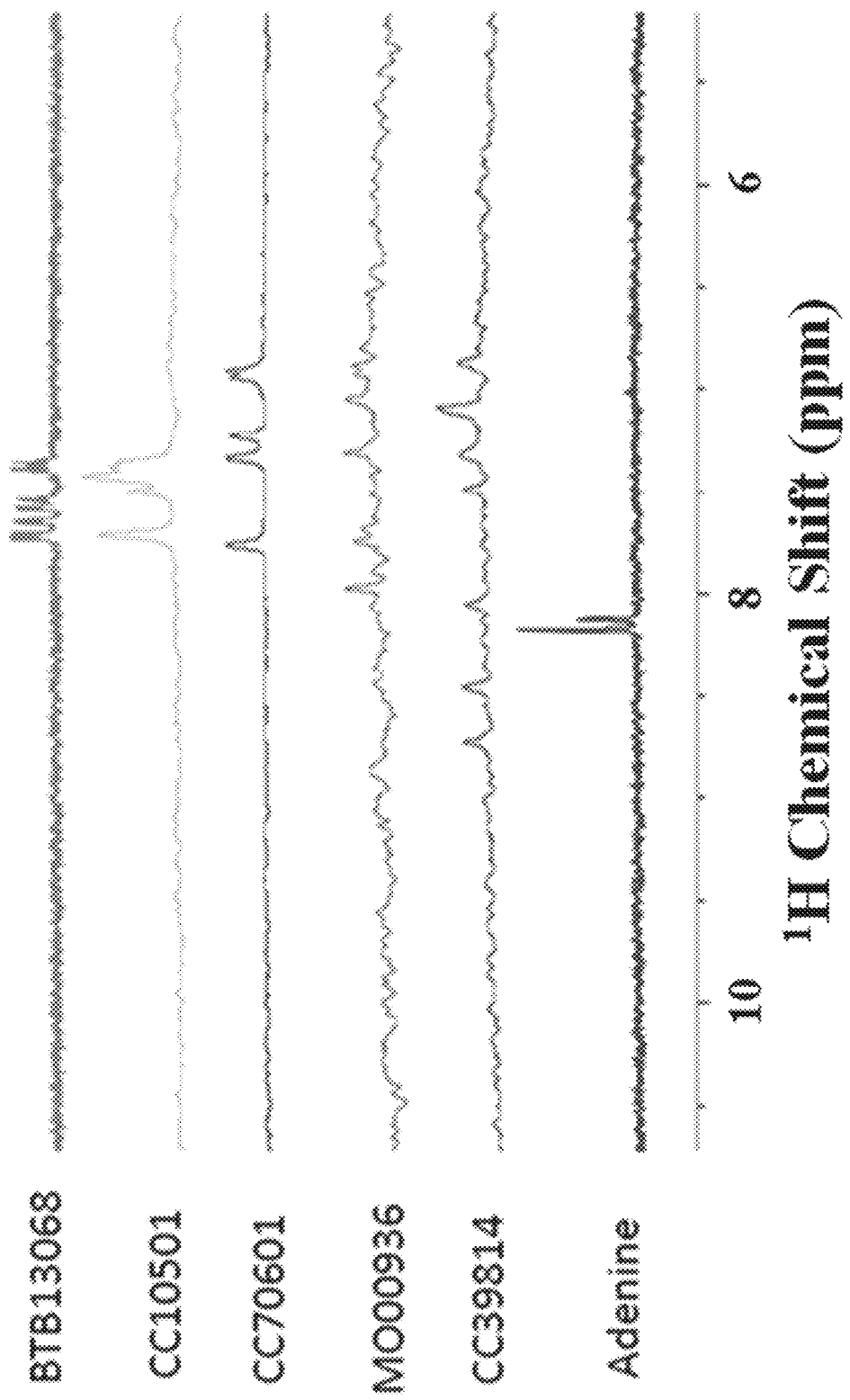
FIG. 8 shows illustrative results from NMR Saturation Transfer Difference (STD) experiments to demonstrate binding of Adenine and 5 Maybridge Fragments to RTA. The protein and ligand concentrations were 20 and 400 µM, respectively. Peaks in these difference spectra arise from magnetization transfer from the RTA protein to the bound ligand.

The ability of the fragments to inhibit the depurination activity of RTA by qRT-PCR using yeast and rat liver ribosomes was examined. The qRT-PCR method measures the depurination level directly after isolation of the depurinated rRNA, and is therefore subject to less interference by fragments than the reporter-based assays. Due to the sensitivity differences between yeast and rat liver ribosomes, different concentrations of RTA were used on the basis of their linear response ranges. The level of depurination inhibition and the affinity data for the 79 fragments are provided (FIG. 6). Several fragments demonstrated good affinity and consistent inhibition of both yeast and rate liver ribosomes, and were accordingly selected for dose-dependent inhibition activity studies (FIG. 7). These results show that these fragments inhibit the activity of RTA better than the positive controls, adenine, and P11. Using ligand-based NMR it is shown that several fragments bind RTA (FIG. 8). Several effective fragments were identified (FIG. 9).

Example 4: X-Ray Crystallography Analysis of Fragments with RTA

The co-crystallization of RTA with three fragments (CC10501, CC70601 and BTB13068) was done using sitting drop vapor diffusion method at 22° C. with varied crystallization conditions (Table 1). 5 mg/ml RTA was mixed with inhibitors in 1:5 molar ratio and incubated for two hours on ice. The incubated samples were screened by using the Microlytic (MCSG1-4) and Hampton (crystal screenHT) crystallization conditions. The crystallization drops were set up in 96-well INTELLI plates (ART ROBBINS) using the CRYSTAL-GRYPHON crystallization robot (ART ROBBINS). Each crystallization drop contained 0.5 μL of enzyme inhibitor mixture and 0.5 μL of well solution. The volume of the well solution was 70 μL. Good quality crystals were obtained in one week.

TABLE 1

| Crystallization and crystal handling | | | | |
|---|---|---|---|---|
| Complex structures | Crystallization conditions | Cryoprotectant solution | Space group | PDB ID |
| RTA + CC10501 | 200 mM Sodium Acetate, 20% (w/v) PEG 3350 | 200 mM Sodium Acetate, 20% (w/v) PEG 3350, 20% ethylene glycol, 1.0 mM CC10501 | $P6_322$ | 6URX |
| RTA + CC70601 | 200 mM Ammonium Iodide, 20% (w/v) PEG 3350 | 200 mM Ammonium Iodide, 20% (w/v) PEG 3350, 20% ethylene glycol, 1.0 mM CC70601 | $P6_322$ | 6URW |
| RTA + BTB13068 | 100 mM Tris pH 7.0, 200 mM Magnesium Chloride, 2.5M Sodium Chloride | 100 mM Tris pH 7.0, 200 mM Magnesium Chloride, 2.5M Sodium Chloride, 20% ethylene glycol, 1.0 mM BTB13068 | $P4_32_12$ | 6URY |

The diffraction data were collected from 1.54 to 2.40 Å resolutions at LRL-CAT beam line (Argonne National Laboratory, Argonne, IL) at 0.97931 Å wavelength. All the diffraction data were processed using iMOSFLM and scaled by AIMLESS program of the CCP4 suite in different space group. The quality of the data was analyzed using the SFCHECK and XTRIAGE. The Matthews coefficient (Vm) calculations was done to calculate the number of monomer molecules present in the unit cells.

The crystal structures of RTA in complex with fragment inhibitors were solved by molecular replacement using PHASER. The chain-A of wild-type RTA (PDB ID: 1RTC) structure was used as the initial phasing model. The model obtained from PHASER was manually adjusted and completed using the graphics program COOT. The structure refinement was performed by REFMAC5 program, using standard protocols for the NCS refinement. The inhibitor molecules were left out from the models in the beginning of the refinement. After building all the water into the structures, inhibitor molecules were fitted in their respective electron densities and the structure of RTA with these fragments were solved.

Figure 10A:
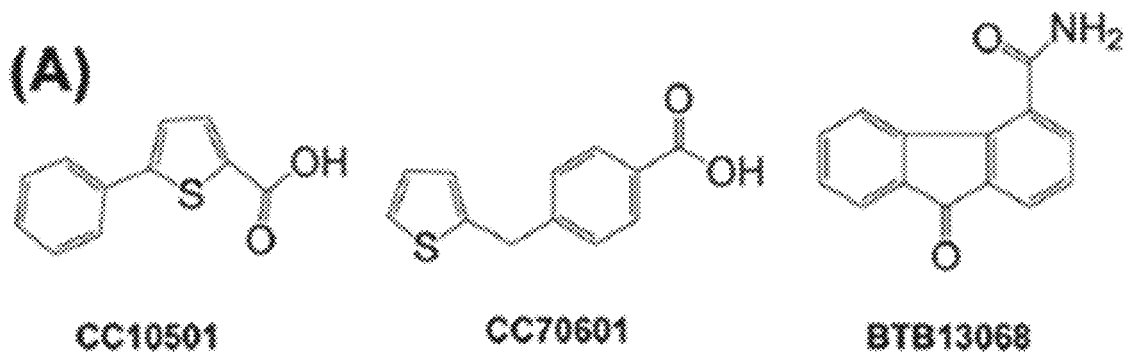
FIGS. 10A-10B provide illustrative inhibitory fragments co-crystallized with RTA.
Figure 10B:
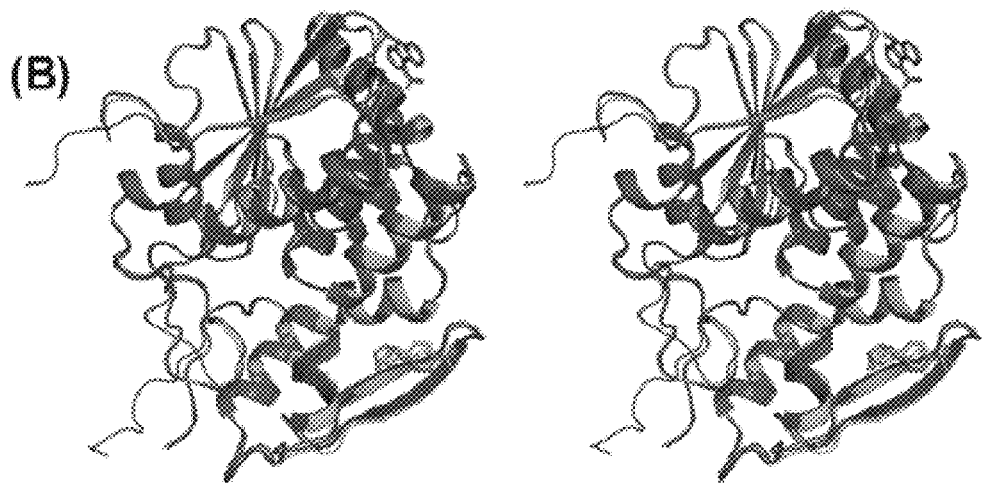
Figure 11:
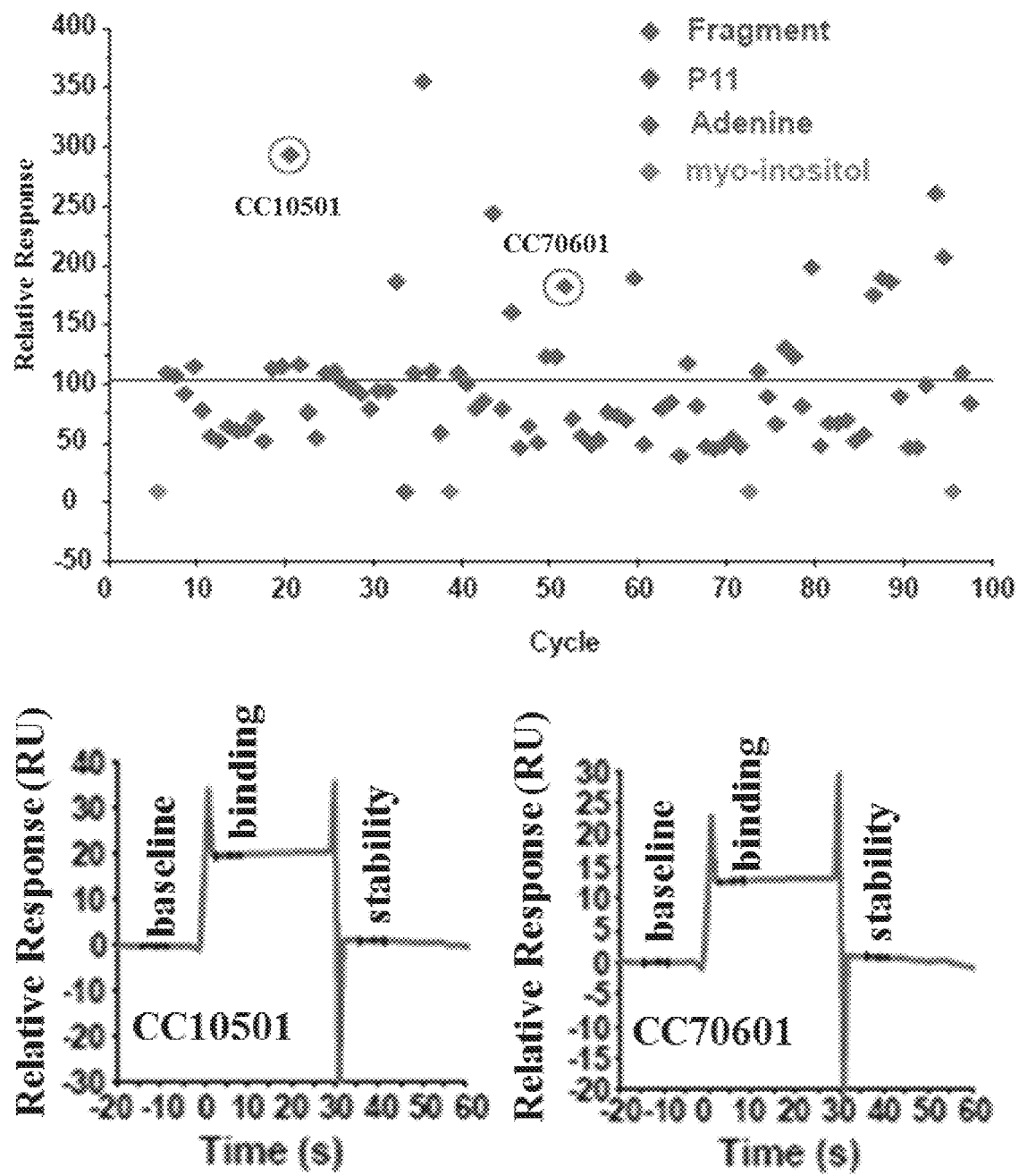
FIG. 11 provides illustrative results of a single-dose screening from one plate. Both positive and negative controls were tested repeatedly in between the screening cycles. DMSO corrections were run at the beginning, after 50 cycles and at the end of the screening cycles. Interaction sensorgrams of CC10501 and CC70601 are also provided.
Figure 12A:
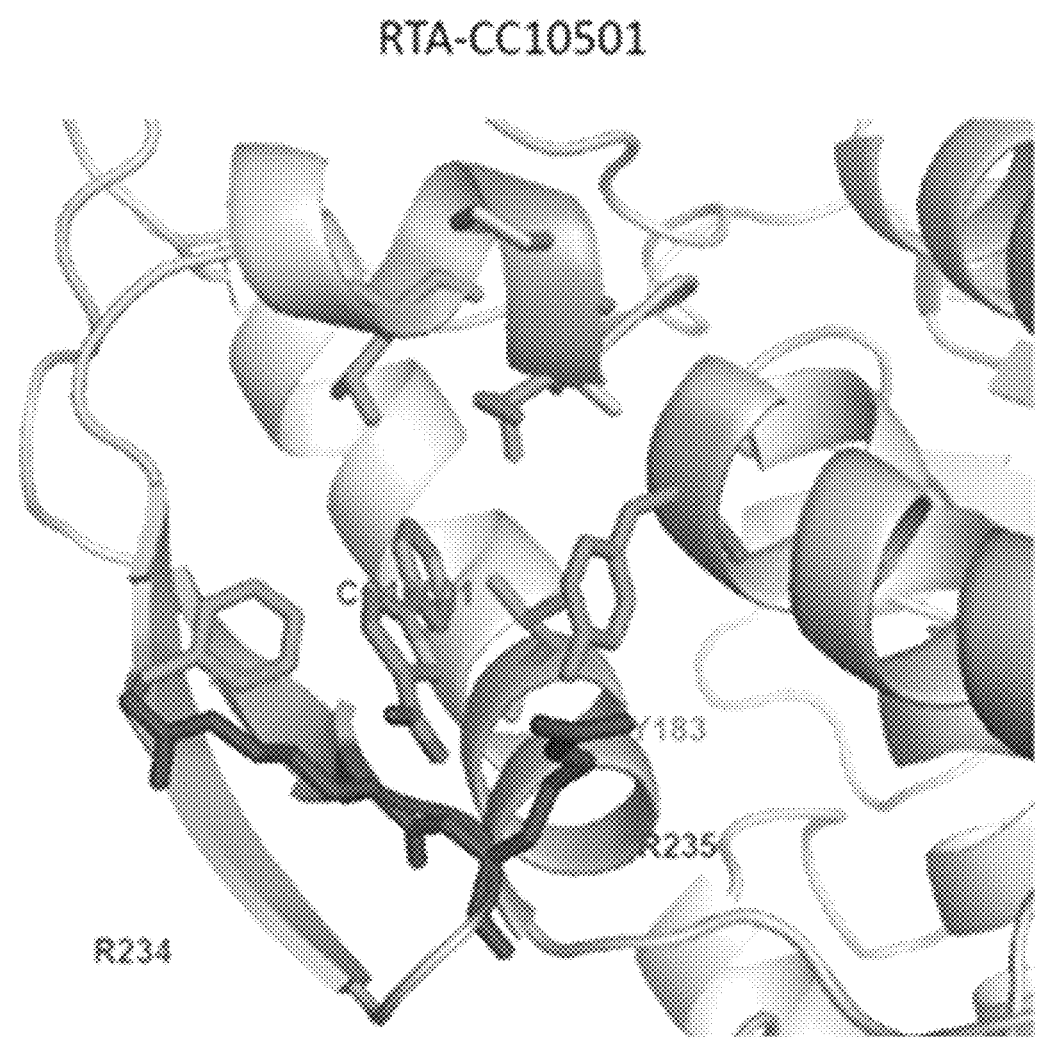
Figure 12B:
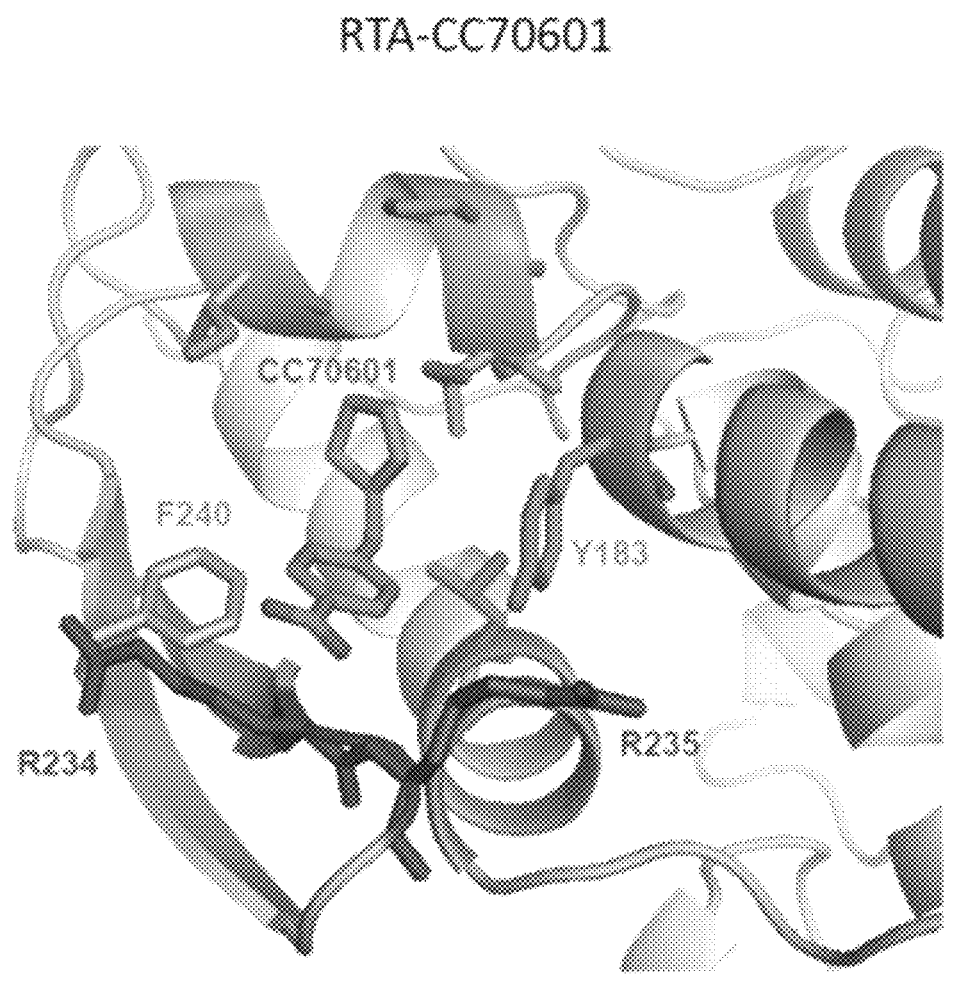
Figure 14:
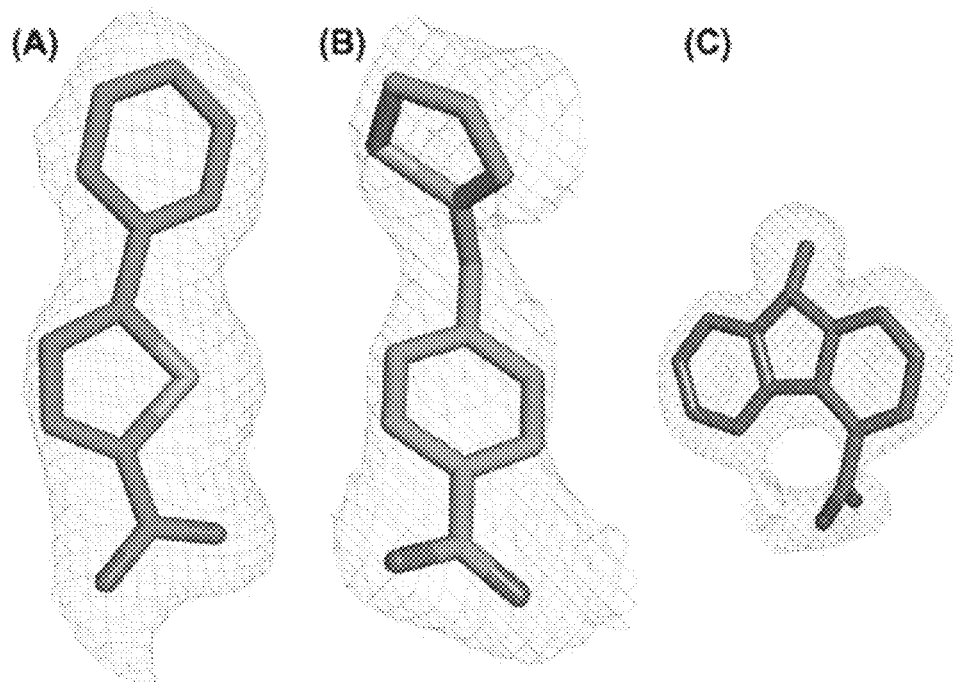
FIG. 14 provides an illustrative omit density map ($F_o$-$F_c$) of CC10501, CC70601, and BTB13068 inhibitors bound to the RTA. The omit map was calculated after 15 cycle of omit refinement by REFMAC6, leaving out the inhibitors. The contour levels are at 2.5σ.

RTA was co-crystallized with CC10501, CC70601, and BTB13068 (FIG. 10A). Both CC10501 and CC70601 showed square shaped sensograms in the binding level screen and bound RTA better than the positive controls (FIG. 11). Molecular replacement using PHASER was done to solve the crystal structures of the complexes (FIG. 10B). X-ray crystallography analysis indicated that CC10501 and CC70601 bind to the ribosome binding site of RTA (FIGS. 12A and 12B). CC10601 and CC70601 complex structures were solved in the P6₃22 space group with a monomer in the asymmetric unit. The BTB13068 complex was solved in space group P4₃212 with a dimer in the asymmetric unit. Except a few N and C terminal residues, the electron density was observed clearly for the entire polypeptide backbone structure. The side chain electron density of a few surface residues was also not observed in the structures (Table 2). All amino acid residues were found to be in the most favored or allowed regions of the Ramachandran plot except for a few residues found in high B-factor loops (FIGS. 13A and 13B). The electron density corresponding to the inhibitors were well resolved in the structure (FIG. 14).

TABLE 2

Missing amino acid side chains in the RTA complex structures.
The letter in parentheses indicates the RTA monomers.

| RTA complex structures | Missing side chain residues |
|---|---|
| RTA + CC10501 | Pro3 (A), Lys4 (A) |
| RTA + CC70601 | Pro3 (A), Lys4 (A), Tyr243 (A) |
| RTA + BTB13068 | Arg196 (A), Gln266 (A), Pro3 (B), Gln5 (B), Pro262 (B) |

Figure 15A:
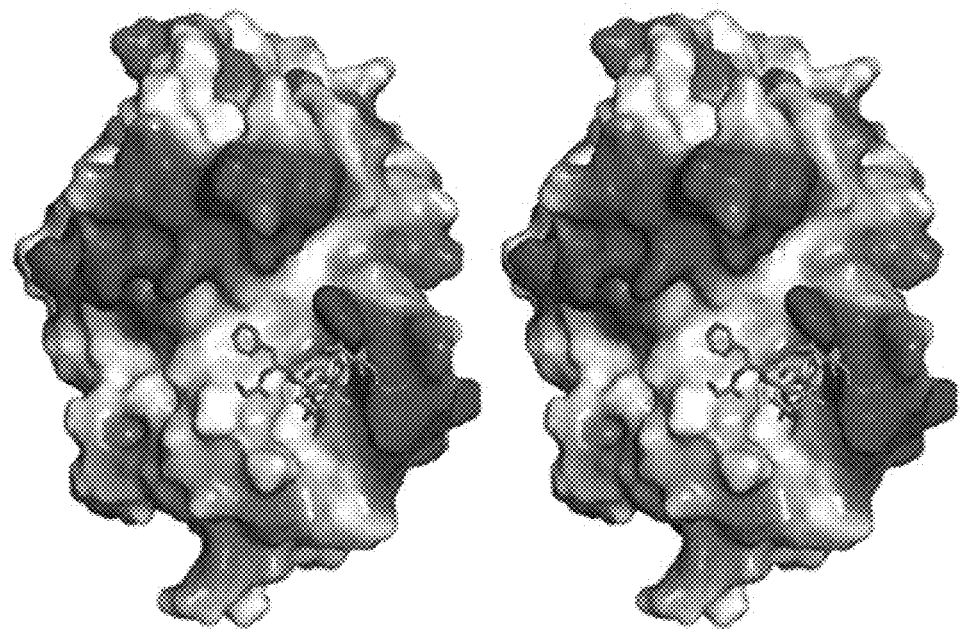
FIGS. 15A-15B show illustrative superposition of the RTA-inhibitor complexes with the P stalk peptide (stereoview).
Figure 15B:
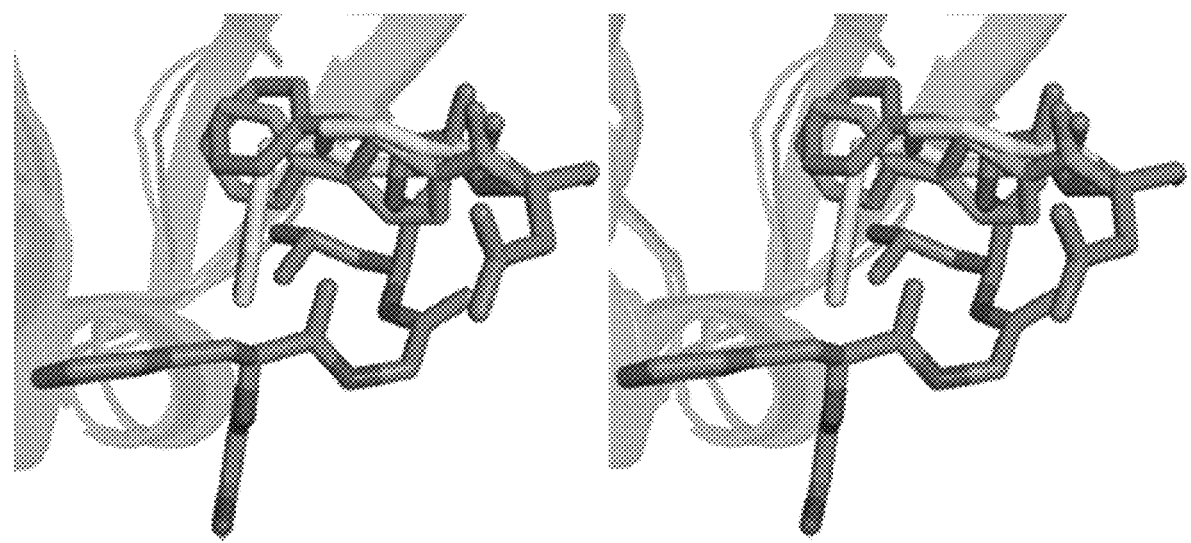
Figure 16A:
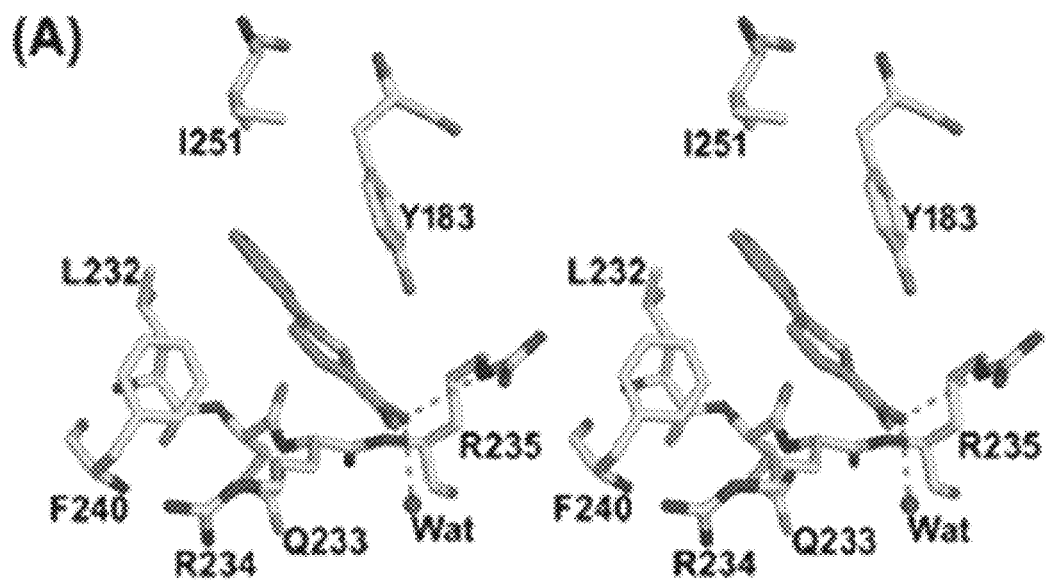
FIGS. 16A-16C provide illustrative binding interactions of RTA in complex with inhibitors (stereoview). Inhibitor complexes of CC10501 (FIG. 16A), CC70601 (FIG. 16B), and BTB13068 (FIG. 16C) are provided. Amino acids interacting with inhibitors from RTA are highlighted. Selected hydrogen bond interactions are shown with orange dotted lines. The RTA residues interacting with inhibitors within 4 Å are highlighted.
Figure 16B:
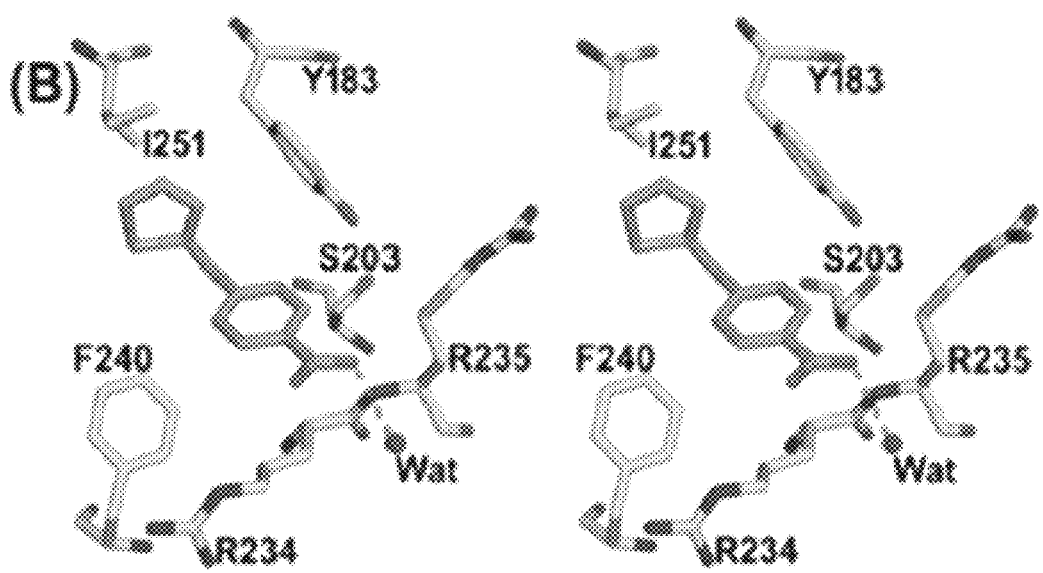
Figure 16C:
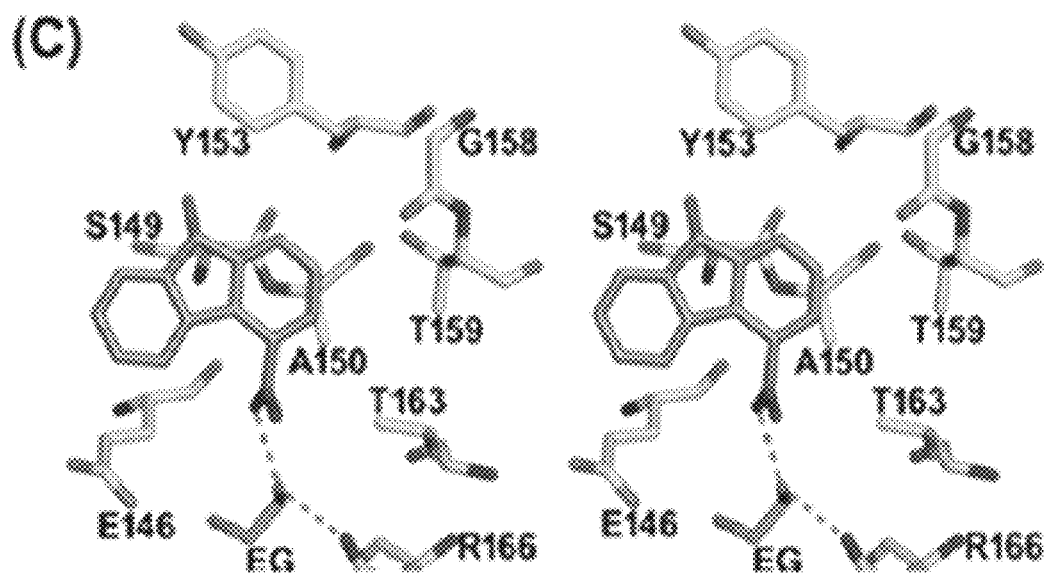
Figure 17:
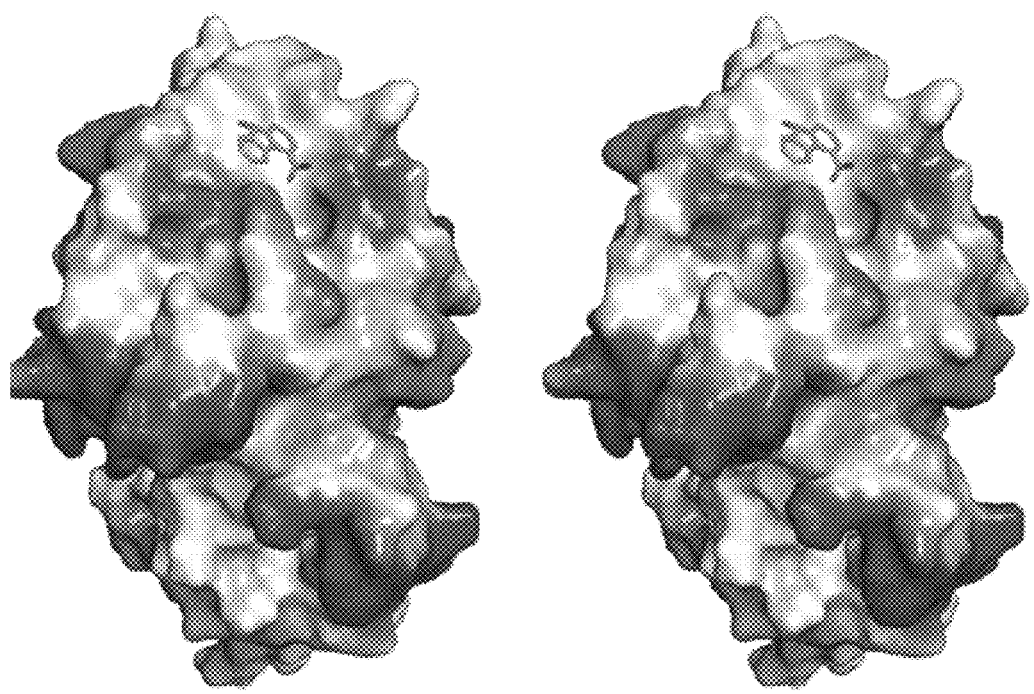
FIG. 17 provides an illustrative electrostatic surface representation (stereoview) of BTB13068 binding in a remote hydrophobic pocket close to helix D4. The binding of BTB13068 is mostly driven by hydrophobic interactions.

The crystal structure of RTA with the C-terminal amino acid sequence of P proteins (SDDDMGFGLFD; PDB ID: 5GU4) established that Phe111 and the penultimate Phe114 residues bind to the hydrophobic pocket of the RTA occupied by the B chain lectin (RTB) in intact ricin. Inhibitors CC10501 and CC70601 bind in the hydrophobic site occupied by Phe114 of the P protein C-termini, thereby precluding the anchoring of RTA to the ribosome (FIGS. 15A-15B). Structural analysis suggests similar binding contacts for CC10501 and CC70601, confirmed by their similar binding constants. CC10501 showed more favorable stacking interactions with the aromatic ring of the inhibitor than CC70601 (FIGS. 16A-16B). BTB13068 binds close to the helix D of the RTA to interact with Glu146, Ser149, Ala150, Try153, Gly158, Thr159, and Thr163, all within 4 Å contacts (FIG. 16C and FIG. 17). The position of the BTB13068 binding is 31 Å away from the P6 hydrophobic pocket and on the surface of RTA. The binding of BTB13068 is unlikely to prevent P protein interaction with RTA and, therefore, without wishing to be bound by theory, may act by preventing conformational changes related to adenine depurination.

Figure 18A:
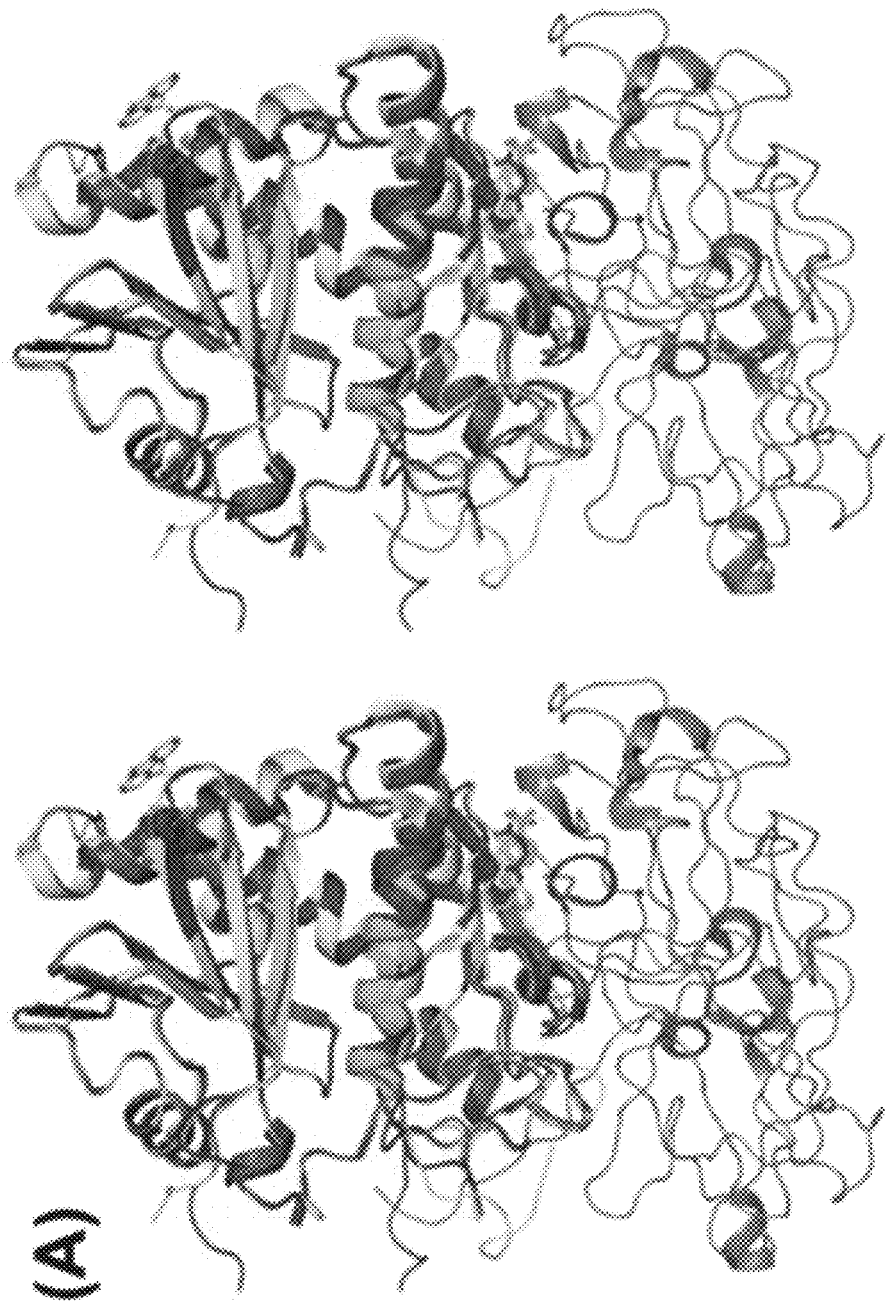
FIGS. 18A-18B show an illustrative superposition of the RTA structure in complex with inhibitors with the RTA-RTB complex.
Figure 18B:
Figure 19A:
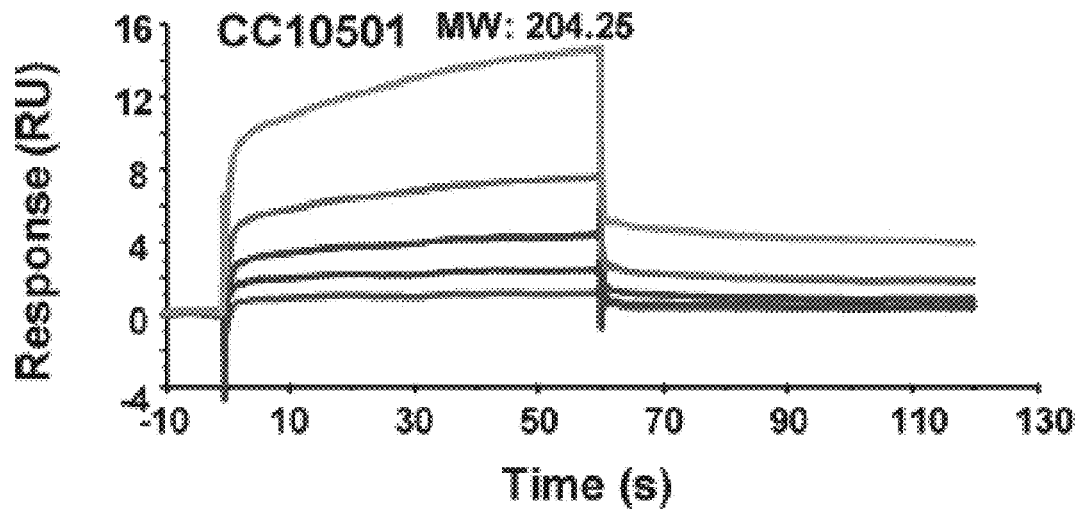
FIGS. 19A-19C show illustrative binding sensorgrams of the three fragments to RTA; CC10501 (FIG. 19A), CC70601 (FIG. 19B), and BTB13068 (FIG. 19C). The fragment concentrations were 12.5, 25, 50, 100, and 200 μM. The binding measurements were repeated five different times using four different chips with three replicates each time.
Figure 19B:
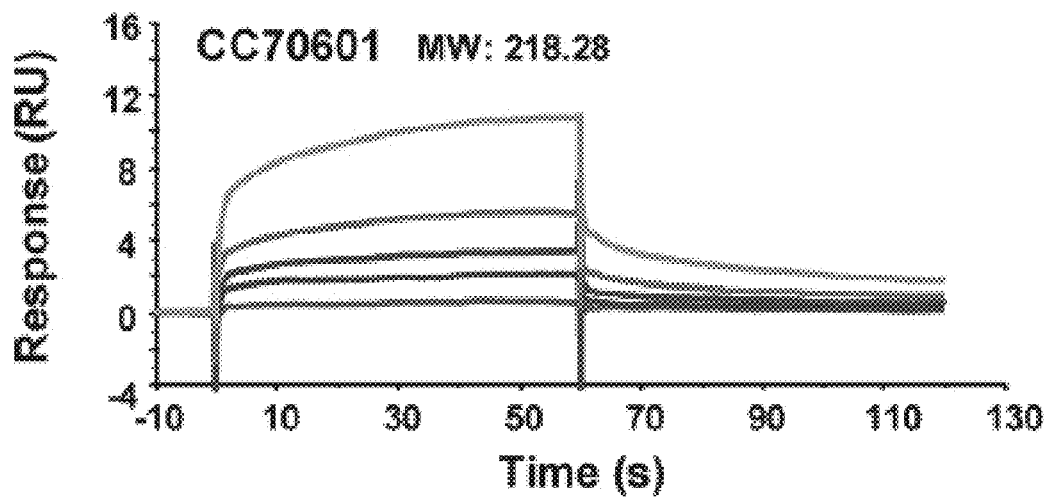
Figure 19C:
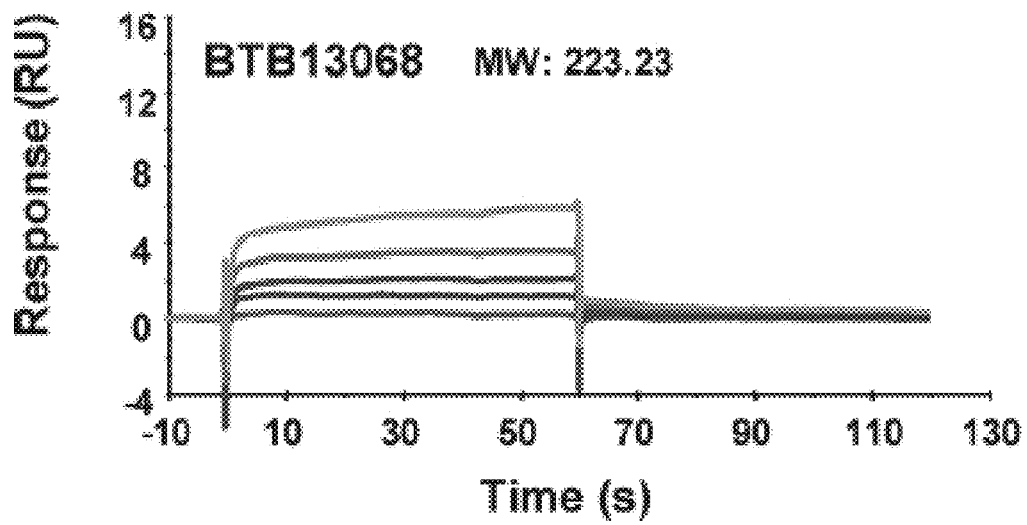
Figure 20A:
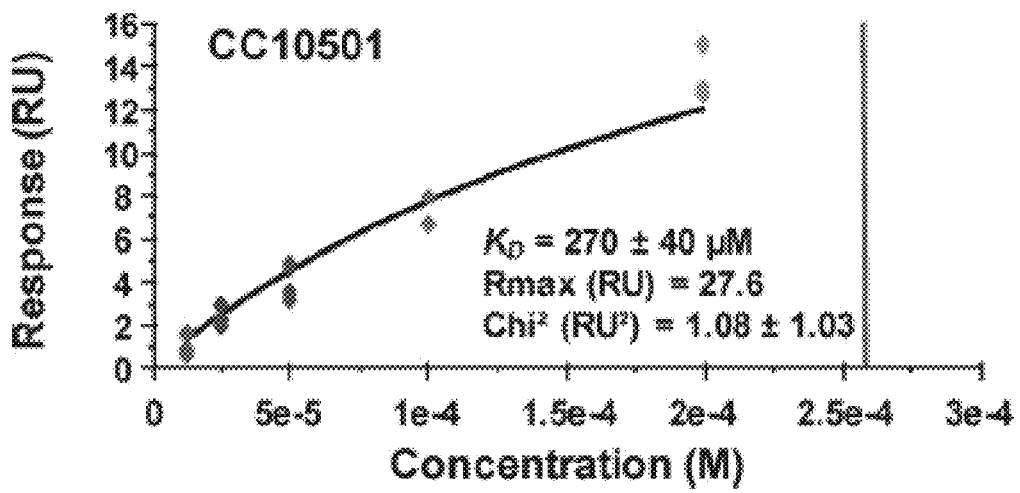
FIGS. 20A-20C show illustrative kinetic fittings resulting of the binding sensorgrams resulting from binding of the three fragments to RTA: CC10501 (FIG. 20A), CC70601 (FIG. 20B), and BTB13068 (FIG. 20C). The $K_D$ values are shown as the mean±standard deviation. The steady state affinity constant $R_{max}$ model with global fitting was used to determine the $K_D$ values for CC10501 and CC70601. The surface activity was calculated on the basis of the binding affinity of P6 was 69%. The steady state affinity model with global fitting was used to determine the $K_D$ value for BTB13068 using the Biacore T200 evaluation software 3.0.
Figure 20B:
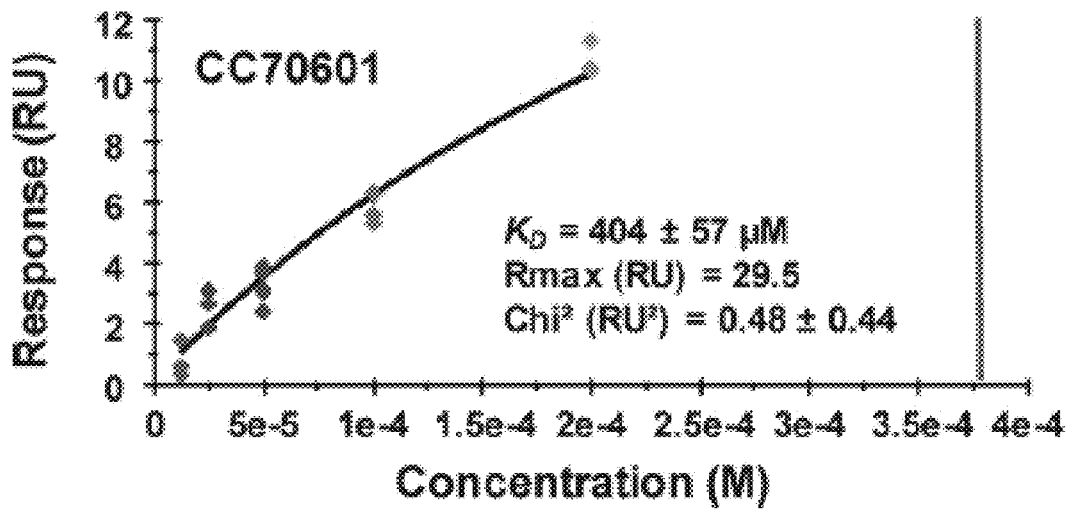
Figure 20C:
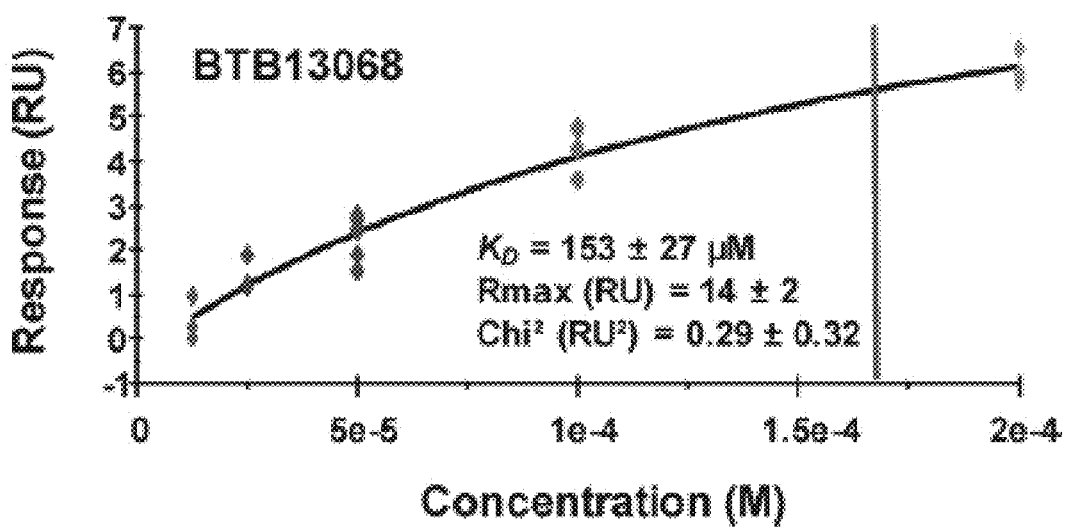

The RTA complex with CC10501 was determined to 1.99 Å resolution. CC10501 is bound in the hydrophobic pocket of RTA where Phe114 of the P protein also binds. In ricin hologoxin, this hydrophobic pocket interacts with Phe262 of RTB (FIGS. 18A-18B). The aromatic ring of CC10501 has π-π stacking with Tyr183 as well as π-T stacking with Phe240 of RTA. Other residues in the hydrophobic interaction with the CC10501 aromatic ring are Leu232 and Ile251. The O1 of the inhibitor is in the hydrogen bond interaction with Water258 (wat258), NE (Arg235), and backbone N (Arg235) (FIG. 16A).

The structure of RTA with CC70601 was solved to 2.40 Å resolution in the space group P6₃22. CC70601 is also bound in the same hydrophobic pocket of RTA as the CC10501 inhibitor. The binding of CC70601 is stabilized primarily by hydrophobic interactions. The aromatic ring of CC70601 is in offset stacking with Tyr183 and Phe240, whereas the thiophene ring of the inhibitor has a hydrophobic interaction with Ile251. The O1 of the inhibitor has a hydrogen bond with wat127 (FIG. 16B).

The structure of BTB13068 with RTA was determined at 1.54 Å resolution in space group P4₃212. There are two monomers of RTA in the asymmetric unit in which BTB130608 is bound between both subunits of RTA. BTB13068 is bound with the 0.5 occupancy at the dimer symmetry interface. One hydrogen bond interaction is observed between O1 of the inhibitor with O1 of an ethylene glycol molecule, also bound in the symmetry interface. The other amino acids, which are within 4 Å of BTB13068, are Glu146, Ser149, Ala150, Try153, Gly158, Thr159, and Thr163 (FIG. 16C). The same residues from the symmetry related monomer are also interacting with BTB13068.

Figure 21A:
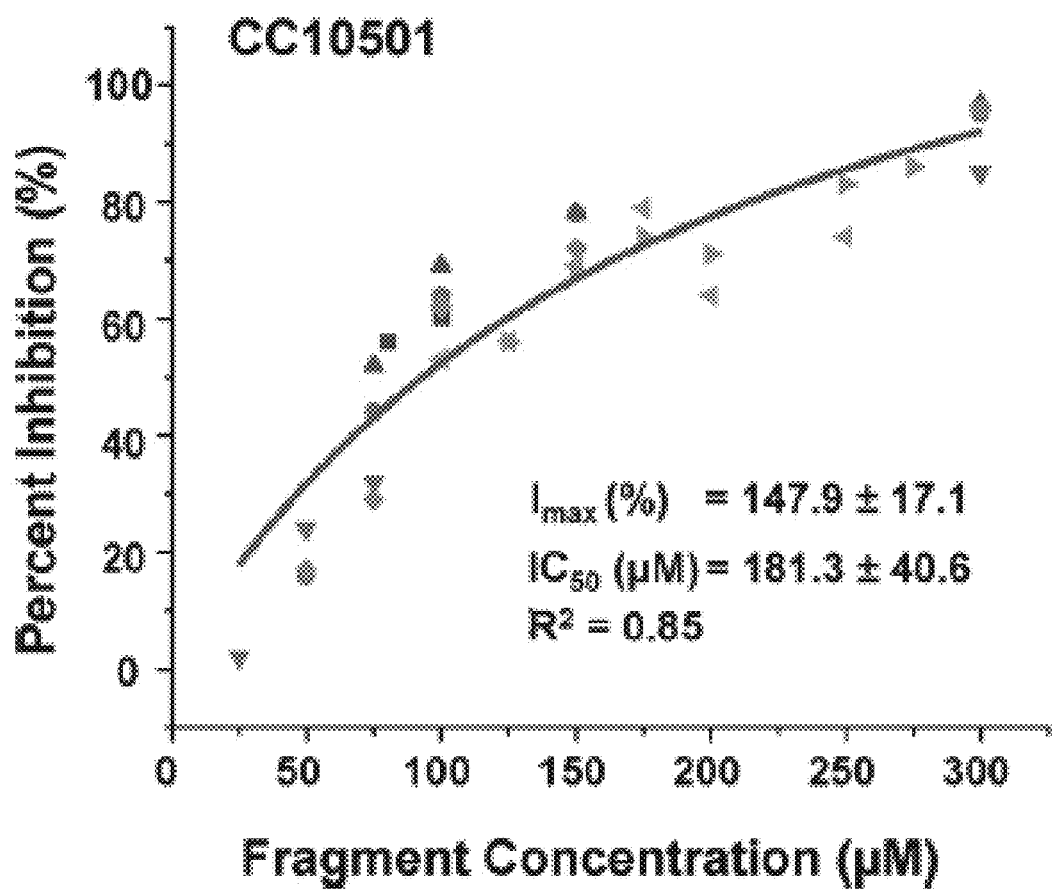
FIGS. 21A-21C provide illustrative 50% inhibitory concentration ($IC_{50}$) of fragments against RTA: CC10501 (FIG. 21A), CC70601 (FIG. 21B), and BTB13068 (FIG. 21C). Different colors indicate different measurements, which we repeated 4 to 6 times. The Michaelis-Menten model was used to fit the inhibition curves using the Origin software.
Figure 21B:
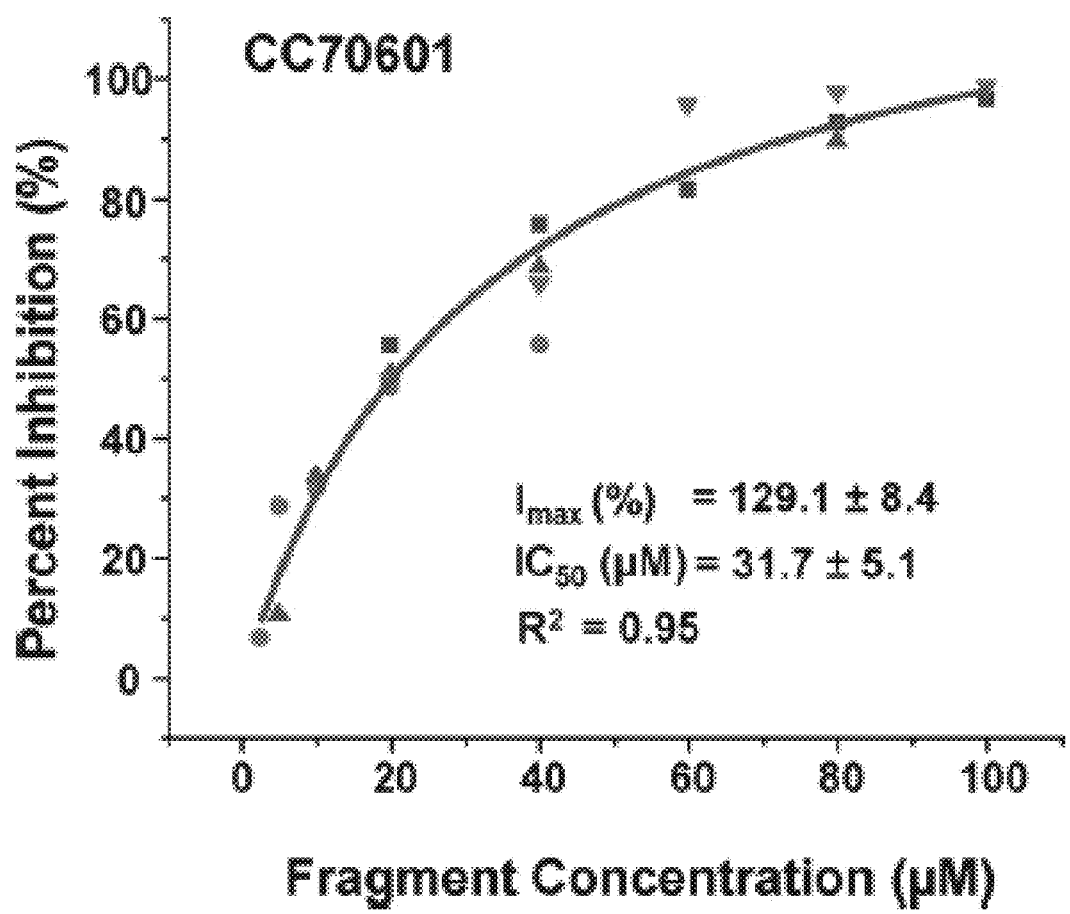
Figure 21C:
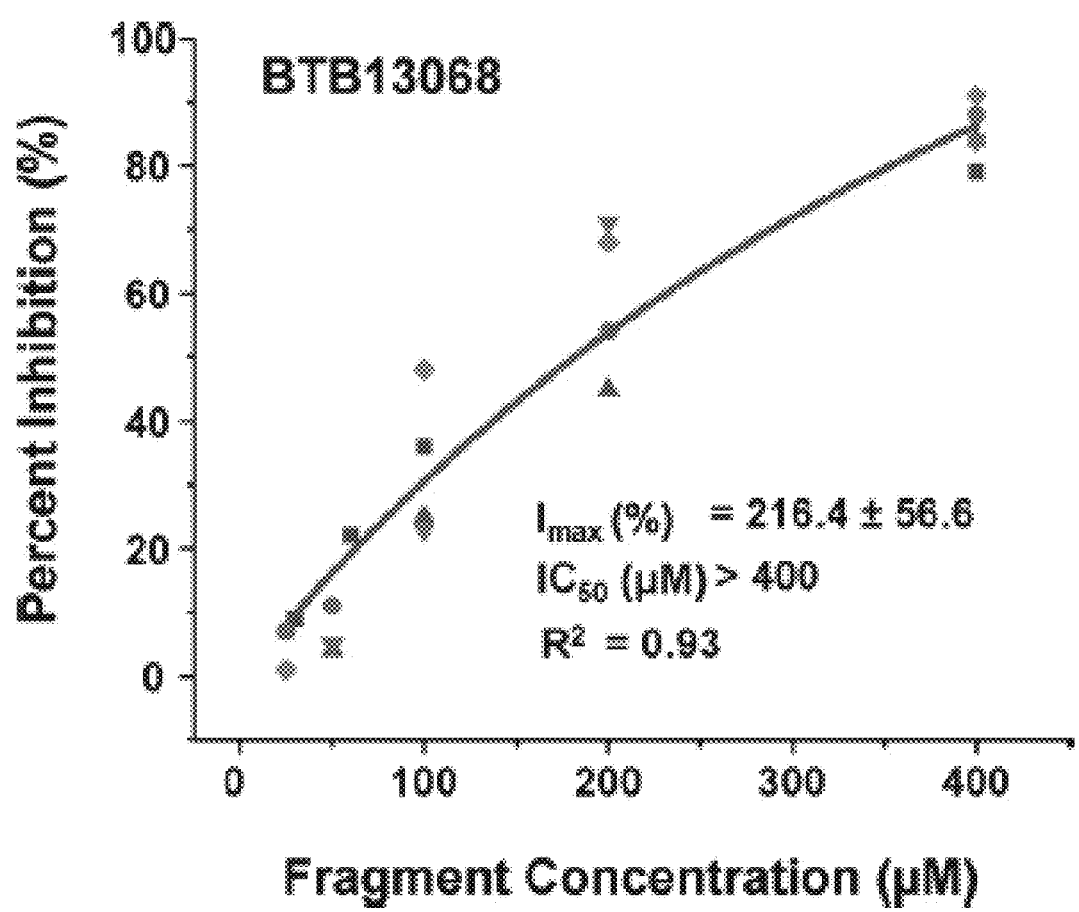
Figure 22:
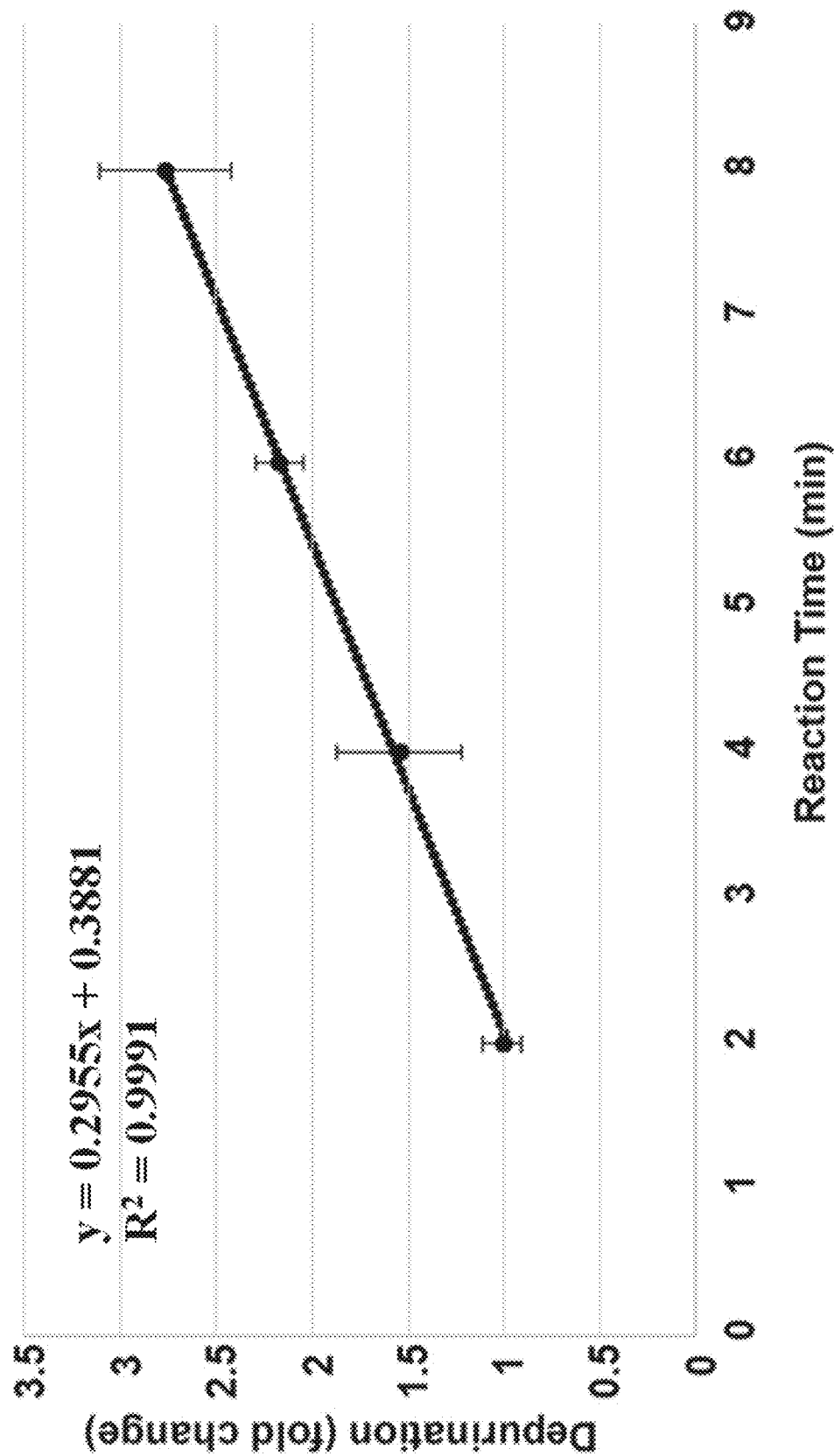
FIG. 22 shows an illustrative time course of depurination under the conditions employed for the 50% inhibitory concentration ($IC_{50}$) experiments with fragments against RTA. The data are expressed as the mean±standard deviation of three to four technical replicates.

Example 5: Affinity ($K_D$) and the $IC_{50}$ of CC10501, CC70601, and BTB13068 Fragments The affinity of the three fragments for RTA was determined using Biacore T200 at 12.5, 25, 50, 100, and 200 μM in triplicate measurements. The results were fitted globally (FIGS. 19A-19C and FIGS. 20A-20C). Due to the lower affinity and propensity to aggregate at higher concentrations, the data for CC10501 and CC70601 were fitted with the "Steady State Affinity Constant $R_{max}$ model" using 69% surface activity calculated on the basis of the binding affinity of the P6 peptide. CC10501 and CC70601 had similar $K_D$ values of 270 and 404 μM, respectively, while BTB13068 had a slightly lower $K_D$ of 150 μM. The 50% inhibitor activity ($IC_{50}$) was determined by qRT-PCR. The data for the percent inhibition at different fragment concentrations for all three fragments were fitted with Michaelis-Menten kinetics using Origin software (FIGS. 21A-21C). The depurination rate was linear over the 8 min time course (FIG. 22). CC70601 gave the best inhibitory activity with an $IC_{50}$ of 32 μM. CC10501 was 5.6-fold weaker with an $IC_{50}$ of 181 μM, and BTB13068 gave the weakest $IC_{50}$, which was greater than 400 μM.

Example 6: Optimization of the Fragments

Figure 23:
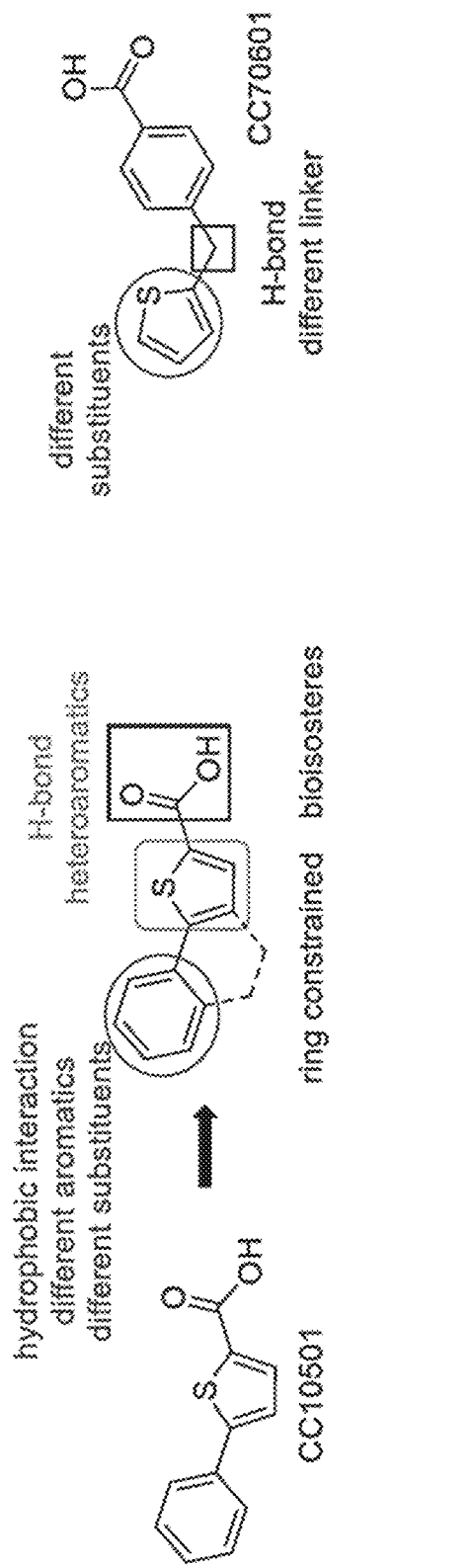
FIG. 23 shows an illustrative summary of the medicinal chemistry efforts towards improvement of CC10501 and CC70601.

CC10501 and CC70601 were identified as lead compounds and served as the basis for the development of compounds with greater affinity (FIG. 23). Informed by the crystal structures of the aforementioned compounds with RTA, more than 180 compounds were designed, obtained, and evaluated.

Figure 24:
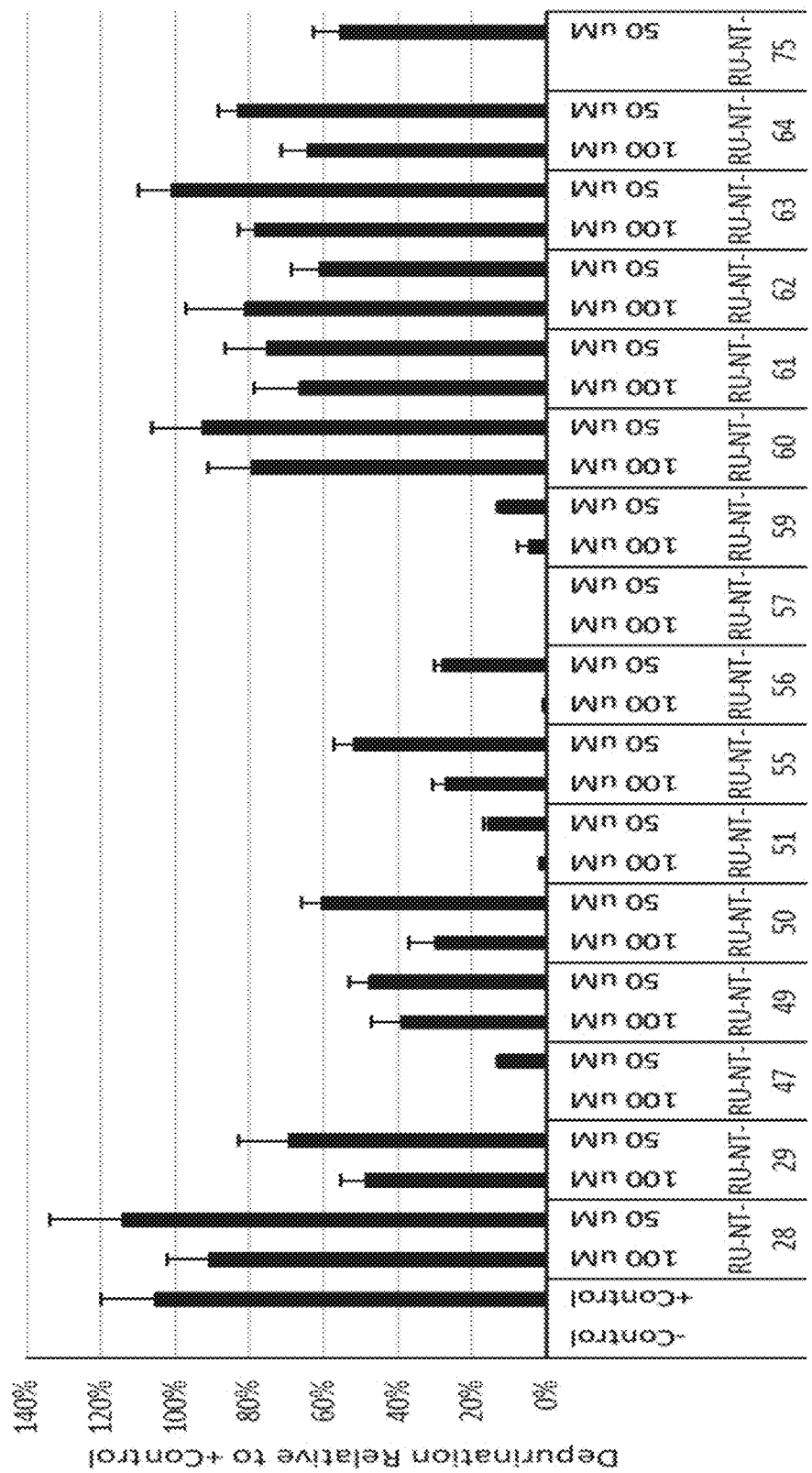
FIG. 24 shows an illustrative inhibition of RTA depurination by fragment inhibitors with inhibitor concentrations of 50 μM and 100 μM, wherein yeast ribosomes were treated with 1.0 nM RTA, as determined by qRT-PCR.
Figure 25A:
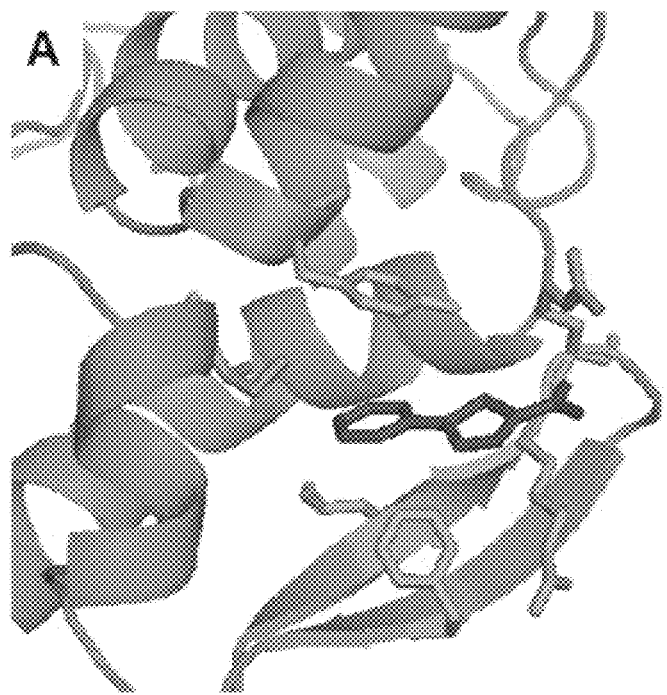
FIGS. 25A-25B provide illustrative binding interactions of RTA in complex with CC10501 (FIG. 25A) and RU-NT-70 (FIG. 25B).
Figure 25B:
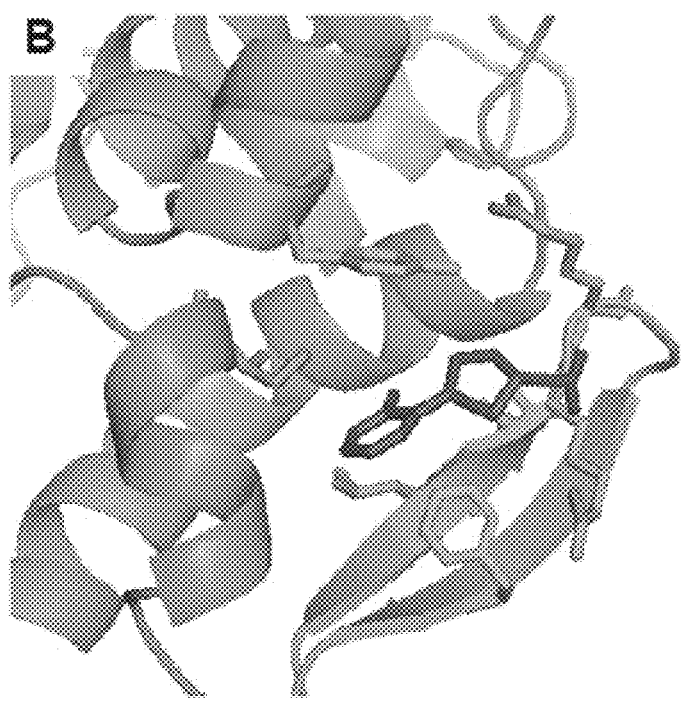

Using CC10501 as a starting point, in certain embodiments bioisosteric groups replacing the carboxylic acid moiety were explored, revealing improved affinity and inhibitory activity of tetrazole functionality. In other embodiments, analogues with strategically placed heteroatoms to engage in hydrogen-bonding were also employed. In yet other embodiments, in order to enhance the hydrophobic interaction, different hydrophobic fragments were incorporated opposite to the position of the carboxylic acid on the thiophene ring. In yet other embodiments, fused tricyclic compounds were explored to improve the steric interaction with the hydrophobic pocket. In yet other embodiments, a variety of substituents including alkyl, cycloalkyl, halo, alkoxy, $CF_3$, phenyl, benzyl, hydroxyl, cyano, acetyl, and alkynyl substituents were incorporated on a phenyl ring. In yet other embodiments, the distance between the thiophene and additional aromatic substituents were varied. Four compounds demonstrated the highest affinity and inhibitory activity (FIG. 24). The x-ray structure of one of such compounds, RU-NT-70, was solved in complex with RTA, demonstrating binding to RTA at the P protein binding pocket in an analogous manner as CC10501 (FIGS. 25A-25B).

TABLE 3

Structure, inhibitory, and binding data for selected analogues against RTA

| Code | MW | Structure | KD (µM) | IC$_{50}$ (µM) | Percent inhibition at 100 µM | Percent inhibition at 50 µM |
|---|---|---|---|---|---|---|
| CC10501 | 204 | 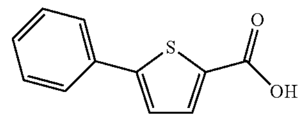 [SMILES: O=C(O)c1ccc(-c2ccccc2)s1] | 270 | — | — | — |
| RU-NT-028 | 204 | 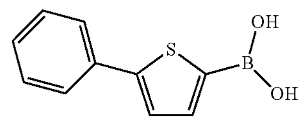 [SMILES: OB(O)c1ccc(-c2ccccc2)s1] | 33 | — | 9 | 0 |
| RU-NT-029 | 228 | 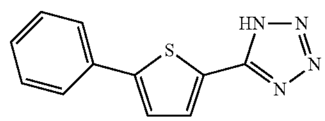 [SMILES: c1ccc(-c2ccc(-c3nnn[nH]3)s2)cc1] | 46 | — | 51 | 31 |
| RU-NT-047 | 246 | 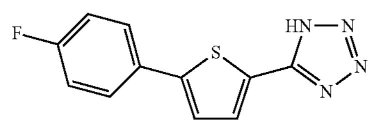 [SMILES: Fc1ccc(-c2ccc(-c3nnn[nH]3)s2)cc1] | 80 | — | 100 | 87 |
| RU-NT-057 | 242 | 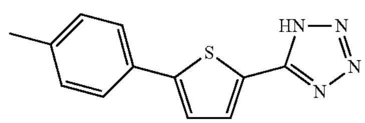 [SMILES: Cc1ccc(-c2ccc(-c3nnn[nH]3)s2)cc1] | 106 | — | 100 | 100 |
| RU-NT-059 | 248 | 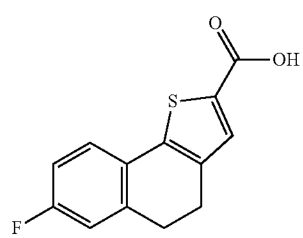 [SMILES: O=C(O)c1cc2c(s1)-c1ccc(F)cc1CC2] | 42 | — | 95 | 88 |
| RU-NT-060 | 230 | 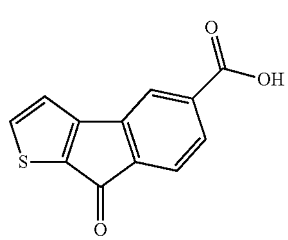 [SMILES: O=C(O)c1ccc2c(c1)-c1ccsc1C2=O] | 73 | — | 21 | 8 |

TABLE 3-continued

Structure, inhibitory, and binding data for selected analogues against RTA

| Code | MW | Structure | KD (µM) | IC$_{50}$ (µM) | Percent inhibition at 100 µM | Percent inhibition at 50 µM |
|---|---|---|---|---|---|---|
| RU-NT-061 | 308 | (7-bromo-4,5-dihydronaphtho[1,2-b]thiophene-2-carboxylic acid) | 94 | — | 34 | 25 |
| RU-NT-062 | 244 | (7-methyl-4,5-dihydronaphtho[1,2-b]thiophene-2-carboxylic acid) | 70 | — | 20

US 12,427,135 B2
TABLE 3-continued
Structure, inhibitory, and binding data for selected analogues against RTA
| Code | MW | Structure | KD (μM) | IC$_{50}$ (μM) | Percent inhibition at 100 μM | Percent inhibition at 50 μM |
|---|---|---|---|---|---|---|
| RU-NT-082 | 254 |  | 209 | |

TABLE 3-continued

Structure, inhibitory, and binding data for selected analogues against RTA

| Code | MW | Structure | KD (μM) | IC$_{50}$ (μM) | Percent inhibition at 100 μM | Percent inhibition at 50 μM |
|---|---|---|---|---|---|---|
| RU-NT-122 | 233 | 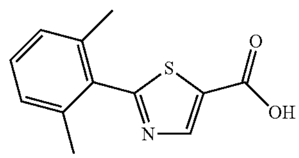 [SMILES: Cc1cccc(C)c1-c1ncc(C(=O)O)s1] | 163 | | | 100 |
| RU-NT-126 | 246 | 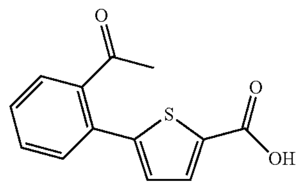 [SMILES: CC(=O)c1ccccc1-c1ccc(C(=O)O)s1] | 93 | | | 99 |
| RU-NT-128 | 256 | 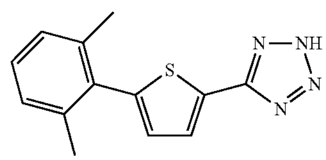 [SMILES: Cc1cccc(C)c1-c1ccc(-c2nn[nH]n2)s1] | 108 | | | 100 |
| RU-NT-131 | 244 | 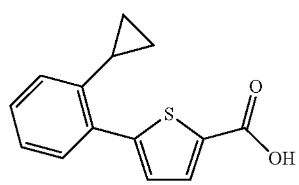 [SMILES: O=C(O)c1ccc(-c2ccccc2C2CC2)s1] | 145 | | | 82 |
| RU-NT-136 | 246 | 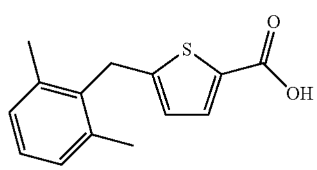 [SMILES: Cc1cccc(C)c1Cc1ccc(C(=O)O)s1] | 72 | 7 | | |
| CC70601 | 218 | 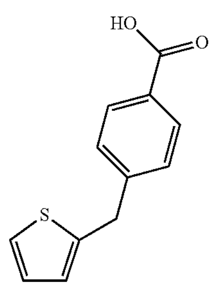 [SMILES: O=C(O)c1ccc(Cc2cccs2)cc1] | 404 | 32 | | |
| RU-NT-036 | 274 | 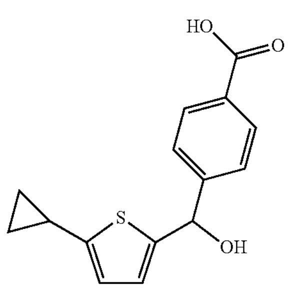 [SMILES: O=C(O)c1ccc(C(O)c2ccc(C3CC3)s2)cc1] | greater | | | similar |

TABLE 3-continued

Structure, inhibitory, and binding data for selected analogues against RTA

| Code | MW | Structure | KD (μM) | IC$_{50}$ (μM) | Percent inhibition at 100 μM | Percent inhibition at 50 μM |
|---|---|---|---|---|---|---|
| RU-NT-037 | 242 | 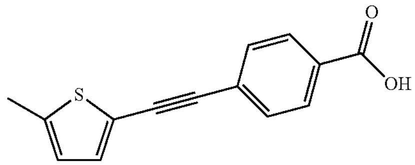 [SMILES: Cc1ccc(C#Cc2ccc(C(=O)O)cc2)s1] | | | | |
| RU-NT-038 | 246 | 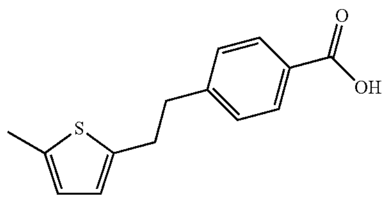 [SMILES: Cc1ccc(CCc2ccc(C(=O)O)cc2)s1] | than | | | to |
| RU-NT-039 | 260 | 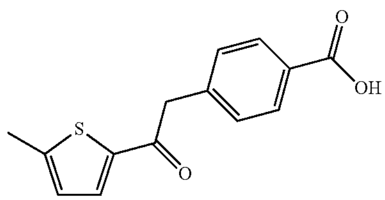 [SMILES: Cc1ccc(C(=O)Cc2ccc(C(=O)O)cc2)s1] | | | | |
| RU-NT-040 | 274 | 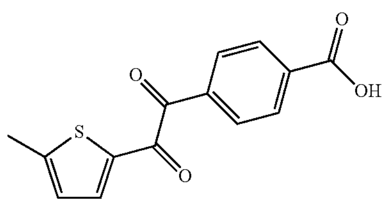 [SMILES: Cc1ccc(C(=O)C(=O)c2ccc(C(=O)O)cc2)s1] | CC70601 | | | CC70601 |
| RU-NT-041 | 339 | 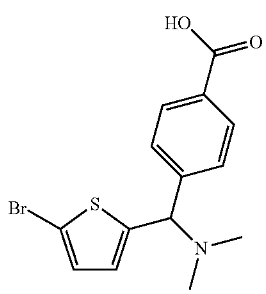 [SMILES: CN(C)C(c1ccc(C(=O)O)cc1)c1ccc(Br)s1] | | | | |
| RU-NT-042 | 258 | 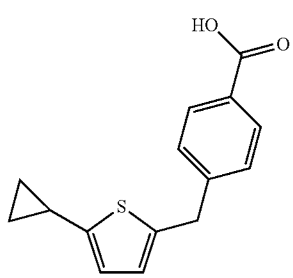 [SMILES: O=C(O)c1ccc(Cc2ccc(C3CC3)s2)cc1] | | | | |

TABLE 3-continued

Structure, inhibitory, and binding data for selected analogues against RTA

| Code | MW | Structure | KD (μM) | IC$_{50}$ (μM) | Percent inhibition at 100 μM | Percent inhibition at 50 μM |
|---|---|---|---|---|---|---|
| RU-NT-045 | 325 | 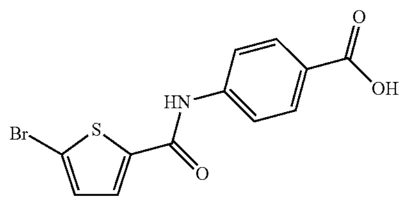 [SMILES: O=C(O)c1ccc(NC(=O)c2ccc(Br)s2)cc1] | | | | |
| RU-NT-046 | 246 | 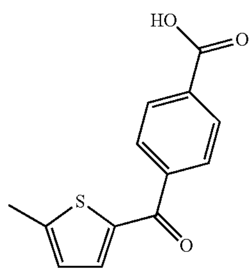 [SMILES: Cc1ccc(C(=O)c2ccc(C(=O)O)cc2)s1] | | | | |
| RU-NT-048 | 232 | 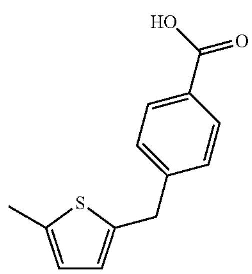 [SMILES: Cc1ccc(Cc2ccc(C(=O)O)cc2)s1] | | | | |
| RU-NT-049 | 201 | 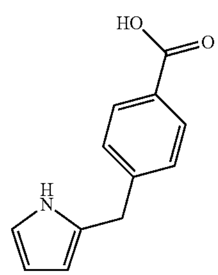 [SMILES: O=C(O)c1ccc(Cc2ccc[nH]2)cc1] | 67 | | 61 | 53 |
| RU-NT-050 | 202 | 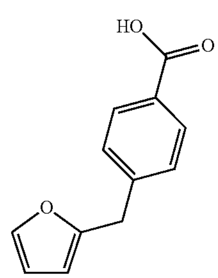 [SMILES: O=C(O)c1ccc(Cc2ccco2)cc1] | 57 | | 71 | 40 |

TABLE 3-continued

Structure, inhibitory, and binding data for selected analogues against RTA

| Code | MW | Structure | KD (μM) | IC$_{50}$ (μM) | Percent inhibition at 100 μM | Percent inhibition at 50 μM |
|---|---|---|---|---|---|---|
| RU-NT-051 | 260 | 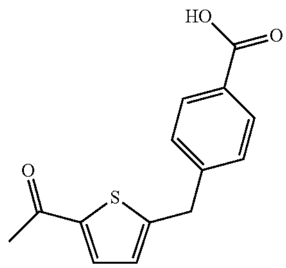 [SMILES: CC(=O)c1ccc(Cc2ccc(C(=O)O)cc2)s1] | 62 | | 98 | 84 |
| RU-NT-055 | 242 | 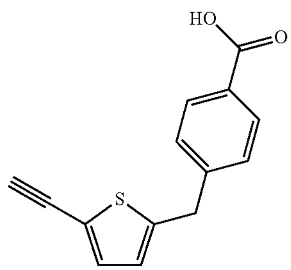 [SMILES: C#Cc1ccc(Cc2ccc(C(=O)O)cc2)s1] | 93 | | 73 | 48 |
| RU-NT-056 | 246 | 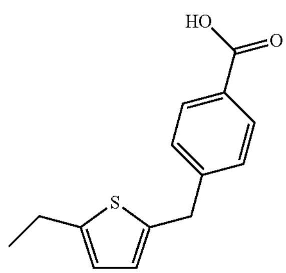 [SMILES: CCc1ccc(Cc2ccc(C(=O)O)cc2)s1] | 60 | | 99 | 72 |
| RU-NT-135 | 310 | 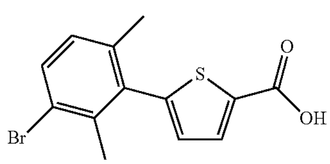 [SMILES: Cc1ccc(Br)c(C)c1-c1ccc(C(=O)O)s1] | 109 | | | |
| RU-NT-165 | 246 | 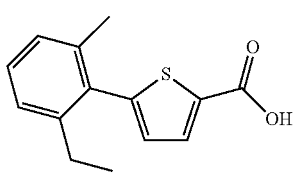 [SMILES: CCc1cccc(C)c1-c1ccc(C(=O)O)s1] | 282 | | | |
| RU-NT-083 | 254 | 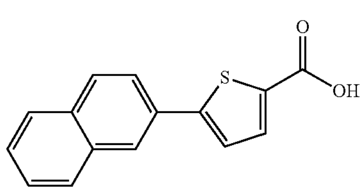 [SMILES: O=C(O)c1ccc(-c2ccc3ccccc3c2)s1] | 369 | — | 82 | 61 |
| RU-NT-084 | 258 | 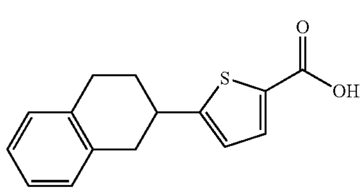 [SMILES: O=C(O)c1ccc(C2CCc3ccccc3C2)s1] | 826 | — | 30 | 26 |

TABLE 3-continued

Structure, inhibitory, and binding data for selected analogues against RTA

| Code | MW | Structure | KD (µM) | IC$_{50}$ (µM) | Percent inhibition at 100 µM | Percent inhibition at 50 µM |
|---|---|---|---|---|---|---|
| RU-NT-086 | 262 | 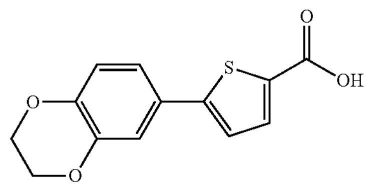 [SMILES: O=C(O)c1ccc(-c2ccc3c(c2)OCCO3)s1] | 826 | — | 30 | 26 |
| RU-NT-087 | 262 | 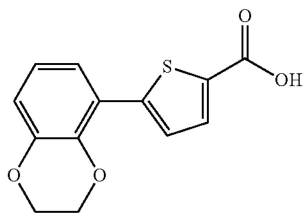 [SMILES: O=C(O)c1ccc(-c2cccc3c2OCCO3)s1] | 384 | — | 71 | 36 |
| RU-NT-89 | 270 | 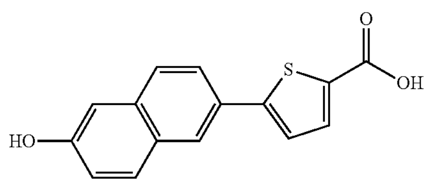 [SMILES: O=C(O)c1ccc(-c2ccc3cc(O)ccc3c2)s1] | 386 | — | — | — |
| RU-NT-105 | 246 | 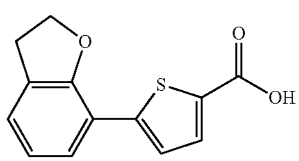 [SMILES: O=C(O)c1ccc(-c2cccc3c2OCC3)s1] | 1184 ± 193 | | 54 ± 7 | |

Figure 26:
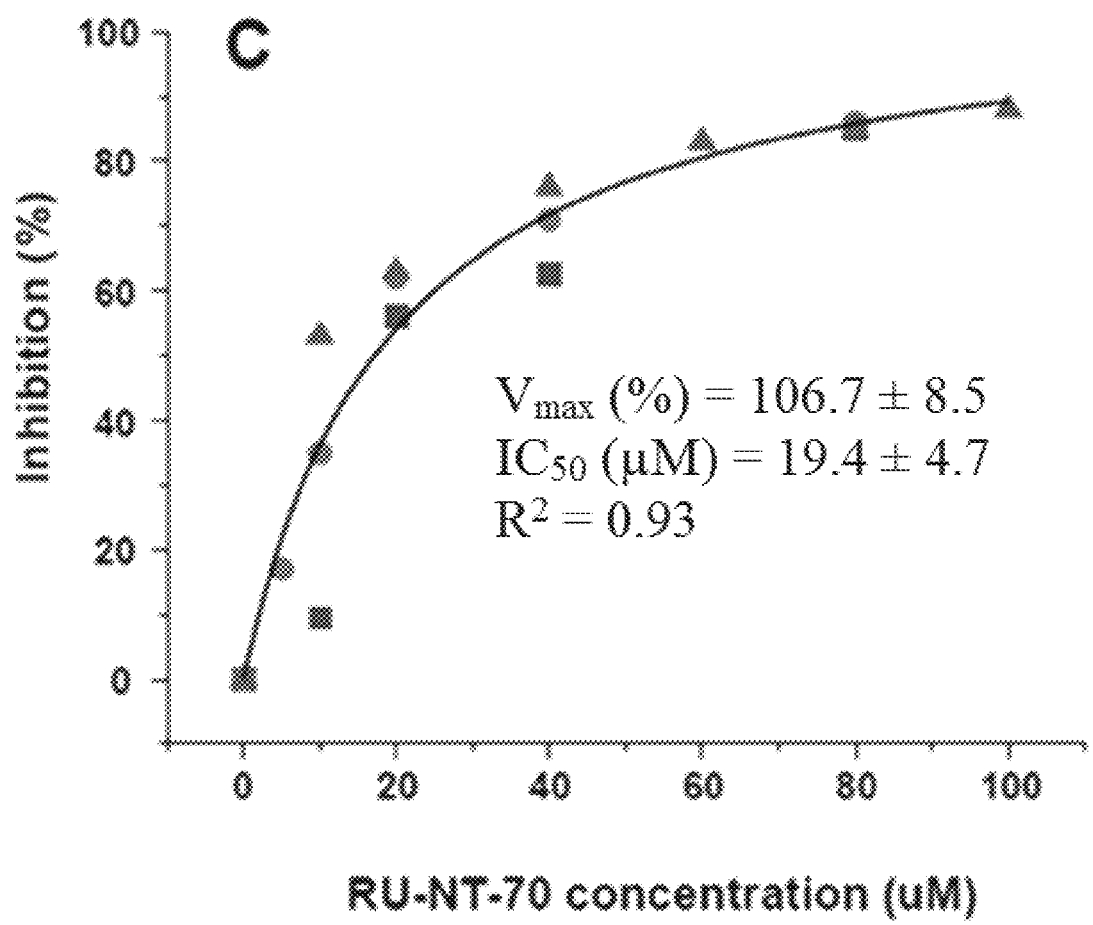
FIG. 26 shows an illustrative inhibitory concentration ($IC_{50}$) of RU-NT-70 against RTA, wherein the measurements were repeated 4 to 6 times. The Michaelis-Menten model was used to fit the inhibition curves using the Origin software.
Figure 27A:
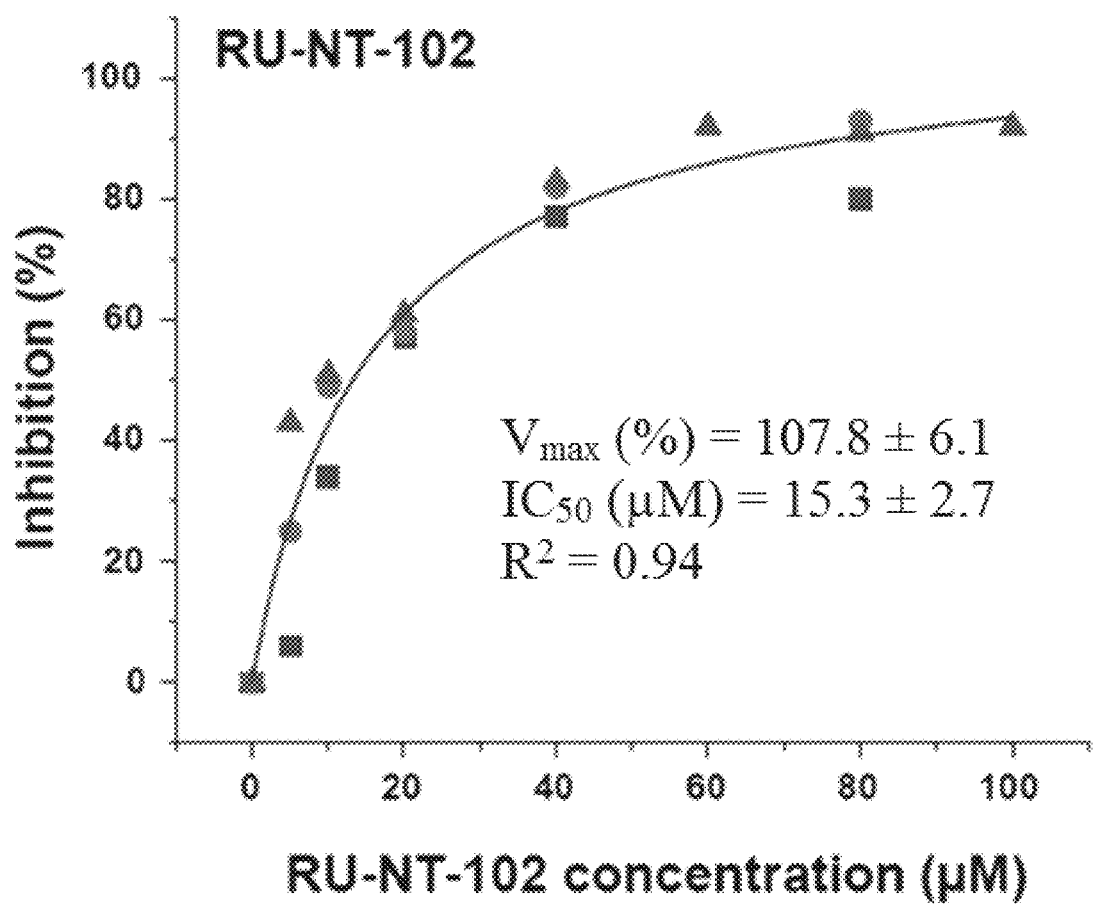
FIGS. 27A-27B show illustrative 50% inhibitory concentration ($IC_{50}$) of RU-NT-102 (FIG. 27A) and RU-NT-136 (FIG. 27B) against RTA. Depurination inhibitory activity of the fragments was determined by qRT-PCR and fragment concentrations were varied depending on the inhibitory activity of the fragment. The different measurements which were repeated 4 to 6 times. The Michaelis-Menten model was used to fit the inhibition curves using the Origin software.
Figure 27B:
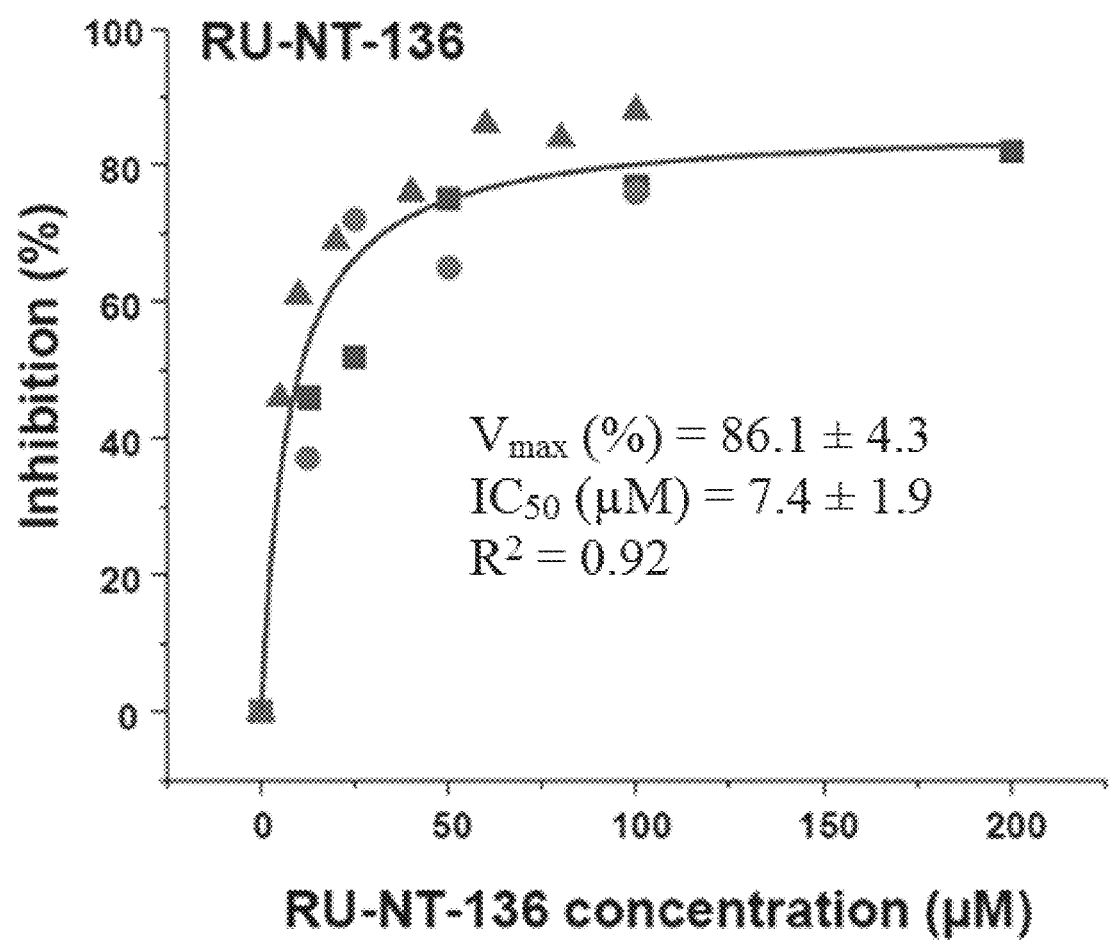
Figure 30:
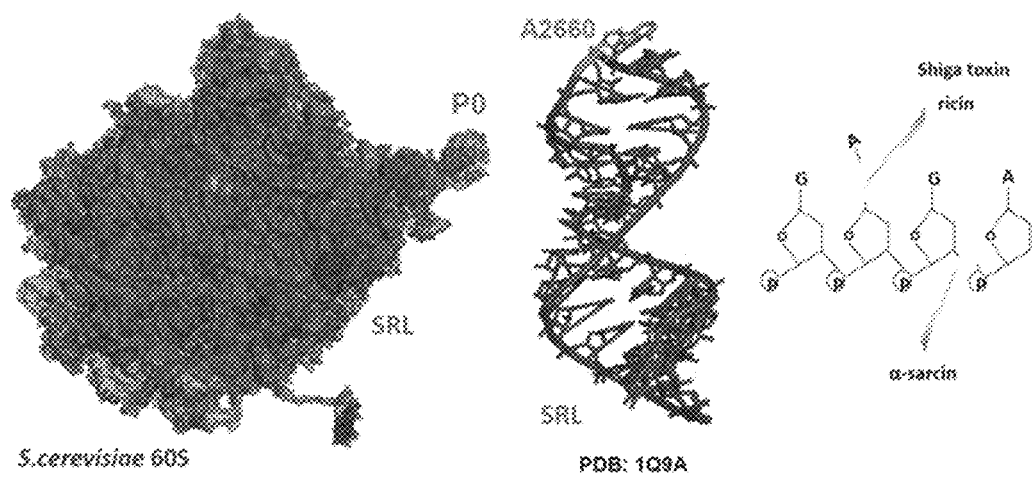
FIG. 30 illustrates that ricin and Stxs depurinate the sarcin/ricin loop (SRL) of the 28S rRNA and inhibits translation.
Figure 31:
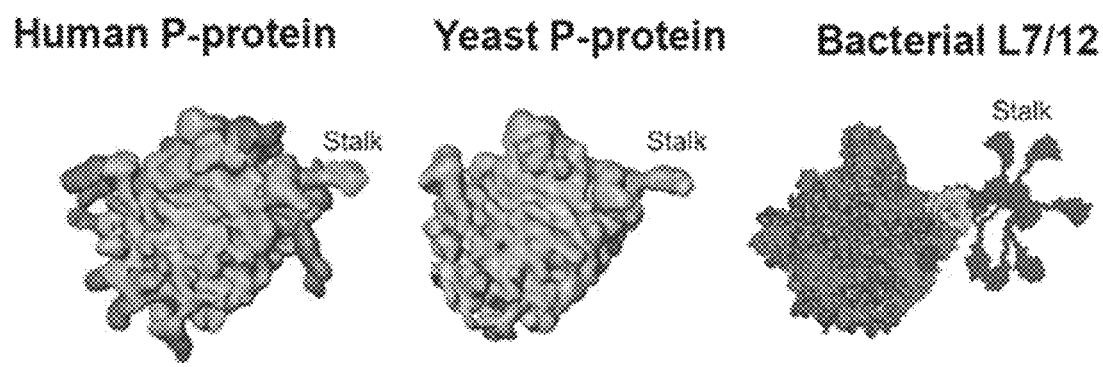
FIG. 31 show illustrative structures of bacterial, yeast, and human stalk.
Figure 34:
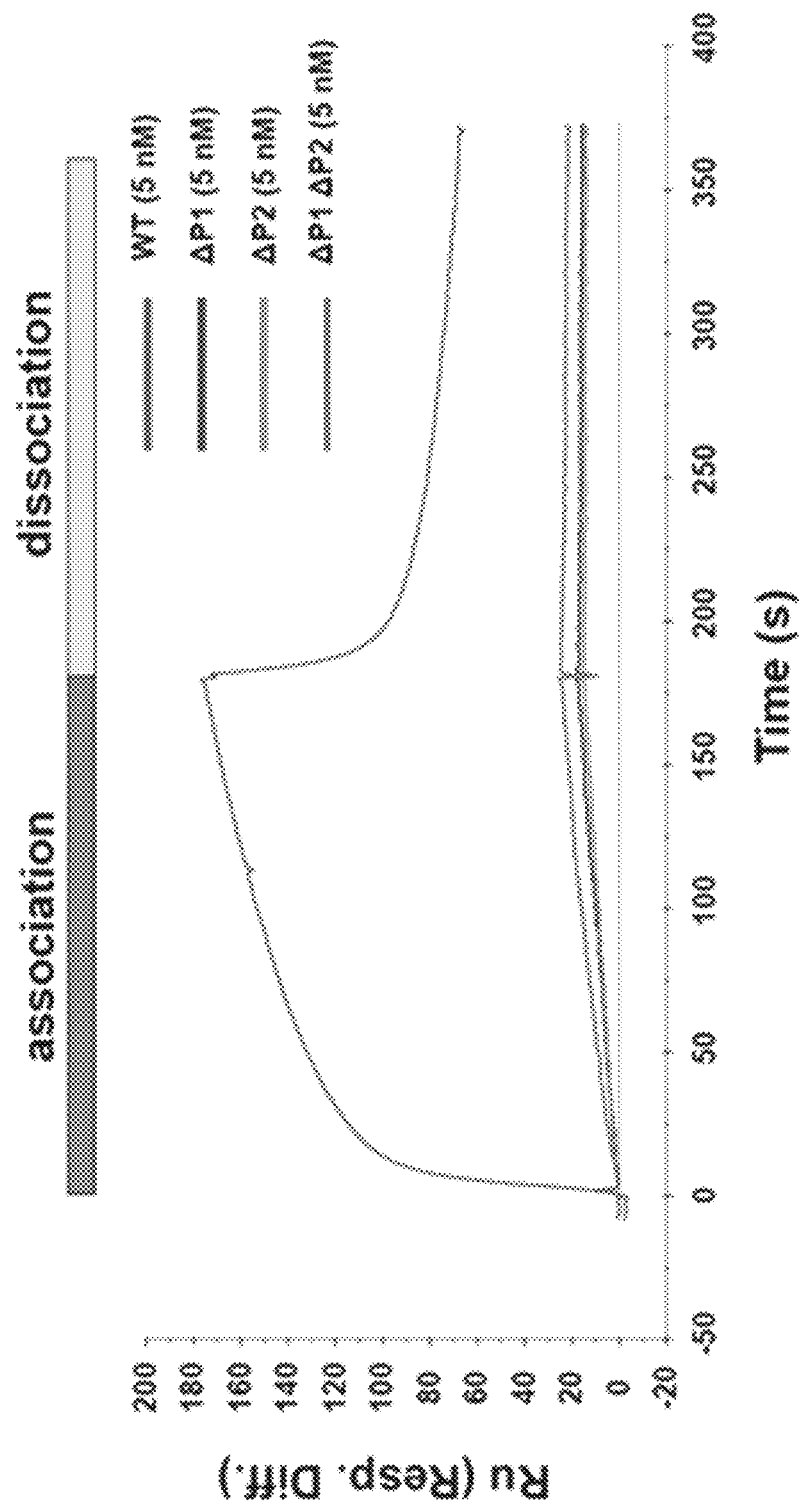
FIG. 34 shows that RTA binding to ribosomes is reduced in the ΔP1 and ΔP2 mutants. Biacore 3000 was used to examine the interaction between N-His RTA as the ligand and ribosomes (5 nM) isolated from the ΔP1, ΔP2 and ΔP1 ΔP2 mutants as the analyte.
Figure 35:
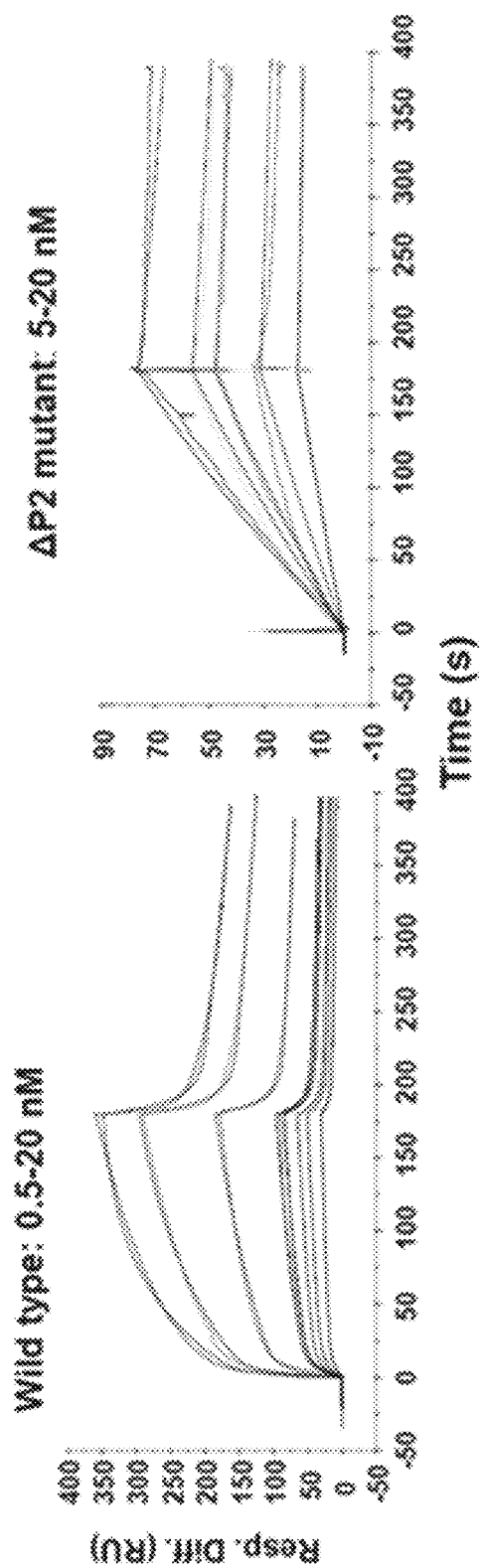
FIG. 35 shows that RTA interacts with wild type ribosomes via two distinct types of electrostatic interactions.
Figure 37:
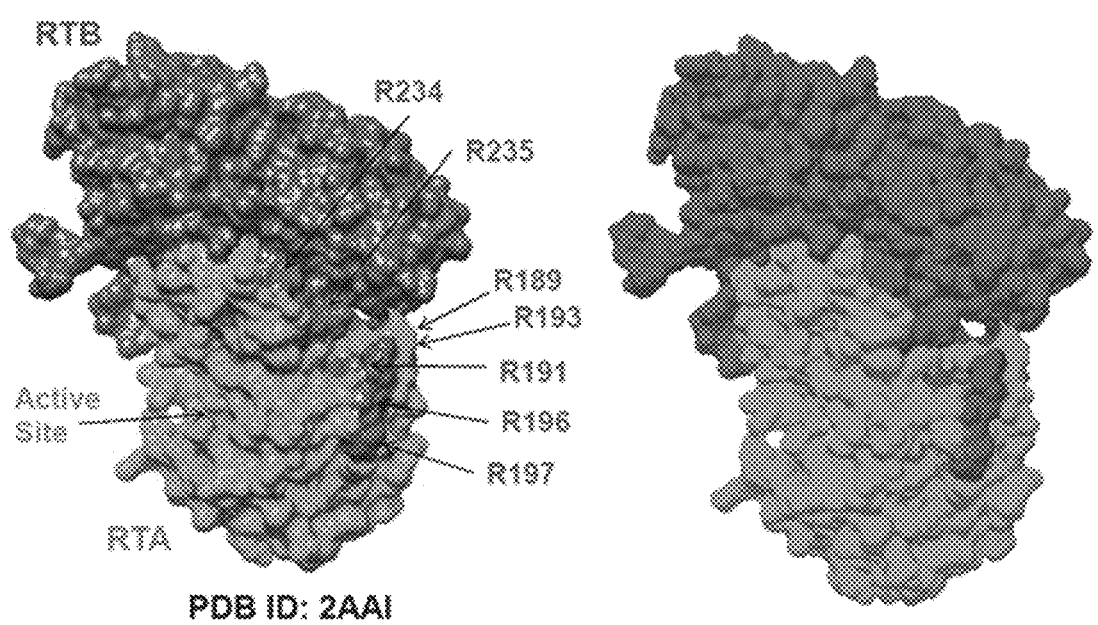
FIG. 37 shows that P stalk binding site of RTA is at the RTA/RTB interface.
Figure 38:
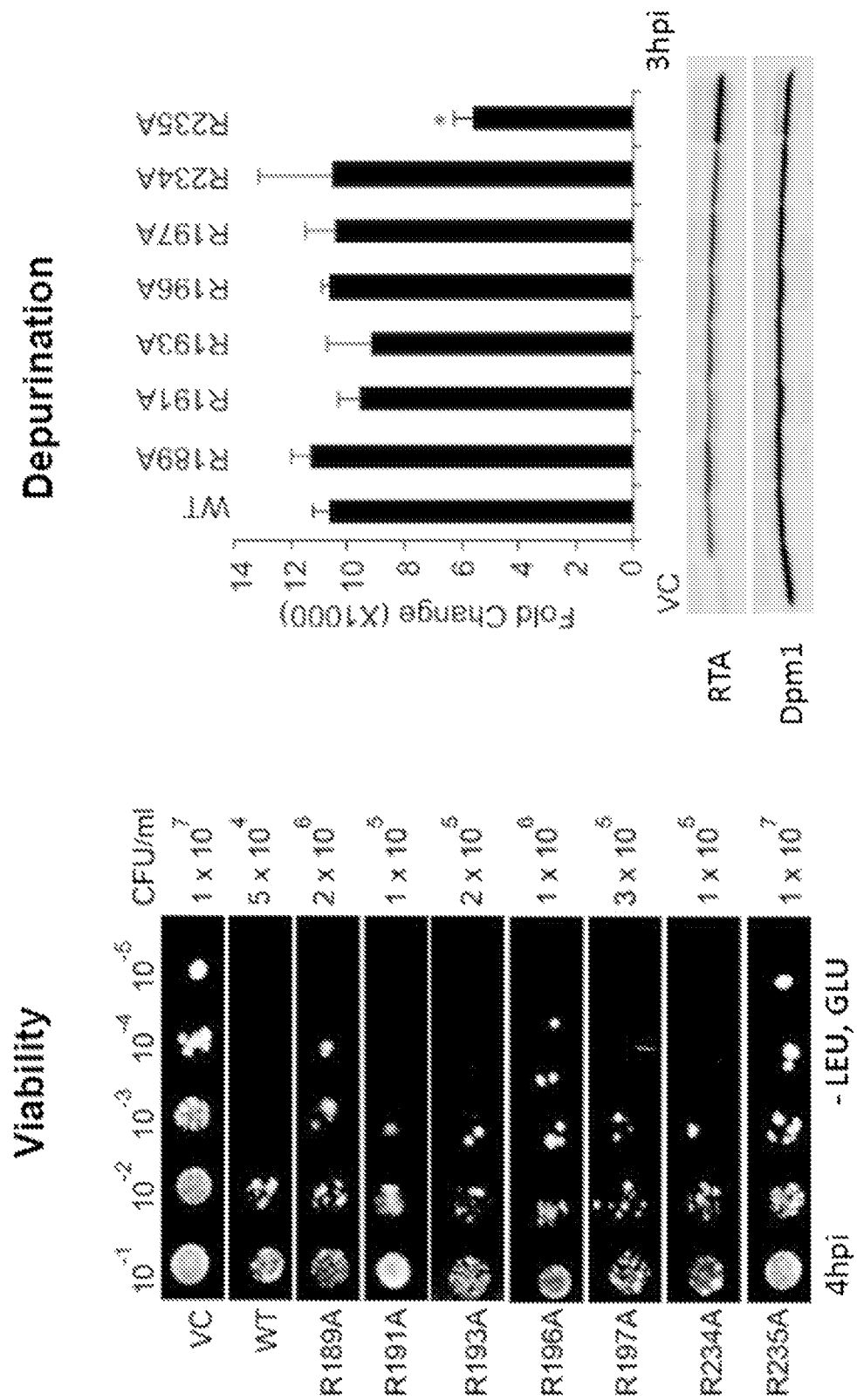
FIG. 38 shows that R235A mutation causes the greatest reduction in toxicity in yeast.
Figure 39:
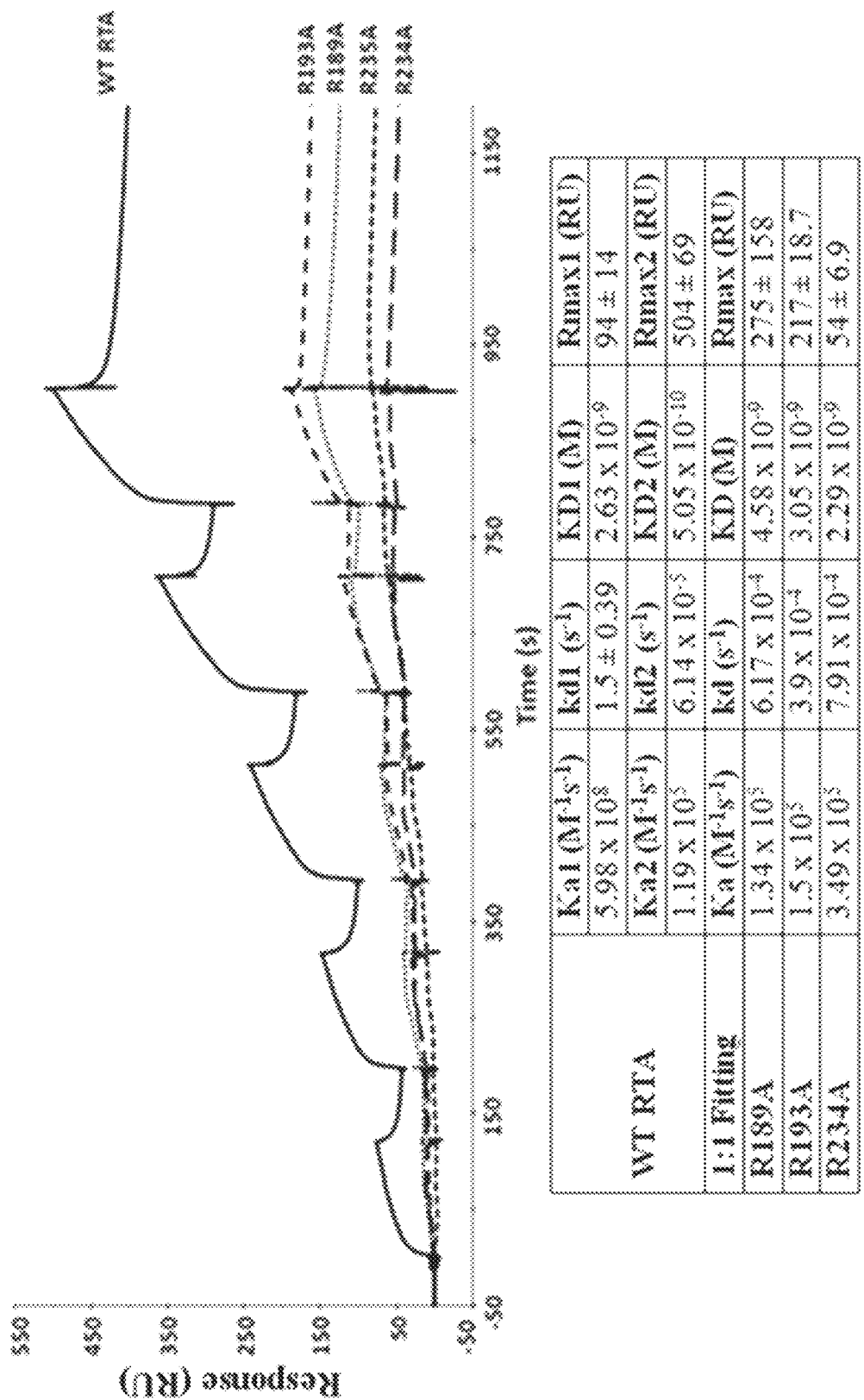
FIG. 39 illustrates that arginine mutations disrupt the interactions with the P stalk.
Figure 42:
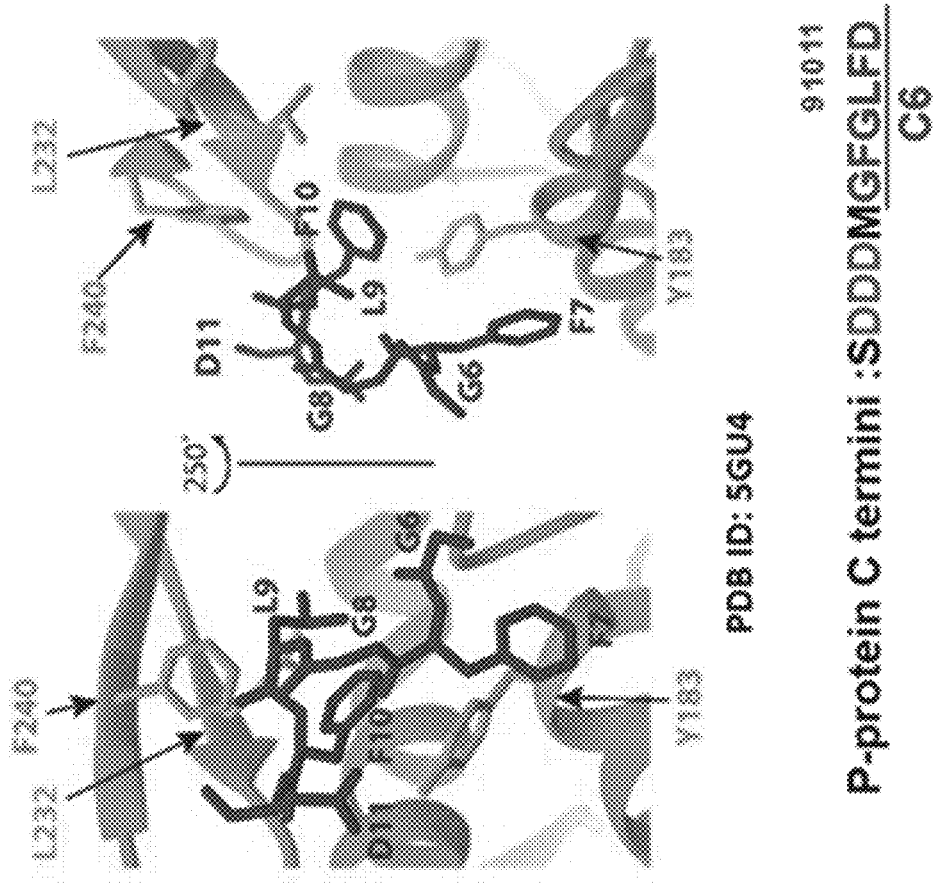
Figure 44:
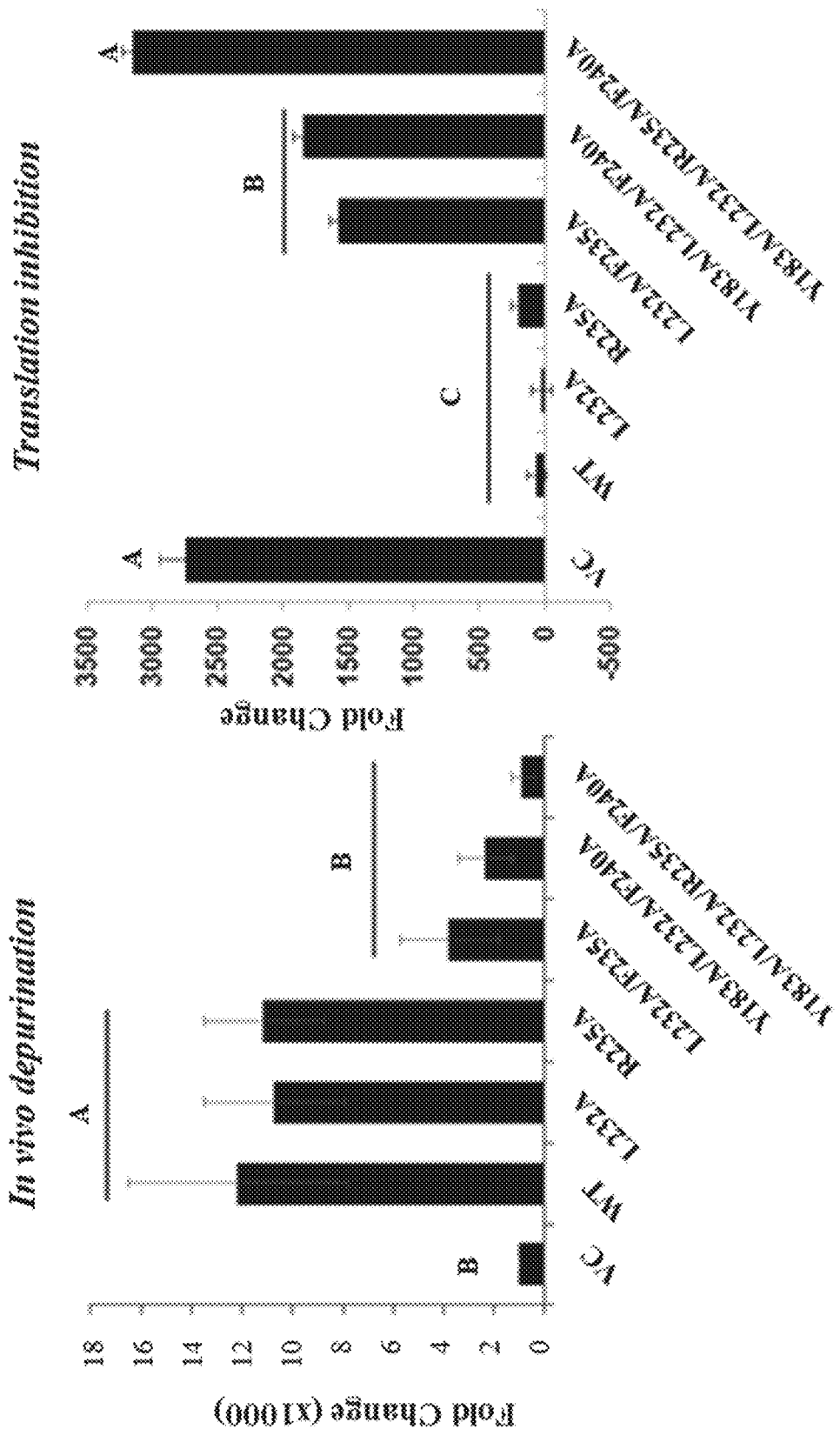
Figure 46A:
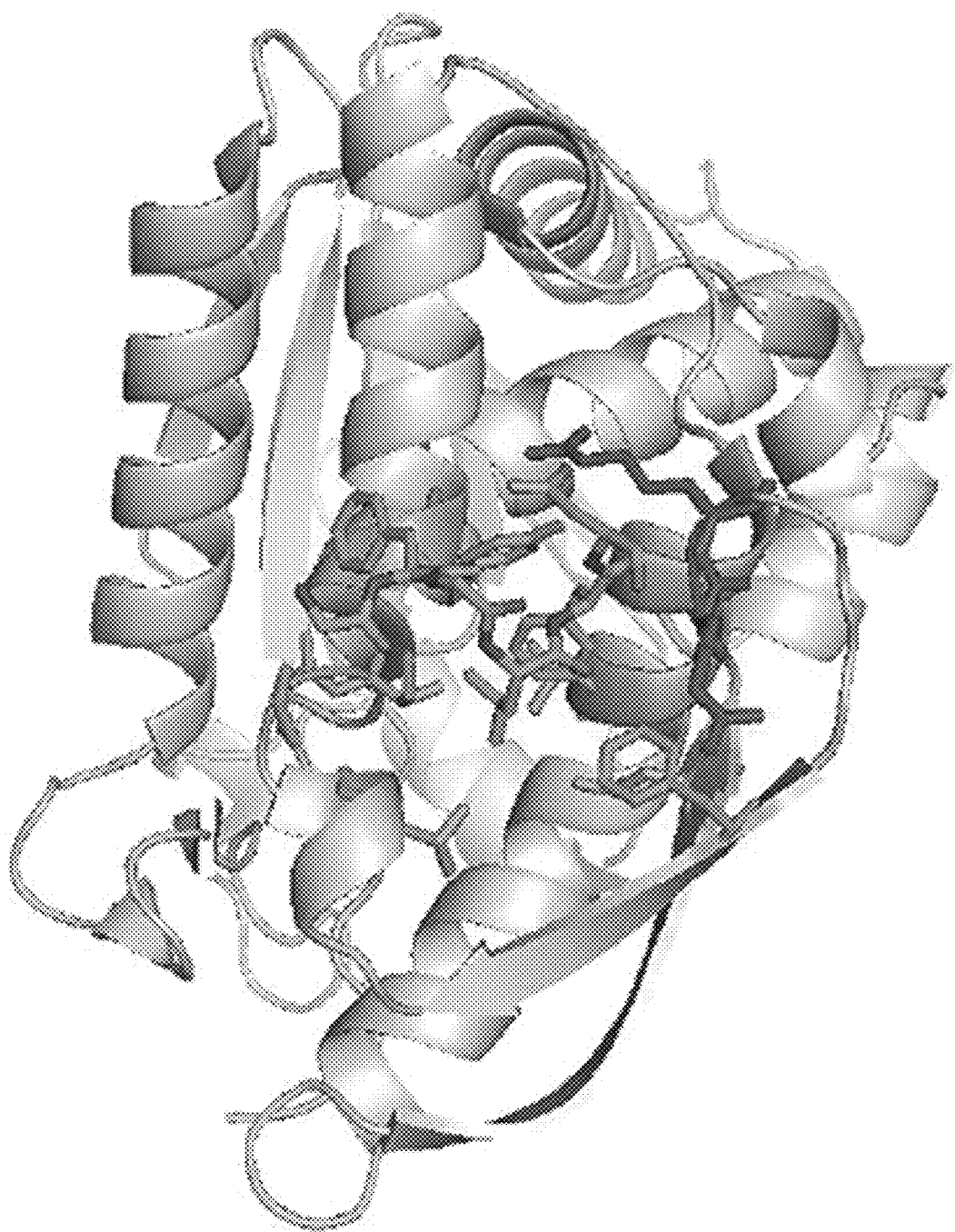
Figure 46B:
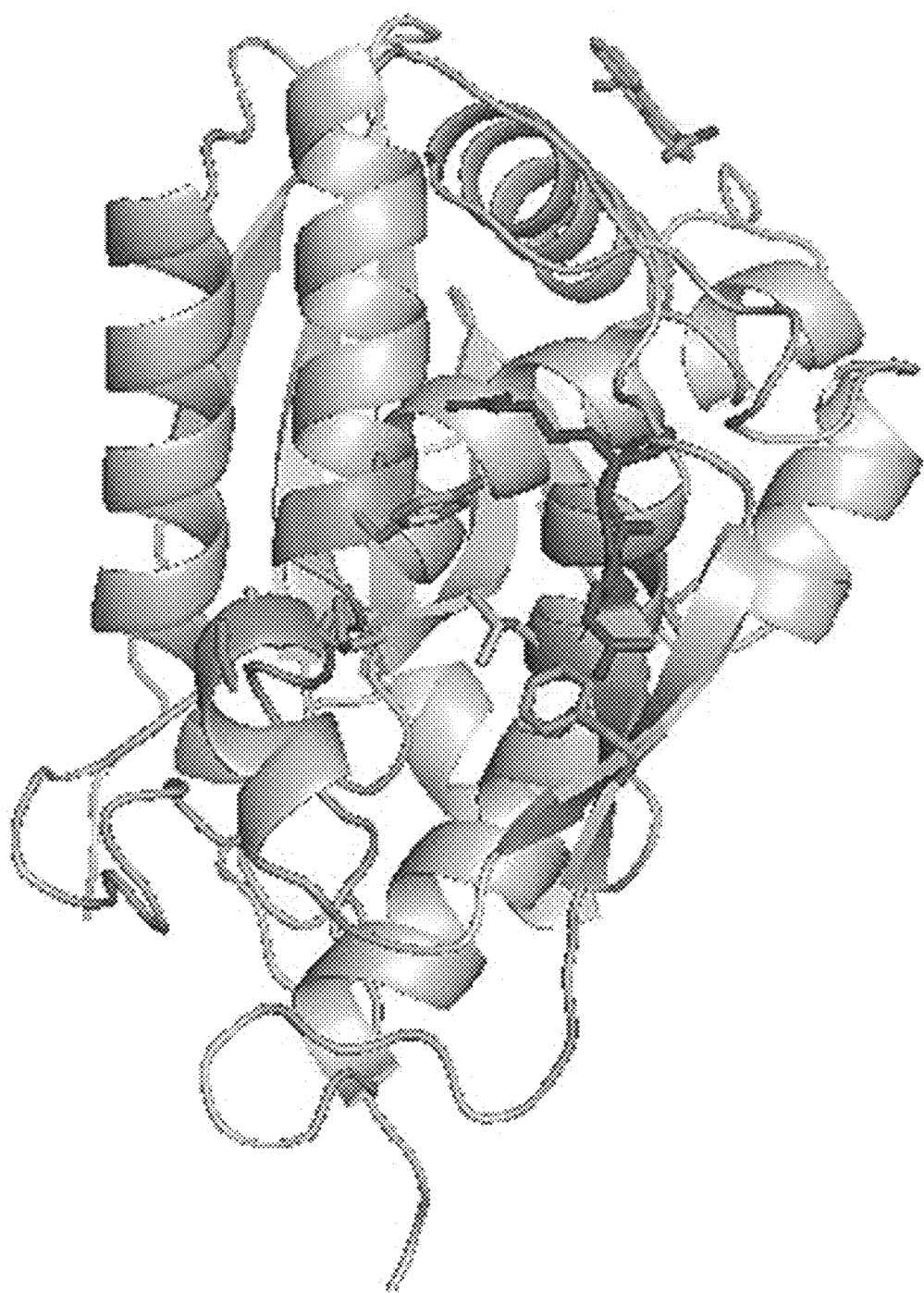
Figure 46C:
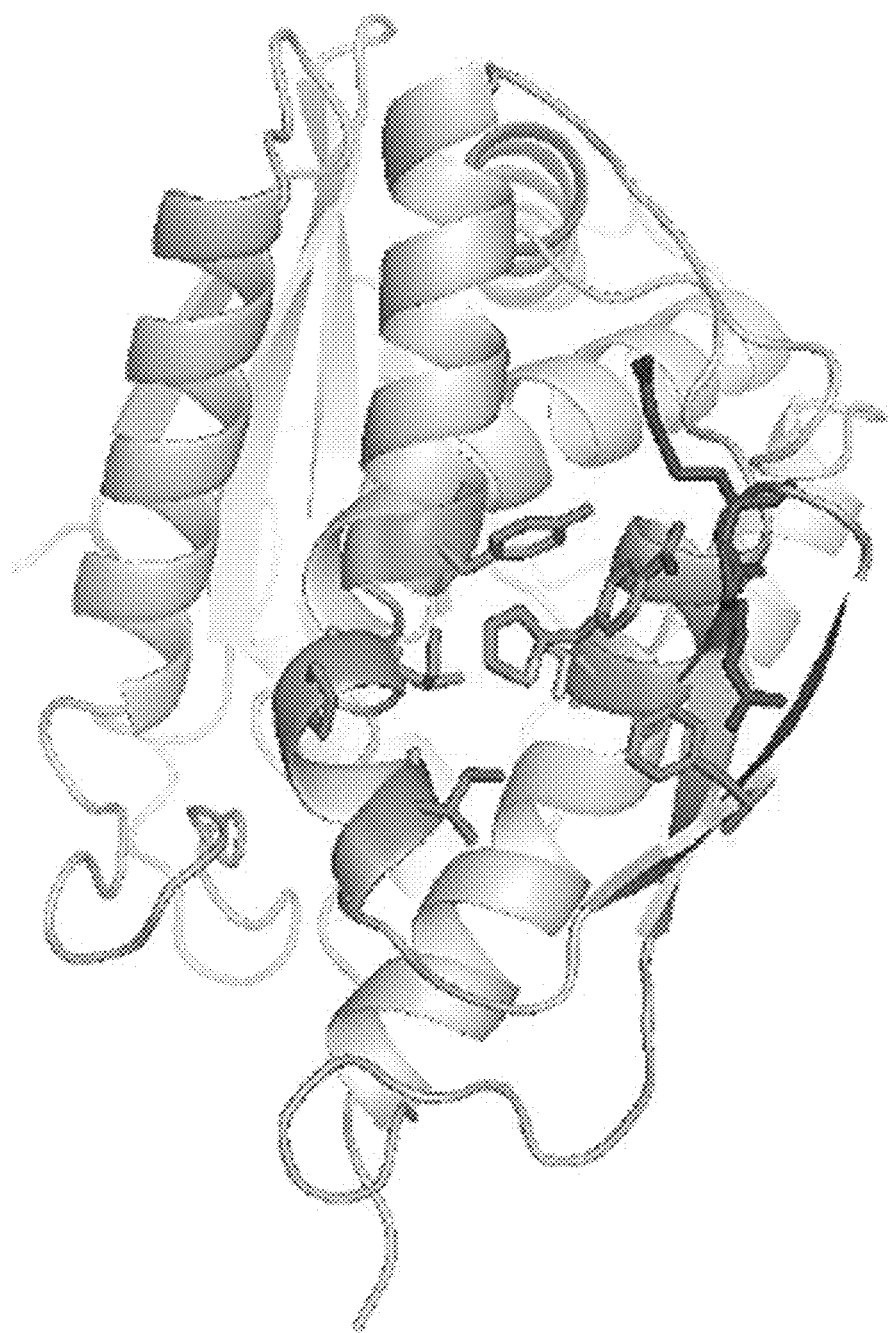
Figure 46D:
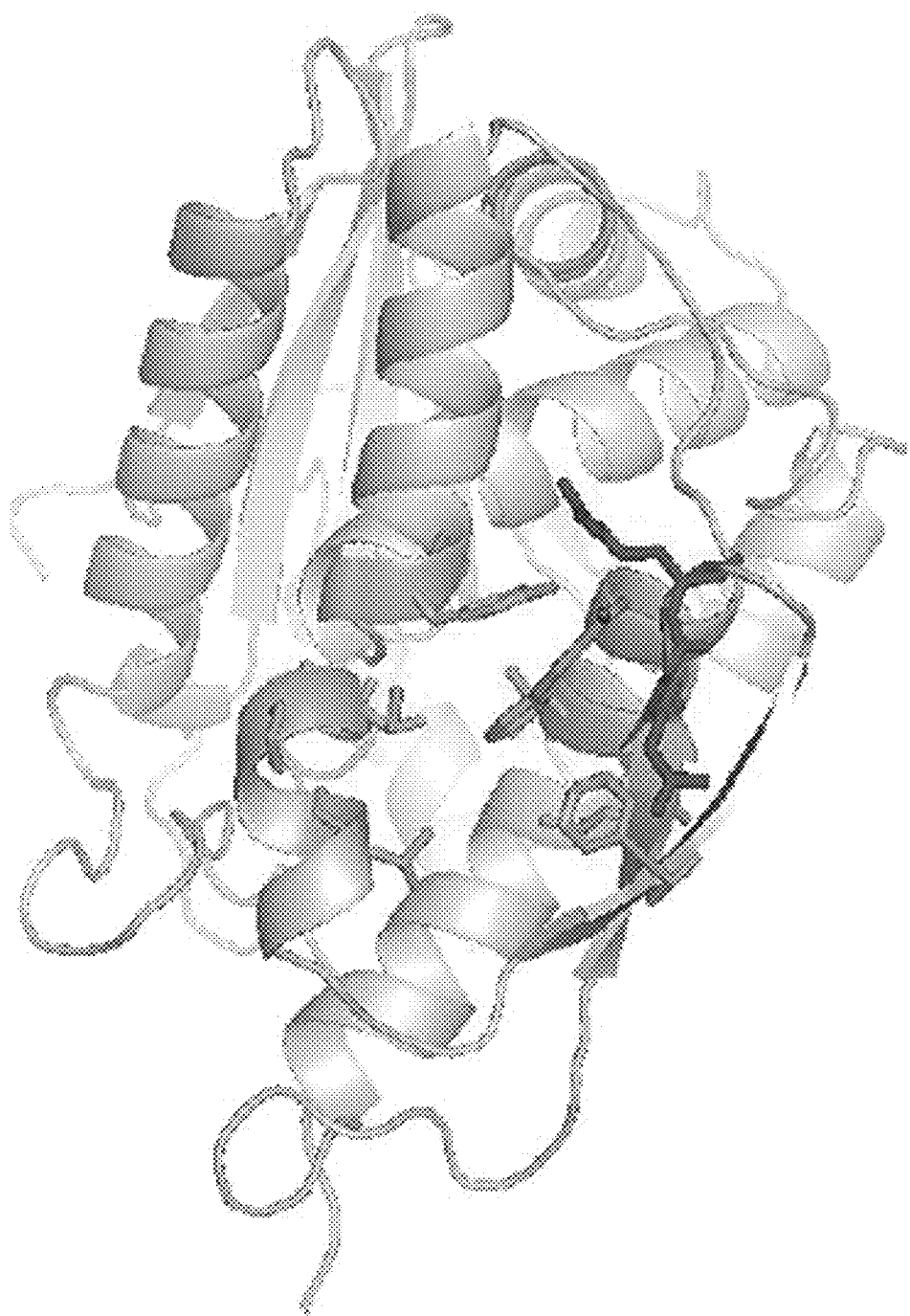
Figure 47A:
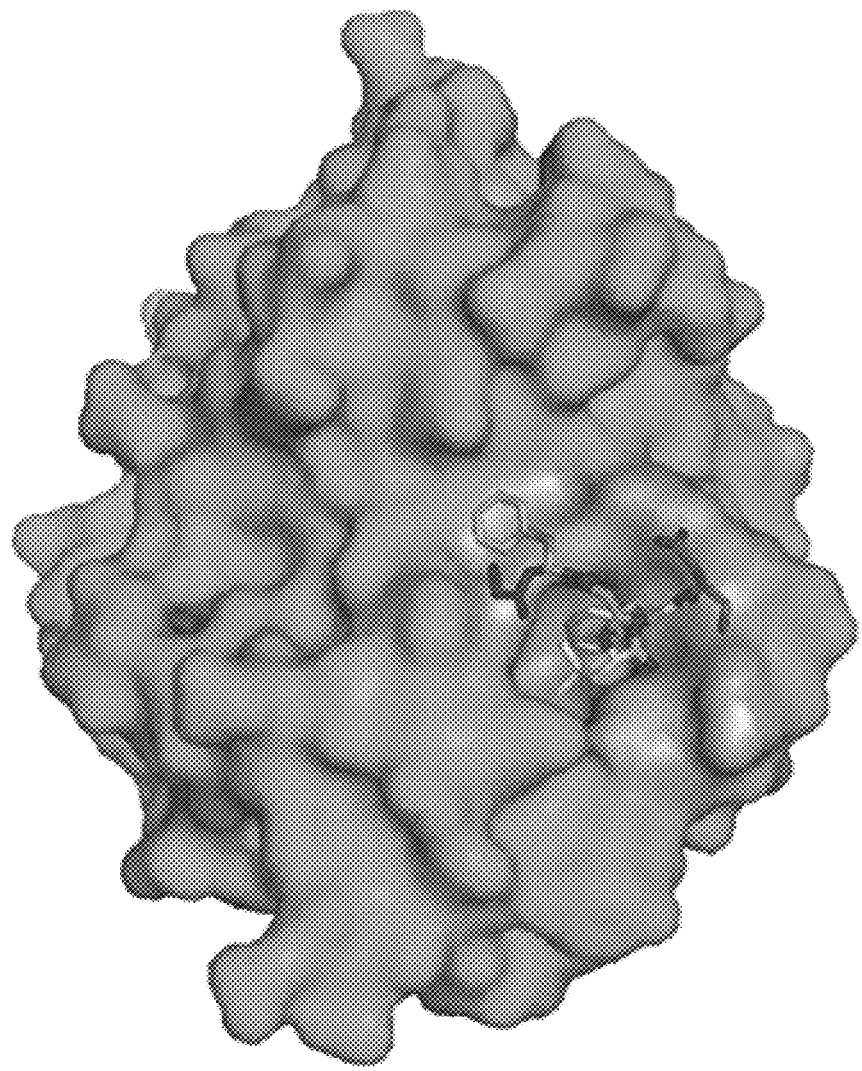
Figure 47B:
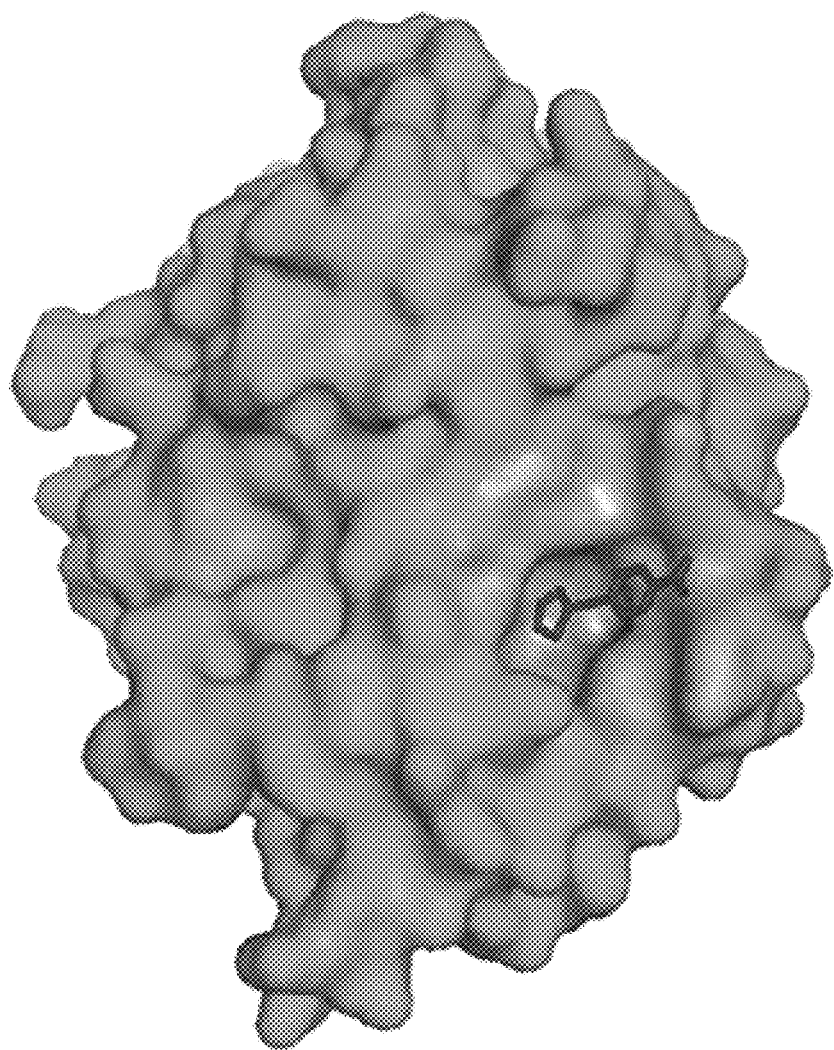
Figure 47C:
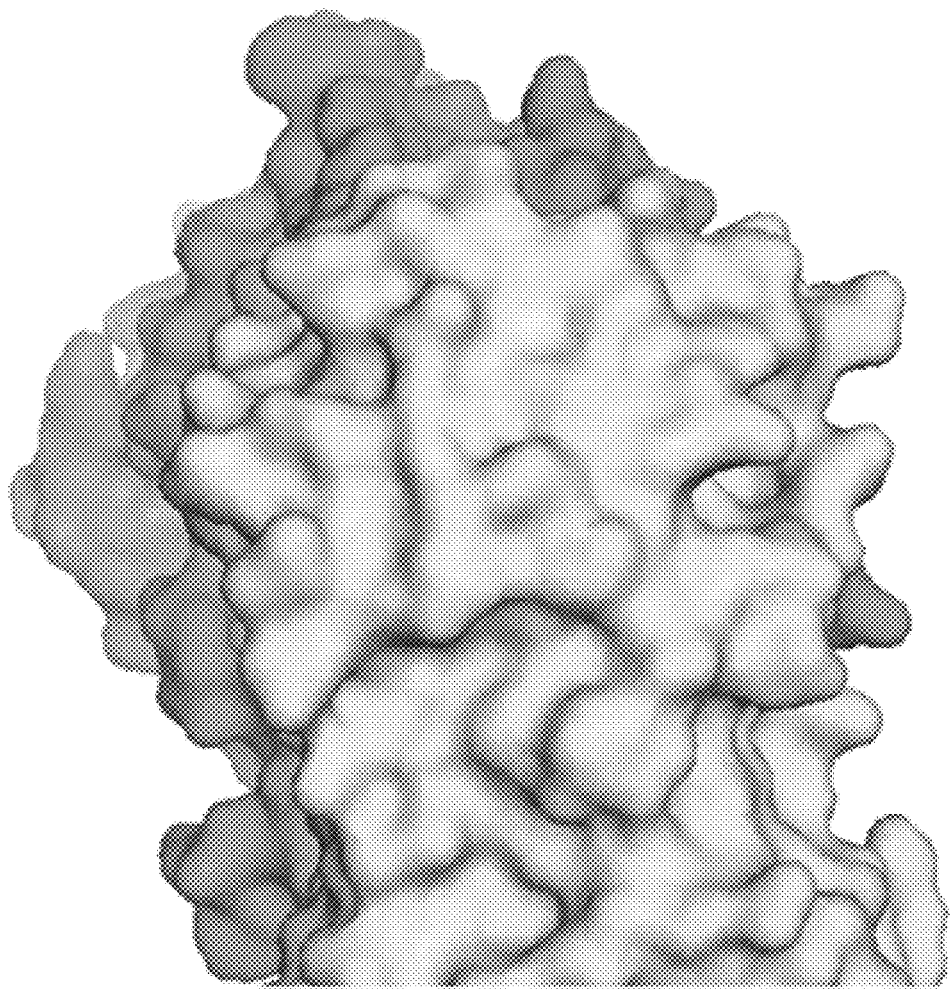
Figure 49A:
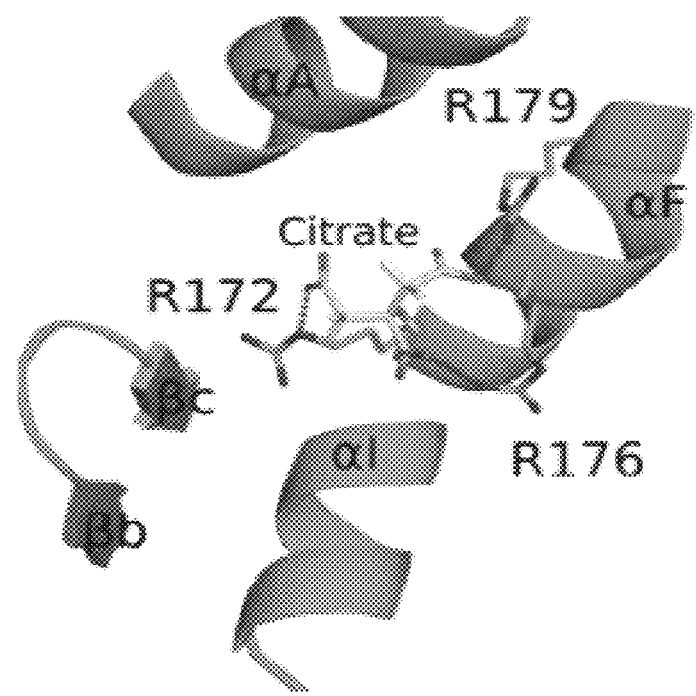
Figure 49B:
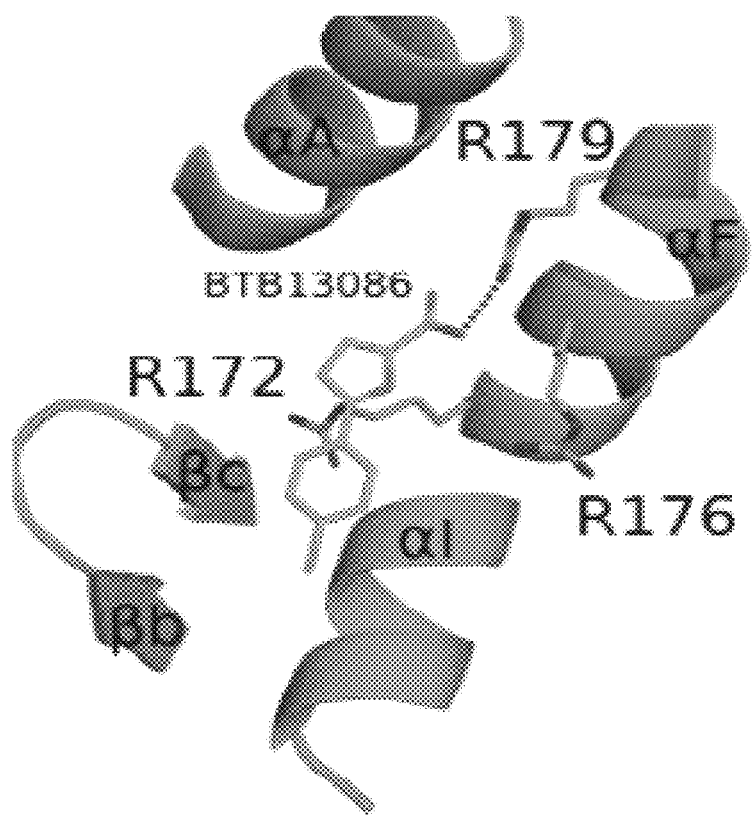
Figure 49C:
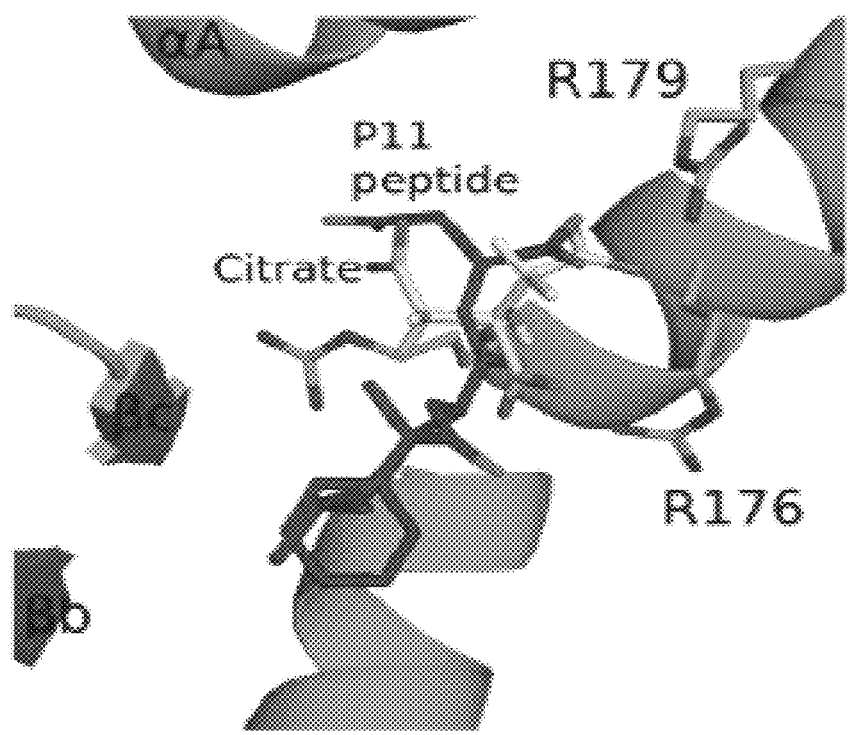
Figure 49D:
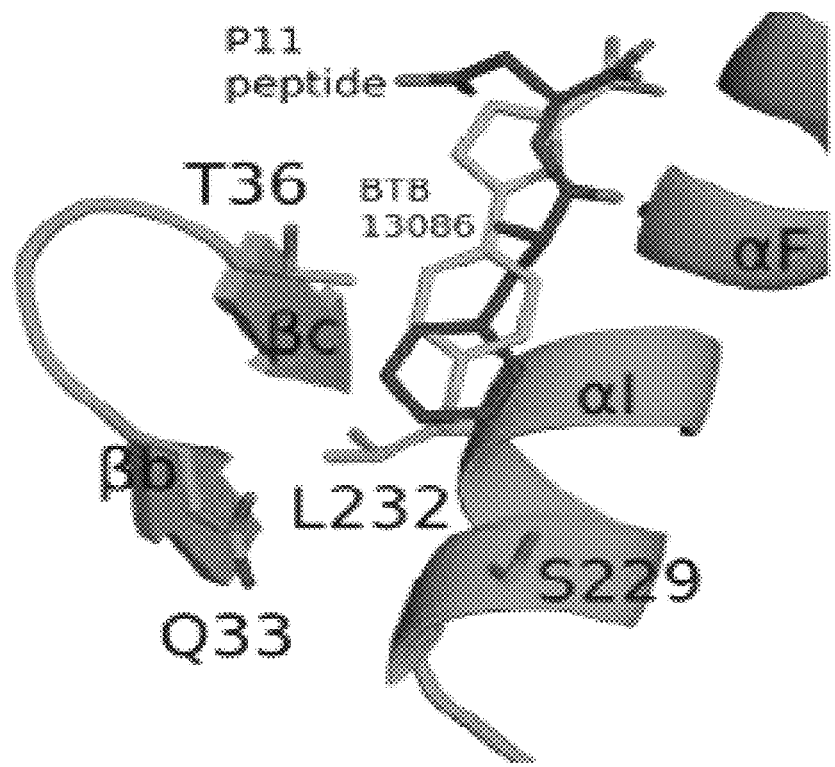
Figure 50:
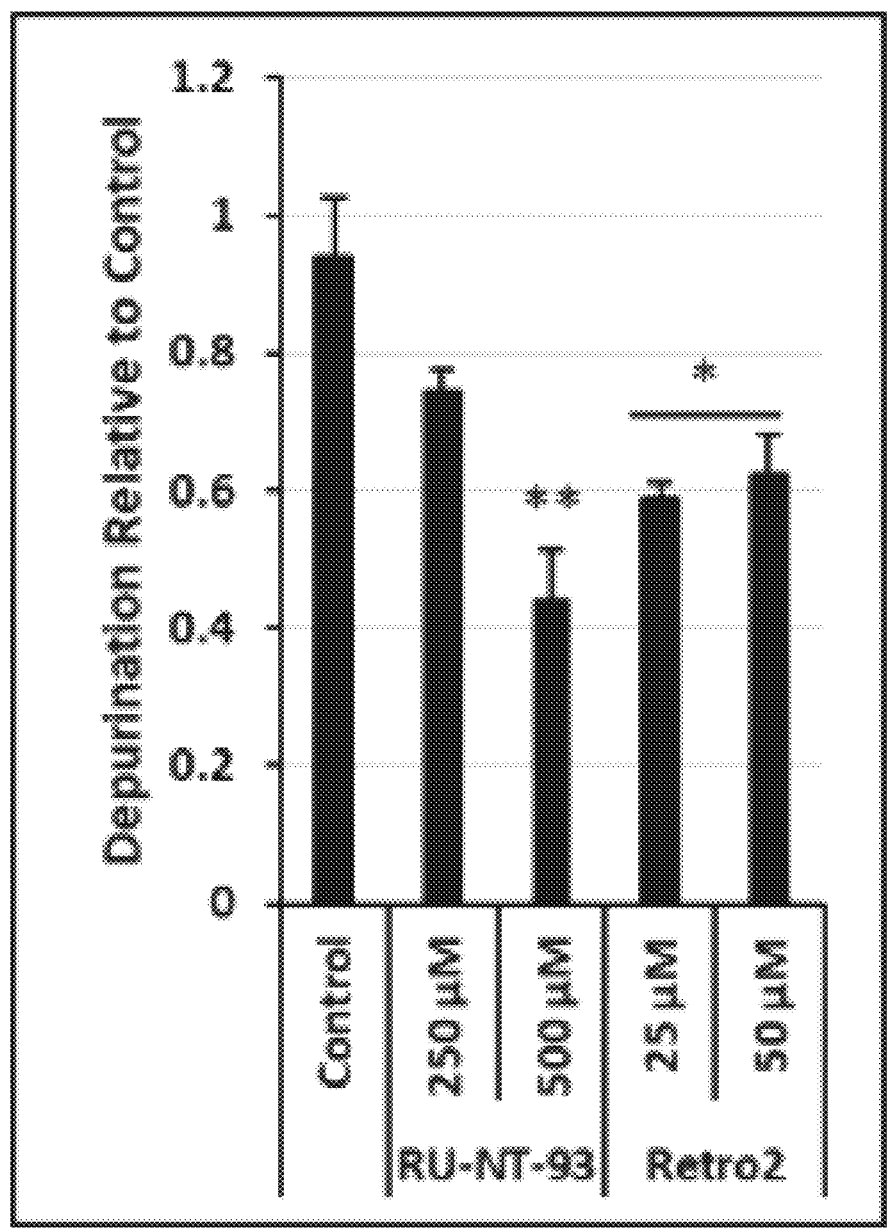
Figure 51:
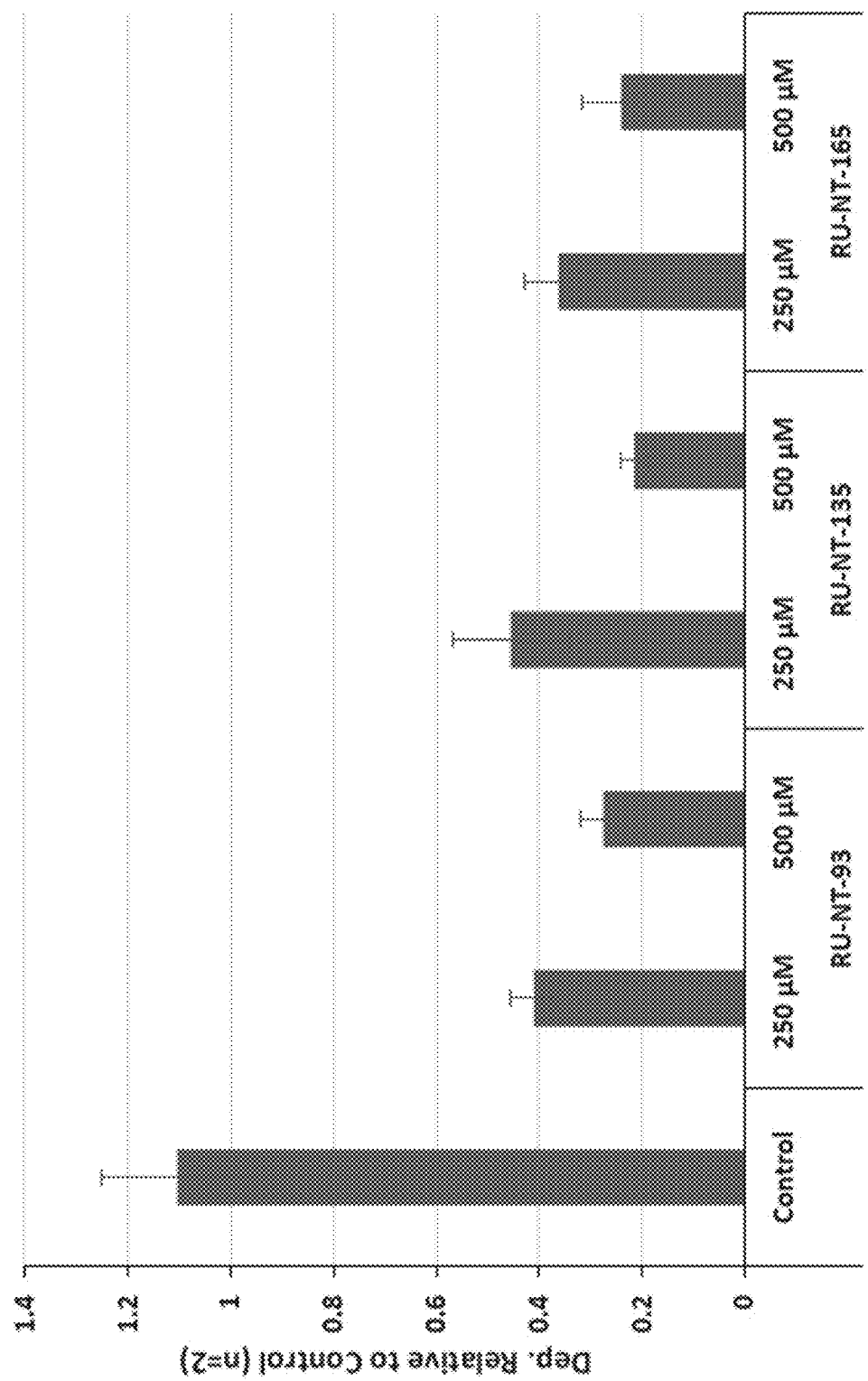
Figure 52:
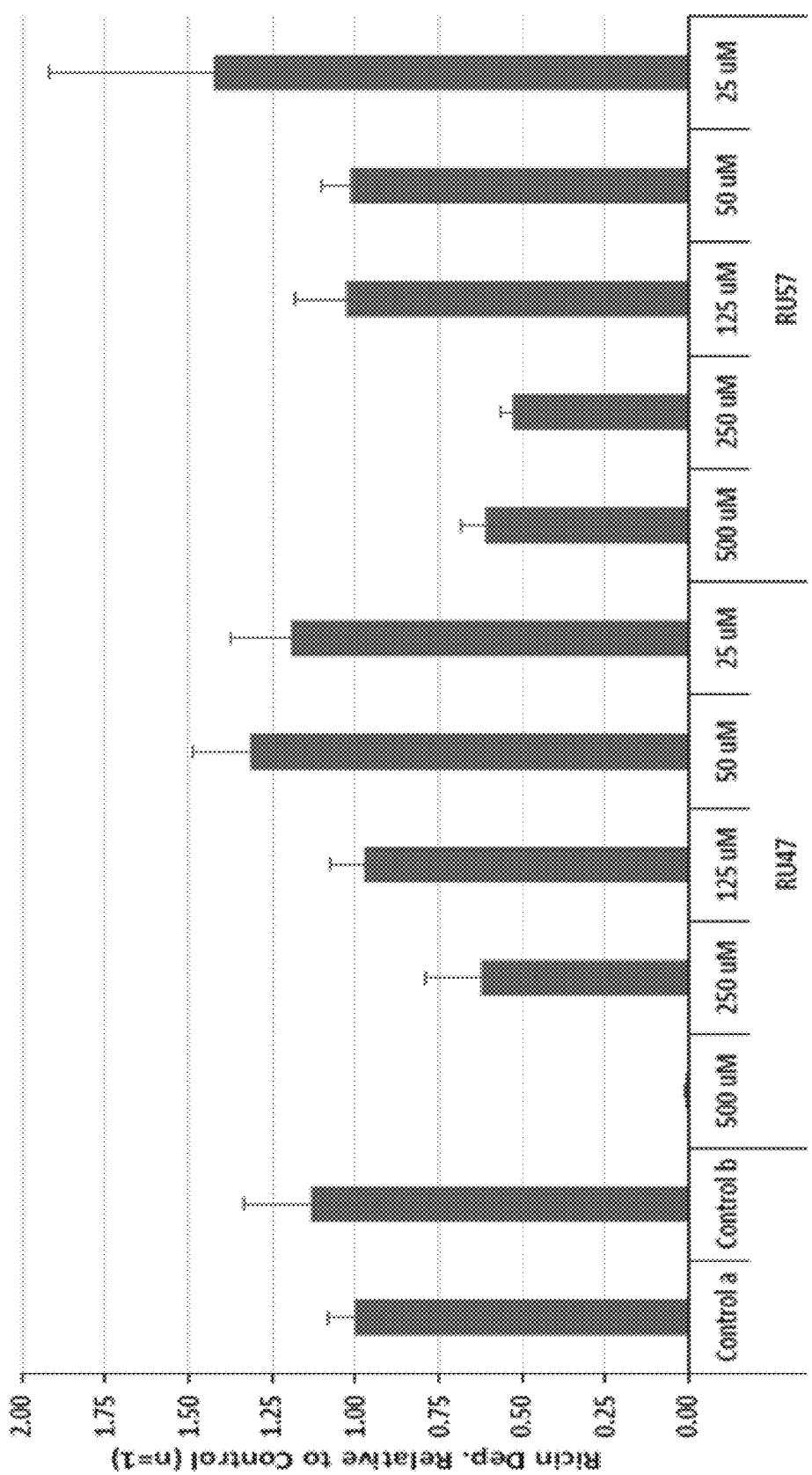

Example 7: Affinity (K$_D$) and the IC$_{50}$ of RU-NT-70, RU-NT-93, RU-NT-102, and RU-NT-136 for RTA The affinity of RU-NT-70, RU-NT-93, RU-NT-102, and RU-NT-136 for RTA was determined using Biacore T200 at 12.5, 25, 50, 100 and 200 µM in triplicate measurements. The results were filled globally. RU-NT-70, RU-NT-93, RU-NT-102, and RU-NT-136 had similar KID values of 72, 62, 67, and 72 µM, respectively, compared to CC10501 with a K$_D$ of 270 µM. These results indicated that the analogues had higher affinity for RTA than the original compound, CC10501. The 5000 inhibitory activity (IC$_{50}$) was determined by qRT-PCR. The data for the percent inhibition at different fragment concentrations were filled with Michaelis-Menten kinetics using Origin software. RU-NT-93 and RU-NT-136 gave the best inhibitory activity with IC$_{50}$ values of 8 and 7.4 µM, respectively (FIG. 27B). RU-NT-70 and RU-NT-102 also had strong inhibitory activity with IC$_{50}$ values of 19 and 15 µM respectively (FIG. 26 and FIG. 27A).

Example 8: Inhibition of Stx2A Depurination

On the basis of the co-crystal structures of Stx2a with certain fragments, it was hypothesized that the rational design of Stx2A fragment inhibitors having an optimal contact with the positively charged region of Stx2A and added interactions with the non-ionic region within the P stalk binding pocket, should improve the binding affinity and/or the binding specificity, ultimately generating more potent Shiga toxin inhibitors.

Compounds of the present disclosure, including but not limited to RU-NT-47 and RU-NT-57 showed affinity and dose-dependent inhibitory activity against Stx2A in vitro and inhibited depurination by Stx2a holotoxin in Vero cells. RU-NT-128, showed protection against Stx2a in Vero cells. RU-NT-62 and PD00589 showed dose-dependent inhibition of Stx2A1 depurination activity in yeast ribosomes in vitro and protected Vero cells against depurination by Stx2a holotoxin in vivo.

TABLE 4

| Inhibitors against Shiga toxin 2a (Stx2a) | | | | | | | | | |
|---|---|---|---|---|---|---|---|---|---|
| | KD (mM) | % inhibition Stx2A1 in yeast ribosome (μM) | | | % Inhibition Stx2a depurination in Vero cell (μM) | | | | |
| Compound | Stx2A1 | 200 | 100 | 50 | 500 | 250 | 125 | 50 | 25 |
| RU-NT-047 | 1.2 | — | 82 | 74 | 94 | 59 | 15 | 11 | 8 |
| RU-NT-057 | 1.51 | — | 100 | 98 | 99 | 75 | 53 | 22 | 15 |
| RU-NT-128 | — | — | — | — | 13 | 19 | — | — | — |
| PD00589 | 0.629 | 80 | 51 | 45 | 36 | 18 | — | — | — |
| RU-NT-062 | 1.6 | 58 | 35 | — | 56 | 15 | — | — | — |
| BTB13086 | 0.575 | IC$_{50}$ = 194 ± μM | | | — | — | — | — | — |
| RU-NT-078 | 0.606 | 70 | 64 | — | — | — | — | — | — |

TABLE 4-continued

| | Inhibitors against Shiga toxin 2a (Stx2a) | | | | | | | | |
|---|---|---|---|---|---|---|---|---|---|
| | KD (mM) | % inhibition Stx2A1 in yeast ribosome (µM) | | | % Inhibition Stx2a depurination in Vero cell (µM) | | | | |
| Compound | Stx2A1 | 200 | 100 | 50 | 500 | 250 | 125 | 50 | 25 |
| MO01112 | 0.579 | 91 | 83 | — | — | — | — | — | — |
| SPB02181 | 0.487 | 62 | 82 | — | — | — | — | — | — |

Example 9: In Vivo Inhibition of Ricin Depurination

The inhibitory activity of RU-NT-93 was compared to Retro-2, the most potent ricin inhibitor, which has been shown to protect mice against ricin by blocking retrograde trafficking. RU-NT-93 (500 µM) inhibited depurination by ricin holotoxin in Vero cells significantly more than the recommended level (25-50 µM) of Retro-2. Two hours of exposure to 200 µM ricin depurinated within the linear range. One-hour preincubation with each compound was used as recommended for Retro-2, although it was not necessary for RU-NT-93. These results suggest that inhibition of ribosome binding may protect cells at a higher level than inhibition of toxin trafficking.

Further, RU-NT-135 and RU-NT-165 showed dose-dependent inhibition of depurination by ricin both in Vero cells and in the lung epithelial cell line (i.e., 1549). Both compounds showed similar protection as RU-NT-93 in A549 cells and in Vero cells. RU-NT-136 (IC$_{50}$=7.5 µM) showed less protection from depurination by ricin in Vero cells as compared to RU-NT-135 and RU-NT-165. RU-NT-47 and RU-NT-57 showed protection against Shiga toxin in vitro and in cell based assays, and also showed dose-dependent protection against ricin holotoxin in Vero cells. Thus, these compounds protected Vero cells from depurination by both ricin and Shiga toxin 2.

Compounds RU-NT-82 and RU-NT-85 were found to have IC$_{50}$ values of 36 µM and 12 µM, respectively, against yeast ribosomes in vitro. Further, both compounds showed dose-dependent inhibition of depurination by ricin toxin in Vero cells. RU-NT-87 also inhibited depurination by ricin toxin in Vero cells.

TABLE 5

| | In vivo inhibition of ricin depurination | | | | |
|---|---|---|---|---|---|
| | KD (mM) | % Inhibition of ricin depurination in Vero cells | | % Inhibition of ricin depurination A549 cells | |
| Compound | RTA | 500 µM | 250 µM | 200 µM | 500 µM | 250 µM |
| RU-NT-047 | — | 99 | 42 | — | — | — |
| RU-NT-057 | — | 43 | 51 | — | 91 | 67 |

TABLE 5-continued

In vivo inhibition of ricin depurination

| Compound | KD (mM) RTA | % Inhibition of ricin depurination in Vero cells | | | % Inhibition of ricin depurination A549 cells | |
|---|---|---|---|---|---|---|
| | | 500 μM | 250 μM | 200 μM | 500 μM | 250 μM |
| RU-NT-93 | 98 | 85 | 700 | 38/30 | 75 | 63 |
| RU-NT-135 | 109 | 100 | 76 | — | 81 | 67 |
| RU-NT-136 | 72 | 28 | 34 | 34 | — | — |
| RU-NT-165 | 282 | 85 | 81 | — | 78 | 67 |
| PD00589 | 210 | 83 | 71 | — | — | — |
| RU-NT-059 | 473 ± 27 | 90 | 68 | 57 | — | — |

TABLE 5-continued

In vivo inhibition of ricin depurination

| Compound | KD (mM) RTA | % Inhibition of ricin depurination in Vero cells | | | % Inhibition of ricin depurination A549 cells | |
|---|---|---|---|---|---|---|
| | | 500 μM | 250 μM | 200 μM | 500 μM | 250 μM |
| RU-NT-060 | 73 | — | — | — | — | — |
| RU-NT-062 | 70 | 41 | 11 | — | — | — |
| RU-NT-082 | — | 82 | 50 | — | — | — |
| RU-NT-085 | — | 73 | 46 | — | — | — |
| RU-NT-087 | — | 48 | 30 | — | — | — |

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

Enumerated Embodiments

The following enumerated embodiments are provided, the numbering of which is not to be construed as designating levels of importance.

Embodiment 1 provides a method of treating, ameliorating, and/or preventing toxicity caused by a ribosome inactivating protein (RIP) in a subject, the method comprising administering to the subject a therapeutically effective amount of a compound of Formula (I), or a salt, solvate, stereoisomer, geometric isomer, and/or tautomer thereof:

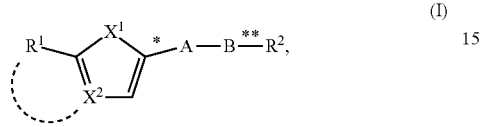

(I)

wherein:

A is a bond or an optionally substituted $C_1$-$C_2$ linker selected from the group consisting of optionally substituted $C_1$-$C_2$ alkylene, —CH=CH—, —C≡C—,

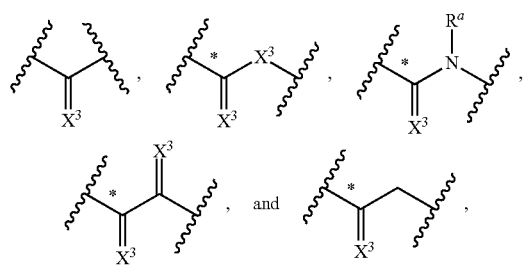

wherein, if present, the $C_1$-$C_2$ alkylene is optionally substituted with at least one substituent selected from the group consisting of hydroxyl, $C_1$-$C_6$ alkoxy, $N(R^a)(R^a)$, and halogen, wherein * indicates the bond from A to the 5-membered ring;

B is selected from the group consisting of a bond,

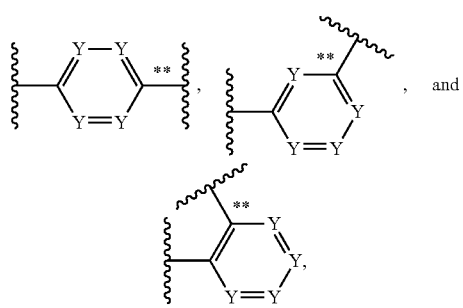

wherein ** indicates the bond from B to $R^2$;

$R^1$ is selected from the group consisting of H, optionally substituted aryl, optionally substituted heteroaryl, optionally substituted benzyl, optionally substituted $C_1$-$C_6$ alkyl, optionally substituted $C_3$-$C_6$ cycloalkyl, optionally substituted heterocycloalkyl, optionally substituted $C_2$-$C_6$ alkenyl, optionally substituted $C_2$-$C_6$ alkynyl, $C(O)$—$C_1$-$C_6$ alkyl, $C(O)$-aryl, $C(O)NR^a_2$, cyano, and halogen, wherein each optional substituent comprises at least one substituent selected from the group consisting of $C_1$-$C_6$ alkyl, $C_2$-$C_6$ alkenyl, $C_1$-$C_6$ cycloalkyl, $C_1$-$C_6$ alkoxy, hydroxyl, $NR^a_2$, $C(O)$—$C_1$-$C_6$ alkyl, CN, $CF_3$, $NO_2$, and $C(O)$-aryl, wherein two adjacent optional $C_1$-$C_6$ alkyl, $C_1$-$C_6$ cycloalkyl, $C_1$-$C_6$ alkoxy, and $C(O)$—$C_1$-$C_6$ alkyl substituents may optionally combine to form a 5 or 6-membered fused ring, wherein each optionally substituted aryl, optionally substituted heteroaryl, optionally substituted benzyl, optionally substituted $C_1$-$C_6$ alkyl, optionally substituted $C_2$-$C_6$ alkenyl, or optional substituent thereof, may optionally combine with $X^2$ to form a 5, 6, or 7-membered fused ring;

$R^2$ is selected from the group consisting of

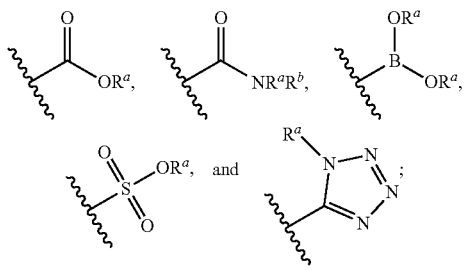

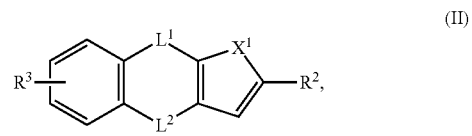

each occurrence of $R^a$ is independently selected from the group consisting of H, $C_1$-$C_6$ alkyl, $C_1$-$C_6$ alkoxy, benzyl, and aryl;

$R^b$ is selected from the group consisting of H, $C_1$-$C_6$ alkyl, $C_1$-$C_6$ alkoxy, benzyl, aryl, hydroxyl, and $C_1$-$C_6$ hydroxyalkyl;

$X^1$ is selected from the group consisting of S, O, and $NR^a$;

$X^2$ is CH or N;

each occurrence of $X^3$ is independently O or S;

each occurrence of Y is independently CH or N, wherein 0-3 Y are N in a given ring.

Embodiment 2 provides the method of embodiment 1, wherein the compound of Formula (I) comprises a compound of Formula II:

$$\text{(II)}$$

wherein:

$R^3$ is selected from the group consisting of $C_1$-$C_6$ alkyl, $C_2$-$C_6$ alkenyl, $C_1$-$C_6$ cycloalkyl, $C_1$-$C_6$ alkoxy, hydroxyl, $NR^a_2$, $C(O)$—$C_1$-$C_6$ alkyl, CN, $CF_3$, $NO_2$, and $C(O)$-aryl;

$L^1$ and $L^2$ are each independently a bond or optionally substituted $C_1$-$C_2$ alkyl.

Embodiment 3 provides the method of any of Embodiments 1-2, wherein the compound of Formula (I) is not 4-(thiophen-2-ylmethyl)benzoic acid.

Embodiment 4 provides the method of any of Embodiments 1-3 wherein $R^1$ is selected from the group consisting of: CN, Br, Me, Et, Ph,

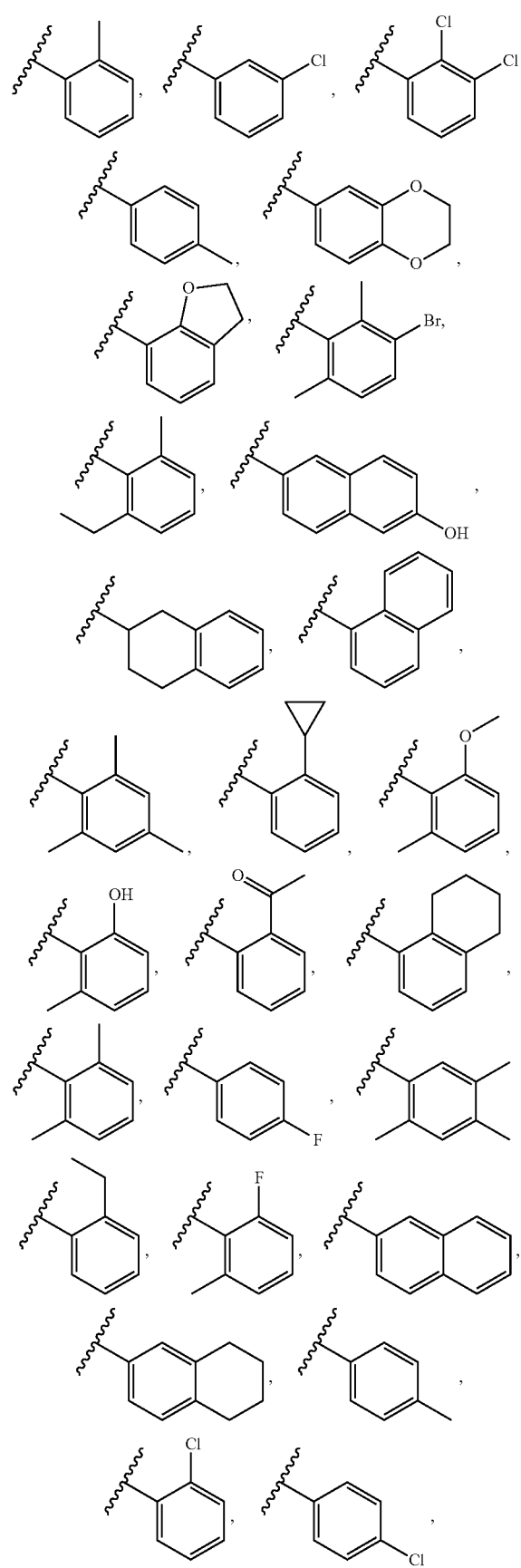
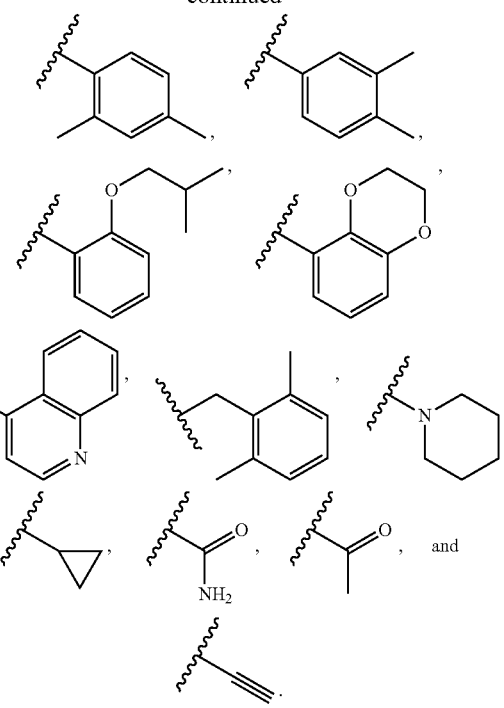
Embodiment 5 provides the method of any of Embodiments 1-4, wherein $R^2$ is selected from the group consisting of
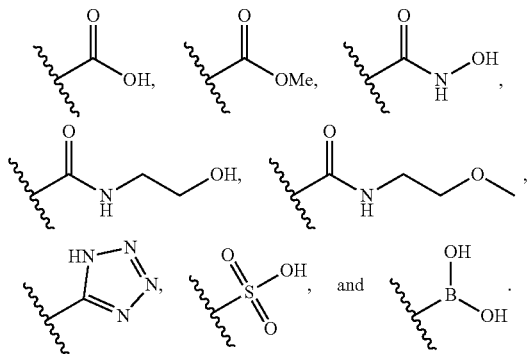
Embodiment 6 provides the method of any of Embodiments 1-5, wherein A is a bond.
Embodiment 7 provides the method of any of Embodiments 1-6, wherein A is selected from the group consisting of:
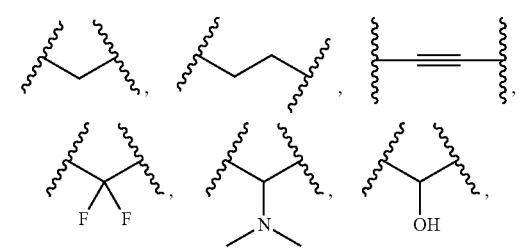

-continued

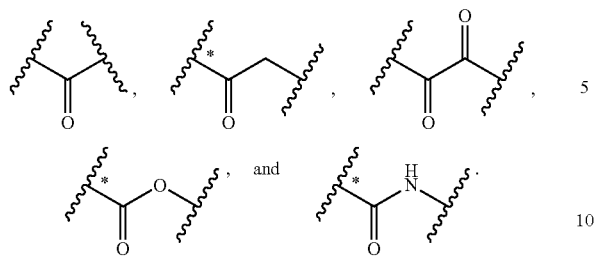

Embodiment 8 provides the method of any of Embodiments 1-7, wherein B is a bond.

Embodiment 9 provides the method of any of Embodiments 1-8, wherein B is

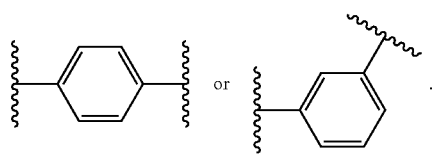 [SMILES: *c1ccc(*)cc1 ; *c1cccc(*)c1]

Embodiment 10 provides the method of any of Embodiments 1-9, wherein $R^3$ is selected from the group consisting of F, Br, Me, $NMe_2$, and OMe.

Embodiment 11 provides the method of any of Embodiments 1-10, wherein $L^1$ is a bond or —$CH_2$—.

Embodiment 12 provides the method of any of Embodiments 1-11, wherein —$CH_2$— or —$CH_2CH_2$—.

Embodiment 13 provides the method of any of Embodiments 1-12, wherein the compound of Formula (I) is selected from the group consisting of:

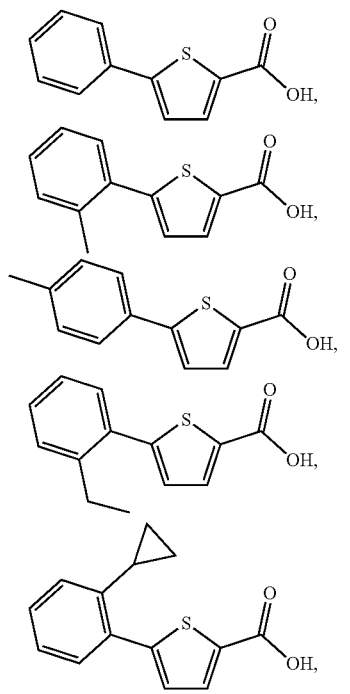

-continued

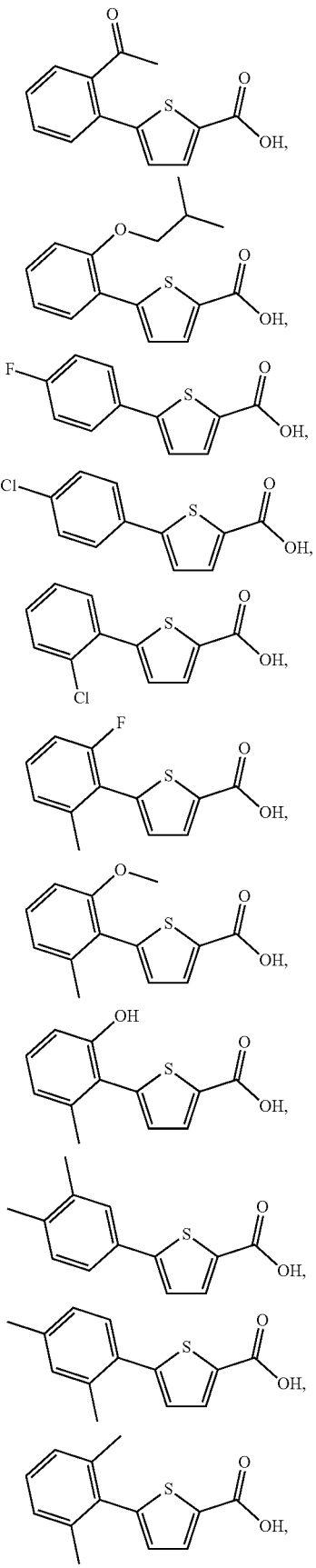

-continued
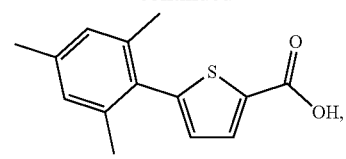
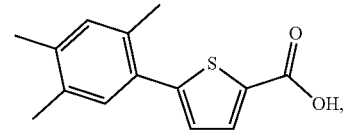
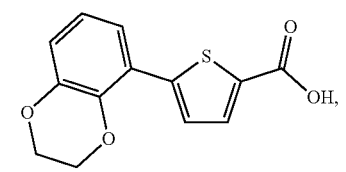
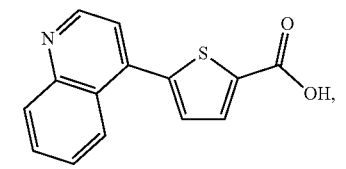
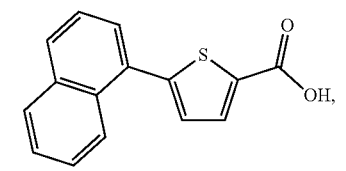
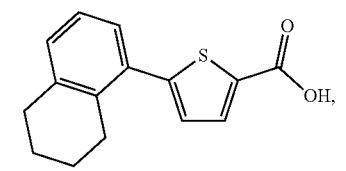
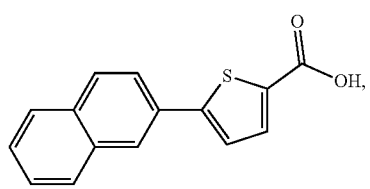
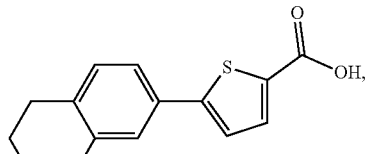
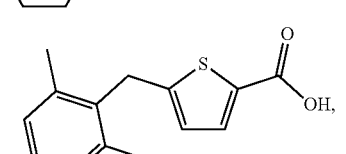
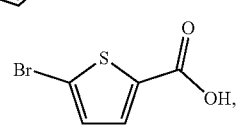
-continued
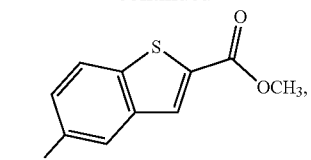
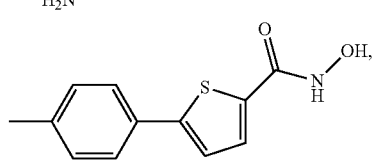
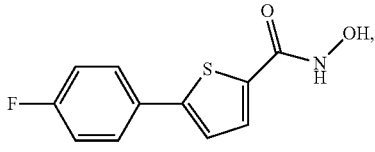
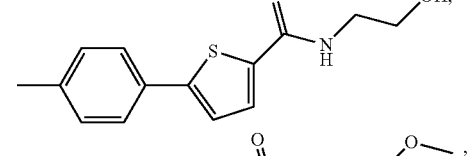
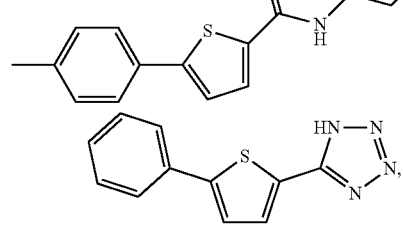
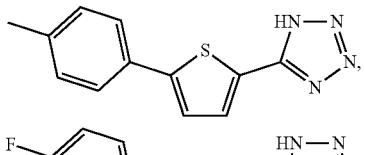
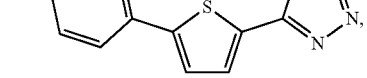
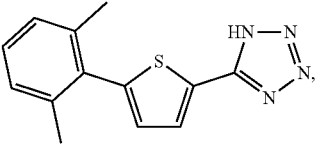
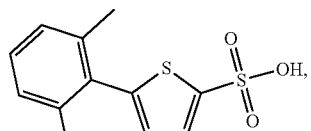
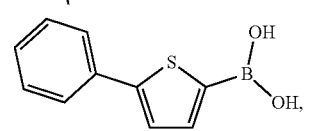
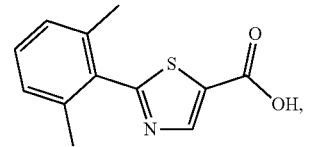

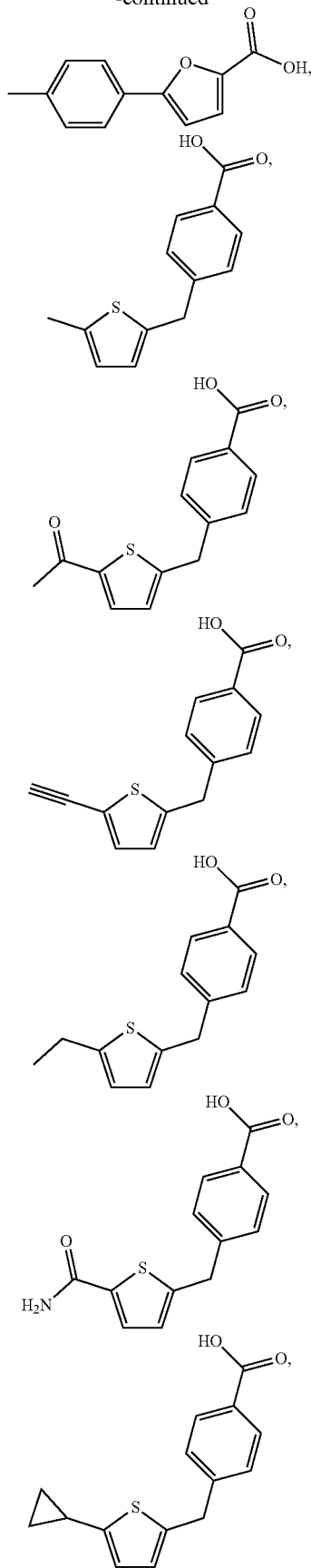
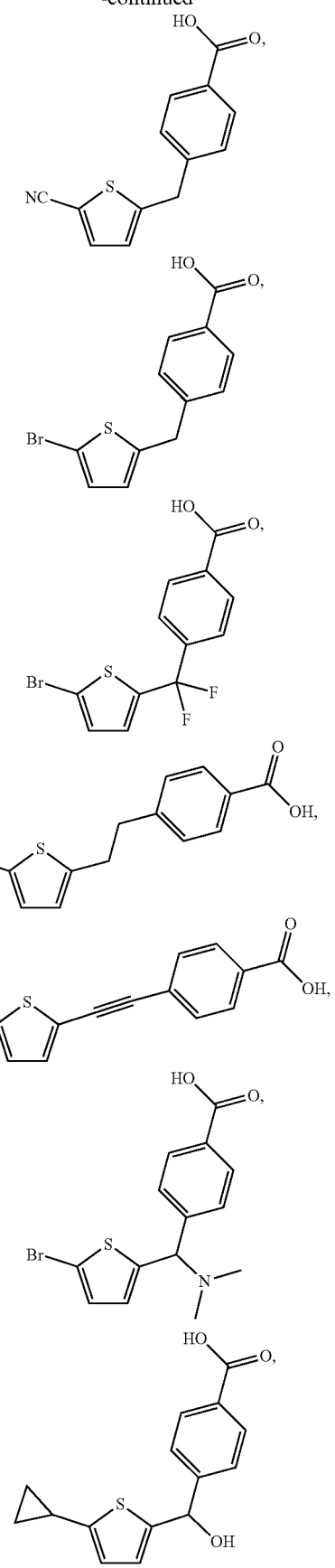

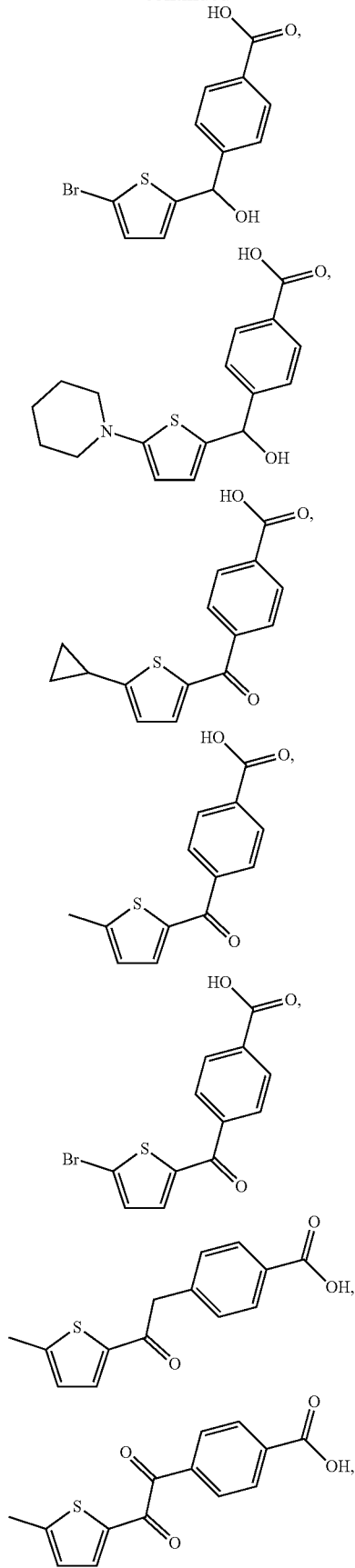
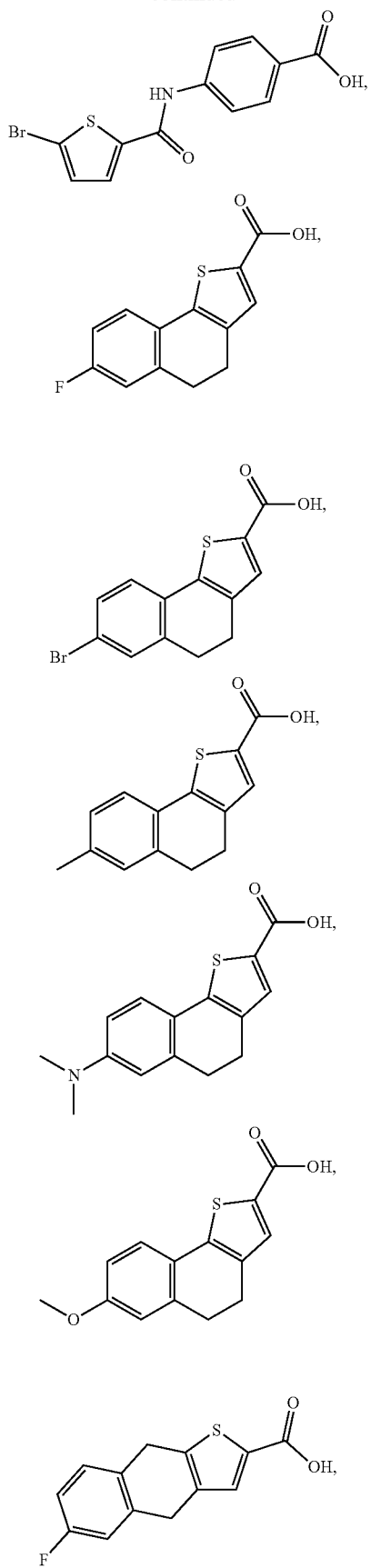

139
-continued
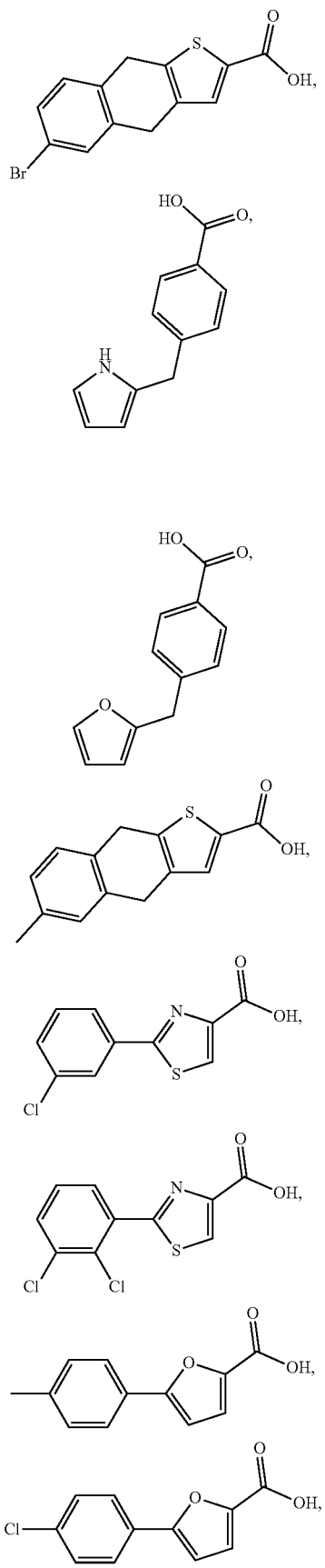
140
-continued
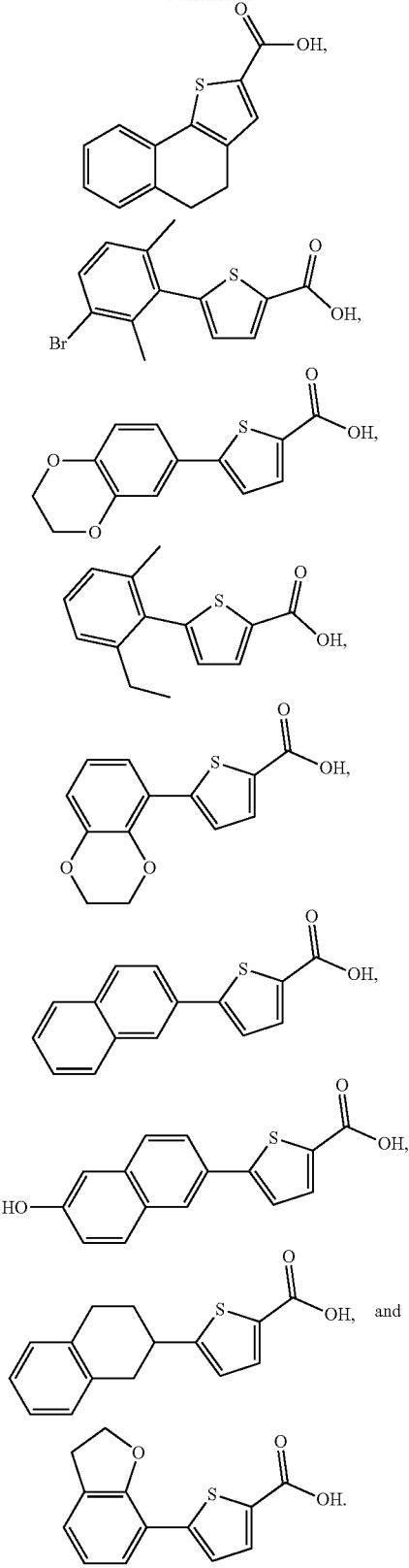
Embodiment 14 provides a method of treating, ameliorating, or preventing toxicity caused by a ribosome inactivating protein (RIP) in a subject, the method comprising administering to the subject a therapeutically effective amount of a compound, or a salt, solvate, stereoisomer, geometric isomer, and/or tautomer thereof, selected from the group consisting of:

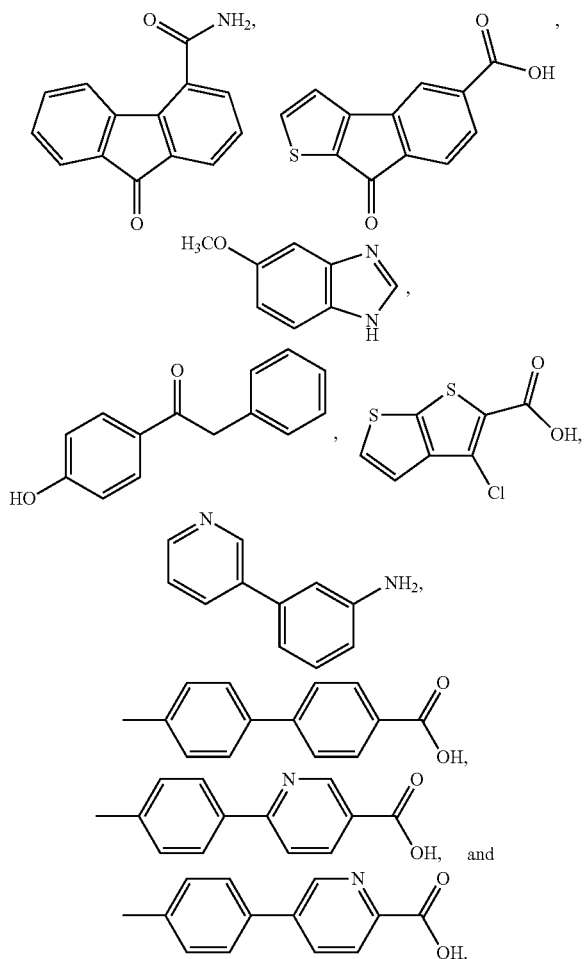

and

Embodiment 15 provides the method of any of Embodiments 1-14, wherein the RIP is ricin.

Embodiment 16 provides the method of any of Embodiments 1-15, wherein the compound inhibits depurination activity of the RIP.

Embodiment 17 provides the method of any of Embodiments 1-16, wherein the compound inhibits interaction of the RIP with a ribosome.

Embodiment 18 provides the method of any of Embodiments 1-17, wherein the compound inhibits interaction of the active A chain (RTA) of the RIP with a ribosome.

Embodiment 19 provides the method of any of Embodiments 1-18, wherein the compound binds to the ribosome binding site of the RTA.

Embodiment 20 provides the method of any of Embodiments 1-19, wherein the compound binds to the ribosome binding site of RTA with a dissociation constant ranging from about 0.3 μM to about 300 μM.

Embodiment 21 provides the method of any of Embodiments 1-20, wherein the compound inhibits the RTA depurination activity with an $IC_{50}$ ranging from about 2 μM to about 150 μM.

Embodiment 22 provides the method of any of Embodiments 1-21, wherein the ribosome inactivating protein (RIP) is either a type I or type II RIP.

Embodiment 23 provides the method of any of Embodiments 1-22, wherein the compound is administered as a pharmaceutical composition to the subject.

Embodiment 24 provides the method of any of Embodiments 1-23, wherein the subject is administered at least one additional agent useful for treating, ameliorating, and/or preventing the toxicity caused by RIP.

Embodiment 25 provides the method of any of Embodiments 1-24, wherein the at least one additional agent is selected from the group consisting of immunotherapeutics and vaccines.

Embodiment 26 provides the method of any of Embodiments 1-25, wherein administering the compound to the subject allows for administering a lower dose of the at least one additional agent as compared to the dose of the at least one additional agent alone that is required to achieve similar results in treating, ameliorating, and/or preventing toxicity caused by RIP.

Embodiment 27 provides the method of any of Embodiments 1-26, wherein the compound and the at least one additional agent are co-administered to the subject.

Embodiment 28 provides the method of any of Embodiments 1-27, wherein the compound and the at least one additional agent are co-formulated.

Embodiment 29 provides the method of any of Embodiments 1-28, wherein the subject is a mammal.

Embodiment 30 provides the method of any of Embodiments 1-29, wherein the subject is a human.

Embodiment 31 provides a compound, or salt, solvate, stereoisomer, geometric isomer, and/or tautomer thereof, selected from the group consisting of:

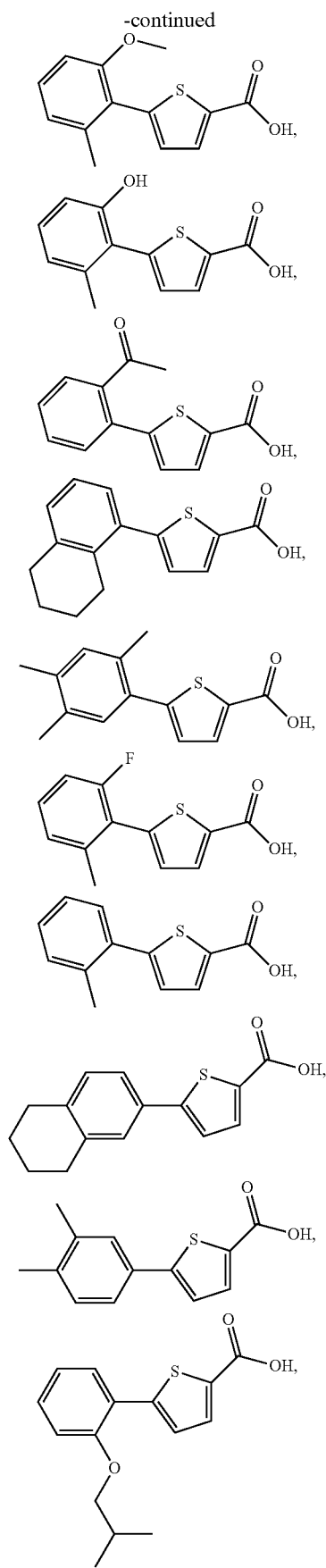
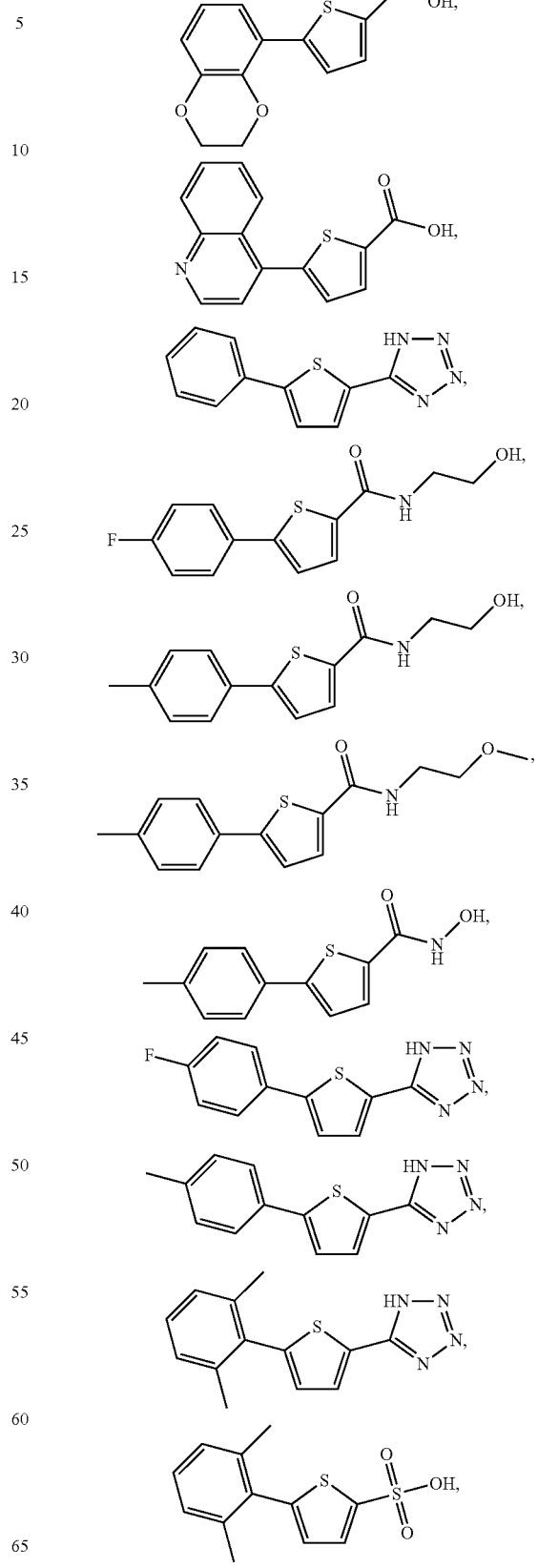

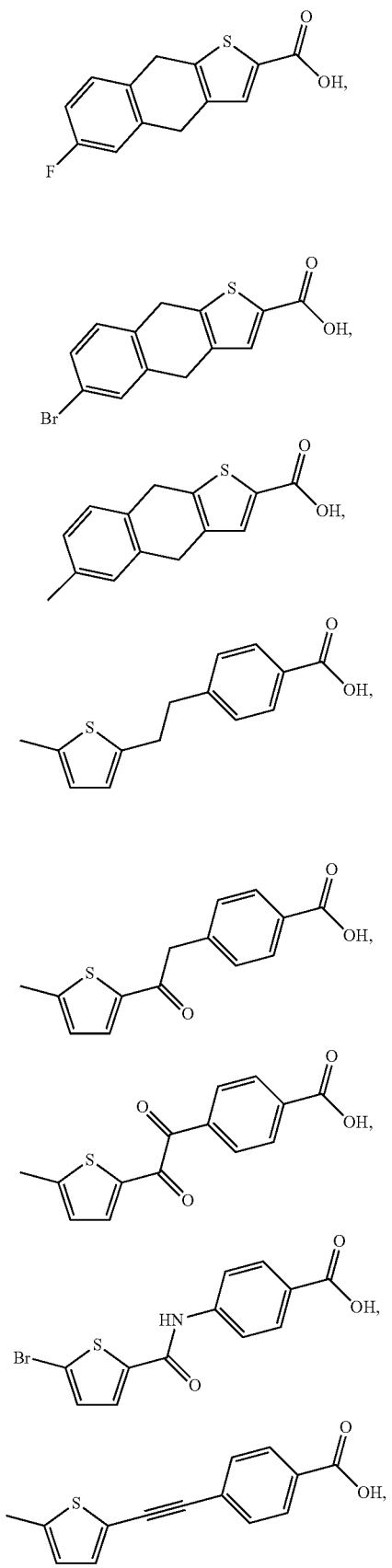
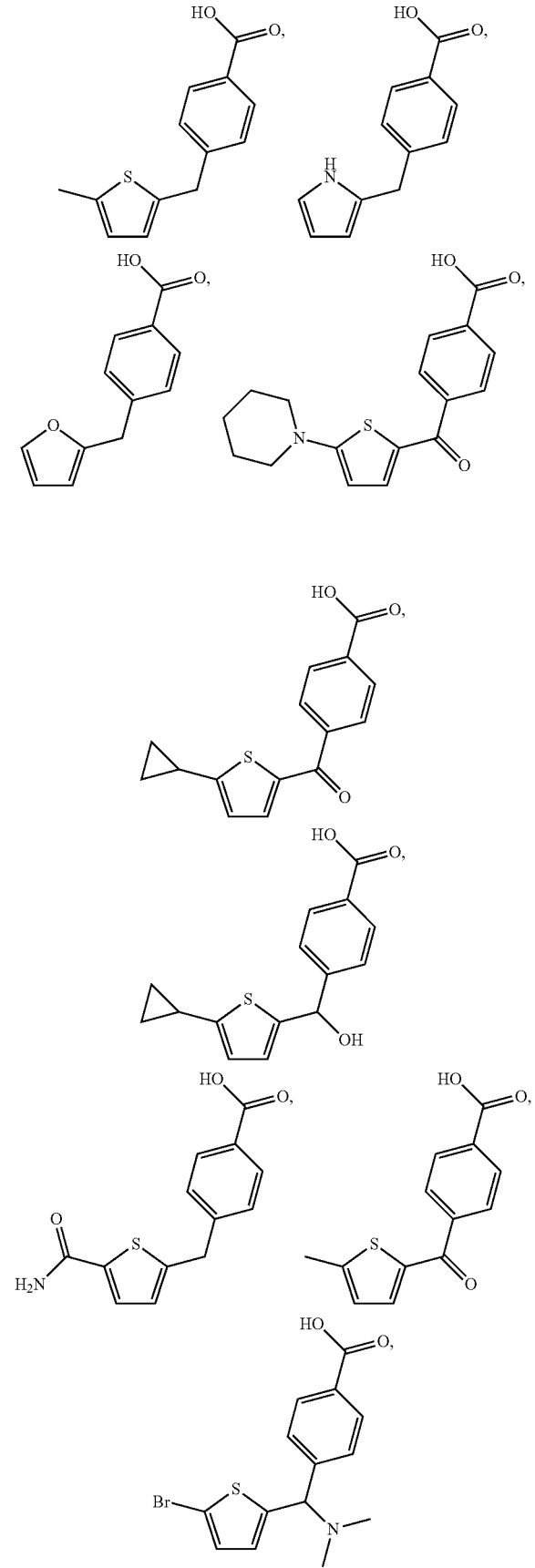

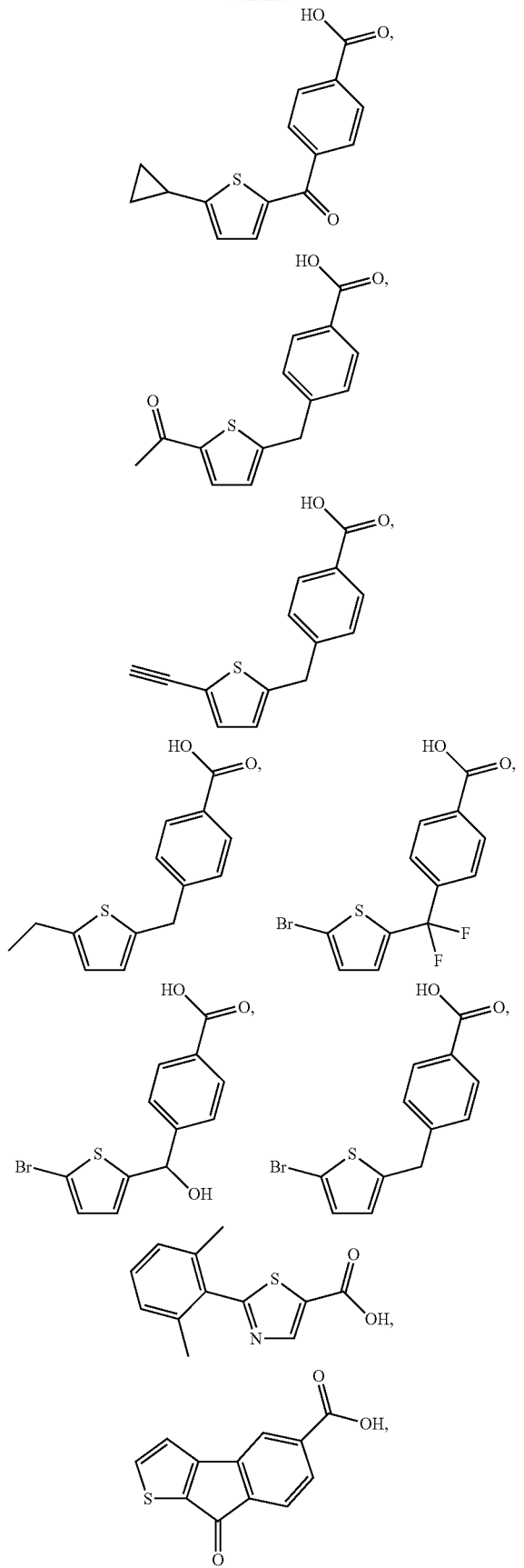
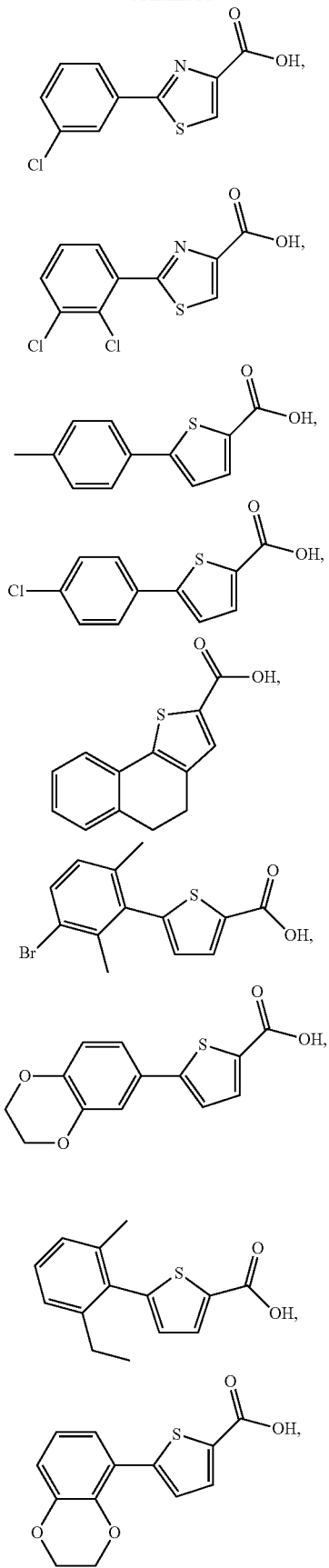

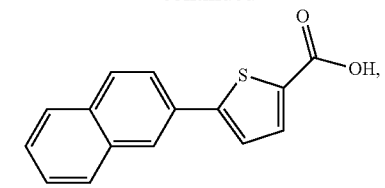
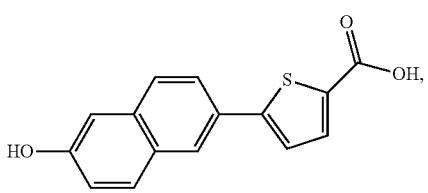
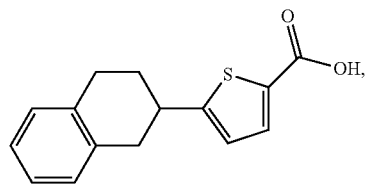
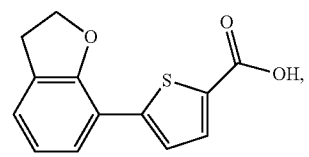
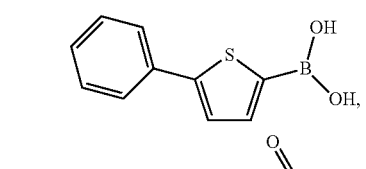
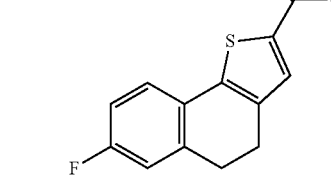
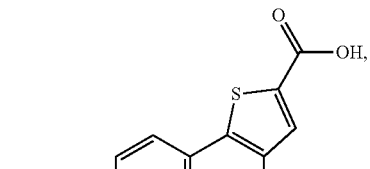
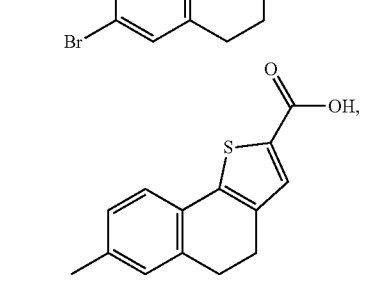
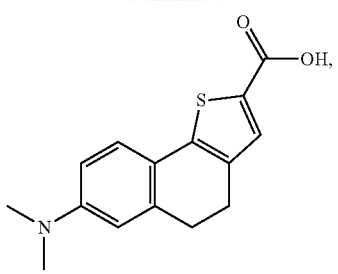
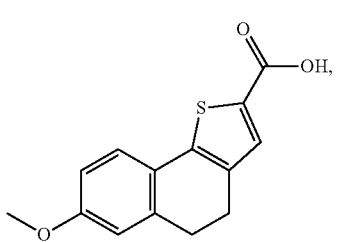
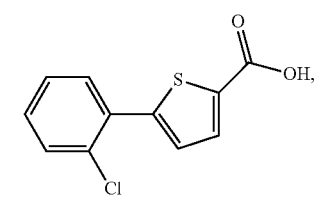
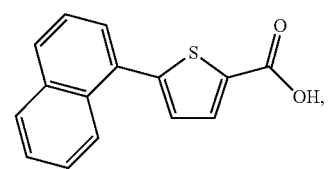
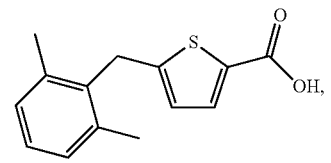
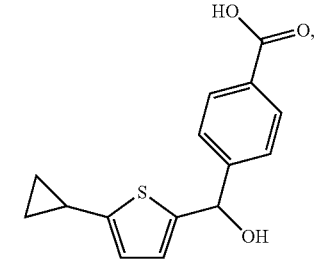

What is claimed is:

1. A method of treating or ameliorating toxicity caused by a ribosome inactivating protein (RIP) in a subject, the method comprising administering to the subject a therapeutically effective amount of a compound of Formula (I), or a salt, solvate, stereoisomer, geometric isomer, or tautomer thereof:

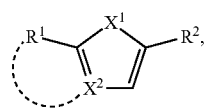
(I)

wherein:
$R^1$ is optionally substituted aryl,
wherein each optional substituent comprises at least one substituent selected from the group consisting of $C_1$-$C_6$ alkyl, $C_1$-$C_6$ cycloalkyl, $C_1$-$C_6$ alkoxy, halogen, hydroxyl, $NR^a_2$, C(O)—$C_1$-$C_6$ alkyl, CN, $CF_3$, $NO_2$, and C(O)-aryl,
wherein two adjacent optional $C_1$-$C_6$ alkyl or $C_1$-$C_6$ alkoxy substituents may optionally combine to form a 5 or 6-membered fused ring;
$R^2$ is selected from the group consisting of

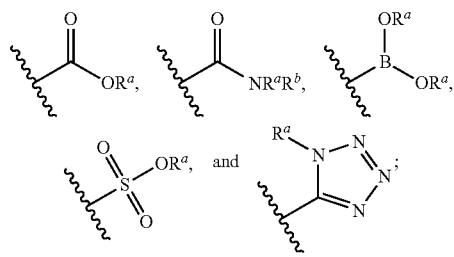

each occurrence of $R^a$ is independently selected from the group consisting of H, $C_1$-$C_6$ alkyl, $C_1$-$C_6$ alkoxy, benzyl, and aryl;
$R^b$ is selected from the group consisting of H, $C_1$-$C_6$ alkyl, $C_1$-$C_6$ alkoxy, benzyl, aryl, hydroxyl, and $C_1$-$C_6$ hydroxyalkyl;

$X^1$ is selected from the group consisting of S and O; and $X^2$ is CH, N, or C, wherein if $X^2$ is C, the optionally substituted aryl in $R^1$ combines with $X^2$ to form a 5, 6, or 7-membered fused ring.

2. The method of claim 1, wherein the compound of Formula (I) comprises a compound of Formula (II):

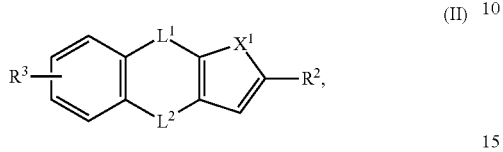

wherein:

$R^3$ is selected from the group consisting of $C_1$-$C_6$ alkyl, $C_1$-$C_6$ cycloalkyl, $C_1$-$C_6$ alkoxy, halogen, hydroxyl, $NR^a{}_2$, C(O)—$C_1$-$C_6$ alkyl, CN, $CF_3$, $NO_2$, and C(O)-aryl;

$L^1$ is a bond; and $L^2$ is optionally substituted $C_1$-$C_2$ alkyl.

3. The method of claim 1, wherein $R^1$ is selected from the group consisting of:

Ph,

4. The method of claim 1, wherein $R^2$ is selected from the group consisting of:

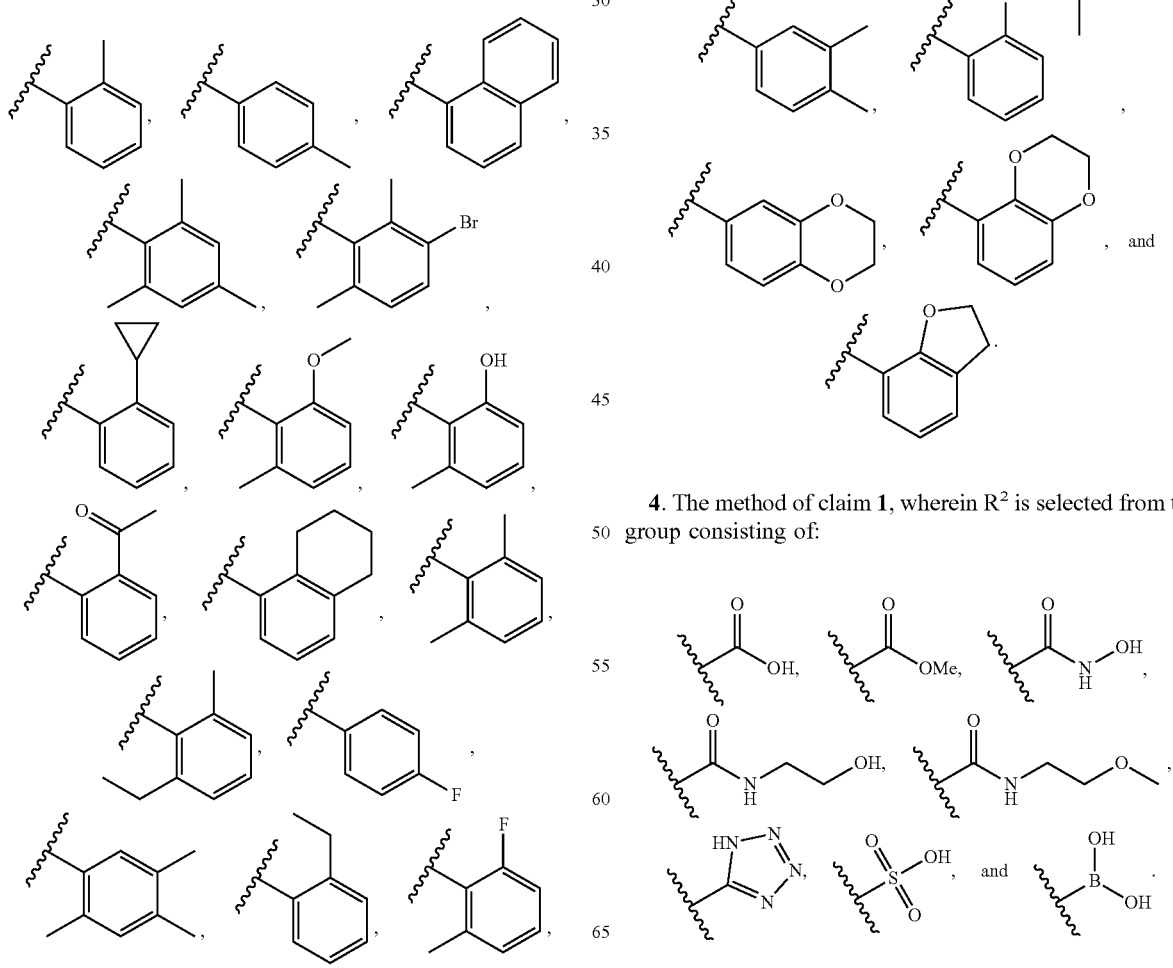

5. The method of claim 2, wherein $R^3$ is selected from the group consisting of halogen, Me, $NMe_2$, and OMe, wherein the halogen is F or Br.

6. The method of claim 2, wherein $L^2$ is $-CH_2-$ or $-CH_2CH_2-$.

7. A method of treating or ameliorating toxicity caused by a ribosome inactivating protein (RIP) in a subject, the method comprising administering to the subject a therapeutically effective amount of a compound selected from the group consisting of:

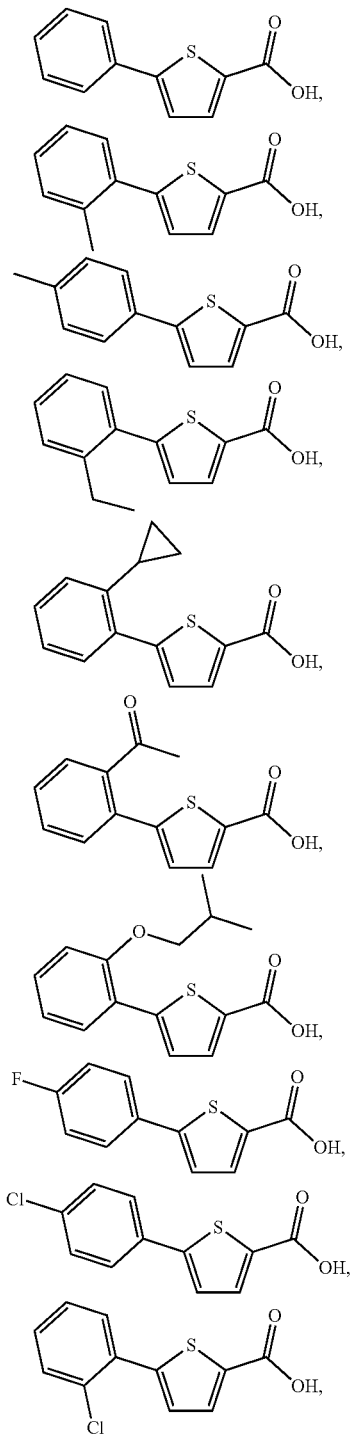

-continued

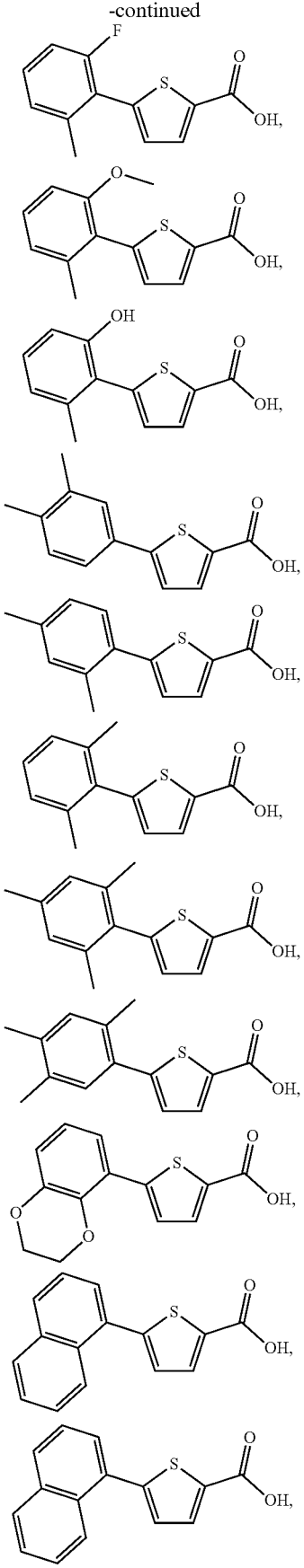

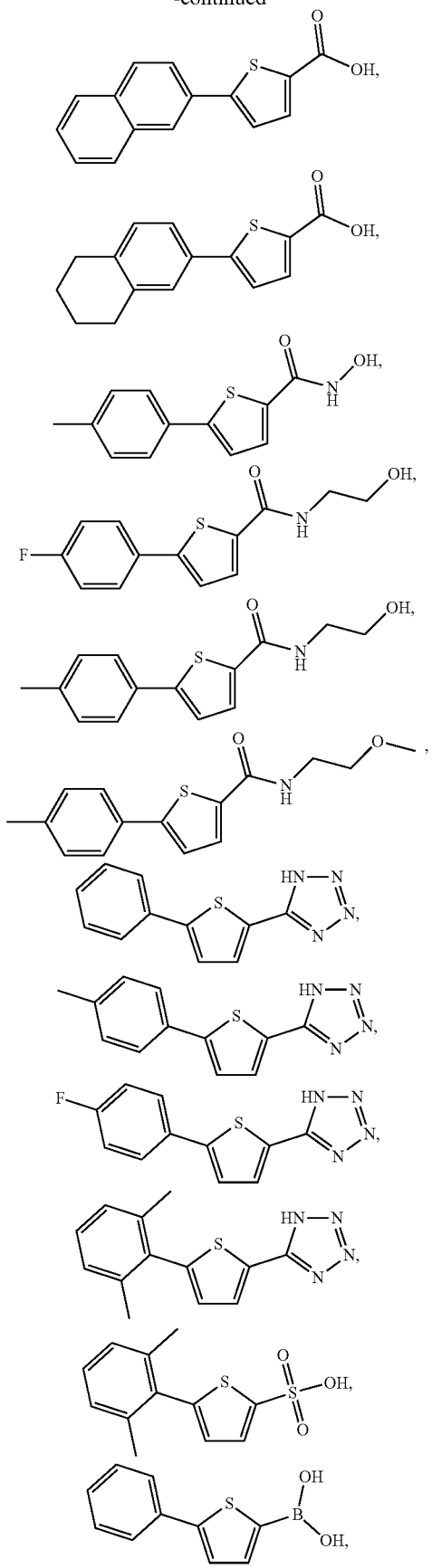
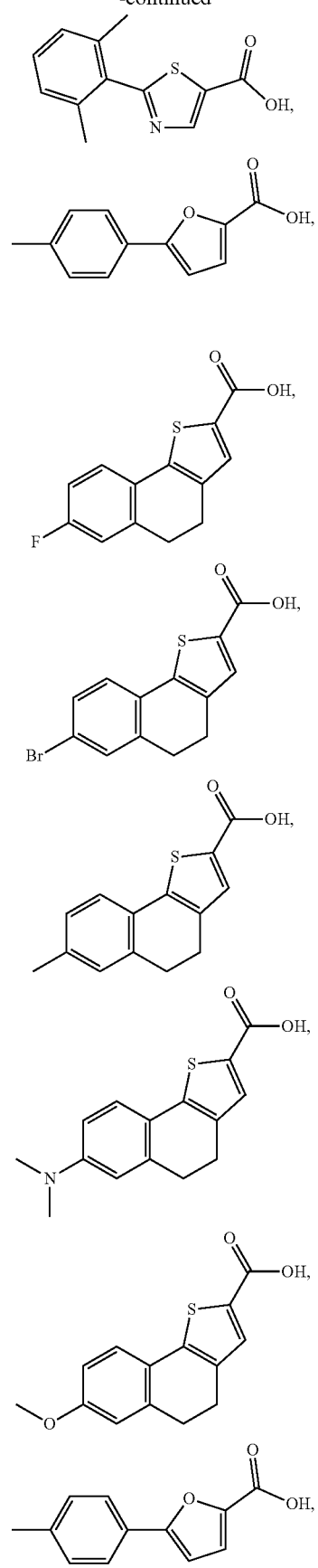

-continued

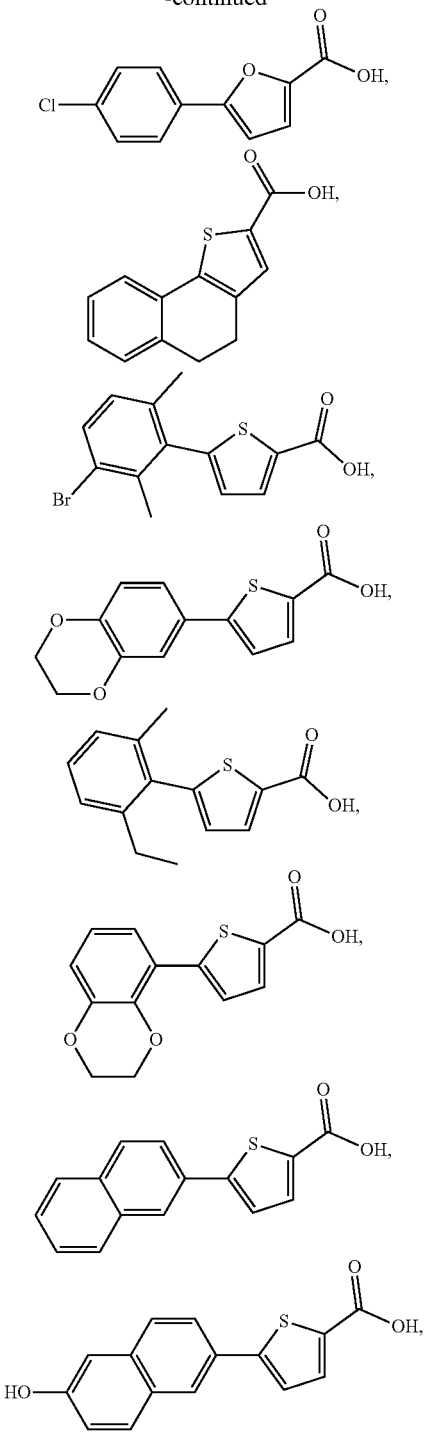

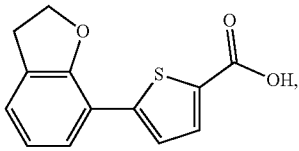 [SMILES: O=C(O)c1ccc(-c2cccc3c2OCC3)s1]

, or a salt, solvate, stereoisomer, geometric isomer, or tautomer thereof.

8. The method of claim 1, wherein the RIP is ricin or Shiga toxin 2a (Stx2a).

9. The method of claim 1, wherein the compound inhibits depurination activity of the RIP.

10. The method of claim 1, wherein the compound inhibits interaction of the RIP with a ribosome.

11. The method of claim 10, wherein the compound inhibits interaction of the active A chain (RTA) of the RIP with a ribosome.

12. The method of claim 11, wherein the compound binds to the ribosome binding site of the RTA.

13. The method of claim 12, wherein the compound binds to the ribosome binding site of RTA with a dissociation constant ranging from about 0.3 μM to about 300 μM.

14. The method of claim 12, wherein the compound inhibits the RTA depurination activity with an $IC_{50}$ ranging from about 2 μM to about 150 μM.

15. The method of claim 1, wherein the ribosome inactivating protein (RIP) is either a type I or type II RIP.

16. The method of claim 1, wherein the compound is administered as a pharmaceutical composition to the subject.

17. The method of claim 1, wherein the subject is administered at least one additional agent useful for treating, ameliorating, and/or preventing the toxicity caused by RIP.

18. The method of claim 17, wherein the at least one additional agent is selected from the group consisting of immunotherapeutics and vaccines.

19. The method of claim 17, wherein administering the compound to the subject allows for administering a lower dose of the at least one additional agent as compared to the dose of the at least one additional agent alone that is required to achieve similar results in treating, ameliorating, and/or preventing toxicity caused by RIP.

20. The method of claim 17, wherein the compound and the at least one additional agent are co-administered to the subject.

21. The method of claim 17, wherein the compound and the at least one additional agent are co-formulated.

22. The method of claim 1, wherein the subject is a mammal.

23. The method of claim 22, wherein the subject is a human.

* * * * *